United States Patent
Saunders et al.

(10) Patent No.: US 8,557,965 B2
(45) Date of Patent: Oct. 15, 2013

(54) SINGLE VARIABLE DOMAINS AGAINST NOTCH PATHWAY MEMBERS

(75) Inventors: Michael John Scott Saunders, Brussels (BE); Johannes Joseph Wilhelmus De Haard, Oudelande (NL); Edward Dolk, Utrecht (NL); Renee De Bruin, Utrecht (NL); Peter Vanlandschoot, Bellem (BE)

(73) Assignee: Ablynx N.V., Zwijnaarde (BE)

( * ) Notice: Subject to any disclaimer, the term of this patent is extended or adjusted under 35 U.S.C. 154(b) by 140 days.

(21) Appl. No.: 12/934,766

(22) PCT Filed: Apr. 7, 2009

(86) PCT No.: PCT/EP2009/054139
§ 371 (c)(1),
(2), (4) Date: Jan. 7, 2011

(87) PCT Pub. No.: WO2009/124931
PCT Pub. Date: Oct. 15, 2009

(65) Prior Publication Data
US 2011/0105733 A1   May 5, 2011

Related U.S. Application Data

(60) Provisional application No. 61/042,854, filed on Apr. 7, 2008.

(51) Int. Cl.
*C07K 16/00* (2006.01)
*C07K 16/18* (2006.01)
*C07K 16/22* (2006.01)
*C07K 16/28* (2006.01)
*C07K 14/475* (2006.01)
*C07K 14/705* (2006.01)

(52) U.S. Cl.
USPC .................. 530/387.1; 530/387.3; 530/350

(58) Field of Classification Search
None
See application file for complete search history.

(56) References Cited

FOREIGN PATENT DOCUMENTS

| WO | WO 01/90190    | 11/2001 |
|----|----------------|---------|
| WO | WO 2005/054434 | 6/2005  |
| WO | WO 2006/068822 | 6/2006  |
| WO | WO 2007/145840 | 12/2007 |

OTHER PUBLICATIONS

Jang et al. (Molec. Immunol. 35:1207-1217 (1998)).*
Brorson et al. (J. Immunol. 163:6694-6701 (1999)).*
Colman (Research in Immunol. 145:33-36 (1994)).*
Wu et al. J Mol Biol 294: 151-162, 1999.*
Rudikoff et al. Proc Natl Acad Sci USA 79: 1979-1983, 1982.*
Deffar et al. Nanobodies—the new concept in antibody engineering. African J Biotechnol 8(12): 2645-2652, 2009.*
Vanlandschoot et al. Nanobodies: New ammunition to battle viruses. Antiviral Res 92: 389-407, 2011.*
Vincke et al. General strategy to humanize a camelid single-domain antibody and identification of a universal humanized nanobody scaffold. J Biol Chem 284(5): 3273-3284, 2009.*
Deschacht et al. A novel promoscuous class of camelid single-domain antibody contributes to the antigen-binding repertoire. J Immunol 184: 5696-5704, 2010.*
Muyldermans, S. Single domain camel antibodies: current status. Rev Molec Biotechnol 74: 277-302, 2001.*
Hamers-Casterman, C. et al., "Naturally occurring antibodies devoid of light chains," *Nature* 1993; 363(6428):446-448.
Sutphin, R.M. et al., "Notch agonists: Emerging as a feasible therapeutic approach in AML," Database Accession No. PREV200700258166 and *Blood* Nov. 2006; 108(11), Part 1, p. 412A.
Jurynczyk, M. et al., "Notch3 Inhibition in Myelin-Reactive T Cells Down-Regulates Protein Kinase Cθ and Attenuates Experimental Autoimmune Encephalomyelitis," *The Journal of Immunology* Feb. 2008; 180(4,15): 2634-2640.

* cited by examiner

*Primary Examiner* — Bridget E Bunner
(74) *Attorney, Agent, or Firm* — Wolf, Greenfield & Sacks, P.C.

(57) ABSTRACT

The present invention relates to amino acid sequences (also referred to herein as "single variable domain(s) of the invention". "Nanobody™ of the invention" or "Nanobodies™ of the invention", ilpolypeptide(s) of the invention") that are directed against (as defined herein) members of the Notch signalling pathway such as the four mammalian members of the Notch Receptors (Notch-1, Notch-2, Notch-3, Notch-4, hereinafter also "Notch Receptors") and the five mammalian members of the Notch Ligands (the Delta-like family with "DLL1", "DLL3", "DLL4" wherein "DLL" stands for Delta-like ligand; the Jagged family with "Jagged-1", "Jagged-2", hereinafter also "Notch Ligands"), as well as to constructs that comprise or essentially consist of one or more such single variable domain(s) (also referred to herein as "construct of the invention" and "constructs of the invention", "Nanobody™ of the invention" or "Nanobodies™ of the invention", respectively). In particular, this invention relates to Notch pathway interfering single variable domains down- or up-regulating Notch signaling (also referred to herein "Notch-antagonists" or "Notch-agonists").

13 Claims, 7 Drawing Sheets

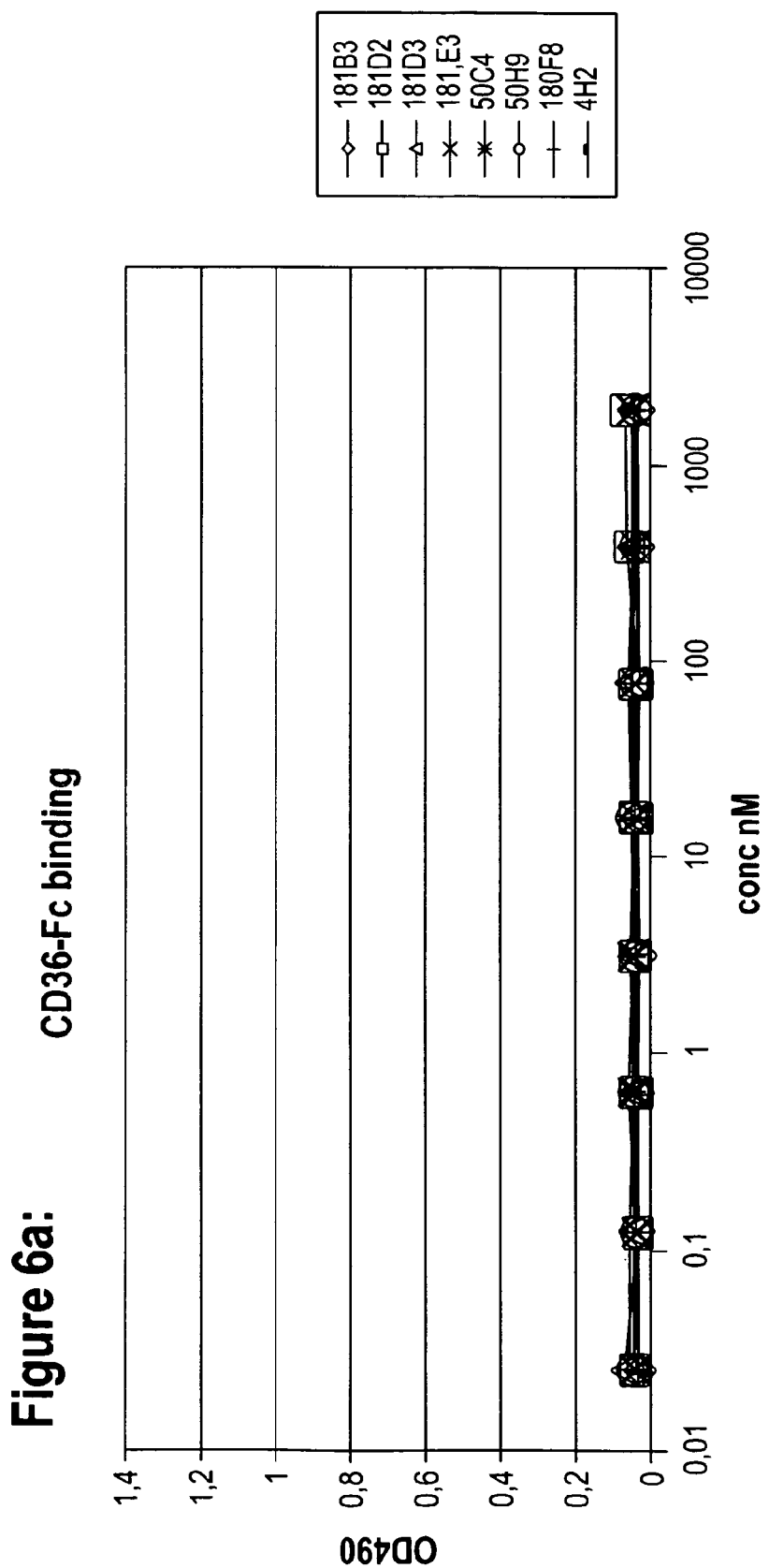

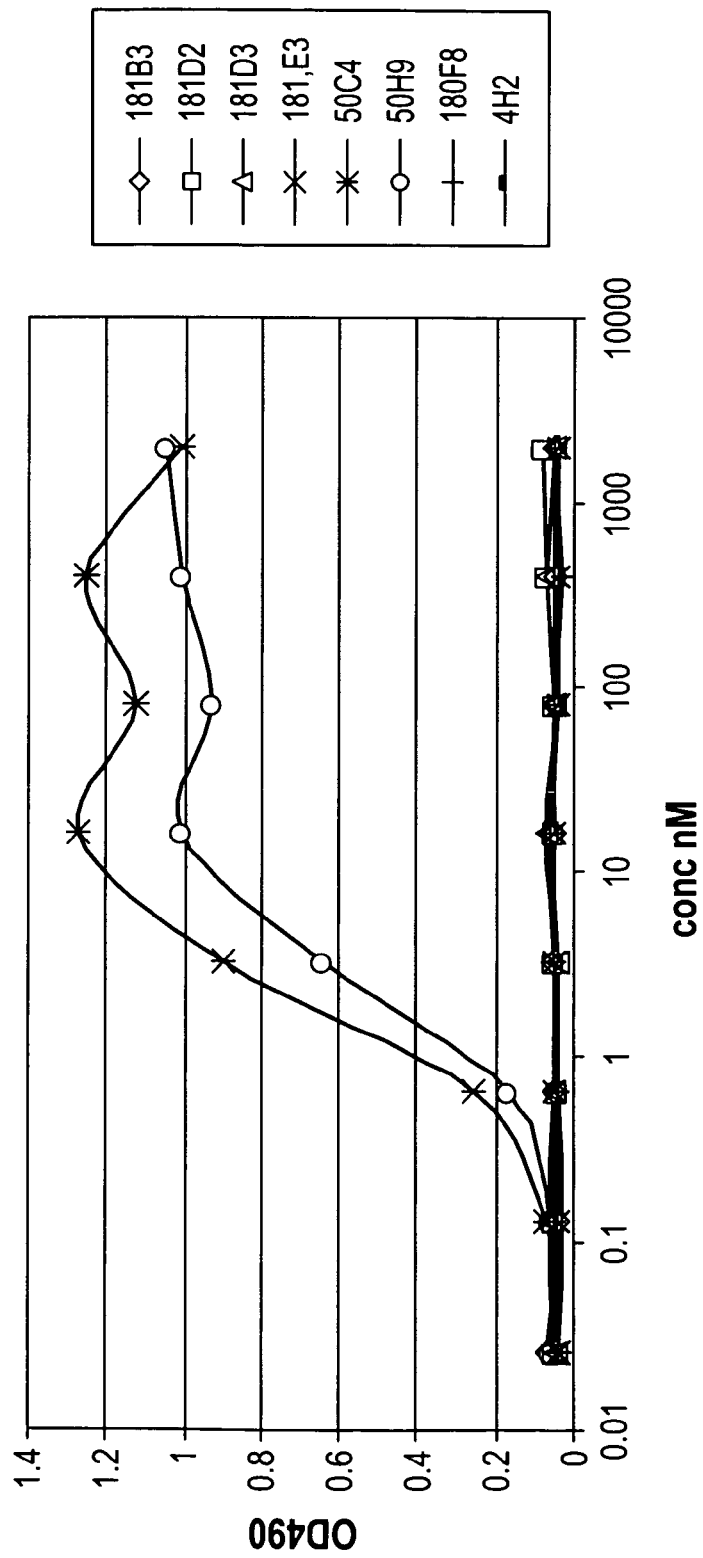

SINGLE VARIABLE DOMAINS AGAINST NOTCH PATHWAY MEMBERS

RELATED APPLICATIONS

Figure 1:
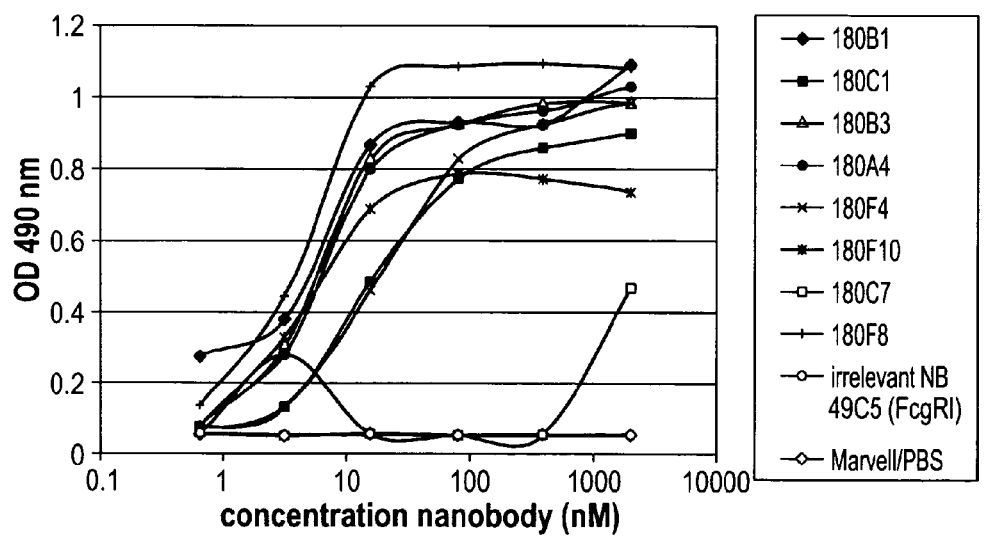

This application is a national stage filing under 35 U.S.C. §371 of international application PCT/EP2009/054139, filed Apr. 7, 2009, which was published under PCT Article 21(2) in English, and claims the benefit under 35 U.S.C. §119(e) of U.S. provisional application Ser. No. 61/042,854, filed Apr. 7, 2008, the disclosures of which are incorporated by reference herein in their entireties.

The present invention relates to amino acid sequences (also referred to herein as "single variable domain(s) of the invention", "Nanobody™ of the invention" or "Nanobodies™ of the invention", "polypeptide(s) of the invention") that are directed against (as defined herein) members of the Notch signalling pathway such as the four mammalian members of the Notch Receptors (Notch-1, Notch-2, Notch-3, Notch-4, hereinafter also "Notch Receptors") and the five mammalian members of the Notch Ligands (the Delta-like family with "DLL1", "DLL3", "DLL4" wherein "DLL" stands for Delta-like ligand; the Jagged family with "Jagged-1", "Jagged-2", hereinafter also "Notch Ligands"), as well as to constructs that comprise or essentially consist of one or more such single variable domain(s) (also referred to herein as "construct of the invention" and "constructs of the invention", "Nanobody™ of the invention" or "Nanobodies™ of the invention", respectively). In particular, this invention relates to Notch pathway interfering single variable domains down- or up-regulating Notch signaling (also referred to herein as "Notch-antagonists" or "Notch-agonists").

The invention also relates to nucleic acids encoding such single variable domains or constructs (also referred to herein as "nucleic acids of the invention", "nucleic acid of the invention", "nucleotide sequence of the invention" or "nucleotide sequences of the invention"); to methods for preparing such single variable domains or constructs; to host cells expressing or capable of expressing such single variable domains or constructs; to compositions, and in particular to pharmaceutical compositions, that comprise such single variable domains or constructs; and to uses of such single variable domains, constructs, nucleic acids, host cells and/or compositions, in particular for prophylactic, therapeutic or diagnostic purposes, such as the uses in cancer, immunomodulation and neurodegenerative disorders and in particular the prophylactic, therapeutic or diagnostic purposes mentioned herein.

Other aspects, embodiments, advantages and applications of the invention will become clear from the further description herein.

The Notch pathway is known to control cell fate choices in many tissues during development and differentiation. As for cancer, numerous observations suggest that chronically active Notch signalling is associated with the transformed phenotype in many cells. Overexpression of apparently full-length Notch receptors and ligands is observed in several common epithelial malignancies and tumor cell lines. In other cases, activated Notch signalling results from deletions that produce constitutively active Notch receptors (Miele et al., supra). Examples of possibly suitable uses of a polypeptide of the invention in cancer are mainly in the form of Notch-antagonists and are for example: cervical carcinomas, pre-neoplastic lesions in cervical epithelium, endometrial carcinomas, T-cell acute lymphoblastic leukaemia (T-ALL), acute promyelocytic leukaemia, erythroleukemia, glioblastoma multiforme, neuroblastoma and medulloblastoma to pleural mesothelioma (Miele et al, supra), disease with excessive angiogenesis (Thurston G. et. Al, 2007, Nature 7, 327-331). Blockade of DLL4 inhibits tumour growth by promoting non-productive angiogenesis (WO2007070671).

As for neurodegenerative disorders, Notch signalling has been known for many years to play a pivotal role in the development of the central nervous system and, more recently also in neuropathology. Examples of possibly suitable uses of a polypeptide of the invention in neurodegenerative diseases are mainly in the form of Notch-agonists and are for example: CADASIL, Alzheimer's disease, familial Alzheimer's disease, demyelinating disorders such as Multiple Sclerosis, neurological lesions such as spinal cord injuries, stroke (Miele et al., supra).

As for immunomodulation, considerable evidence points to multiple roles of Notch signalling in the immune system. It is well established that Notch signalling plays a role in T-cell maturation, in particular by inhibiting the "differentiation" program that is triggered after activation of T-cells by a cognate interaction. Hence, Notch-agonists may be used for immunosuppressive or tolerogenic interferences (uses in transplantation/graft versus host diseases); Notch-antagonists may amplify an immune response.

The single variable domains and constructs of the present invention can generally be used to modulate, and in particular inhibit and/or prevent, binding of Notch Ligands to Notch Receptors, and thus to modulate, and in particular inhibit or prevent, the signalling that is mediated by Notch Ligands and/or Notch Receptors, to modulate the biological pathways in which Notch Ligands and/or Notch Receptors are involved, and/or to modulate the biological mechanisms, responses and effects associated with such signalling or these pathways.

As such, the single variable domains and constructs of the present invention can be used for the prevention and treatment (as defined herein) of cancer, neurodegenerative diseases and immunomodulatory diseases. Generally, cancer, neurodegenerative diseases and immunomodulatory diseases can be defined as diseases and disorders that can be prevented and/or treated, respectively, by suitably administering to a subject in need thereof (i.e. having the disease or disorder or at least one symptom thereof and/or at risk of attracting or developing the disease or disorder) of either a polypeptide or composition of the invention (and in particular, of a pharmaceutically active amount thereof) and/or of a known active principle active against members of the Notch signalling pathway members of the Notch signalling pathway or a biological pathway or mechanism in which members of the Notch signalling pathway is involved (and in particular, of a pharmaceutically active amount thereof). Examples of such cancer, neurodegenerative diseases and immunomodulatory diseases will be clear to the skilled person based on the disclosure herein, and for example include the following diseases and disorders: Alzheimer, cervical carcinomas, pre-neoplastic lesions in cervical epithelium, endometrial carcinomas, T-cell acute lymphoblastic leukaemia (T-ALL), acute promyelocytic leukaemia, erythroleukemia, glioblastoma multiforme, neuroblastoma and medulloblastoma to pleural mesothelioma (Miele et al, supra), disease with excessive angiogenesis (Thurston G. et. Al, 2007, Nature 7, 327-331), CADASIL, Alzheimer's disease, familial Alzheimer's disease, demyelinating disorders such as Multiple Sclerosis, neurological lesions such as spinal cord injuries, stroke (Miele et al., supra), transplantation/graft versus host diseases.

In particular, the single variable domains and constructs of the present invention can be used for the prevention and treatment of cancer, neurodegenerative diseases and immunomodulatory diseases which are characterized by excessive and/or unwanted signaling mediated by members of the Notch signalling pathway or by the pathway(s) in which members of the Notch signalling pathway are involved. Examples of such cancer, neurodegenerative diseases and immunomodulatory diseases will again be clear to the skilled person based on the disclosure herein.

Thus, without being limited thereto, the single variable domains of the invention can for example be used to prevent and/or to treat all diseases and disorders that are currently being prevented or treated with active principles that can modulate Notch pathway-mediated signalling, such as those mentioned in the prior art cited above. It is also envisaged that the single variable domains of the invention can be used to prevent and/or to treat all diseases and disorders for which treatment with such active principles is currently being developed, has been proposed, or will be proposed or developed in future. In addition, it is envisaged that, because of their favourable properties as further described herein, the single variable domains of the present invention may be used for the prevention and treatment of other diseases and disorders than those for which these known active principles are being used or will be proposed or developed; and/or that the single variable domains of the present invention may provide new methods and regimens for treating the diseases and disorders described herein.

Other applications and uses of the single variable domains of the invention will become clear to the skilled person from the further disclosure herein.

Generally, it is an object of the invention to provide pharmacologically active agents, as well as constructs comprising the same, that can be used in the diagnosis, prevention and/or treatment of cancer, neurodegenerative diseases and immunomodulatory diseases and of the further diseases and disorders mentioned herein; and to provide methods for the diagnosis, prevention and/or treatment of such diseases and disorders that involve the administration and/or use of such agents and constructs.

In particular, it is an object of the invention to provide such pharmacologically active agents, constructs and/or methods that have certain advantages compared to the agents, constructs and/or methods that are currently used and/or known in the art. These advantages will become clear from the further description below.

More in particular, it is an object of the invention to provide therapeutic proteins that can be used as pharmacologically active agents, as well as constructs comprising the same, for the diagnosis, prevention and/or treatment of cancer, neurodegenerative diseases and immunomodulatory diseases and of the further diseases and disorders mentioned herein; and to provide methods for the diagnosis, prevention and/or treatment of such diseases and disorders that involve the administration and/or the use of such therapeutic proteins and constructs.

Accordingly, it is a specific object of the present invention to provide single variable domains that are directed against (as defined herein) members of the Notch signalling pathway, in particular against members of the Notch signalling pathway from a warm-blooded animal, more in particular against members of the Notch signalling pathway from a mammal, and especially against human members of the Notch signalling pathway, and to provide single variable domains comprising or essentially consisting of at least one such amino acid sequence.

In particular, it is a specific object of the present invention to provide such single variable domains that are suitable for prophylactic, therapeutic and/or diagnostic use in a warm-blooded animal, and in particular in a mammal, and more in particular in a human being.

More in particular, it is a specific object of the present invention to provide such single variable domains that can be used for the prevention, treatment, alleviation and/or diagnosis of one or more diseases, disorders or conditions associated with members of the Notch signalling pathway and/or mediated by members of the Notch signalling pathway (such as the diseases, disorders and conditions mentioned herein) in a warm-blooded animal, in particular in a mammal, and more in particular in a human being.

It is also a specific object of the invention to provide such single variable domains that can be used in the preparation of pharmaceutical or veterinary compositions for the prevention and/or treatment of one or more diseases, disorders or conditions associated with and/or mediated by members of the Notch signalling pathway (such as the diseases, disorders and conditions mentioned herein) in a warm-blooded animal, in particular in a mammal, and more in particular in a human being.

In the invention, generally, these objects are achieved by the use of the amino acid sequences, proteins, single variable domains and constructs that are described herein.

In general, the invention provides single variable domains that are directed against (as defined herein) and/or can specifically bind (as defined herein) to members of the Notch signalling pathway; as well as compounds and constructs, and in particular proteins and single variable domains, that comprise at least one such amino acid sequence.

More in particular, the invention provides single variable domains that can bind to members of the Notch signalling pathway with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein; as well as compounds and constructs, and in particular proteins and single variable domains, that comprise at least one such amino acid sequence.

In particular, single variable domains of the invention are preferably such that they:

bind to members of the Notch signalling pathway with a dissociation constant ($K_D$) of $10^{-5}$ to $10^{-12}$ moles/liter or less, and preferably and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles);

and/or such that they:

bind to members of the Notch signalling pathway with a $k_{on}$-rate of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$;

and/or such that they:

bind to members of the Notch signalling pathway with a $k_{off}$-rate between 1 $s^{-1}$ ($t_{1/2}$=0.69 s) and $10^{-6}$ $s^{-1}$ (providing a near irreversible complex with a $t_{1/2}$ of multiple days), preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

Preferably, a monovalent amino acid sequence of the invention (or a polypeptide that contains only one amino acid sequence of the invention) is preferably such that it will bind to members of the Notch signalling pathway with an affinity less than 500 nM, preferably less than 200 nM, more preferably less than 10 nM, such as less than 500 pM.

Some preferred IC50 values for binding of the single variable domains or single variable domains of the invention to members of the Notch signalling pathway will become clear from the further description and examples herein.

For binding to members of the Notch signalling pathway, an amino acid sequence of the invention will usually contain within its amino acid sequence one or more amino acid residues or one or more stretches of amino acid residues (i.e. with each "stretch" comprising two or amino acid residues that are adjacent to each other or in close proximity to each other, i.e. in the primary or tertiary structure of the amino acid sequence) via which the single variable domains of the invention can bind to members of the Notch signalling pathway, which amino acid residues or stretches of amino acid residues thus form the "site" for binding to members of the Notch signalling pathway (also referred to herein as the "antigen binding site").

The single variable domains provided by the invention are preferably in essentially isolated form (as defined herein), or form part of a protein or polypeptide of the invention (as defined herein), which may comprise or essentially consist of one or more single variable domains of the invention and which may optionally further comprise one or more further single variable domains (all optionally linked via one or more suitable linkers). For example, and without limitation, the one or more single variable domains of the invention may be used as a binding unit in such a protein or polypeptide, which may optionally contain one or more further single variable domains that can serve as a binding unit (i.e. against one or more other targets than members of the Notch signalling pathway), so as to provide a monovalent, multivalent or multispecific polypeptide of the invention, respectively, all as described herein. Such a protein or polypeptide may also be in essentially isolated form (as defined herein).

The single variable domains of the invention as such preferably essentially consist of a single amino acid chain that is not linked via disulphide bridges to any other amino acid sequence or chain (but that may or may not contain one or more intramolecular disulphide bridges. For example, it is known that Nanobodies—as described herein—may sometimes contain a disulphide bridge between CDR3 and CDR1 or FR2). However, it should be noted that one or more single variable domains of the invention may be linked to each other and/or to other single variable domains (e.g. via disulphide bridges) to provide peptide constructs that may also be useful in the invention (for example Fab' fragments, F(ab')$_2$ fragments, ScFv constructs, "diabodies" and other multispecific constructs. Reference is for example made to the review by Holliger and Hudson, Nat Biotechnol. 2005 September; 23(9):1126-36).

Generally, when an amino acid sequence of the invention (or a compound, construct or polypeptide comprising the same) is intended for administration to a subject (for example for therapeutic and/or diagnostic purposes as described herein), it is preferably either an amino acid sequence that does not occur naturally in said subject; or, when it does occur naturally in said subject, in essentially isolated form (as defined herein).

It will also be clear to the skilled person that for pharmaceutical use, the single variable domains of the invention (as well as compounds, constructs and single variable domains comprising the same) are preferably directed against human members of the Notch signalling pathway; whereas for veterinary purposes, the single variable domains of the invention are preferably directed against members of the Notch signalling pathway from the species to be treated, or are at least cross-reactive with members of the Notch signalling pathway from the species to be treated.

Furthermore, an amino acid sequence of the invention may optionally, and in addition to the at least one binding site for binding against members of the Notch signalling pathway, contain one or more further binding sites for binding against other antigens, proteins or targets.

The efficacy of the single variable domains of the invention, and of constructs comprising the same, can be tested using any suitable in vitro assay, cell-based assay, in vivo assay and/or animal model known per se, or any combination thereof, depending on the specific disease or disorder involved. Suitable assays and animal models will be clear to the skilled person, and for example include mouse models for various diseases where a member of the Notch signalling pathway is involved have been developed (T. Gridley, Human Molecular Genetics, 2003, Vol., 12, Review Issue 1, R9-R13), as well as the assays and animal models used in the experimental part below and in the prior art cited herein.

Also, according to the invention, single variable domains that are directed against members of the Notch signalling pathway from a first species of warm-blooded animal may or may not show cross-reactivity with members of the Notch signalling pathway from one or more other species of warm-blooded animal. For example, single variable domains directed against human members of the Notch signalling pathway may or may not show cross reactivity with members of the Notch signalling pathway from one or more other species of primates (such as, without limitation, monkeys from the genus *Macaca* (such as, and in particular, cynomolgus monkeys (*Macaca fascicularis*) and/or rhesus monkeys (*Macaca mulatta*)) and baboon (*Papio ursinus*)) and/or with members of the Notch signalling pathway from one or more species of animals that are often used in animal models for diseases (for example mouse, rat, rabbit, pig or dog), and in particular in animal models for diseases and disorders associated with members of the Notch signalling pathway (such as the species and animal models mentioned herein). In this respect, it will be clear to the skilled person that such cross-reactivity, when present, may have advantages from a drug development point of view, since it allows the single variable domains against human members of the Notch signalling pathway to be tested in such disease models.

More generally, single variable domains of the invention that are cross-reactive with members of the Notch signalling pathway from multiple species of mammal will usually be advantageous for use in veterinary applications, since it will allow the same amino acid sequence or polypeptide to be used across multiple species. Thus, it is also encompassed within the scope of the invention that single variable domains directed against members of the Notch signalling pathway from one species of animal (such as single variable domains against human members of the Notch signalling pathway) can be used in the treatment of another species of animal, as long as the use of the/or single variable domains provide the desired effects in the species to be treated.

The present invention is in its broadest sense also not particularly limited to or defined by a specific antigenic determinant, epitope, part, domain, subunit or confirmation (where applicable) of members of the Notch signalling pathway against which the single variable domains of the invention are directed. For example, the single variable domains may or may not be directed against an "interaction site" (as defined herein). However, it is generally assumed and preferred that the single variable domains of the invention are preferably directed against an interaction site (as defined herein), and in particular against at least partly either the ligand site or the receptor site of the ligand-receptor interaction sites). Thus, in one preferred, but non-limiting aspect, the single variable domains of the invention are directed against ligand-receptor interaction site of the Notch Ligands (supra) or/and are directed against the ligand-receptor interaction site of the Notch Receptors (supra), and are as further defined herein.

As further described herein, a polypeptide of the invention may contain two or more single variable domains of the invention that are directed against members of the Notch signaling pathway. Generally, such single variable domains will bind to members of the Notch signalling pathway with increased avidity compared to a single amino acid sequence of the invention. Such a polypeptide may for example comprise two single variable domains of the invention that are directed against the same antigenic determinant, epitope, part, domain, subunit or confirmation (where applicable) of members of the Notch signalling pathway (which may or may not be an interaction site); or comprise at least one "first" amino acid sequence of the invention that is directed against a first same antigenic determinant, epitope, part, domain, subunit or confirmation (where applicable) of members of the Notch signalling pathway (which may or may not be an interaction site); and at least one "second" amino acid sequence of the invention that is directed against a second antigenic determinant, epitope, part, domain, subunit or confirmation (where applicable) different from the first (and which again may or may not be an interaction site). Preferably, in such "biparatopic" single variable domains of the invention, at least one amino acid sequence of the invention is directed against an interaction site (as defined herein), although the invention in its broadest sense is not limited thereto.

Also, when the target is part of a binding pair (for example, a receptor-ligand binding pair), the single variable domains may be such that they compete with the cognate binding partner (e.g. the ligand, receptor or other binding partner, as applicable) for binding to the target, and/or such that they (fully or partially) neutralize binding of the binding partner to the target.

It is also within the scope of the invention that, where applicable, an amino acid sequence of the invention can bind to two or more antigenic determinants, epitopes, parts, domains, subunits or confirmations of members of the Notch signalling pathway. In such a case, the antigenic determinants, epitopes, parts, domains or subunits of members of the Notch signalling pathway to which the single variable domains of the invention bind may be essentially the same (for example, if members of the Notch signalling pathway contains repeated structural motifs or occurs in a multimeric form) or may be different (and in the latter case, the single variable domains of the invention may bind to such different antigenic determinants, epitopes, parts, domains, subunits of members of the Notch signalling pathway with an affinity and/or specificity which may be the same or different). Also, for example, when members of the Notch signalling pathway exists in an activated conformation and in an inactive conformation, the single variable domains of the invention may bind to either one of these confirmation, or may bind to both these confirmations (i.e. with an affinity and/or specificity which may be the same or different). Also, for example, the single variable domains of the invention may bind to a conformation of members of the Notch signalling pathway in which it is bound to a pertinent ligand, may bind to a conformation of members of the Notch signalling pathway in which it not bound to a pertinent ligand, or may bind to both such confirmations (again with an affinity and/or specificity which may be the same or different).

It is also expected that the single variable domains of the invention will generally bind to all naturally occurring or synthetic analogs, variants, mutants, alleles, parts and fragments of the members of the Notch signalling pathway; or at least to those analogs, variants, mutants, alleles, parts and fragments of members of the Notch signalling pathway that contain one or more antigenic determinants or epitopes that are essentially the same as the antigenic determinant(s) or epitope(s) to which the single variable domains of the invention bind in members of the Notch signalling pathway (e.g. in wild-type members of the Notch signalling pathway). Again, in such a case, the single variable domains of the invention may bind to such analogs, variants, mutants, alleles, parts and fragments with an affinity and/or specificity that are the same as, or that are different from (i.e. higher than or lower than), the affinity and specificity with which the single variable domains of the invention bind to (wild-type) members of the Notch signalling pathway. It is also included within the scope of the invention that the single variable domains of the invention bind to some analogs, variants, mutants, alleles, parts and fragments of the members of the Notch signalling pathway, but not to others.

When members of the Notch signalling pathway exists in a monomeric form and in one or more multimeric forms, it is within the scope of the invention that the single variable domains of the invention only bind to members of the Notch signalling pathway in monomeric form, only bind to members of the Notch signalling pathway in multimeric form, or bind to both the monomeric and the multimeric form. Again, in such a case, the single variable domains of the invention may bind to the monomeric form with an affinity and/or specificity that are the same as, or that are different from (i.e. higher than or lower than), the affinity and specificity with which the single variable domains of the invention bind to the multimeric form.

Also, when members of the Notch signalling pathway can associate with other proteins or single variable domains to form protein complexes (e.g. with multiple subunits), it is within the scope of the invention that the single variable domains of the invention bind to members of the Notch signalling pathway in its non-associated state, bind to members of the Notch signalling pathway in its associated state, or bind to both. In all these cases, the single variable domains of the invention may bind to such multimers or associated protein complexes with an affinity and/or specificity that may be the same as or different from (i.e. higher than or lower than) the affinity and/or specificity with which the single variable domains of the invention bind to members of the Notch signalling pathway in its monomeric and non-associated state.

Also, as will be clear to the skilled person, proteins or single variable domains that contain two or more single variable domains directed against members of the Notch signalling pathway may bind with higher avidity to members of the Notch signalling pathway than the corresponding monomeric amino acid sequence(s). For example, and without limitation, proteins or single variable domains that contain two or more single variable domains directed against different epitopes of members of the Notch signalling pathway may (and usually will) bind with higher avidity than each of the different monomers, and proteins or single variable domains that contain two or more single variable domains directed against members of the Notch signalling pathway may (and usually will) bind also with higher avidity.

Generally, the single variable domains of the invention will at least bind to those forms of members of the Notch signalling pathway (including monomeric, multimeric and associated forms) that are the most relevant from a biological and/or therapeutic point of view, as will be clear to the skilled person.

It is also within the scope of the invention to use parts, fragments, analogs, mutants, variants, alleles and/or derivatives of the single variable domains of the invention, and/or to use proteins or single variable domains comprising or essentially consisting of one or more of such parts, fragments, analogs, mutants, variants, alleles and/or derivatives, as long as these are suitable for the uses envisaged herein. Such parts, fragments, analogs, mutants, variants, alleles and/or derivatives will usually contain (at least part of) a functional antigen-binding site for binding against members of the Notch signalling pathway; and more preferably will be capable of specific binding to members of the Notch signalling pathway, and even more preferably capable of binding to members of the Notch signalling pathway with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein. Some non-limiting examples of such parts, fragments, analogs, mutants, variants, alleles, derivatives, proteins and/or single variable domains will become clear from the further description herein. Additional fragments or single variable domains of the invention may also be provided by suitably combining (i.e. by linking or genetic fusion) one or more (smaller) parts or fragments as described herein.

In one specific, but non-limiting aspect of the invention, which will be further described herein, such analogs, mutants, variants, alleles, derivatives have an increased half-life in serum (as further described herein) compared to the amino acid sequence from which they have been derived. For example, an amino acid sequence of the invention may be linked (chemically or otherwise) to one or more groups or moieties that extend the half-life (such as PEG), so as to provide a derivative of an amino acid sequence of the invention with increased half-life.

In one specific, but non-limiting aspect, the amino acid sequence of the invention may be an amino acid sequence that comprises an immunoglobulin fold or may be an amino acid sequence that, under suitable conditions (such as physiological conditions) is capable of forming an immunoglobulin fold (i.e. by folding). Reference is inter alia made to the review by Halaby et al., J. (1999) Protein Eng. 12, 563-71. Preferably, when properly folded so as to form an immunoglobulin fold, such an amino acid sequence is capable of specific binding (as defined herein) to members of the Notch signalling pathway; and more preferably capable of binding to members of the Notch signalling pathway with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein. Also, parts, fragments, analogs, mutants, variants, alleles and/or derivatives of such single variable domains are preferably such that they comprise an immunoglobulin fold or are capable for forming, under suitable conditions, an immunoglobulin fold.

In particular, but without limitation, the single variable domains of the invention may be single variable domains that essentially consist of 4 framework regions (FR1 to FR4 respectively) and 3 complementarity determining regions (CDR1 to CDR3 respectively); or any suitable fragment of such an amino acid sequence (which will then usually contain at least some of the amino acid residues that form at least one of the CDR's, as further described herein).

The single variable domains of the invention may in particular be an immunoglobulin sequence or a suitable fragment thereof, and more in particular be an immunoglobulin variable domain sequence or a suitable fragment thereof, such as light chain variable domain sequence (e.g. a $V_L$-sequence) or a suitable fragment thereof; or a heavy chain variable domain sequence (e.g. a $V_H$-sequence) or a suitable fragment thereof. When the amino acid sequence of the invention is a heavy chain variable domain sequence, it may be a heavy chain variable domain sequence that is derived from a conventional four-chain antibody (such as, without limitation, a $V_H$ sequence that is derived from a human antibody) or be a so-called $V_{HH}$-sequence (as defined herein) that is derived from a so-called "heavy chain antibody" (as defined herein).

However, it should be noted that the invention is not limited as to the origin of the amino acid sequence of the invention (or of the nucleotide sequence of the invention used to express it), nor as to the way that the amino acid sequence or nucleotide sequence of the invention is (or has been) generated or obtained. Thus, the single variable domains of the invention may be naturally occurring single variable domains (from any suitable species) or synthetic or semi-synthetic amino acid sequences. In a specific but non-limiting aspect of the invention, the amino acid sequence is a naturally occurring immunoglobulin sequence (from any suitable species) or a synthetic or semi-synthetic immunoglobulin sequence, including but not limited to "humanized" (as defined herein) immunoglobulin sequences (such as partially or fully humanized mouse or rabbit immunoglobulin sequences, and in particular partially or fully humanized VHH sequences or Nanobodies), "camelized" (as defined herein) immunoglobulin sequences, as well as immunoglobulin sequences that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing. Reference is for example made to the standard handbooks, as well as to the further description and prior art mentioned herein.

Similarly, the nucleotide sequences of the invention may be naturally occurring nucleotide sequences or synthetic or semi-synthetic sequences, and may for example be sequences that are isolated by PCR from a suitable naturally occurring template (e.g. DNA or RNA isolated from a cell), nucleotide sequences that have been isolated from a library (and in particular, an expression library), nucleotide sequences that have been prepared by introducing mutations into a naturally occurring nucleotide sequence (using any suitable technique known per se, such as mismatch PCR), nucleotide sequence that have been prepared by PCR using overlapping primers, or nucleotide sequences that have been prepared using techniques for DNA synthesis known per se.

The amino acid sequence of the invention may in particular be a domain antibody (or an amino acid sequence that is suitable for use as a domain antibody), a single domain antibody (or an amino acid sequence that is suitable for use as a single domain antibody), a "dAb" (or an amino acid sequence that is suitable for use as a dAb) or a Nanobody™ (as defined herein, and including but not limited to a $V_{HH}$ sequence); other single variable domains, or any suitable fragment of any one thereof. For a general description of (single) domain antibodies, reference is also made to the prior art cited above, as well as to EP 0 368 684. For the term "dAb's", reference is for example made to Ward et al. (Nature 1989 Oct. 12; 341 (6242): 544-6), to Holt et al., Trends Biotechnol., 2003, 21(11):484-490; as well as to for example WO 06/030220, WO 06/003388 and other published patent applications of Domantis Ltd. It should also be noted that, although less preferred in the context of the present invention because they are not of mammalian origin, single domain antibodies or single variable domains can be derived from certain species of shark (for example, the so-called "IgNAR domains", see for example WO 05/18629).

In particular, the amino acid sequence or single variable domain(s) of the invention may be a Nanobody® (as defined herein) or a suitable fragment thereof [Note: Nanobody®, Nanobodies® and Nanoclone® are registered trademarks of Ablynx N.V.]. Such Nanobodies directed against members of the Notch signalling pathway will also be referred to herein as "Nanobodies of the invention".

For a general description of Nanobodies, reference is made to the further description below, as well as to the prior art cited herein. In this respect, it should however be noted that this description and the prior art mainly described Nanobodies of the so-called "$V_H3$ class" (i.e. Nanobodies with a high degree of sequence homology to human germline sequences of the $V_H3$ class such as DP-47, DP-51 or DP-29), which Nanobodies form a preferred aspect of this invention. It should however be noted that the invention in its broadest sense generally covers any type of Nanobody directed against members of the Notch signalling pathway, and for example also covers the Nanobodies belonging to the so-called "$V_H4$ class" (i.e. Nanobodies with a high degree of sequence homology to human germline sequences of the $V_H4$ class such as DP-78), as for example described in the U.S. provisional application 60/792,279 by Ablynx N.V. entitled "DP-78-like Nanobodies" filed on Apr. 14, 2006 (see also PCT/EP2007/003259).

Generally, Nanobodies (in particular VHH sequences and partially humanized Nanobodies) can in particular be characterized by the presence of one or more "Hallmark residues" (as described herein) in one or more of the framework sequences (again as further described herein).

Thus, generally, a Nanobody can be defined as an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which one or more of the Hallmark residues are as further defined herein.

In particular, a Nanobody can be an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which the framework sequences are as further defined herein.

More in particular, a Nanobody can be an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:
i) preferably one or more of the amino acid residues at positions 11, 37, 44, 45, 47, 83, 84, 103, 104 and 108 according to the Kabat numbering are chosen from the Hallmark residues mentioned in Table A-3 below;
and in which:
ii) said amino acid sequence has at least 80% amino acid identity with at least one of the single variable domains of SEQ ID NO's: 1 to 22, in which for the purposes of determining the degree of amino acid identity, the amino acid residues that form the CDR sequences (indicated with X in the sequences of SEQ ID NO's: 1 to 22) are disregarded.

In these Nanobodies, the CDR sequences are generally as further defined herein.

Thus, the invention also relates to such Nanobodies that can bind to (as defined herein) and/or are directed against members of the Notch signalling pathway, to suitable fragments thereof, as well as to single variable domains that comprise or essentially consist of one or more of such Nanobodies and/or suitable fragments.

SEQ ID NO's [255-269] give the single variable domains of a number of VHH sequences that have been raised against members of the Notch signalling pathway.

In particular, the invention in some specific aspects provides:

single variable domains that are directed against (as defined herein) members of the Notch signalling pathway and that have at least 80%, preferably at least 85%, such as 90% or 95% or more sequence identity with at least one of the single variable domains of SEQ ID NO's: [255-269] (see Table A-1A for reference to sequences, same reference to the SEQ ID NO's: [255-269] applies throughout of the application even if Table A-1A reference is not given). These single variable domains may further be such that they neutralize binding of the cognate ligand to members of the Notch signalling pathway; and/or compete with the cognate ligand for binding to members of the Notch signalling pathway; and/or are directed against an interaction site (as defined herein) on members of the Notch signalling pathway (such as the ligand binding site);

single variable domains that cross-block (as defined herein) the binding of at least one of the single variable domains of SEQ ID NO's: [255-269] to members of the Notch signalling pathway and/or that compete with at least one of the single variable domains of SEQ ID NO's: [255-269] for binding to members of the Notch signalling pathway. Again, these single variable domains may further be such that they neutralize binding of the cognate ligand to members of the Notch signalling pathway; and/or compete with the cognate ligand for binding to members of the Notch signalling pathway; and/or are directed against an interaction site (as defined herein) on members of the Notch signalling pathway (such as the ligand binding site);

which single variable domains may be as further described herein (and may for example be Nanobodies); as well as single variable domains of the invention that comprise one or more of such single variable domains (which may be as further described herein, and may for example be bispecific and/or biparatopic single variable domains as described herein), and nucleic acid sequences that encode such single variable domains. Such single variable domains do not include any naturally occurring ligands.

In some other specific aspects, the invention provides:

single variable domains of the invention that are specific for (as defined herein) FcgR3, FcgR1, FcgR2 and pIgR; which single variable domains of the invention may be as further described herein (and may for example be Nanobodies); as well as single variable domains of the invention that comprise one or more of such single variable domains (which may be as further described herein, and may for example be bispecific and/or biparatopic single variable domains as described herein), and nucleic acid sequences that encode such single variable domains. Such single variable domains do not include any naturally occurring ligands.

Accordingly, some particularly preferred Nanobodies of the invention are Nanobodies which can bind (as further defined herein) to and/or are directed against to members of the Notch signalling pathway and which:

i) have at least 80% amino acid identity with at least one of the single variable domains of SEQ ID NO's: [255-269], in which for the purposes of determining the degree of amino acid identity, the amino acid residues that form the CDR sequences are disregarded. In this respect, reference is also made to Table A-1B (same reference to the SEQ ID NO's of the frameworks applies throughout of the application even if Table A-1B reference is not given), which lists the framework 1 sequences (SEQ ID NO's: [126-143]), framework 2 sequences (SEQ ID NO's: [162-179]), framework 3 sequences (SEQ ID NO's: [198-215]) and framework 4 sequences (SEQ ID NO's: [234-251]) of the Nanobodies of SEQ ID NO's: [255-269] (with respect to the amino acid residues at positions 1 to 4 and 27 to 30 of the framework 1 sequences, reference is also made to the comments made below. Thus, for determining the degree of amino acid identity, these residues are preferably disregarded);

and in which:

ii) preferably one or more of the amino acid residues at positions 11, 37, 44, 45, 47, 83, 84, 103, 104 and 108 according to the Kabat numbering are chosen from the Hallmark residues mentioned in Table A-3 below.

In these Nanobodies, the CDR sequences are generally as further defined herein.

Again, such Nanobodies may be derived in any suitable manner and from any suitable source, and may for example be naturally occurring VHH sequences (i.e. from a suitable species of Camelid) or synthetic or semi-synthetic amino acid sequences, including but not limited to "humanized" (as defined herein) Nanobodies, "camelized" (as defined herein) immunoglobulin sequences (and in particular camelized heavy chain variable domain sequences), as well as Nanobodies that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing as further described herein. Also, when a Nanobody comprises a $V_{HH}$ sequence, said Nanobody may be suitably humanized, as further described herein, so as to provide one or more further (partially or fully) humanized Nanobodies of the invention. Similarly, when a Nanobody comprises a synthetic or semi-synthetic sequence (such as a partially humanized sequence), said Nanobody may optionally be further suitably humanized, again as described herein, again so as to provide one or more further (partially or fully) humanized Nanobodies of the invention.

In particular, humanized Nanobodies may be single variable domains that are as generally defined for Nanobodies in the previous paragraphs, but in which at least one amino acid residue is present (and in particular, in at least one of the framework residues) that is and/or that corresponds to a humanizing substitution (as defined herein). Some preferred, but non-limiting humanizing substitutions (and suitable combinations thereof) will become clear to the skilled person based on the disclosure herein. In addition, or alternatively, other potentially useful humanizing substitutions can be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined can be introduced into said $V_{HH}$ sequence (in any manner known per se, as further described herein) and the resulting humanized VHH sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person based on the disclosure herein. Also, based on the foregoing, (the framework regions of) a Nanobody may be partially humanized or fully humanized.

Some particularly preferred humanized Nanobodies of the invention are humanized variants of the Nanobodies of SEQ ID NO's: [255-269].

Thus, some other preferred Nanobodies of the invention are Nanobodies which can bind (as further defined herein) to members of the Notch signalling pathway and which:

i) are a humanized variant of one of the single variable domains of SEQ ID NO's: [255-269]; and/or ii) have at least 80% amino acid identity with at least one of the single variable domains of SEQ ID NO's: [255-269] in which for the purposes of determining the degree of amino acid identity, the amino acid residues that form the CDR sequences are disregarded;

and in which:

i) preferably one or more of the amino acid residues at positions 11, 37, 44, 45, 47, 83, 84, 103, 104 and 108 according to the Kabat numbering are chosen from the Hallmark residues mentioned in Table A-3 below.

According to another specific aspect of the invention, the invention provides a number of stretches of amino acid residues (i.e. small peptides) that are particularly suited for binding to members for the Notch signalling pathway. These stretches of amino acid residues may be present in, and/or may be corporated into, an amino acid sequence of the invention, in particular in such a way that they form (part of) the antigen binding site of an amino acid sequence of the invention. As these stretches of amino acid residues were first generated as CDR sequences of heavy chain antibodies or VHH sequences that were raised against members of the Notch signalling pathway (or may be based on and/or derived from such CDR sequences, as further described herein), they will also generally be referred to herein as "CDR sequences" (i.e. as CDR1, CDR2 and CDR3, respectively). It should however be noted that the invention in its broadest sense is not limited to a specific structural role or function that these stretches of amino acid residues may have in an amino acid sequence of the invention, as long as these stretches of amino acid residues allow the amino acid sequence of the invention to bind to members for the Notch signalling pathway. Thus, generally, the invention in its broadest sense comprises any amino acid sequence that is capable of binding to members of the Notch signalling pathway and that comprises one or more CDR sequences as described herein, and in particular a suitable combination of two or more such CDR sequences, that are suitably linked to each other via one or more further amino acid sequences, such that the entire amino acid sequence forms a binding domain and/or binding unit that is capable of binding to members for the Notch signalling pathway. It should however also be noted that the presence of only one such CDR sequence in an amino acid sequence of the invention may by itself already be sufficient to provide an amino acid sequence of the invention that is capable of binding to members for the Notch signalling pathway, reference is for example again made to the so-called "Expedite fragments" described in WO 03/050531.

Thus, in another specific, but non-limiting aspect, the amino acid sequence of the invention may be an amino acid sequence that comprises at least one amino acid sequence that is chosen from the group consisting of the CDR1, CDR2 and CDR3 that are described herein in Table A-1B (same reference to the SEQ ID NO's of the CDRs applies throughout of the application even if Table A-1B reference is not given). In particular, an amino acid sequence of the invention may be an amino acid sequence that comprises at least one antigen binding site, wherein said antigen binding site comprises at least one amino acid sequence that is chosen from the group consisting of the CDR1, CDR2 and CDR3 that are described herein (or any suitable combination thereof).

Generally, in this aspect of the invention, the amino acid sequence of the invention may be any amino acid sequence that comprises at least one stretch of amino acid residues, in which said stretch of amino acid residues has an amino acid sequence that corresponds to the sequence of at least one of the CDR sequences described herein. Such an amino acid sequence may or may not comprise an immunoglobulin fold. For example, and without limitation, such an amino acid sequence may be a suitable fragment of an immunoglobulin sequence that comprises at least one such CDR sequence, but that is not large enough to form a (complete) immunoglobulin fold (reference is for example again made to the "Expedite fragments" described in WO 03/050531). Alternatively, such an amino acid sequence may be a suitable "protein scaffold" that comprises least one stretch of amino acid residues that corresponds to such a CDR sequence (i.e. as part of its antigen binding site). Suitable scaffolds for presenting single variable domains will be clear to the skilled person, and for example comprise, without limitation, to binding scaffolds based on or derived from immunoglobulins (i.e. other than the immunoglobulin sequences already described herein), protein scaffolds derived from protein A domains (such as Affibodies™), tendamistat, fibronectin, lipocalin, CTLA-4, T-cell receptors, designed ankyrin repeats, avimers and PDZ domains (Binz et al., Nat. Biotech 2005, Vol 23:1257), and binding moieties based on DNA or RNA including but not limited to DNA or RNA aptamers (Ulrich et al., Comb Chem High Throughput Screen 2006 9(8):619-32).

Again, any amino acid sequence of the invention that comprises one or more of these CDR sequences is preferably such that it can specifically bind (as defined herein) to members for the Notch signalling pathway, and more in particular such that it can bind to members of the Notch signalling pathway with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein), that is as defined herein.

More in particular, the single variable domains according to this aspect of the invention may be any amino acid sequence that comprises at least one antigen binding site, wherein said antigen binding site comprises at least two single variable domains that are chosen from the group consisting of the CDR1 described herein, the CDR2 described herein and the CDR3 described herein, such that (i) when the first amino acid sequence is chosen from the CDR1 described herein, the second amino acid sequence is chosen from the CDR2 described herein or the CDR3 described herein; (ii) when the first amino acid sequence is chosen from the CDR2 described herein, the second amino acid sequence is chosen from the CDR1 described herein or the CDR3 described herein; or (iii) when the first amino acid sequence is chosen from the CDR2 described herein, the second amino acid sequence is chosen from the CDR1 described herein or the CDR3 described herein.

Even more in particular, the single variable domains of the invention may be single variable domains that comprise at least one antigen binding site, wherein said antigen binding site comprises at least three single variable domains that are chosen from the group consisting of the CDR1 described herein, the CDR2 described herein and the CDR3 described herein, such that the first amino acid sequence is chosen from the CDR1 described herein, the second amino acid sequence is chosen from the CDR2 described herein, and the third amino acid sequence is chosen from the CDR3 described herein. Preferred combinations of CDR1, CDR2 and CDR3 will become clear from the further description herein. As will be clear to the skilled person, such an amino acid sequence is preferably an immunoglobulin sequence (as further described herein), but it may for example also be any other amino acid sequence that comprises a suitable scaffold for presenting said CDR sequences.

Thus, in one specific, but non-limiting aspect, the invention relates to an amino acid sequence directed against members for the Notch signalling pathway, that comprises one or more stretches of amino acid residues chosen from the group consisting of:
a) the single variable domains of SEQ ID NO's: [144-161];
b) single variable domains that have at least 80% amino acid identity with at least one of the single variable domains of SEQ ID NO's: [144-161];
c) single variable domains that have 3, 2, or 1 amino acid difference with at least one of the single variable domains of SEQ ID NO's: [144-161];
d) the single variable domains of SEQ ID NO's: [180-197];
e) single variable domains that have at least 80% amino acid identity with at least one of the single variable domains of SEQ ID NO's: [180-197];
f) single variable domains that have 3, 2, or 1 amino acid difference with at least one of the single variable domains of SEQ ID NO's: [180-197];
g) the single variable domains of SEQ ID NO's: [216-233];
h) single variable domains that have at least 80% amino acid identity with at least one of the single variable domains of SEQ ID NO's: [216-233];
i) single variable domains that have 3, 2, or 1 amino acid difference with at least one of the single variable domains of SEQ ID NO's: [216-233];
or any suitable combination thereof.

When an amino acid sequence of the invention contains one or more single variable domains according to b) and/or c):
i) any amino acid substitution in such an amino acid sequence according to b) and/or c) is preferably, and compared to the corresponding amino acid sequence according to a), a conservative amino acid substitution, (as defined herein);
and/or
ii) the amino acid sequence according to b) and/or c) preferably only contains amino acid substitutions, and no amino acid deletions or insertions, compared to the corresponding amino acid sequence according to a);
and/or
iii) the amino acid sequence according to b) and/or c) may be an amino acid sequence that is derived from an amino acid sequence according to a) by means of affinity maturation using one or more techniques of affinity maturation known per se.

Similarly, when an amino acid sequence of the invention contains one or more single variable domains according to e) and/or f):

i) any amino acid substitution in such an amino acid sequence according to e) and/or f) is preferably, and compared to the corresponding amino acid sequence according to d), a conservative amino acid substitution, (as defined herein); and/or
ii) the amino acid sequence according to e) and/or f) preferably only contains amino acid substitutions, and no amino acid deletions or insertions, compared to the corresponding amino acid sequence according to d); and/or
iii) the amino acid sequence according to e) and/or f) may be an amino acid sequence that is derived from an amino acid sequence according to d) by means of affinity maturation using one or more techniques of affinity maturation known per se.

Also, similarly, when an amino acid sequence of the invention contains one or more single variable domains according to h) and/or i):
i) any amino acid substitution in such an amino acid sequence according to h) and/or i) is preferably, and compared to the corresponding amino acid sequence according to g), a conservative amino acid substitution, (as defined herein); and/or
ii) the amino acid sequence according to h) and/or i) preferably only contains amino acid substitutions, and no amino acid deletions or insertions, compared to the corresponding amino acid sequence according to g); and/or
iii) the amino acid sequence according to h) and/or i) may be an amino acid sequence that is derived from an amino acid sequence according to g) by means of affinity maturation using one or more techniques of affinity maturation known per se.

It should be understood that the last preceding paragraphs also generally apply to any single variable domains of the invention that comprise one or more single variable domains according to b), c), e), f), h) or i), respectively.

In this specific aspect, the amino acid sequence preferably comprises one or more stretches of amino acid residues chosen from the group consisting of:
i) the single variable domains of SEQ ID NO's: [144-161];
ii) the single variable domains of SEQ ID NO's: [180-197]; and
iii) the single variable domains of SEQ ID NO's: [216-233]; or any suitable combination thereof.

Also, preferably, in such an amino acid sequence, at least one of said stretches of amino acid residues forms part of the antigen binding site for binding against members for the Notch signalling pathway.

In a more specific, but again non-limiting aspect, the invention relates to an amino acid sequence directed against members for the Notch signalling pathway that comprise two or more stretches of amino acid residues chosen from the group consisting of:
a) the single variable domains of SEQ ID NO's: [144-161];
b) single variable domains that have at least 80% amino acid identity with at least one of the single variable domains of SEQ ID NO's: [144-161];
c) single variable domains that have 3, 2, or 1 amino acid difference with at least one of the single variable domains of SEQ ID NO's: [144-161];
d) the single variable domains of SEQ ID NO's: [180-197];
e) single variable domains that have at least 80% amino acid identity with at least one of the single variable domains of SEQ ID NO's: [180-197];
f) single variable domains that have 3, 2, or 1 amino acid difference with at least one of the single variable domains of SEQ ID NO's: [180-197];
g) the single variable domains of SEQ ID NO's: [216-233];
h) single variable domains that have at least 80% amino acid identity with at least one of the single variable domains of SEQ ID NO's: [216-233];
i) single variable domains that have 3, 2, or 1 amino acid difference with at least one of the single variable domains of SEQ ID NO's: [216-233];
such that (i) when the first stretch of amino acid residues corresponds to one of the single variable domains according to a), b) or c), the second stretch of amino acid residues corresponds to one of the single variable domains according to d), e), f), g), h) or i); (ii) when the first stretch of amino acid residues corresponds to one of the single variable domains according to d), e) or f), the second stretch of amino acid residues corresponds to one of the single variable domains according to a), b), c), g), h) or i); or (iii) when the first stretch of amino acid residues corresponds to one of the single variable domains according to g), h) or i), the second stretch of amino acid residues corresponds to one of the single variable domains according to a), b), c), d), e) or f).

In this specific aspect, the amino acid sequence preferably comprises two or more stretches of amino acid residues chosen from the group consisting of:
i) the single variable domains of SEQ ID NO's: [144-161];
ii) the single variable domains of SEQ ID NO's: [180-197]; and
iii) the single variable domains of SEQ ID NO's: [216-233];
such that, (i) when the first stretch of amino acid residues corresponds to one of the single variable domains of SEQ ID NO's: [144-161], the second stretch of amino acid residues corresponds to one of the single variable domains of SEQ ID NO's: [180-197] or of SEQ ID NO's: [216-233]; (ii) when the first stretch of amino acid residues corresponds to one of the single variable domains of SEQ ID NO's: [180-197], the second stretch of amino acid residues corresponds to one of the single variable domains of SEQ ID NO's: [144-161] or of SEQ ID NO's: [216-233]; or (iii) when the first stretch of amino acid residues corresponds to one of the single variable domains of SEQ ID NO's: [216-233], the second stretch of amino acid residues corresponds to one of the single variable domains of SEQ ID NO's: [144-161] or of SEQ ID NO's: [180-197].

Also, in such an amino acid sequence, the at least two stretches of amino acid residues again preferably form part of the antigen binding site for binding against members for the Notch signalling pathway.

In an even more specific, but non-limiting aspect, the invention relates to an amino acid sequence directed against members for the Notch signalling pathway, that comprises three or more stretches of amino acid residues, in which the first stretch of amino acid residues is chosen from the group consisting of:
a) the single variable domains of SEQ ID NO's: [144-161];
b) single variable domains that have at least 80% amino acid identity with at least one of the single variable domains of SEQ ID NO's: [144-161];
c) single variable domains that have 3, 2, or 1 amino acid difference with at least one of the single variable domains of SEQ ID NO's: [144-161];
the second stretch of amino acid residues is chosen from the group consisting of:
d) the single variable domains of SEQ ID NO's: [180-197];

e) single variable domains that have at least 80% amino acid identity with at least one of the single variable domains of SEQ ID NO's: [180-197];
f) single variable domains that have 3, 2, or 1 amino acid difference with at least one of the single variable domains of SEQ ID NO's: [180-197];
and the third stretch of amino acid residues is chosen from the group consisting of:
g) the single variable domains of SEQ ID NO's: [216-233];
h) single variable domains that have at least 80% amino acid identity with at least one of the single variable domains of SEQ ID NO's: [216-233];
i) single variable domains that have 3, 2, or 1 amino acid difference with at least one of the single variable domains of SEQ ID NO's: [216-233].

Preferably, in this specific aspect, the first stretch of amino acid residues is chosen from the group consisting of the single variable domains of SEQ ID NO's: [144-161]; the second stretch of amino acid residues is chosen from the group consisting of the single variable domains of SEQ ID NO's: [180-197]; and the third stretch of amino acid residues is chosen from the group consisting of the single variable domains of SEQ ID NO's: [216-233].

Again, preferably, in such an amino acid sequence, the at least three stretches of amino acid residues forms part of the antigen binding site for binding against members for the Notch signalling pathway.

Preferred combinations of such stretches of single variable domains will become clear from the further disclosure herein.

Preferably, in such single variable domains the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the single variable domains of SEQ ID NO's: [255-269]. This degree of amino acid identity can for example be determined by determining the degree of amino acid identity (in a manner described herein) between said amino acid sequence and one or more of the sequences of SEQ ID NO's: [255-269], in which the amino acid residues that form the framework regions are disregarded. Also, such single variable domains of the invention can be as further described herein.

Also, such single variable domains are preferably such that they can specifically bind (as defined herein) to members for the Notch signalling pathway; and more in particular bind to members of the Notch signalling pathway with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein.

When the amino acid sequence of the invention essentially consists of 4 framework regions (FR1 to FR4, respectively) and 3 complementarity determining regions (CDR1 to CDR3, respectively), the amino acid sequence of the invention is preferably such that:
CDR1 is chosen from the group consisting of:
a) the single variable domains of SEQ ID NO's: [144-161];
b) single variable domains that have at least 80% amino acid identity with at least one of the single variable domains of SEQ ID NO's: [144-161];
c) single variable domains that have 3, 2, or 1 amino acid difference with at least one of the single variable domains of SEQ ID NO's: [144-161];
and/or
CDR2 is chosen from the group consisting of:
d) the single variable domains of SEQ ID NO's: [180-197];
e) single variable domains that have at least 80% amino acid identity with at least one of the single variable domains of SEQ ID NO's: [180-197];
f) single variable domains that have 3, 2, or 1 amino acid difference with at least one of the single variable domains of SEQ ID NO's: [180-197];
and/or
CDR3 is chosen from the group consisting of:
g) the single variable domains of SEQ ID NO's: [216-233];
h) single variable domains that have at least 80% amino acid identity with at least one of the single variable domains of SEQ ID NO's: [216-233];
i) single variable domains that have 3, 2, or 1 amino acid difference with at least one of the single variable domains of SEQ ID NO's: [216-233].

In particular, such an amino acid sequence of the invention may be such that CDR1 is chosen from the group consisting of the single variable domains of SEQ ID NO's: [144-161]; and/or CDR2 is chosen from the group consisting of the single variable domains of SEQ ID NO's: [180-197]; and/or CDR3 is chosen from the group consisting of the single variable domains of SEQ ID NO's: [216-233].

In particular, when the amino acid sequence of the invention essentially consists of 4 framework regions (FR1 to FR4, respectively) and 3 complementarity determining regions (CDR1 to CDR3, respectively), the amino acid sequence of the invention is preferably such that:
CDR1 is chosen from the group consisting of:
a) the single variable domains of SEQ ID NO's: [144-161];
b) single variable domains that have at least 80% amino acid identity with at least one of the single variable domains of SEQ ID NO's: [144-161];
c) single variable domains that have 3, 2, or 1 amino acid difference with at least one of the single variable domains of SEQ ID NO's: [144-161];
and
CDR2 is chosen from the group consisting of:
d) the single variable domains of SEQ ID NO's: [180-197];
e) single variable domains that have at least 80% amino acid identity with at least one of the single variable domains of SEQ ID NO's: [180-197];
f) single variable domains that have 3, 2, or 1 amino acid difference with at least one of the single variable domains of SEQ ID NO's: [180-197];
and
CDR3 is chosen from the group consisting of:
g) the single variable domains of SEQ ID NO's: [216-233];
h) single variable domains that have at least 80% amino acid identity with at least one of the single variable domains of SEQ ID NO's: [216-233];
i) single variable domains that have 3, 2, or 1 amino acid difference with at least one of the single variable domains of SEQ ID NO's: [216-233]; or any suitable fragment of such an amino acid sequence In particular, such an amino acid sequence of the invention may be such that CDR1 is chosen from the group consisting of the single variable domains of SEQ ID NO's: [144-161]; and CDR2 is chosen from the group consisting of the single variable domains of SEQ ID NO's: [180-197]; and CDR3 is chosen from the group consisting of the single variable domains of SEQ ID NO's: [216-233].

Again, preferred combinations of CDR sequences will become clear from the further description herein.

Also, such single variable domains are preferably such that they can specifically bind (as defined herein) to members for the Notch signalling pathway; and more in particular bind to members of the Notch signalling pathway with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein.

In one preferred, but non-limiting aspect, the invention relates to an amino acid sequence that essentially consists of 4 framework regions (FR1 to FR4, respectively) and 3 complementarity determining regions (CDR1 to CDR3, respectively), in which the CDR sequences of said amino acid sequence have at least 70% amino acid identity, preferably at least 80% amino acid identity, more preferably at least 90% amino acid identity, such as 95% amino acid identity or more or even essentially 100% amino acid identity with the CDR sequences of at least one of the single variable domains of SEQ ID NO's: [255-269]. This degree of amino acid identity can for example be determined by determining the degree of amino acid identity (in a manner described herein) between said amino acid sequence and one or more of the sequences of SEQ ID NO's: [255-269], in which the amino acid residues that form the framework regions are disregarded. Such single variable domains of the invention can be as further described herein.

In such an amino acid sequence of the invention, the framework sequences may be any suitable framework sequences, and examples of suitable framework sequences will be clear to the skilled person, for example on the basis the standard handbooks and the further disclosure and prior art mentioned herein.

The framework sequences are preferably (a suitable combination of) immunoglobulin framework sequences or framework sequences that have been derived from immunoglobulin framework sequences (for example, by humanization or camelization). For example, the framework sequences may be framework sequences derived from a light chain variable domain (e.g. a $V_L$-sequence) and/or from a heavy chain variable domain (e.g. a $V_H$-sequence). In one particularly preferred aspect, the framework sequences are either framework sequences that have been derived from a $V_{HH}$-sequence (in which said framework sequences may optionally have been partially or fully humanized) or are conventional $V_H$ sequences that have been camelized (as defined herein).

The framework sequences are preferably such that the amino acid sequence of the invention is a domain antibody (or an amino acid sequence that is suitable for use as a domain antibody); is a single domain antibody (or an amino acid sequence that is suitable for use as a single domain antibody); is a "dAb" (or an amino acid sequence that is suitable for use as a dAb); or is a Nanobody™ (including but not limited to $V_{HH}$ sequence). Again, suitable framework sequences will be clear to the skilled person, for example on the basis the standard handbooks and the further disclosure and prior art mentioned herein.

In particular, the framework sequences present in the single variable domains of the invention may contain one or more of Hallmark residues (as defined herein), such that the amino acid sequence of the invention is a Nanobody™. Some preferred, but non-limiting examples of (suitable combinations of) such framework sequences will become clear from the further disclosure herein.

Again, as generally described herein for the single variable domains of the invention, it is also possible to use suitable fragments (or combinations of fragments) of any of the foregoing, such as fragments that contain one or more CDR sequences, suitably flanked by and/or linked via one or more framework sequences (for example, in the same order as these CDR's and framework sequences may occur in the full-sized immunoglobulin sequence from which the fragment has been derived). Such fragments may also again be such that they comprise or can form an immunoglobulin fold, or alternatively be such that they do not comprise or cannot form an immunoglobulin fold.

In one specific aspect, such a fragment comprises a single CDR sequence as described herein (and in particular a CDR3 sequence), that is flanked on each side by (part of) a framework sequence (and in particular, part of the framework sequence(s) that, in the immunoglobulin sequence from which the fragment is derived, are adjacent to said CDR sequence. For example, a CDR3 sequence may be preceded by (part of) a FR3 sequence and followed by (part of) a FR4 sequence). Such a fragment may also contain a disulphide bridge, and in particular a disulphide bridge that links the two framework regions that precede and follow the CDR sequence, respectively (for the purpose of forming such a disulphide bridge, cysteine residues that naturally occur in said framework regions may be used, or alternatively cysteine residues may be synthetically added to or introduced into said framework regions). For a further description of these "Expedite fragments", reference is again made to WO 03/050531, as well as to the US provisional application of Ablynx N.V. entitled "Peptides capable of binding to serum proteins" of Ablynx N.V. (inventors: Revets, Hilde Adi Pierrette; Kolkman, Joost Alexander; and Hoogenboom, Hendricus Renerus Jacobus Mattheus) filed on Dec. 5, 2006 (see also PCT/EP2007/063348).

In another aspect, the invention relates to a compound or construct, and in particular a protein or polypeptide (also referred to herein as a "compound of the invention" or "polypeptide of the invention", respectively) that comprises or essentially consists of one or more single variable domains of the invention (or suitable fragments thereof), and optionally further comprises one or more other groups, residues, moieties or binding units. As will become clear to the skilled person from the further disclosure herein, such further groups, residues, moieties, binding units or single variable domains may or may not provide further functionality to the amino acid sequence of the invention (and/or to the compound or construct in which it is present) and may or may not modify the properties of the amino acid sequence of the invention.

For example, such further groups, residues, moieties or binding units may be one or more additional amino acid sequences, such that the compound or construct is a (fusion) protein or (fusion) polypeptide. In a preferred but non-limiting aspect, said one or more other groups, residues, moieties or binding units are immunoglobulin sequences. Even more preferably, said one or more other groups, residues, moieties or binding units are chosen from the group consisting of domain antibodies, single variable domains that are suitable for use as a domain antibody, single domain antibodies, single variable domains that are suitable for use as a single domain antibody, "dAb"'s, single variable domains that are suitable for use as a dAb, or Nanobodies.

Alternatively, such groups, residues, moieties or binding units may for example be chemical groups, residues, moieties, which may or may not by themselves be biologically and/or pharmacologically active. For example, and without limitation, such groups may be linked to the one or more single variable domains of the invention so as to provide a "derivative" of an amino acid sequence or polypeptide of the invention, as further described herein.

Also within the scope of the present invention are compounds or constructs, that comprises or essentially consists of one or more derivatives as described herein, and optionally further comprises one or more other groups, residues, moieties or binding units, optionally linked via one or more linkers. Preferably, said one or more other groups, residues, moieties or binding units are amino acid sequences.

In the compounds or constructs described above, the one or more single variable domains of the invention and the one or more groups, residues, moieties or binding units may be linked directly to each other and/or via one or more suitable linkers or spacers. For example, when the one or more groups, residues, moieties or binding units are amino acid sequences, the linkers may also be amino acid sequences, so that the resulting compound or construct is a fusion (protein) or fusion (polypeptide).

As will be clear from the further description above and herein, this means that the single variable domains of the invention can be used as "building blocks" to form single variable domains of the invention, i.e. by suitably combining them with other groups, residues, moieties or binding units, in order to form compounds or constructs as described herein (such as, without limitations, the biparatopic. bi/multivalent and bi/multispecific single variable domains of the invention described herein) which combine within one molecule one or more desired properties or biological functions.

The compounds or single variable domains of the invention can generally be prepared by a method which comprises at least one step of suitably linking the one or more single variable domains of the invention to the one or more further groups, residues, moieties or binding units, optionally via the one or more suitable linkers, so as to provide the compound or polypeptide of the invention. Single variable domains of the invention can also be prepared by a method which generally comprises at least the steps of providing a nucleic acid that encodes a polypeptide of the invention, expressing said nucleic acid in a suitable manner, and recovering the expressed polypeptide of the invention. Such methods can be performed in a manner known per se, which will be clear to the skilled person, for example on the basis of the methods and techniques further described herein.

The process of designing/selecting and/or preparing a compound or polypeptide of the invention, starting from an amino acid sequence of the invention, is also referred to herein as "formatting" said amino acid sequence of the invention; and an amino acid of the invention that is made part of a compound or polypeptide of the invention is said to be "formatted" or to be "in the format of" said compound or polypeptide of the invention. Examples of ways in which an amino acid sequence of the invention can be formatted and examples of such formats will be clear to the skilled person based on the disclosure herein; and such formatted single variable domains form a further aspect of the invention.

In one specific aspect of the invention, a compound of the invention or a polypeptide of the invention may have an increased half-life, compared to the corresponding amino acid sequence of the invention. Some preferred, but non-limiting examples of such compounds and single variable domains will become clear to the skilled person based on the further disclosure herein, and for example comprise single variable domains or single variable domains of the invention that have been chemically modified to increase the half-life thereof (for example, by means of pegylation); single variable domains of the invention that comprise at least one additional binding site for binding to a serum protein (such as serum albumin); or single variable domains of the invention that comprise at least one amino acid sequence of the invention that is linked to at least one moiety (and in particular at least one amino acid sequence) that increases the half-life of the amino acid sequence of the invention. Examples of single variable domains of the invention that comprise such half-life extending moieties or single variable domains will become clear to the skilled person based on the further disclosure herein; and for example include, without limitation, single variable domains in which the one or more single variable domains of the invention are suitable linked to one or more serum proteins or fragments thereof (such as (human) serum albumin or suitable fragments thereof) or to one or more binding units that can bind to serum proteins (such as, for example, domain antibodies, single variable domains that are suitable for use as a domain antibody, single domain antibodies, single variable domains that are suitable for use as a single domain antibody, "dAb'"s, single variable domains that are suitable for use as a dAb, or Nanobodies that can bind to serum proteins such as serum albumin (such as human serum albumin), serum immunoglobulins such as IgG, or transferrin; reference is made to the further description and references mentioned herein); single variable domains in which an amino acid sequence of the invention is linked to an Fc portion (such as a human Fc) or a suitable part or fragment thereof; or single variable domains in which the one or more single variable domains of the invention are suitable linked to one or more small proteins or peptides that can bind to serum proteins (such as, without limitation, the proteins and peptides described in WO 91/01743, WO 01/45746, WO 02/076489 and to the US provisional application of Ablynx N.V. entitled "Peptides capable of binding to serum proteins" of Ablynx N.V. filed on Dec. 5, 2006 (see also PCT/EP2007/063348).

Generally, the compounds or single variable domains of the invention with increased half-life preferably have a half-life that is at least 1.5 times, preferably at least 2 times, such as at least 5 times, for example at least 10 times or more than 20 times, greater than the half-life of the corresponding amino acid sequence of the invention per se. For example, the compounds or single variable domains of the invention with increased half-life may have a half-life that is increased with more than 1 hours, preferably more than 2 hours, more preferably more than 6 hours, such as more than 12 hours, or even more than 24, 48 or 72 hours, compared to the corresponding amino acid sequence of the invention per se.

In a preferred, but non-limiting aspect of the invention, such compounds or single variable domains of the invention have a serum half-life that is increased with more than 1 hours, preferably more than 2 hours, more preferably more than 6 hours, such as more than 12 hours, or even more than 24, 48 or 72 hours, compared to the corresponding amino acid sequence of the invention per se.

In another preferred, but non-limiting aspect of the invention, such compounds or single variable domains of the invention exhibit a serum half-life in human of at least about 12 hours, preferably at least 24 hours, more preferably at least 48 hours, even more preferably at least 72 hours or more. For example, compounds or single variable domains of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

In another aspect, the invention relates to a nucleic acid that encodes an amino acid sequence of the invention or a polypeptide of the invention (or a suitable fragment thereof). Such a nucleic acid will also be referred to herein as a "nucleic acid of the invention" and may for example be in the form of a genetic construct, as further described herein.

In another aspect, the invention relates to a host or host cell that expresses (or that under suitable circumstances is capable of expressing) an amino acid sequence of the invention and/or a polypeptide of the invention; and/or that contains a nucleic acid of the invention. Some preferred but non-limiting examples of such hosts or host cells will become clear from the further description herein.

The invention further relates to a product or composition containing or comprising at least one amino acid sequence of the invention, at least one polypeptide of the invention (or a suitable fragment thereof) and/or at least one nucleic acid of the invention, and optionally one or more further components of such constructs known per se, i.e. depending on the intended use of the composition. Such a product or composition may for example be a pharmaceutical composition (as described herein), a veterinary composition or a product or composition for diagnostic use (as also described herein). Some preferred but non-limiting examples of such products or constructs will become clear from the further description herein.

The invention also relates to the use of an amino acid sequence, Nanobody or polypeptide of the invention, or of a composition comprising the same, in (methods or constructs for) modulating members of the Notch signalling pathway, either in vitro (e.g. in an in vitro or cellular assay) or in vivo (e.g. in an a single cell or in a multicellular organism, and in particular in a mammal, and more in particular in a human being, such as in a human being that is at risk of or suffers from cancer, neurodegenerative diseases and immunomodulatory diseases).

The invention also relates to methods for modulating members of the Notch signalling pathway, either in vitro (e.g. in an in vitro or cellular assay) or in vivo (e.g. in an a single cell or multicellular organism, and in particular in a mammal, and more in particular in a human being, such as in a human being that is at risk of or suffers from cancer, neurodegenerative diseases and immunomodulatory diseases), which method comprises at least the step of contacting members of the Notch signalling pathway with at least one amino acid sequence, Nanobody or polypeptide of the invention, or with a composition comprising the same, in a manner and in an amount suitable to modulate members of the Notch signalling pathway, with at least one amino acid sequence, Nanobody or polypeptide of the invention.

The invention also relates to the use of an one amino acid sequence, Nanobody or polypeptide of the invention in the preparation of a composition (such as, without limitation, a pharmaceutical composition or preparation as further described herein) for modulating members of the Notch signalling pathway, either in vitro (e.g. in an in vitro or cellular assay) or in vivo (e.g. in an a single cell or multicellular organism, and in particular in a mammal, and more in particular in a human being, such as in a human being that is at risk of or suffers from cancer, neurodegenerative diseases and immunomodulatory diseases).

In the context of the present invention, "modulating" or "to modulate" generally means either reducing or inhibiting the activity of, or alternatively increasing the activity of, members of the Notch signalling pathway, as measured using a suitable in vitro, cellular or in vivo assay (such as those mentioned herein). In particular, "modulating" or "to modulate" may mean either reducing or inhibiting the activity of, or alternatively increasing the activity of members of the Notch signalling pathway, as measured using a suitable in vitro, cellular or in vivo assay (such as those mentioned herein), by at least 1%, preferably at least 5%, such as at least 10% or at least 25%, for example by at least 50%, at least 60%, at least 70%, at least 80%, or 90% or more, compared to activity of members of the Notch signalling pathway in the same assay under the same conditions but without the presence of the amino acid sequence, Nanobody or polypeptide of the invention.

As will be clear to the skilled person, "modulating" may also involve effecting a change (which may either be an increase or a decrease) in affinity, avidity, specificity and/or selectivity of members of the Notch signalling pathway for one or more of its targets, ligands or substrates; and/or effecting a change (which may either be an increase or a decrease) in the sensitivity of members of the Notch signalling pathway for one or more conditions in the medium or surroundings in which members of the Notch signalling pathway is present (such as pH, ion strength, the presence of co-factors, etc.), compared to the same conditions but without the presence of the amino acid sequence, Nanobody or polypeptide of the invention. As will be clear to the skilled person, this may again be determined in any suitable manner and/or using any suitable assay known per se, such as the assays described herein or in the prior art cited herein.

"Modulating" may also mean effecting a change (i.e. an activity as an agonist or as an antagonist, respectively) with respect to one or more biological or physiological mechanisms, effects, responses, functions, pathways or activities in which members of the Notch signalling pathway (or in which its substrate(s), ligand(s) or pathway(s) are involved, such as its signalling pathway or metabolic pathway and their associated biological or physiological effects) is involved. Again, as will be clear to the skilled person, such an action as an agonist or an antagonist may be determined in any suitable manner and/or using any suitable (in vitro and usually cellular or in assay) assay known per se, such as the assays described herein or in the prior art cited herein. In particular, an action as an agonist or antagonist may be such that an intended biological or physiological activity is increased or decreased, respectively, by at least 1%, preferably at least 5%, such as at least 10% or at least 25%, for example by at least 50%, at least 60%, at least 70%, at least 80%, or 90% or more, compared to the biological or physiological activity in the same assay under the same conditions but without the presence of the amino acid sequence, Nanobody or polypeptide of the invention.

Modulating may for example involve reducing or inhibiting the binding of members of the Notch signalling pathway to one of its substrates or ligands and/or competing with a natural ligand, substrate for binding to members of the Notch signalling pathway. Modulating may also involve activating members of the Notch signalling pathway or the mechanism or pathway in which it is involved. Modulating may be reversible or irreversible, but for pharmaceutical and pharmacological purposes will usually be in a reversible manner.

The invention further relates to methods for preparing or generating the amino acid sequences, single variable domains, nucleic acids, host cells, products and constructs described herein. Some preferred but non-limiting examples of such methods will become clear from the further description herein.

Generally, these methods may comprise the steps of:
a) providing a set, collection or library of amino acid sequences; and
b) screening said set, collection or library of single variable domains for single variable domains that can bind to and/or have affinity for members for the Notch signalling pathway;

and c) isolating the amino acid sequence(s) that can bind to and/or have affinity for members for the Notch signalling pathway.

In such a method, the set, collection or library of single variable domains may be any suitable set, collection or library of amino acid sequences. For example, the set, collection or library of single variable domains may be a set, collection or library of immunoglobulin sequences (as described herein), such as a naïve set, collection or library of immunoglobulin sequences; a synthetic or semi-synthetic set, collection or library of immunoglobulin sequences; and/or a set, collection or library of immunoglobulin sequences that have been subjected to affinity maturation.

Also, in such a method, the set, collection or library of single variable domains may be a set, collection or library of heavy chain variable domains (such as $V_H$ domains or $V_{HH}$ domains) or of light chain variable domains. For example, the set, collection or library of single variable domains may be a set, collection or library of domain antibodies or single domain antibodies, or may be a set, collection or library of single variable domains that are capable of functioning as a domain antibody or single domain antibody.

In a preferred aspect of this method, the set, collection or library of single variable domains may be an immune set, collection or library of immunoglobulin sequences, for example derived from a mammal that has been suitably immunized with members of the Notch signalling pathway or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

In the above methods, the set, collection or library of single variable domains may be displayed on a phage, phagemid, ribosome or suitable micro-organism (such as yeast), such as to facilitate screening. Suitable methods, techniques and host organisms for displaying and screening (a set, collection or library of) single variable domains will be clear to the person skilled in the art, for example on the basis of the further disclosure herein. Reference is also made to the review by Hoogenboom in Nature Biotechnology, 23, 9, 1105-1116 (2005).

In another aspect, the method for generating single variable domains comprises at least the steps of:

a) providing a collection or sample of cells expressing amino acid sequences;

b) screening said collection or sample of cells for cells that express an amino acid sequence that can bind to and/or have affinity for members for the Notch signalling pathway;

and c) either (i) isolating said amino acid sequence; or (ii) isolating from said cell a nucleic acid sequence that encodes said amino acid sequence, followed by expressing said amino acid sequence.

For example, when the desired amino acid sequence is an immunoglobulin sequence, the collection or sample of cells may for example be a collection or sample of B-cells. Also, in this method, the sample of cells may be derived from a mammal that has been suitably immunized with members of the Notch signalling pathway or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

The above method may be performed in any suitable manner, as will be clear to the skilled person. Reference is for example made to EP 0 542 810, WO 05/19824, WO 04/051268 and WO 04/106377. The screening of step b) is preferably performed using a flow cytometry technique such as FACS. For this, reference is for example made to Lieby et al., Blood, Vol. 97, No. 12, 3820 (2001).

In another aspect, the method for generating an amino acid sequence directed against members of the Notch signalling pathway may comprise at least the steps of:

a) providing a set, collection or library of nucleic acid sequences encoding amino acid sequences;

b) screening said set, collection or library of nucleic acid sequences for nucleic acid sequences that encode an amino acid sequence that can bind to and/or has affinity for members for the Notch signalling pathway;

and c) isolating said nucleic acid sequence, followed by expressing said amino acid sequence.

In such a method, the set, collection or library of nucleic acid sequences encoding single variable domains may for example be a set, collection or library of nucleic acid sequences encoding a naïve set, collection or library of immunoglobulin sequences; a set, collection or library of nucleic acid sequences encoding a synthetic or semi-synthetic set, collection or library of immunoglobulin sequences; and/or a set, collection or library of nucleic acid sequences encoding a set, collection or library of immunoglobulin sequences that have been subjected to affinity maturation.

Also, in such a method, the set, collection or library of nucleic acid sequences may encode a set, collection or library of heavy chain variable domains (such as $V_H$ domains or $V_{HH}$ domains) or of light chain variable domains. For example, the set, collection or library of nucleic acid sequences may encode a set, collection or library of domain antibodies or single domain antibodies, or a set, collection or library of single variable domains that are capable of functioning as a domain antibody or single domain antibody.

In a preferred aspect of this method, the set, collection or library of single variable domains may be an immune set, collection or library of nucleic acid sequences, for example derived from a mammal that has been suitably immunized with members of the Notch signalling pathway or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

The set, collection or library of nucleic acid sequences may for example encode an immune set, collection or library of heavy chain variable domains or of light chain variable domains. In one specific aspect, the set, collection or library of nucleotide sequences may encode a set, collection or library of 255-269.

In the above methods, the set, collection or library of nucleotide sequences may be displayed on a phage, phagemid, ribosome or suitable micro-organism (such as yeast), such as to facilitate screening. Suitable methods, techniques and host organisms for displaying and screening (a set, collection or library of) nucleotide sequences encoding single variable domains will be clear to the person skilled in the art, for example on the basis of the further disclosure herein. Reference is also made to the review by Hoogenboom in Nature Biotechnology, 23, 9, 1105-1116 (2005).

The invention also relates to single variable domains that are obtained by the above methods, or alternatively by a method that comprises the one of the above methods and in addition at least the steps of determining the nucleotide sequence or amino acid sequence of said immunoglobulin sequence; and of expressing or synthesizing said amino acid sequence in a manner known per se, such as by expression in a suitable host cell or host organism or by chemical synthesis.

Also, following the steps above, one or more single variable domains of the invention may be suitably humanized (or alternatively camelized); and/or the amino acid sequence(s) thus obtained may be linked to each other or to one or more other suitable single variable domains (optionally via one or more suitable linkers) so as to provide a polypeptide of the invention. Also, a nucleic acid sequence encoding an amino acid sequence of the invention may be suitably humanized (or alternatively camelized) and suitably expressed; and/or one or more nucleic acid sequences encoding an amino acid sequence of the invention may be linked to each other or to one or more nucleic acid sequences that encode other suitable single variable domains (optionally via nucleotide sequences that encode one or more suitable linkers), after which the nucleotide sequence thus obtained may be suitably expressed so as to provide a polypeptide of the invention.

The invention further relates to applications and uses of the amino acid sequences, compounds, constructs, single variable domains, nucleic acids, host cells, products and constructs described herein, as well as to methods for the prevention and/or treatment for diseases and disorders associated with members for the Notch signalling pathway. Some preferred but non-limiting applications and uses will become clear from the further description herein.

The invention also relates to the amino acid sequences, compounds, constructs, single variable domains, nucleic acids, host cells, products and compositions described herein for use in therapy.

In particular, the invention also relates to the amino acid sequences, compounds, constructs, single variable domains, nucleic acids, host cells, products and compositions described herein for use in therapy of a disease or disorder that can be prevented or treated by administering, to a subject in need thereof, of (a pharmaceutically effective amount of) an amino acid sequence, compound, construct or polypeptide as described herein.

More in particular, the invention relates to the amino acid sequences, compounds, constructs, single variable domains, nucleic acids, host cells, products and compositions described herein for use in therapy of cancer, neurodegenerative diseases and immunomodulatory diseases.

Other aspects, embodiments, advantages and applications of the invention will also become clear from the further description herein, in which the invention will be described and discussed in more detail with reference to the Nanobodies of the invention and single variable domains of the invention comprising the same, which form some of the preferred aspects of the invention.

As will become clear from the further description herein, Nanobodies generally offer certain advantages (outlined herein) compared to "dAb's" or similar (single) domain antibodies or immunoglobulin sequences, which advantages are also provided by the Nanobodies of the invention. However, it will be clear to the skilled person that the more general aspects of the teaching below can also be applied (either directly or analogously) to other single variable domains of the invention.

DETAILED DESCRIPTION OF THE INVENTION

In the present description, examples and claims:

a) Unless indicated or defined otherwise, all terms used have their usual meaning in the art, which will be clear to the skilled person. Reference is for example made to the standard handbooks, such as Sambrook et al, "Molecular Cloning: A Laboratory Manual" (2nd. Ed.), Vols. 1-3, Cold Spring Harbor Laboratory Press (1989); F. Ausubel et al, eds., "Current protocols in molecular biology", Green Publishing and Wiley Interscience, New York (1987); Lewin, "Genes II", John Wiley & Sons, New York, N.Y., (1985); Old et al., "Principles of Gene Manipulation: An Introduction to Genetic Engineering", 2nd edition, University of California Press, Berkeley, Calif. (1981); Roitt et al., "Immunology" (6th. Ed.), Mosby/Elsevier, Edinburgh (2001); Roitt et al., Roitt's Essential Immunology, 10$^{th}$ Ed. Blackwell Publishing, UK (2001); and Janeway et al., "Immunobiology" (6th Ed.), Garland Science Publishing/Churchill Livingstone, N.Y. (2005), as well as to the general background art cited herein;

b) Unless indicated otherwise, the term "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively). In addition, the term "sequence" as used herein (for example in terms like "immunoglobulin sequence", "antibody sequence", "variable domain sequence", "$V_{HH}$ sequence" or "protein sequence"), should generally be understood to include both the relevant amino acid sequence as well as nucleic acids or nucleotide sequences encoding the same, unless the context requires a more limited interpretation. Also, the term "nucleotide sequence" as used herein also encompasses a nucleic acid molecule with said nucleotide sequence, so that the terms "nucleotide sequence" and "nucleic acid" should be considered equivalent and are used interchangeably herein;

c) Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta, Adv. Drug Deliv. Rev. 2006, 58 (5-6): 640-56; Levin and Weiss, Mol. Biosyst. 2006, 2(1): 49-57; Irving et al., J. Immunol. Methods, 2001, 248(1-2), 31-45; Schmitz et al., Placenta, 2000, 21 Suppl. A, S106-12, Gonzales et al., Tumour Biol., 2005, 26(1), 31-43, which describe techniques for protein engineering, such as affinity maturation and other techniques for improving the specificity and other desired properties of proteins such as immunoglobulins.

d) Amino acid residues will be indicated according to the standard three-letter or one-letter amino acid code, as mentioned in Table A-2;

TABLE A-2

| one-letter and three-letter amino acid code | | | |
|---|---|---|---|
| Nonpolar, uncharged (at pH 6.0-7.0)[3] | Alanine | Ala | A |
| | Valine | Val | V |
| | Leucine | Leu | L |

TABLE A-2-continued one-letter and three-letter amino acid code

|  | Isoleucine | Ile | I |
|---|---|---|---|
|  | Phenylalanine | Phe | F |
|  | Methionine[1] | Met | M |
|  | Tryptophan | Trp | W |
|  | Proline | Pro | P |
| Polar, | Glycine[2] | Gly | G |
| uncharged | Serine | Ser | S |
| (at pH 6.0-7.0) | Threonine | Thr | T |
|  | Cysteine | Cys | C |
|  | Asparagine | Asn | N |
|  | Glutamine | Gln | Q |
|  | Tyrosine | Tyr | Y |
| Polar, | Lysine | Lys | K |
| charged | Arginine | Arg | R |
| (at pH 6.0-7.0) | Histidine[4] | His | H |
|  | Aspartate | Asp | D |
|  | Glutamate | Glu | E |

Notes:
[1]Sometimes also considered to be a polar uncharged amino acid.
[2]Sometimes also considered to be a nonpolar uncharged amino acid.
[3]As will be clear to the skilled person, the fact that an amino acid residue is referred to in this Table as being either charged or uncharged at pH 6.0 to 7.0 does not reflect in any way on the charge said amino acid residue may have at a pH lower than 6.0 and/or at a pH higher than 7.0; the amino acid residues mentioned in the Table can be either charged and/or uncharged at such a higher or lower pH, as will be clear to the skilled person.
[4]As is known in the art, the charge of a His residue is greatly dependant upon even small shifts in pH, but a His residue can generally be considered essentially uncharged at a pH of about 6.5.

e) For the purposes of comparing two or more nucleotide sequences, the percentage of "sequence identity" between a first nucleotide sequence and a second nucleotide sequence may be calculated by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position).

Alternatively, the degree of sequence identity between two or more nucleotide sequences may be calculated using a known computer algorithm for sequence alignment such as NCBI Blast v2.0, using standard settings.

Some other techniques, computer algorithms and settings for determining the degree of sequence identity are for example described in WO 04/037999, EP 0 967 284, EP 1 085 089, WO 00/55318, WO 00/78972, WO 98/49185 and GB 2 357 768-A.

Usually, for the purpose of determining the percentage of "sequence identity" between two nucleotide sequences in accordance with the calculation method outlined hereinabove, the nucleotide sequence with the greatest number of nucleotides will be taken as the "first" nucleotide sequence, and the other nucleotide sequence will be taken as the "second" nucleotide sequence;

f) For the purposes of comparing two or more amino acid sequences, the percentage of "sequence identity" between a first amino acid sequence and a second amino acid sequence (also referred to herein as "amino acid identity") may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e. as an "amino acid difference" as defined herein.

Alternatively, the degree of sequence identity between two single variable domains may be calculated using a known computer algorithm, such as those mentioned above for determining the degree of sequence identity for nucleotide sequences, again using standard settings.

Usually, for the purpose of determining the percentage of "sequence identity" between two single variable domains in accordance with the calculation method outlined hereinabove, the amino acid sequence with the greatest number of amino acid residues will be taken as the "first" amino acid sequence, and the other amino acid sequence will be taken as the "second" amino acid sequence.

Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, GB-A-3 357 768, WO 98/49185, WO 00/46383 and WO 01/09300; and (preferred) types and/or combinations of such substitutions may be selected on the basis of the pertinent teachings from WO 04/037999 as well as WO 98/49185 and from the further references cited therein.

Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp.

Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

Any amino acid substitutions applied to the single variable domains described herein may also be based on the analysis of the frequencies of amino acid variations between homologous proteins of different species developed by Schulz et al., Principles of Protein Structure, Springer-Verlag, 1978, on the analyses of structure forming potentials developed by Chou and Fasman, Biochemistry 13: 211, 1974 and Adv. Enzymol., 47: 45-149, 1978, and on the analysis of hydrophobicity patterns in proteins developed by Eisenberg et al., Proc. Natl. Acad. Sci. USA 81: 140-144, 1984; Kyte & Doolittle; J Molec. Biol. 157: 105-132, 198 1, and Goldman et al., Ann. Rev. Biophys. Chem. 15: 321-353, 1986, all incorporated herein in their entirety by reference. Information on the primary, secondary and tertiary structure of Nanobodies is given in the description herein and in the general background art cited above. Also, for this purpose, the crystal structure of a $V_{HH}$ domain from a llama is for example given by Desmyter et al., Nature Structural Biology, Vol. 3, 9, 803 (1996); Spinelli et al., Natural Structural Biology (1996); 3, 752-757; and Decanniere et al., Structure, Vol. 7, 4, 361 (1999). Further information about some of the amino acid residues that in conventional $V_H$ domains form the $V_H/V_L$ interface and potential camelizing substitutions on these positions can be found in the prior art cited above.

g) nucleic acid sequences are said to be "exactly the same" if they have 100% sequence identity (as defined herein) over their entire length;

h) When comparing two amino acid sequences, the term "amino acid difference" refers to an insertion, deletion or substitution of a single amino acid residue on a position of the first sequence, compared to the second sequence; it being understood that two single variable domains can contain one, two or more such amino acid differences;

i) When a nucleotide sequence or amino acid sequence is said to "comprise" another nucleotide sequence or amino acid sequence, respectively, or to "essentially consist of" another nucleotide sequence or amino acid sequence, this may mean that the latter nucleotide sequence or amino acid sequence has been incorporated into the firstmentioned nucleotide sequence or amino acid sequence, respectively, but more usually this generally means that the firstmentioned nucleotide sequence or amino acid sequence comprises within its sequence a stretch of nucleotides or amino acid residues, respectively, that has the same nucleotide sequence or amino acid sequence, respectively, as the latter sequence, irrespective of how the firstmentioned sequence has actually been generated or obtained (which may for example be by any suitable method described herein). By means of a non-limiting example, when a Nanobody of the invention is said to comprise a CDR sequence, this may mean that said CDR sequence has been incorporated into the Nanobody of the invention, but more usually this generally means that the Nanobody of the invention contains within its sequence a stretch of amino acid residues with the same amino acid sequence as said CDR sequence, irrespective of how said Nanobody of the invention has been generated or obtained. It should also be noted that when the latter amino acid sequence has a specific biological or structural function, it preferably has essentially the same, a similar or an equivalent biological or structural function in the firstmentioned amino acid sequence (in other words, the firstmentioned amino acid sequence is preferably such that the latter sequence is capable of performing essentially the same, a similar or an equivalent biological or structural function). For example, when a Nanobody of the invention is said to comprise a CDR sequence or framework sequence, respectively, the CDR sequence and framework are preferably capable, in said Nanobody, of functioning as a CDR sequence or framework sequence, respectively. Also, when a nucleotide sequence is said to comprise another nucleotide sequence, the firstmentioned nucleotide sequence is preferably such that, when it is expressed into an expression product (e.g. a polypeptide), the amino acid sequence encoded by the latter nucleotide sequence forms part of said expression product (in other words, that the latter nucleotide sequence is in the same reading frame as the firstmentioned, larger nucleotide sequence).

j) A nucleic acid sequence or amino acid sequence is considered to be "(in) essentially isolated (form)"—for example, compared to its native biological source and/or the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid sequence or amino acid sequence is considered "essentially isolated" when it has been purified at least 2-fold, in particular at least 10-fold, more in particular at least 100-fold, and up to 1000-fold or more. A nucleic acid sequence or amino acid sequence that is "in essentially isolated form" is preferably essentially homogeneous, as determined using a suitable technique, such as a suitable chromatographical technique, such as polyacrylamide-gel electrophoresis;

k) The term "domain" as used herein generally refers to a globular region of an amino acid sequence (such as an antibody chain, and in particular to a globular region of a heavy chain antibody), or to a polypeptide that essentially consists of such a globular region. Usually, such a domain will comprise peptide loops (for example 3 or 4 peptide loops) stabilized, for example, as a sheet or by disulfide bonds. The term "binding domain" refers to such a domain that is directed against an antigenic determinant (as defined herein);

l) The term "antigenic determinant" refers to the epitope on the antigen recognized by the antigen-binding molecule (such as a Nanobody or a polypeptide of the invention) and more in particular by the antigen-binding site of said molecule. The terms "antigenic determinant" and "epitope" may also be used interchangeably herein.

m) An amino acid sequence (such as a Nanobody, an antibody, a polypeptide of the invention, or generally an antigen binding protein or polypeptide or a fragment thereof) that can (specifically) bind to, that has affinity for and/or that has specificity for a specific antigenic determinant, epitope, antigen or protein (or for at least one part, fragment or epitope thereof) is said to be "against" or "directed against" said antigenic determinant, epitope, antigen or protein.

n) The term "specificity" refers to the number of different types of antigens or antigenic determinants to which a particular antigen-binding molecule or antigen-binding protein (such as a Nanobody or a polypeptide of the invention) molecule can bind. The specificity of an antigen-binding protein can be determined based on affinity and/or avidity. The affinity, represented by the equilibrium constant for the dissociation of an antigen with an antigen-binding protein ($K_D$), is a measure for the binding strength between an antigenic determinant and an antigen-binding site on the antigen-binding protein: the lesser the value of the $K_D$, the stronger the binding strength between an antigenic determinant and the antigen-binding molecule (alternatively, the affinity can also be expressed as the affinity constant ($K_A$), which is $1/K_D$). As will be clear to the skilled person (for example on the basis of the further disclosure herein), affinity can be determined in a manner known per se, depending on the specific antigen of interest. Avidity is the measure of the strength of binding between an antigen-binding molecule (such as a Nanobody or polypeptide of the invention) and the pertinent antigen. Avidity is related to both the affinity between an antigenic determinant and its antigen binding site on the antigen-binding molecule and the number of pertinent binding sites present on the antigen-binding molecule. Typically, antigen-binding proteins (such as the amino acid sequences, Nanobodies and/or single variable domains of the invention) will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^4$ mol/liter (or any $K_A$ value lower than $10^4$ $M^{-1}$) liters/mol is generally considered to indicate non-specific binding. Preferably, a monovalent immunoglobulin sequence of the invention will bind to the desired antigen with an affinity less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein.

The dissociation constant may be the actual or apparent dissociation constant, as will be clear to the skilled person. Methods for determining the dissociation constant will be clear to the skilled person, and for example include the techniques mentioned herein. In this respect, it will also be clear that it may not be possible to measure dissociation constants of more then $10^{-4}$ moles/liter or $10^{-3}$ moles/liter (e.g., of $10^{-2}$ moles/liter). Optionally, as will also be clear to the skilled person, the (actual or apparent) dissociation constant may be calculated on the basis of the (actual or apparent) association constant ($K_A$), by means of the relationship [$K_D=1/K_A$].

The affinity denotes the strength or stability of a molecular interaction. The affinity is commonly given as by the $K_D$, or dissociation constant, which has units of mol/liter (or M). The affinity can also be expressed as an association constant, $K_A$, which equals $1/K_D$ and has units of (mol/liter)$^{-1}$ (or M$^{-1}$). In the present specification, the stability of the interaction between two molecules (such as an amino acid sequence, Nanobody or polypeptide of the invention and its intended target) will mainly be expressed in terms of the $K_D$ value of their interaction; it being clear to the skilled person that in view of the relation $K_A=1/K_D$, specifying the strength of molecular interaction by its $K_D$ value can also be used to calculate the corresponding $K_A$ value. The $K_D$-value characterizes the strength of a molecular interaction also in a thermodynamic sense as it is related to the free energy (DG) of binding by the well known relation DG=RT·ln($K_D$) (equivalently DG=−RT·ln($K_A$)), where R equals the gas constant, T equals the absolute temperature and ln denotes the natural logarithm.

The $K_D$ for biological interactions which are considered meaningful (e.g. specific) are typically in the range of $10^{-10}$M (0.1 nM) to $10^{-5}$M (10000 nM). The stronger an interaction is, the lower is its $K_D$.

The $K_D$ can also be expressed as the ratio of the dissociation rate constant of a complex, denoted as $k_{off}$, to the rate of its association, denoted $k_{on}$ (so that $K_D=k_{off}/k_{on}$ and $K_A=k_{on}/k_{off}$). The off-rate $k_{off}$ has units s$^{-1}$ (where s is the SI unit notation of second). The on-rate $k_{on}$ has units M$^{-1}$s$^{-1}$. The on-rate may vary between $10^2$ M$^{-1}$s$^{-1}$ to about $10^7$ M$^{-1}$s$^{-1}$, approaching the diffusion-limited association rate constant for bimolecular interactions. The off-rate is related to the half-life of a given molecular interaction by the relation $t_{1/2}=\ln(2)/k_{off}$. The off-rate may vary between $10^{-6}$ s$^{-1}$ (near irreversible complex with a $t_{1/2}$ of multiple days) to 1 s$^{-1}$ ($t_{1/2}=0.69$ s).

The affinity of a molecular interaction between two molecules can be measured via different techniques known per se, such as the well known surface plasmon resonance (SPR) biosensor technique (see for example Ober et al., Intern. Immunology, 13, 1551-1559, 2001) where one molecule is immobilized on the biosensor chip and the other molecule is passed over the immobilized molecule under flow conditions yielding $k_{on}$, $k_{off}$ measurements and hence $K_D$ (or $K_A$) values. This can for example be performed using the well-known BIACORE instruments.

It will also be clear to the skilled person that the measured $K_D$ may correspond to the apparent $K_D$ if the measuring process somehow influences the intrinsic binding affinity of the implied molecules for example by artefacts related to the coating on the biosensor of one molecule. Also, an apparent $K_D$ may be measured if one molecule contains more than one recognition sites for the other molecule. In such situation the measured affinity may be affected by the avidity of the interaction by the two molecules.

Another approach that may be used to assess affinity is the 2-step ELISA (Enzyme-Linked Immunosorbent Assay) procedure of Friguet et al. (J. Immunol. Methods, 77, 305-19, 1985). This method establishes a solution phase binding equilibrium measurement and avoids possible artefacts relating to adsorption of one of the molecules on a support such as plastic.

However, the accurate measurement of $K_D$ may be quite labor-intensive and as consequence, often apparent $K_D$ values are determined to assess the binding strength of two molecules. It should be noted that as long all measurements are made in a consistent way (e.g. keeping the assay conditions unchanged) apparent $K_D$ measurements can be used as an approximation of the true $K_D$ and hence in the present document $K_D$ and apparent $K_D$ should be treated with equal importance or relevance. Finally, it should be noted that in many situations the experienced scientist may judge it to be convenient to determine the binding affinity relative to some reference molecule. For example, to assess the binding strength between molecules A and B, one may e.g. use a reference molecule C that is known to bind to B and that is suitably labelled with a fluorophore or chromophore group or other chemical moiety, such as biotin for easy detection in an ELISA or FACS (Fluorescent activated cell sorting) or other format (the fluorophore for fluorescence detection, the chromophore for light absorption detection, the biotin for streptavidin-mediated ELISA detection). Typically, the reference molecule C is kept at a fixed concentration and the concentration of A is varied for a given concentration or amount of B. As a result an $IC_{50}$ value is obtained corresponding to the concentration of A at which the signal measured for C in absence of A is halved. Provided $K_{D\ ref}$, the $K_D$ of the reference molecule, is known, as well as the total concentration $c_{ref}$ of the reference molecule, the apparent $K_D$ for the interaction A-B can be obtained from following formula: $K_D=IC_{50}/(1+c_{ref}/K_{D\ ref})$. Note that if $c_{ref}<<K_{D\ ref}$, $K_D\approx IC_{50}$. Provided the measurement of the $IC_{50}$ is performed in a consistent way (e.g. keeping $c_{ref}$ fixed) for the binders that are compared, the strength or stability of a molecular interaction can be assessed by the $IC_{50}$ and this measurement is judged as equivalent to $K_D$ or to apparent $K_D$ throughout this text.

o) The half-life of an amino acid sequence, compound or polypeptide of the invention can generally be defined as the time taken for the serum concentration of the amino acid sequence, compound or polypeptide to be reduced by 50%, in vivo, for example due to degradation of the sequence or compound and/or clearance or sequestration of the sequence or compound by natural mechanisms. The in vivo half-life of an amino acid sequence, compound or polypeptide of the invention can be determined in any manner known per se, such as by pharmacokinetic analysis. Suitable techniques will be clear to the person skilled in the art, and may for example generally involve the steps of suitably administering to a warm-blooded animal (i.e. to a human or to another suitable mammal, such as a mouse, rabbit, rat, pig, dog or a primate, for example monkeys from the genus *Macaca* (such as, and in particular, cynomolgus monkeys (*Macaca fascicularis*) and/or rhesus monkeys (*Macaca mulatta*)) and baboon (*Papio ursinus*)) a suitable dose of the amino acid sequence, compound or polypeptide of the invention; collecting blood samples or other samples from said animal; determining the level or concentration of the amino acid sequence, compound or polypeptide of the invention in said blood sample; and calculating, from (a plot of) the data thus obtained, the time until the level or concentration of the amino acid sequence, compound or polypeptide of the invention has been reduced by 50% compared to the initial level upon dosing. Reference is for example made to the Experimental Part below, as well as to the standard handbooks, such as Kenneth, A et al: Chemical Stability of Pharmaceuticals: A Handbook for Pharmacists and Peters et al, Pharmacokinete analysis: A Practical Approach (1996). Reference is also made to "Pharmacokinetics", M Gibaldi & D Perron, published by Marcel Dekker, 2nd Rev. edition (1982).

As will also be clear to the skilled person (see for example pages 6 and 7 of WO 04/003019 and in the further references cited therein), the half-life can be expressed using parameters such as the t1/2-alpha, t1/2-beta and the area under the curve (AUC). In the present specification, an "increase in half-life" refers to an increase in any one of these parameters, such as any two of these parameters, or essentially all three these parameters. As used herein "increase in half-life" or "increased half-life" in particular refers to an increase in the t1/2-beta, either with or without an increase in the t1/2-alpha and/or the AUC or both.

p) In the context of the present invention, "modulating" or "to modulate" generally means either reducing or inhibiting the activity of, or alternatively increasing the activity of, a target or antigen, as measured using a suitable in vitro, cellular or in vivo assay. In particular, "modulating" or "to modulate" may mean either reducing or inhibiting the activity of, or alternatively increasing a (relevant or intended) biological activity of, a target or antigen, as measured using a suitable in vitro, cellular or in vivo assay (which will usually depend on the target or antigen involved), by at least 1%, preferably at least 5%, such as at least 10% or at least 25%, for example by at least 50%, at least 60%, at least 70%, at least 80%, or 90% or more, compared to activity of the target or antigen in the same assay under the same conditions but without the presence of the construct of the invention.

As will be clear to the skilled person, "modulating" may also involve effecting a change (which may either be an increase or a decrease) in affinity, avidity, specificity and/or selectivity of a target or antigen for one or more of its ligands, binding partners, partners for association into a homomultimeric or heteromultimeric form, or substrates; and/or effecting a change (which may either be an increase or a decrease) in the sensitivity of the target or antigen for one or more conditions in the medium or surroundings in which the target or antigen is present (such as pH, ion strength, the presence of co-factors, etc.), compared to the same conditions but without the presence of the construct of the invention. As will be clear to the skilled person, this may again be determined in any suitable manner and/or using any suitable assay known per se, depending on the target or antigen involved.

"Modulating" may also mean effecting a change (i.e. an activity as an agonist, as an antagonist or as a reverse agonist, respectively, depending on the target or antigen and the desired biological or physiological effect) with respect to one or more biological or physiological mechanisms, effects, responses, functions, pathways or activities in which the target or antigen (or in which its substrate(s), ligand(s) or pathway(s) are involved, such as its signalling pathway or metabolic pathway and their associated biological or physiological effects) is involved. Again, as will be clear to the skilled person, such an action as an agonist or an antagonist may be determined in any suitable manner and/or using any suitable (in vitro and usually cellular or in assay) assay known per se, depending on the target or antigen involved. In particular, an action as an agonist or antagonist may be such that an intended biological or physiological activity is increased or decreased, respectively, by at least 1%, preferably at least 5%, such as at least 10% or at least 25%, for example by at least 50%, at least 60%, at least 70%, at least 80%, or 90% or more, compared to the biological or physiological activity in the same assay under the same conditions but without the presence of the construct of the invention.

Modulating may for example also involve allosteric modulation of the target or antigen; and/or reducing or inhibiting the binding of the target or antigen to one of its substrates or ligands and/or competing with a natural ligand, substrate for binding to the target or antigen. Modulating may also involve activating the target or antigen or the mechanism or pathway in which it is involved. Modulating may for example also involve effecting a change in respect of the folding or confirmation of the target or antigen, or in respect of the ability of the target or antigen to fold, to change its confirmation (for example, upon binding of a ligand), to associate with other (sub)units, or to disassociate. Modulating may for example also involve effecting a change in the ability of the target or antigen to transport other compounds or to serve as a channel for other compounds (such as ions).

Modulating may be reversible or irreversible, but for pharmaceutical and pharmacological purposes will usually be in a reversible manner.

q) In respect of a target or antigen, the term "interaction site" on the target or antigen means a site, epitope, antigenic determinant, part, domain or stretch of amino acid residues on the target or antigen that is a site for binding to a ligand, receptor or other binding partner, a catalytic site, a cleavage site, a site for allosteric interaction, a site involved in multimerisation (such as homomerization or heterodimerization) of the target or antigen; or any other site, epitope, antigenic determinant, part, domain or stretch of amino acid residues on the target or antigen that is involved in a biological action or mechanism of the target or antigen. More generally, an "interaction site" can be any site, epitope, antigenic determinant, part, domain or stretch of amino acid residues on the target or antigen to which an amino acid sequence or polypeptide of the invention can bind such that the target or antigen (and/or any pathway, interaction, signalling, biological mechanism or biological effect in which the target or antigen is involved) is modulated (as defined herein).

r) An amino acid sequence or polypeptide is said to be "specific for" a first target or antigen compared to a second target or antigen when is binds to the first antigen with an affinity (as described above, and suitably expressed as a $K_D$ value, $K_A$ value, $K_{off}$ rate and/or $K_{on}$ rate) that is at least 10 times, such as at least 100 times, and preferably at least 1000 times, and up to 10,000 times or more better than the affinity with which said amino acid sequence or polypeptide binds to the second target or polypeptide. For example, the first antigen may bind to the target or antigen with a $K_D$ value that is at least 10 times less, such as at least 100 times less, and preferably at least 1000 times less, such as 10,000 times less or even less than that, than the $K_D$ with which said amino acid sequence or polypeptide binds to the second target or polypeptide. Preferably, when an amino acid sequence or polypeptide is "specific for" a first target or antigen compared to a second target or antigen, it is directed against (as defined herein) said first target or antigen, but not directed against said second target or antigen.

s) The terms "cross-block", "cross-blocked" and "cross-blocking" are used interchangeably herein to mean the ability of an amino acid sequence or other binding agents (such as a polypeptide of the invention) to interfere with the binding of other single variable domains or binding agents of the invention to a given target, herein against a member of the Notch signalling pathway. The extend to which an amino acid sequence or other binding agents of the invention is able to interfere with the binding of another to a member of the Notch signalling pathway, and therefore whether it can be said to cross-block according to the invention, can be determined using competition binding assays. One particularly suitable quantitative assay uses a Biacore machine which can measure the extent of interactions using surface plasmon resonance technology. Another suitable quantitative cross-blocking assay uses an ELISA-based approach to measure competition between amino acid sequence or another binding agent in terms of their binding to the target.

The following generally describes a suitable Biacore assay for determining whether an amino acid sequence or other binding agent cross-blocks or is capable of cross-blocking according to the invention. It will be appreciated that the assay can be used with any of the amino acid sequence or other binding agents described herein. The Biacore machine (for example the Biacore 3000) is operated in line with the manufacturer's recommendations. Thus in one cross-blocking assay, the target protein is coupled to a CM5 Biacore chip using standard amine coupling chemistry to generate a surface that is coated with the target. Typically 200-800 resonance units of the target would be coupled to the chip (an amount that gives easily measurable levels of binding but that is readily saturable by the concentrations of test reagent being used). Two test single variable domains (termed A* and B*) to be assessed for their ability to cross-block each other are mixed at a one to one molar ratio of binding sites in a suitable buffer to create the test mixture. When calculating the concentrations on a binding site basis the molecular weight of an amino acid sequence is assumed to be the total molecular weight of the amino acid sequence divided by the number of target binding sites on that amino acid sequence. The concentration of each amino acid sequence in the test mix should be high enough to readily saturate the binding sites for that amino acid sequence on the target molecules captured on the Biacore chip. The single variable domains in the mixture are at the same molar concentration (on a binding basis) and that concentration would typically be between 1.00 and 1.5 micro-molar (on a binding site basis). Separate solutions containing A* alone and B* alone are also prepared. A* and B* in these solutions should be in the same buffer and at the same concentration as in the test mix. The test mixture is passed over the target-coated Biacore chip and the total amount of binding recorded. The chip is then treated in such a way as to remove the bound single variable domains without damaging the chip-bound target. Typically this is done by treating the chip with 30 mM HCl for 60 seconds. The solution of A* alone is then passed over the target-coated surface and the amount of binding recorded. The chip is again treated to remove all of the bound single variable domains without damaging the chip-bound target. The solution of B* alone is then passed over the target-coated surface and the amount of binding recorded. The maximum theoretical binding of the mixture of A* and B* is next calculated, and is the sum of the binding of each amino acid sequence when passed over the target surface alone. If the actual recorded binding of the mixture is less than this theoretical maximum then the two single variable domains are cross-blocking each other. Thus, in general, a cross-blocking amino acid sequence or other binding agent according to the invention is one which will bind to the target in the above Biacore cross-blocking assay such that during the assay and in the presence of a second amino acid sequence or other binding agent of the invention the recorded binding is between 80% and 0.1% (e.g. 80% to 4%) of the maximum theoretical binding, specifically between 75% and 0.1% (e.g. 75% to 4%) of the maximum theoretical binding, and more specifically between 70% and 0.1% (e.g. 70% to 4%) of maximum theoretical binding (as just defined above) of the two single variable domains or binding agents in combination. The Biacore assay described above is a primary assay used to determine if single variable domains or other binding agents cross-block each other according to the invention. On rare occasions particular single variable domains or other binding agents may not bind to target coupled via amine chemistry to a CM5 Biacore chip (this usually occurs when the relevant binding site on target is masked or destroyed by the coupling to the chip). In such cases cross-blocking can be determined using a tagged version of the target, for example a N-terminal His-tagged version (R & D Systems, Minneapolis, Minn., USA; 2005 cat#1406-ST-025). In this particular format, an anti-His amino acid sequence would be coupled to the Biacore chip and then the His-tagged target would be passed over the surface of the chip and captured by the anti-His amino acid sequence. The cross blocking analysis would be carried out essentially as described above, except that after each chip regeneration cycle, new His-tagged target would be loaded back onto the anti-His amino acid sequence coated surface. In addition to the example given using N-terminal His-tagged [target], C-terminal His-tagged target could alternatively be used. Furthermore, various other tags and tag binding protein combinations that are known in the art could be used for such a cross-blocking analysis (e.g. HA tag with anti-HA antibodies; FLAG tag with anti-FLAG antibodies; biotin tag with streptavidin).

The following generally describes an ELISA assay for determining whether an amino acid sequence or other binding agent directed against a target cross-blocks or is capable of cross-blocking as defined herein. It will be appreciated that the assay can be used with any of the single variable domains (or other binding agents such as single variable domains of the invention) described herein. The general principal of the assay is to have an amino acid sequence or binding agent that is directed against the target coated onto the wells of an ELISA plate. An excess amount of a second, potentially cross-blocking, anti-target amino acid sequence is added in solution (i.e. not bound to the ELISA plate). A limited amount of the target is then added to the wells. The coated amino acid sequence and the amino acid sequence in solution compete for binding of the limited number of target molecules. The plate is washed to remove excess target that has not been bound by the coated amino acid sequence and to also remove the second, solution phase amino acid sequence as well as any complexes formed between the second, solution phase amino acid sequence and target. The amount of bound target is then measured using a reagent that is appropriate to detect the target. An amino acid sequence in solution that is able to cross-block the coated amino acid sequence will be able to cause a decrease in the number of target molecules that the coated amino acid sequence can bind relative to the number of target molecules that the coated amino acid sequence can bind in the absence of the second, solution phase, amino acid sequence. In the instance where the first amino acid sequence, e.g. an Ab-X, is chosen to be the immobilized amino acid sequence, it is coated onto the wells of the ELISA plate, after which the plates are blocked with a suitable blocking solution to minimize non-specific binding of reagents that are subsequently added. An excess amount of the second amino acid sequence, i.e. Ab-Y, is then added to the ELISA plate such that the moles of Ab-Y target binding sites per well are at least 10 fold higher than the moles of Ab-X target binding sites that were used, per well, during the coating of the ELISA plate. Target is then added such that the moles of target added per well are at least 25-fold lower than the moles of Ab-X target binding sites that were used for coating each well. Following a suitable incubation period the ELISA plate is washed and a reagent for detecting the target is added to measure the amount of target specifically bound by the coated anti-target amino acid sequence (in this case Ab-X). The background signal for the assay is defined as the signal obtained in wells with the coated amino acid sequence (in this case Ab-X), second solution phase amino acid sequence (in this case Ab-Y), target buffer only (i.e. no target) and target detection reagents. The positive control signal for the assay is defined as the signal obtained in wells with the coated amino acid sequence (in this case Ab-X), second solution phase amino acid sequence buffer only (i.e. no second solution phase amino acid sequence), target and target detection reagents. The ELISA assay may be run in such a manner so as to have the positive control signal be at least 6 times the background signal. To avoid any artefacts (e.g. significantly different affinities between Ab-X and Ab-Y for [target]) resulting from the choice of which amino acid sequence to use as the coating amino acid sequence and which to use as the second (competitor) amino acid sequence, the cross-blocking assay may to be run in two formats: 1) format 1 is where Ab-X is the amino acid sequence that is coated onto the ELISA plate and Ab-Y is the competitor amino acid sequence that is in solution and 2) format 2 is where Ab-Y is the amino acid sequence that is coated onto the ELISA plate and Ab-X is the competitor amino acid sequence that is in solution. Ab-X and Ab-Y are defined as cross-blocking if, either in format 1 or in format 2, the solution phase anti-target amino acid sequence is able to cause a reduction of between 60% and 100%, specifically between 70% and 100%, and more specifically between 80% and 100%, of the target detection signal {i.e. the amount of target bound by the coated amino acid sequence) as compared to the target detection signal obtained in the absence of the solution phase anti-target amino acid sequence (i.e. the positive control wells).

t) As further described herein, the total number of amino acid residues in a Nanobody can be in the region of 110-120, is preferably 112-115, and is most preferably 113. It should however be noted that parts, fragments, analogs or derivatives (as further described herein) of a Nanobody are not particularly limited as to their length and/or size, as long as such parts, fragments, analogs or derivatives meet the further requirements outlined herein and are also preferably suitable for the purposes described herein;

u) The amino acid residues of a Nanobody are numbered according to the general numbering for $V_H$ domains given by Kabat et al. ("Sequence of proteins of immunological interest", US Public Health Services, NIH Bethesda, Md., Publication No. 91), as applied to $V_{HH}$ domains from Camelids in the article of Riechmann and Muyldermans, J. Immunol. Methods 2000 Jun. 23; 240 (1-2): 185-195 (see for example FIG. 2 of this publication); or referred to herein. According to this numbering, FR1 of a Nanobody comprises the amino acid residues at positions 1-30, CDR1 of a Nanobody comprises the amino acid residues at positions 31-35, FR2 of a Nanobody comprises the amino acids at positions 36-49, CDR2 of a Nanobody comprises the amino acid residues at positions 50-65, FR3 of a Nanobody comprises the amino acid residues at positions 66-94, CDR3 of a Nanobody comprises the amino acid residues at positions 95-102, and FR4 of a Nanobody comprises the amino acid residues at positions 103-113. [In this respect, it should be noted that—as is well known in the art for $V_H$ domains and for $V_{HH}$ domains—the total number of amino acid residues in each of the CDR's may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Generally, however, it can be said that, according to the numbering of Kabat and irrespective of the number of amino acid residues in the CDR's, position 1 according to the Kabat numbering corresponds to the start of FR1 and vice versa, position 36 according to the Kabat numbering corresponds to the start of FR2 and vice versa, position 66 according to the Kabat numbering corresponds to the start of FR3 and vice versa, and position 103 according to the Kabat numbering corresponds to the start of FR4 and vice versa.].

Alternative methods for numbering the amino acid residues of $V_H$ domains, which methods can also be applied in an analogous manner to $V_{HH}$ domains from Camelids and to Nanobodies, are the method described by Chothia et al. (Nature 342, 877-883 (1989)), the so-called "AbM definition" and the so-called "contact definition". However, in the present description, claims and figures, the numbering according to Kabat as applied to $V_{HH}$ domains by Riechmann and Muyldermans will be followed, unless indicated otherwise; and v) The Figures, Sequence Listing and the Experimental Part/Examples are only given to further illustrate the invention and should not be interpreted or construed as limiting the scope of the invention and/or of the appended claims in any way, unless explicitly indicated otherwise herein.

For a general description of heavy chain antibodies and the variable domains thereof, reference is inter alia made to the prior art cited herein, to the review article by Muyldermans in Reviews in Molecular Biotechnology 74 (2001), 277-302; as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1 433 793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference.

In accordance with the terminology used in the art (see the above references), the variable domains present in naturally occurring heavy chain antibodies will also be referred to as "$V_{HH}$ domains", in order to distinguish them from the heavy chain variable domains that are present in conventional 4-chain antibodies (which will be referred to hereinbelow as "$V_H$ domains") and from the light chain variable domains that are present in conventional 4-chain antibodies (which will be referred to hereinbelow as "$V_L$ domains").

As mentioned in the prior art referred to above, $V_{HH}$ domains have a number of unique structural characteristics and functional properties which make isolated $V_{HH}$ domains (as well as Nanobodies based thereon, which share these structural characteristics and functional properties with the naturally occurring $V_{HH}$ domains) and proteins containing the same highly advantageous for use as functional antigen-binding domains or proteins. In particular, and without being limited thereto, $V_{HH}$ domains (which have been "designed" by nature to functionally bind to an antigen without the presence of, and without any interaction with, a light chain variable domain) and Nanobodies can function as a single, relatively small, functional antigen-binding structural unit, domain or protein. This distinguishes the $V_{HH}$ domains from the $V_H$ and $V_L$ domains of conventional 4-chain antibodies, which by themselves are generally not suited for practical application as single antigen-binding proteins or domains, but need to be combined in some form or another to provide a functional antigen-binding unit (as in for example conventional antibody fragments such as Fab fragments; in ScFv's fragments, which consist of a $V_H$ domain covalently linked to a $V_L$ domain).

Because of these unique properties, the use of $V_{HH}$ domains and Nanobodies as single antigen-binding proteins or as antigen binding domains (i.e. as part of a larger protein or polypeptide) offers a number of significant advantages over the use of conventional $V_H$ and $V_L$ domains, scFv's or conventional antibody fragments (such as Fab- or F(ab')$_2$- fragments):

- only a single domain is required to bind an antigen with high affinity and with high selectivity, so that there is no need to have two separate domains present, nor to assure that these two domains are present in the right spatial conformation and configuration (i.e. through the use of especially designed linkers, as with scFv's);
- $V_{HH}$ domains and Nanobodies can be expressed from a single gene and require no post-translational folding or modifications;
- $V_{HH}$ domains and Nanobodies can easily be engineered into multivalent and multispecific formats (as further discussed herein);
- $V_{HH}$ domains and Nanobodies are highly soluble and do not have a tendency to aggregate (as with the mouse-derived "dAb's" described by Ward et al., Nature, Vol. 341, 1989, p. 544);
- $V_{HH}$ domains and Nanobodies are highly stable to heat, pH, proteases and other denaturing agents or conditions (see for example Ewert et al, supra);
- $V_{HH}$ domains and Nanobodies are easy and relatively cheap to prepare, even on a scale required for production. For example, $V_{HH}$ domains, Nanobodies and proteins/single variable domains containing the same can be produced using microbial fermentation (e.g. as further described below) and do not require the use of mammalian expression systems, as with for example conventional antibody fragments;
- $V_{HH}$ domains and Nanobodies are relatively small (approximately 15 kDa, or 10 times smaller than a conventional IgG) compared to conventional 4-chain antibodies and antigen-binding fragments thereof, and therefore show high(er) penetration into tissues (including but not limited to solid tumors and other dense tissues) than such conventional 4-chain antibodies and antigen binding fragments thereof;
- $V_{HH}$ domains and Nanobodies can show so-called cavity-binding properties (inter alia due to their extended CDR3 loop, compared to conventional $V_H$ domains) and can therefore also access targets and epitopes not accessible to conventional 4-chain antibodies and antigen-binding fragments thereof. For example, it has been shown that $V_{HH}$ domains and Nanobodies can inhibit enzymes (see for example WO 97/49805; Transue et al., Proteins 1998 Sep. 1; 32(4): 515-22; Lauwereys et al., EMBO J. 1998 Jul. 1; 17(13): 3512-20).

In a specific and preferred aspect, the invention provides Nanobodies against members for the Notch signalling pathway, and in particular Nanobodies against members of the Notch signalling pathway from a warm-blooded animal, and more in particular Nanobodies against members of the Notch signalling pathway from a mammal, and especially Nanobodies against human members for the Notch signalling pathway, as well as proteins and/or single variable domains comprising at least one such Nanobody.

In particular, the invention provides Nanobodies against members for the Notch signalling pathway, and proteins and/or single variable domains comprising the same, that have improved therapeutic and/or pharmacological properties and/or other advantageous properties (such as, for example, improved ease of preparation and/or reduced costs of goods), compared to conventional antibodies against members of the Notch signalling pathway or fragments thereof, compared to constructs that could be based on such conventional antibodies or antibody fragments (such as Fab' fragments, F(ab')$_2$ fragments, ScFv constructs, "diabodies" and other multispecific constructs (see for example the review by Holliger and Hudson, Nat Biotechnol. 2005 September; 23(9):1126-36)), and also compared to the so-called "dAb's" or similar (single) domain antibodies that may be derived from variable domains of conventional antibodies. These improved and advantageous properties will become clear from the further description herein, and for example include, without limitation, one or more of:

- increased affinity and/or avidity for members for the Notch signalling pathway, either in a monovalent format, in a multivalent format (for example in a bivalent format) and/or in a multispecific format (for example one of the multispecific formats described hereinbelow);
- better suitability for formatting in a multivalent format (for example in a bivalent format);
- better suitability for formatting in a multispecific format (for example one of the multispecific formats described hereinbelow);
- improved suitability or susceptibility for "humanizing" substitutions (as defined herein);
- less immunogenicity, either in a monovalent format, in a multivalent format (for example in a bivalent format) and/or in a multispecific format (for example one of the multispecific formats described hereinbelow);
- increased stability, either in a monovalent format, in a multivalent format (for example in a bivalent format)

and/or in a multispecific format (for example one of the multispecific formats described hereinbelow);

increased specificity towards members for the Notch signalling pathway, either in a monovalent format, in a multivalent format (for example in a bivalent format) and/or in a multispecific format (for example one of the multispecific formats described hereinbelow);

decreased or where desired increased cross-reactivity with members of the Notch signalling pathway from different species;

and/or one or more other improved properties desirable for pharmaceutical use (including prophylactic use and/or therapeutic use) and/or for diagnostic use (including but not limited to use for imaging purposes), either in a monovalent format, in a multivalent format (for example in a bivalent format) and/or in a multispecific format (for example one of the multispecific formats described hereinbelow).

As generally described herein for the single variable domains of the invention, the Nanobodies of the invention are preferably in essentially isolated form (as defined herein), or form part of a protein or polypeptide of the invention (as defined herein), which may comprise or essentially consist of one or more Nanobodies of the invention and which may optionally further comprise one or more further single variable domains (all optionally linked via one or more suitable linkers). For example, and without limitation, the one or more single variable domains of the invention may be used as a binding unit in such a protein or polypeptide, which may optionally contain one or more further single variable domains that can serve as a binding unit (i.e. against one or more other targets than members for the Notch signalling pathway), so as to provide a monovalent, multivalent or multispecific polypeptide of the invention, respectively, all as described herein. In particular, such a protein or polypeptide may comprise or essentially consist of one or more Nanobodies of the invention and optionally one or more (other) Nanobodies (i.e. directed against other targets than members for the Notch signalling pathway), all optionally linked via one or more suitable linkers, so as to provide a monovalent, multivalent or multispecific Nanobody construct, respectively, as further described herein. Such proteins or single variable domains may also be in essentially isolated form (as defined herein).

In a Nanobody of the invention, the binding site for binding against members of the Notch signalling pathway is preferably formed by the CDR sequences. Optionally, a Nanobody of the invention may also, and in addition to the at least one binding site for binding against members for the Notch signalling pathway, contain one or more further binding sites for binding against other antigens, proteins or targets. For methods and positions for introducing such second binding sites, reference is for example made to Keck and Huston, Biophysical Journal, 71, October 1996, 2002-2011; EP 0 640 130; and WO 06/07260.

As generally described herein for the single variable domains of the invention, when a Nanobody of the invention (or a polypeptide of the invention comprising the same) is intended for administration to a subject (for example for therapeutic and/or diagnostic purposes as described herein), it is preferably directed against human members for the Notch signalling pathway; whereas for veterinary purposes, it is preferably directed against members of the Notch signalling pathway from the species to be treated. Also, as with the single variable domains of the invention, a Nanobody of the invention may or may not be cross-reactive (i.e. directed against members of the Notch signalling pathway from two or more species of mammal, such as against human members of the Notch signalling pathway and members of the Notch signalling pathway from at least one of the species of mammal mentioned herein).

Also, again as generally described herein for the single variable domains of the invention, the Nanobodies of the invention may generally be directed against any antigenic determinant, epitope, part, domain, subunit or confirmation (where applicable) of members for the Notch signalling pathway. However, it is generally assumed and preferred that the Nanobodies of the invention (and single variable domains comprising the same) are directed against the receptor-ligand binding epitopes of the members of the Notch signalling pathway.

As already described herein, the amino acid sequence and structure of a Nanobody can be considered—without however being limited thereto—to be comprised of four framework regions or "FR's" (or sometimes also referred to as "FW's"), which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively. Some preferred framework sequences and CDR's (and combinations thereof) that are present in the Nanobodies of the invention are as described herein. Other suitable CDR sequences can be obtained by the methods described herein.

According to a non-limiting but preferred aspect of the invention, (the CDR sequences present in) the Nanobodies of the invention are such that:

the Nanobodies can bind to members of the Notch signalling pathway with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles);

and/or such that:

the Nanobodies can bind to members of the Notch signalling pathway with a $k_{on}$-rate of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$;

and/or such that they:

the Nanobodies can bind to members of the Notch signalling pathway with a $k_{off}$-rate between $1$ $s^{-1}$ ($t_{1/2}$=0.69 s) and $10^{-6}$ $s^{-1}$ (providing a near irreversible complex with a $t_{1/2}$ of multiple days), preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

Preferably, (the CDR sequences present in) the Nanobodies of the invention are such that: a monovalent Nanobody of the invention (or a polypeptide that contains only one Nanobody of the invention) is preferably such that it will bind to members of the Notch signalling pathway with an affinity less than 500 nM, preferably less than 200 nM, more preferably less than 10 nM, such as less than 500 pM.

The affinity of the Nanobody of the invention against members of the Notch signalling pathway can be determined in a manner known per se, for example using the general techniques for measuring $K_D$, $K_A$, $k_{off}$ or $k_{on}$ mentioned herein, as well as some of the specific assays described herein.

Some preferred IC50 values for binding of the Nanobodies of the invention (and of single variable domains comprising the same) to members of the Notch signalling pathway will become clear from the further description and examples herein.

In a preferred but non-limiting aspect, the invention relates to a Nanobody (as defined herein) against members for the Notch signalling pathway, which consists of 4 framework regions (FR1 to FR4 respectively) and 3 complementarity determining regions (CDR1 to CDR3 respectively), in which:

CDR1 is chosen from the group consisting of:
a) the single variable domains of SEQ ID NO's: [144-161];
b) single variable domains that have at least 80% amino acid identity with at least one of the single variable domains of SEQ ID NO's: [144-161];
c) single variable domains that have 3, 2, or 1 amino acid difference with at least one of the single variable domains of SEQ ID NO's: [144-161];
and/or
CDR2 is chosen from the group consisting of:
d) the single variable domains of SEQ ID NO's: [180-197];
e) single variable domains that have at least 80% amino acid identity with at least one of the single variable domains of SEQ ID NO's: [180-197];
f) single variable domains that have 3, 2, or 1 amino acid difference with at least one of the single variable domains of SEQ ID NO's: [180-197];
and/or
CDR3 is chosen from the group consisting of:
g) the single variable domains of SEQ ID NO's: [216-233];
h) single variable domains that have at least 80% amino acid identity with at least one of the single variable domains of SEQ ID NO's: [216-233];
i) single variable domains that have 3, 2, or 1 amino acid difference with at least one of the single variable domains of SEQ ID NO's: [216-233];
or any suitable fragment of such an amino acid sequence.

In particular, according to this preferred but non-limiting aspect, the invention relates to a Nanobody (as defined herein) against members for the Notch signalling pathway, which consists of 4 framework regions (FR1 to FR4 respectively) and 3 complementarity determining regions (CDR1 to CDR3 respectively), in which:

CDR1 is chosen from the group consisting of:
a) the single variable domains of SEQ ID NO's: [144-161];
b) single variable domains that have at least 80% amino acid identity with at least one of the single variable domains of SEQ ID NO's: [144-161];
c) single variable domains that have 3, 2, or 1 amino acid difference with at least one of the single variable domains of SEQ ID NO's: [144-161];
and
CDR2 is chosen from the group consisting of:
d) the single variable domains of SEQ ID NO's: [180-197];
e) single variable domains that have at least 80% amino acid identity with at least one of the single variable domains of SEQ ID NO's: [180-197];
f) single variable domains that have 3, 2, or 1 amino acid difference with at least one of the single variable domains of SEQ ID NO's: [180-197];
and
CDR3 is chosen from the group consisting of:
g) the single variable domains of SEQ ID NO's: [216-233];
h) single variable domains that have at least 80% amino acid identity with at least one of the single variable domains of SEQ ID NO's: [216-233];
i) single variable domains that have 3, 2, or 1 amino acid difference with at least one of the single variable domains of SEQ ID NO's: [216-233];
or any suitable fragment of such an amino acid sequences.

As generally mentioned herein for the single variable domains of the invention, when a Nanobody of the invention contains one or more 144-161 according to b) and/or c):
i) any amino acid substitution in such a CDR according to b) and/or c) is preferably, and compared to the corresponding CDR according to a), a conservative amino acid substitution (as defined herein);
and/or
ii) the CDR according to b) and/or c) preferably only contains amino acid substitutions, and no amino acid deletions or insertions, compared to the corresponding CDR according to a);
and/or
iii) the CDR according to b) and/or c) may be a CDR that is derived from a CDR according to a) by means of affinity maturation using one or more techniques of affinity maturation known per se.

Similarly, when a Nanobody of the invention contains one or more 180-197 according to e) and/or f):
i) any amino acid substitution in such a CDR according to e) and/or f) is preferably, and compared to the corresponding CDR according to d), a conservative amino acid substitution (as defined herein);
and/or
ii) the CDR according to e) and/or f) preferably only contains amino acid substitutions, and no amino acid deletions or insertions, compared to the corresponding CDR according to d);
and/or
iii) the CDR according to e) and/or f) may be a CDR that is derived from a CDR according to d) by means of affinity maturation using one or more techniques of affinity maturation known per se.

Also, similarly, when a Nanobody of the invention contains one or more 216-233 according to h) and/or i):
i) any amino acid substitution in such a CDR according to h) and/or i) is preferably, and compared to the corresponding CDR according to g), a conservative amino acid substitution (as defined herein);
and/or
ii) the CDR according to h) and/or i) preferably only contains amino acid substitutions, and no amino acid deletions or insertions, compared to the corresponding CDR according to g);
and/or
iii) the CDR according to h) and/or i) may be a CDR that is derived from a CDR according to g) by means of affinity maturation using one or more techniques of affinity maturation known per se.

It should be understood that the last three paragraphs generally apply to any Nanobody of the invention that comprises one or more 144-161, 180-197 and/or 216-233 according to b), c), e), f), h) or i), respectively.

Of the Nanobodies of the invention, Nanobodies comprising one or more of the CDR's explicitly listed above are particularly preferred; Nanobodies comprising two or more of the CDR's explicitly listed above are more particularly preferred; and Nanobodies comprising three of the CDR's explicitly listed above are most particularly preferred.

Some particularly preferred, but non-limiting combinations of CDR sequences, as well as preferred combinations of CDR sequences and framework sequences, are mentioned in Table A-1B below, which lists the CDR sequences and framework sequences that are present in a number of preferred (but non-limiting) Nanobodies of the invention. As will be clear to the skilled person, a combination of CDR1, CDR2 and CDR3 that occur in the same clone (i.e. CDR1, CDR2 and CDR3 that are mentioned on the same line in Table A-1B) will usually be preferred (although the invention in its broadest sense is not limited thereto, and also comprises other suitable combinations of the CDR sequences mentioned in Table A-1B). Also, a combination of CDR sequences and framework sequences that occur in the same clone (i.e. CDR sequences and framework sequences that are mentioned on the same line in Table A-1B) will usually be preferred (although the invention in its broadest sense is not limited thereto, and also comprises other suitable combinations of the CDR sequences and framework sequences mentioned in Table A-1B, as well as combinations of such CDR sequences and other suitable framework sequences, e.g. as further described herein).

Also, in the Nanobodies of the invention that comprise the combinations of CDR's mentioned in Table A-1B, each CDR can be replaced by a CDR chosen from the group consisting of single variable domains that have at least 80%, preferably at least 90%, more preferably at least 95%, even more preferably at least 99% sequence identity (as defined herein) with the mentioned CDR's; in which:

i) any amino acid substitution in such a CDR is preferably, and compared to the corresponding CDR sequence mentioned in Table A-1B, a conservative amino acid substitution (as defined herein);

and/or ii) any such CDR sequence preferably only contains amino acid substitutions, and no amino acid deletions or insertions, compared to the corresponding CDR sequence mentioned in Table A-1B;

and/or iii) any such CDR sequence is a CDR that is derived by means of a technique for affinity maturation known per se, and in particular starting from the corresponding CDR sequence mentioned in Table A-1B.

However, as will be clear to the skilled person, the (combinations of) CDR sequences, as well as (the combinations of) CDR sequences and framework sequences mentioned in Table A-1B will generally be preferred.

TABLE A-1A

Preferred single variable domains (Nanobodies ™).
("Clone name" (first column) and "SEQ ID NO: XXX" are also used to refer to the corresponding preferred single variable domain sequence itself and all three terms can be used interchangeably, e.g. terms: "178C4", "SEQ ID NO: 252" and "EVQLVESGGGLVQAGGSLRLSCAASGRTFSDYAMAWFRQAPGKER EFVAAISWSGDSTSYADSVKGRFTISRHNAENTVFLQMNSLKPEDTAVYYCAADRRVRVHGSWYGSEYWGQGTQVTVSS" can be used interchangeably)

| Clone name | Target | SEQ ID NO: | Preferred single variable domains (Nanobodies ™). |
|---|---|---|---|
| >179E6 | DLL4 | 329 | EVQLVESGGGLVQAGGSLRLSCIASGDTSEIYDMGWFRQAPGKEREFVSSIHWRGRGTNYTDSVEGRFTISKDNAKNM VYLQMNSLKPEDTAVYYCAATRLIVYTPTGFRQYFDWGQGAQVTVSS |
| >179H9 | DLL4 | 330 | EVQLVESGGGLVQAGGSLRLSCAASG??F?SDVMGWFRRAPGKEREFVASITTTGNEYYEDSLKGRFTVSRDIAENTM YLEMTNLKPEDTAEYSCAGRLLGSTIRSHEYRYWGQGTQVTVSS |
| >179A10 | DLL4 | 331 | EVQLVESGGGLVQAGGSLRLSCVASGDTSEIYDMGWFRQAPGKEREFVSSIHWGGRGTNYTDSVKGRFTISKDNAKN MVHLQMNSLKPEDTAVYYCAATRLIVYTPTGFRQYFDWGQGTQVTVSS |
| >179D12 | DLL4 | 332 | EVQLVESGGGLVQAGGSLRLSCVASGDTSEIYDMGWFRQAPGKEREFVSSIHWGGRGTNYTDSVKGRFTISKDNAKN MVYLQMNSLKPEDTAVYYCAATRLIVYTPTGFRQYFDWGQGTQVTVSS |
| >179F6 | DLL4 | 333 | EVQLVESGGGLVQAGGSLRLSCAASGSDFSGFLLGWYRQPPGKQRELIAQTTDGGRTNYGDSVKGRFTISRDNAKNT WYLQMDSLKPEDTGVYYCNTFPLTSWGQGTQVTVSS |
| >179F7 | DLL4 | 334 | EVQLVESGGGLVQSGGSLSLSCAASGSVLRINDMGWYRQAPGKTREMVATITRSGVLNYTDSVKGRFTVSRDDAKNT VYLQMSSLKPEDTAVYSCFANIVIRSSGYFNRYWGQGTLVTVSS |
| >178C4 | Jagged-1 | 335 | EVQLVESGGGLVQAGGSLRLSCAASGFTFDDYAIGWFRQAPGKEREGVSCMRGRDGSTYYADSVNGRFTISSDNAKN TVYLQMNSLKPEDTAVYYCAAHTDFACYIGYYSDYDPHDYWGQGTQVTVSS |
| >178A7 | Jagged-1 | 336 | EVQLVESGGGLVQPGGSLRLSCATSGVIFSTAAMGWYRQAPGKSRVLVARMFSDGRTIYAESVKRRFTISRDNAKNTV YLQMNSLEPEDTAVYYCNALQFGAVYWGQGTQVTVSS |
| >178D9 | Jagged-1 | 337 | EVQLVKSGGGLVQPGGSLRLSCAASGSIVSANLIGWYRQAPGKQREGVAFITSGGAINYADSVKGRFTISRDDAKNTVY LQMNSLKPEDTAIYYCNLRQLGNVYWAQGTQVTVSS |
| >178C11 | Jagged-1 | 338 | EVQLVESGGGLVQPGGSLRLSCATSGVIFSTAAMGWYRQAPGKSRVLVARMFSDGRTIYAESVKRRFTISRDNAKNTV YLQMNSLEPEDTAVYYCNALQFGAVYWGQGTQVTVSS |
| >180A4 | Notch-1 | 339 | EVQLVESGGGLVQPGGSLRLSCAASGRTSSPIAMGWFRQAPGKEREFVSGITWSGAYTHYANSVKGRFTISRDSAKNT VYLQMNSLKPEDTAVYYCTTATNSTTGYDYWGQGTQVTVSS |
| >180B1 | Notch-1 | 340 | EVQLVESGGDLVQPGGSLRLSCAASGTVFSNNDMGWSRQAPGKERELVASFTSGGNTVYADAAKGRFTISRDNSKNT VYLEMNSLKPDDTAVYYCRVVDLLRGKLYWGQGTQVTVSS |
| >180B3 | Notch-1 | 341 | EVQLVESGGDLVQPGGSLRLSCAASGTVFSNNDMGWSRQAPGKERELVASFTSGGNTVYADAAKGRFTISRDNSKNT VYLEMNSLKPDDTAVYYCRVVDLLRGKLYWGQGTQVTVSS |

TABLE A-1A-continued

Preferred single variable domains (Nanobodies ™).
("Clone name" (first column) and "SEQ ID NO: XXX" are also used to refer to the corresponding preferred single variable domain sequence itself and all three terms can be used interchangeably, e.g. terms: "178C4", "SEQ ID NO: 252" and "EVQLVESGGGLVQAGGSLRLSCAASGRTFSDYAMAWFRQAPGKER EFVAAISWSGDSTSYADSVKGRFTISRHNAENTVFLQMNSLKPEDTAVYYCAADRRVRVHGSWYGSEYWGQGTQVTVSS" can be used interchangeably)

| Clone name | Target | SEQ ID NO: | Preferred single variable domains (Nanobodies ™). |
|---|---|---|---|
| >180C1 | Notch-1 | 342 | EVQLVESGGDLVQPGGSLRLSCAASRTVFSISDMGWSRQAPGKERELVASISSDNYTVYADAAKGRFTISRDNSKNTVYLEMNSLKPDDTAVYYCRVVDPLRGKLYWGQGTQVTVSS |
| >180C7 | Notch-1 | 343 | EVQLVESGGGLVQAGGSLRLSCAASGGIFGINAVAWYRQAPGKERDWVALIVGEAITRYTDSVSGRFTISRDNAKNTVYLEMNSLKPDDTAVYYCRVVDPLRGKLYWGQGTQVTVSS |
| >180F8 | Notch-1 | 344 | EVQLVESGGDLVQPGGSLRLSCTTSGTVFSINDMGWSRQAPGKGRELVASISSEGTTIYADAAKGRFTISRDNSKNTVYLEMNSLKPDDTAVYYCRVVDPLRGKLYWGQGTQVTVSS |
| >180F4 | Notch-1 | 345 | EVQLVESGGGLVQAGDSLRLSCAVSGGSFSSYTMGWVRQAPGKEREAVASIWRSGGNTYYADSVKGRFTVSRDNAKHTVYLQMNSLKPEDTAVYYCAAASFAPGSRGYDYWGQGTQVTVSS |
| >180F5 | Notch-1 | 346 | EVQLVESGGGLVQPGGSLRLSCAASGRTSSPIAMGWFRQAPGKEREFVSGITWSGAYTHYANSVKGRFTISRDSAKNTVYLQMNSLKPEDTAVYYCTTATNSTTGYDYWGQGTQVTVSS |
| >180F10 | Notch-1 | 347 | EVQLVESGGDLVQPGGSLRLSCAASATVFSNSDMGWSRQAPGKERELVASITTDGNTLYADAAKGRFAIYRDNSKNTVYLEMNSLKPDDTAVYYCRVVDLLRGKLYWGQGTQVTVSS |
| >181G4 | Notch-2 | 348 | EVQLVESGGGLVQAGGSLRLSCAASGSIFSITEMDWYRQAPGKQREWVAGETSDGSTNYADSVKGRFTISRDNANNAVYLQMNRLKPEDTAVYHCAASLRNSGSNVEGRYWGQGTQVTVSS |
| >181B4 | Notch-2 | 349 | EVQLVESGGGLVQPGGSLRLSCAASGRINSMNWYHQAPGKEREWVASITSSGTAIYADSVKGRITISRDNAKNTVYLQMNSLKTEDTGVYYCAANLQNARGSYYGQGTQVTVSS |
| >181D4 | Notch-2 | 350 | EVQLVESGGGLVQPGGSLRLSCAASGFTFGDYAMNWVRQAPGKGLEWVSSISAGGYSTTYADSVKGRFTISRDNAKNTLYLQMNSLNPEDTAVYYCARGDWRYGSRGQGTQVTVSS |
| >181E4 | Notch-2 | 351 | EVQLVESGGGLVQAGGSLRLSCAASGSMSSINAMRWYRQASGKQREPVAEITSEGTIIYADSVKGRFTTSRDNAKNTVYLQMNSLKPEDTGVYYCAADDGARGSYYGQGTQVTVSS |
| >181F4 | Notch-2 | 352 | EVQLVESGGALVQAGGSLRLSCVASGSSFSINDMDWYRQAPGKTREWVAGINEYGGRNYANSVKDRFTISTDNAKNTVYLQMNSLKPEDTGVYYCAATLAKGGGRYWGQGTPVTVSS |
| >181H4 | Notch-2 | 353 | EVKLVESGGGLVQPGGSLRLSCAASGSIFRFNGVDWYRQAPGAEREWVAGFGSGGTTNYADSVKGRFIVSRDNAENTVFLQMNSLKPEDSAVYFCAASIEGVSGRYYGQGTQVTVSS |
| >181A5 | Notch-2 | 354 | EVQLVESGGGLVQAGGSLRLSCVVSGSILSINTMDWYRQAPGNEREWVGGITDGGRSNYADSVKDRFTIYRANAKNTVYLQMNSLKPEDTAVYYCAADLRGGIATTGRYWGQGTQVTVSS |
| >181C10 | Notch-2 | 355 | EVQLVESGGGLVQAGGSLRLSCAASGMTTIGPMGWYRQGPGKQRELVARITGGGSTNYVDSAKGRFTISRDNAKNAVYLQMNNLKLDDTAVYYCNAYGSGSDYLPIDYWGQGTQVTVSS |
| >181C11 | Notch-2 | 356 | EVQLVESGGGLVQAGGSLRLSCAASGMTTIGPMGWYRQGPGKQRELVARITGGGSTNYVDSAKGRFTISRDNAKNMGYLQMNNLKLDDTAIYYCYAYGSGSDYLPTDYWGQGTQVTVSS |
| >181D11 | Notch-2 | 357 | EVQLVESGGGLVQAGGSLRLSCAASGMTTIGPMGWYRQGPGKQRELVARITGGGSTNYVDSAKGRFTISRHNAKNMVYLQMNNLKLDDTAVYYCNAYGSGSDYLPMDYWGQGTQVTVSS |

TABLE A-1B

Preferred combinations of CDR sequences, preferred combinations of framework sequences, and preferred combinations of framework and CDR sequences.
("ID" refers to the SEQ ID NO and is referenced e.g. below whereas "ID"/"ID SEQ ID NO" number on the right of the sequence refers to corresponding sequence)

| Preferred combinations | FR1 | ID | CDR1 | ID | FR2 | ID | CDR2 | ID |
|---|---|---|---|---|---|---|---|---|
| 1 | EVQLVESGGGLVQAGGSLRLSCIASGDTSE | 126 | IYDMG | 155 | WFRQAPGKEREFVS | 184 | SIHWRGRGTNYTDSVEG | 213 |
| 2 | EVQLVESGGGLVQAGG | 127 | SDVMG | 156 | WFRRAPGKEREFVA | 185 | SITTTGNEYYEDSLKG | 214 |

TABLE A-1B-continued

Preferred combinations of CDR sequences, preferred combinations of framework sequences, and preferred combinations of framework and CDR sequences. ("ID" refers to the SEQ ID NO and is referenced e.g. below whereas "ID"/"ID SEQ ID NO" number on the right of the sequence refers to corresponding sequence)

| | | | | | | | | |
|---|---|---|---|---|---|---|---|---|
| | SLRLSCAAS GxxFx | | | | | | | |
| 3 | EVQLVESG GGLVQAGG SLRLSCVAS GDTSE | 128 | IYDMG | 157 | WFRQAPGKE REFVS | 186 | SIHWGGRGTN YTDSVKG | 215 |
| 4 | EVQLVESG GGLVQAGG SLRLSCVAS GDTSE | 129 | IYDMG | 158 | WFRQAPGKE REFVS | 187 | SIHWGGRGTN YTDSVKG | 216 |
| 5 | EVQLVESG GGLVQAGG SLRLSCAAS GSDFS | 130 | GFLLG | 159 | WYRQPPGKQ RELIA | 188 | QTTDGGRTNY GDSVKG | 217 |
| 6 | EVQLVESG GGLVQSGG SLSLSCAAS GSVLR | 131 | INDMG | 160 | WYRQAPGKT REMVA | 189 | TITRSGVLNYT DSVKG | 218 |
| 7 | EVQLVESG GGLVQAGG SLRLSCAAS GFTFD | 132 | DYAIG | 161 | WFRQAPGKE REGVS | 190 | CMRGRDGST YYADSVNG | 219 |
| 8 | EVQLVESG GGLVQPGG SLRLSCATS GVIFS | 133 | TAAMG | 162 | WYRQAPGKS RVLVA | 191 | RMFSDGRTIY AESVKR | 220 |
| 9 | EVQLVKSG GGLVQPGG SLRLSCAAS GSIVS | 134 | ANLIG | 163 | WYRQAPGKQ REGVA | 192 | FITSGGAINYA DSVKG | 221 |
| 10 | EVQLVESG GGLVQPGG SLRLSCATS GVIFS | 135 | TAAMG | 164 | WYRQAPGKS RVLVA | 193 | RMFSDGRTIY AESVKR | 222 |
| 11 | EVQLVESG GGLVQPGG SLRLSCAAS GRTSS | 136 | PIAMG | 165 | WFRQAPGKE REFVS | 194 | GITWSGAYTH YANSVKG | 223 |
| 12 | EVQLVESG GDLVQPGG SLRLSCAAS GTVFS | 137 | NNDMG | 166 | WSRQAPGKE RELVA | 195 | SFTSGGNTVY ADAAKG | 224 |
| 13 | EVQLVESG GDLVQPGG SLRLSCAAS GTVFS | 138 | NNDMG | 167 | WSRQAPGKE RELVA | 196 | SFTSGGNTVY ADAAKG | 225 |
| 14 | EVQLVESG GDLVQPGG SLRLSCAAS RTVFS | 139 | ISDMG | 168 | WSRQAPGKE RELVA | 197 | SISSDNYTVYA DAAKG | 226 |
| 15 | EVQLVESG GGLVQAGG SLRLSCAAS GGIFG | 140 | INAVA | 169 | WYRQAPGKE RDWVA | 198 | LIVGEAITRYT DSVSG | 227 |
| 16 | EVQLVESG GDLVQPGG SLRLSCTTS GTVFS | 141 | INDMG | 170 | WSRQAPGKG RELVA | 199 | SISSEGTTIYA DAAKG | 228 |

TABLE A-1B-continued

Preferred combinations of CDR sequences, preferred combinations of framework sequences, and preferred combinations of framework and CDR sequences. ("ID" refers to the SEQ ID NO and is referenced e.g. below whereas "ID"/"ID SEQ ID NO" number on the right of the sequence refers to corresponding sequence)

| | | | | | | | | |
|---|---|---|---|---|---|---|---|---|
| 17 | EVQLVESGGGLVQAGDSLRLSCAVSGGSFS | 142 | SYTMG | 171 | WVRQAPGKEREAVA | 200 | SIWRSGGNTYYADSVKG | 229 |
| 18 | EVQLVESGGGLVQPGGSLRLACAASGRTSS | 143 | PIAMG | 172 | WFRQAPGKEREFVS | 201 | GITWSGAYTHYANSVKG | 230 |
| 19 | EVQLVESGGDLVQPGGSLRLSCAASATVFS | 144 | NSDMG | 173 | WSRQAPGKERELVA | 202 | SITTDGNTLYADAAKG | 231 |
| 20 | EVQLVESGGGLVQAGGSLRLSCAASGSIFS | 145 | ITEMD | 174 | WYRQAPGKQREWVA | 203 | GETSDGSTNYADSVKG | 232 |
| 21 | EVQLVESGGGLVQPGGSLRLSCAASGRINS | 146 | MN | 175 | WYHQAPGKEREWVA | 204 | SITSSGTAIYADSVKG | 233 |
| 22 | EVQLVESGGGLVQPGGSLRLSCAASGFTFG | 147 | DYAMN | 176 | WVRQAPGKGLEWVS | 205 | SISAGGYSTTYADSVKG | 234 |
| 23 | EVQLVESGGGLVQAGGSLRLSCAASGSMSS | 148 | INAMR | 177 | WYRQASGKQREPVA | 206 | EITSEGTIIYADSVKG | 235 |
| 24 | EVQLVESGGALVQAGGSLRLSCVASGSSFS | 149 | INDMD | 178 | WYRQAPGKTREWVA | 207 | GINEYGGRNYANSVKD | 236 |
| 25 | EVKLVESGGGLVQPGGSLRLSCAASGSIFR | 150 | FNGVD | 179 | WYRQAPGAEREWVA | 208 | GFGSGGTTNYADSVKG | 237 |
| 26 | EVQLVESGGGLVQAGGSLRLSCVVSGSILS | 151 | INTMD | 180 | WYRQAPGNEREWVG | 209 | GITDGGRSNYADSVKD | 238 |
| 27 | EVQLVESGGGLVQAGGSLRLSCAASGMTTI | 152 | GPMG | 181 | WYRQGPGKQRELVA | 210 | RITGGSTNYVDSAKG | 239 |
| 28 | EVQLVESGGGLVQAGGSLRLSCAASGMTTI | 153 | GPMG | 182 | WYRQGPGKQRELVA | 211 | RITGGGSTNYVDSAKG | 240 |
| 29 | EVQLVESGGGLVQAGGSLRLSCAASGMTTI | 154 | GPMG | 183 | WYRQGPGKQRELVA | 212 | RITGGGSTNYVDSAKG | 241 |

| Preferred combinations | FR3 | ID | CDR3 | ID | FR4 | ID |
|---|---|---|---|---|---|---|
| 1 | RFTISKDNAKNMVYLQMNSLKPEDTAVYYCAA | 242 | TRLIVYTPTGFRQYFD | 271 | WGQGAQVTVSS | 300 |

TABLE A-1B-continued

Preferred combinations of CDR sequences, preferred combinations of framework sequences, and preferred combinations of framework and CDR sequences. ("ID" refers to the SEQ ID NO and is referenced e.g. below whereas "ID"/"ID SEQ ID NO" number on the right of the sequence refers to corresponding sequence)

| | | | | | | | |
|---|---|---|---|---|---|---|---|
| 2 | RFTVSRDIA ENTMYLEMT NLKPEDTAE YSCAG | 243 | RLLGSTIRSHEY RY | 272 | WGQGTQ VTVSS | 301 | |
| 3 | RFTISKDNA KNMVHLQM NSLKPEDTA VYYCAA | 244 | TRLIVYTPTGFR QYFD | 273 | WGQGTQ VTVSS | 302 | |
| 4 | RFTISKDNA KNMVYLQM NSLKPEDTA VYYCAA | 245 | TRLIVYTPTGFR QYFD | 274 | WGQGTQ VTVSS | 303 | |
| 5 | RFTISRDNA KNTWYLQM DSLKPEDTG VYYCNT | 246 | FPLTS | 275 | WGQGTQ VTVSS | 304 | |
| 6 | RFTVSRDDA KNTVYLQMS SLKPEDTAV YSCFA | 247 | NIVIRSSGYFNR Y | 276 | WGQGTLV TVSS | 305 | |
| 7 | RFTISSDNA KNTVYLQMN SLKPEDTAV YYCAA | 248 | HTDFACYIGYYS DYDPHDY | 277 | WGQGTQ VTVSS | 306 | |
| 8 | RFTISRDNA KNTVYLQMN SLEPEDTAV YYCNA | 249 | LQFGAVY | 278 | WGQGTQ VTVSS | 307 | |
| 9 | RFTISRDDA KNTVYLQMN SLKPEDTAIY YCNL | 250 | RQLGNVY | 279 | WAQGTQ VTVSS | 308 | |
| 10 | RFTISRDNA KNTVYLQMN SLEPEDTAV YYCNA | 251 | LQFGAVY | 280 | WGQGTQ VTVSS | 309 | |
| 11 | RFTISRDSA KNTVYLQMN SLKPEDTAV YYCTT | 252 | ATNSTTGYDY | 281 | WGQGTQ VTVSS | 310 | |
| 12 | RFTISRDNS KNTVYLEMN SLKPDDTAV YYCRV | 253 | VDLLRGKLY | 282 | WGQGTQ VTVSS | 311 | |
| 13 | RFTISRDNS KNTVYLEMN SLKPDDTAV YYCRV | 254 | VDLLRGKLY | 283 | WGQGTQ VTVSS | 312 | |
| 14 | RFTISRDNS KNTVYLEMN SLKPDDTAV YYCRV | 255 | VDPLRGKLY | 284 | WGQGTQ VTVSS | 313 | |
| 15 | RFTISRDNA KNTVYLEMN SLKPDDTAV YYCRV | 256 | VDPLRGKLY | 285 | WGQGTQ VTVSS | 314 | |
| 16 | RFTISRDNS KNTVYLEMN SLKPDDTAV YYCRV | 257 | VDPLRGKLY | 286 | WGQGTQ VTVSS | 315 | |

TABLE A-1B-continued

Preferred combinations of CDR sequences, preferred combinations of framework sequences, and preferred combinations of framework and CDR sequences. ("ID" refers to the SEQ ID NO and is referenced e.g. below whereas "ID"/"ID SEQ ID NO" number on the right of the sequence refers to corresponding sequence)

| | | | | | | |
|---|---|---|---|---|---|---|
| 17 | RFTVSRDNA KHTVYLQMN SLKPEDTAV YYCAA | 258 | ASFAPGSRGYDY | 287 | WGQGTQ VTVSS | 316 |
| 18 | RFTISRDSA KNTVYLQMN SLKPEDTAV YYCTT | 259 | ATNSTTGYDY | 288 | WGQGTQ VTVSS | 317 |
| 19 | RFAIYRDNS KNTVYLEMN SLKPDDTAV YYCRV | 260 | VDLLRGKLY | 289 | WGTQGTQ VTVSS | 318 |
| 20 | RFTISRDNA NNAVYLQM NRLKPEDTA VYHCAA | 261 | SLRNSGSNVEG RY | 290 | WGQGTQ VTVSS | 319 |
| 21 | RITISRDNAK NTVYLQMNS LKTEDTGVY YCAA | 262 | NLQNARGSY | 291 | YGQGTQV TVSS | 320 |
| 22 | RFTISRDNA KNTLYLQMN SLNPEDTAV YYCAR | 263 | GDWRYGS | 292 | RGQGTQV TVSS | 321 |
| 23 | RFTTSRDNA KNTVYLQMN SLKPEDTGV YYCAA | 264 | DDGARGSY | 293 | YGQGTQV TVSS | 322 |
| 24 | RFTISTDNAK NTVYLQMNS LKPEDTGVY YCAA | 265 | TLAKGGGRY | 294 | WGQGTP VTVSS | 323 |
| 25 | RFIVSRDNA ENTVFLQMN SLKPEDSAV YFCAA | 266 | SIEGVSGRY | 295 | YGQGTQV TVSS | 324 |
| 26 | RFTIYRANA KNTVYLQMN SLKPEDTAV YYCAA | 267 | DLRGGIATTGRY | 296 | WGQGTQ VTVSS | 325 |
| 27 | RFTISRDNA KNAVYLQMN NLKLDDTAV YYCNA | 268 | YGSGSDYLPIDY | 297 | WGQGTQ VTVSS | 326 |
| 28 | RFTISRDNA KNMGYLQM NNLKLDDTAI YYCYA | 269 | YGSGSDYLPTDY | 298 | WGQGTQ VTVSS | 327 |
| 29 | RFTISRHNA KNMVYLQM NNLKLDDTA VYYCNA | 270 | YGSGSDYLPMDY | 299 | WGQGTQ VTVSS | 328 |

Thus, in the Nanobodies of the invention, at least one of the CDR1, CDR2 and CDR3 present is suitably chosen from the group consisting of the CDR1, CDR2 and CDR3, respectively, listed in Table A-1B; or from the group of CDR1, CDR2 and CDR3, respectively, that have at least 80%, preferably at least 90%, more preferably at least 95%, even more preferably at least 99% "sequence identity" (as defined herein) with at least one of the CDR1, CDR2 and CDR3, respectively, listed in Table A-1B; and/or from the group consisting of the CDR1, CDR2 and CDR3, respectively, that have 3, 2 or only 1 "amino acid difference(s)" (as defined herein) with at least one of the CDR1, CDR2 and CDR3, respectively, listed in Table A-1B.

In this context, by "suitably chosen" is meant that, as applicable, a CDR1 sequence is chosen from suitable CDR1 (i.e. as defined herein), a CDR2 sequence is chosen from suitable CDR2 (i.e. as defined herein), and a CDR3 sequence is chosen from suitable CDR3 sequence (i.e. as defined herein), respectively. More in particular, the CDR sequences are preferably chosen such that the Nanobodies of the invention bind to members of the Notch signalling pathway with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein.

In particular, in the Nanobodies of the invention, at least the CDR3 sequence present is suitably chosen from the group consisting of the CDR3 listed in Table A-1B or from the group of CDR3 that have at least 80%, preferably at least 90%, more preferably at least 95%, even more preferably at least 99% sequence identity with at least one of the CDR3 listed in Table A-1B; and/or from the group consisting of the CDR3 that have 3, 2 or only 1 amino acid difference(s) with at least one of the CDR3 listed in Table A-1B.

Preferably, in the Nanobodies of the invention, at least two of the CDR1, CDR2 and CDR3 present are suitably chosen from the group consisting of the CDR1, CDR2 and CDR3, respectively, listed in Table A-1B or from the group consisting of CDR1, CDR2 and CDR3, respectively, that have at least 80%, preferably at least 90%, more preferably at least 95%, even more preferably at least 99% sequence identity with at least one of the CDR1, CDR2 and CDR3, respectively, listed in Table A-1B; and/or from the group consisting of the CDR1, CDR2 and CDR3, respectively, that have 3, 2 or only 1 "amino acid difference(s)" with at least one of the CDR1, CDR2 and CDR3, respectively, listed in Table A-1B.

In particular, in the Nanobodies of the invention, at least the CDR3 sequence present is suitably chosen from the group consisting of the CDR3 listed in Table A-1B or from the group of CDR3 that have at least 80%, preferably at least 90%, more preferably at least 95%, even more preferably at least 99% sequence identity with at least one of the CDR3 listed in Table A-1B, respectively; and at least one of the CDR1 and CDR2 present is suitably chosen from the group consisting of the CDR1 and 180-197, respectively, listed in Table A-1B or from the group of CDR1 and CDR2, respectively, that have at least 80%, preferably at least 90%, more preferably at least 95%, even more preferably at least 99% sequence identity with at least one of the CDR1 and CDR2, respectively, listed in Table A-1B; and/or from the group consisting of the CDR1 and CDR2, respectively, that have 3, 2 or only 1 amino acid difference(s) with at least one of the CDR1 and CDR2, respectively, listed in Table A-1B.

Most preferably, in the Nanobodies of the invention, all three CDR1, CDR2 and CDR3 present are suitably chosen from the group consisting of the CDR1, CDR2 and CDR3, respectively, listed in Table A-1B or from the group of CDR1, CDR2 and CDR3, respectively, that have at least 80%, preferably at least 90%, more preferably at least 95%, even more preferably at least 99% sequence identity with at least one of the CDR1, CDR2 and CDR3, respectively, listed in Table A-1B; and/or from the group consisting of the CDR1, CDR2 and CDR3, respectively, that have 3, 2 or only 1 amino acid difference(s) with at least one of the CDR1, CDR2 and CDR3, respectively, listed in Table A-1B.

Even more preferably, in the Nanobodies of the invention, at least one of the CDR1, CDR2 and CDR3 present is suitably chosen from the group consisting of the CDR1, CDR2 and CDR3, respectively, listed in Table A-1B. Preferably, in this aspect, at least one or preferably both of the other two CDR sequences present are suitably chosen from CDR sequences that have at least 80%, preferably at least 90%, more preferably at least 95%, even more preferably at least 99% sequence identity with at least one of the corresponding CDR sequences, respectively, listed in Table A-1B; and/or from the group consisting of the CDR sequences that have 3, 2 or only 1 amino acid difference(s) with at least one of the corresponding sequences, respectively, listed in Table A-1B.

In particular, in the Nanobodies of the invention, at least the CDR3 sequence present is suitably chosen from the group consisting of the CDR3 listed in Table A-1B. Preferably, in this aspect, at least one and preferably both of the CDR1 and CDR2 present are suitably chosen from the groups of CDR1 and CDR2, respectively, that have at least 80%, preferably at least 90%, more preferably at least 95%, even more preferably at least 99% sequence identity with the CDR1 and CDR2, respectively, listed in Table A-1B; and/or from the group consisting of the CDR1 and CDR2, respectively, that have 3, 2 or only 1 amino acid difference(s) with at least one of the CDR1 and CDR2, respectively, listed in Table A-1B.

Even more preferably, in the Nanobodies of the invention, at least two of the CDR1, CDR2 and CDR3 present are suitably chosen from the group consisting of the CDR1, CDR2 and CDR3, respectively, listed in Table A-1B. Preferably, in this aspect, the remaining CDR sequence present is suitably chosen from the group of CDR sequences that have at least 80%, preferably at least 90%, more preferably at least 95%, even more preferably at least 99% sequence identity with at least one of the corresponding CDR sequences listed in Table A-1B; and/or from the group consisting of CDR sequences that have 3, 2 or only 1 amino acid difference(s) with at least one of the corresponding sequences listed in Table A-1B.

In particular, in the Nanobodies of the invention, at least the CDR3 sequence is suitably chosen from the group consisting of the 216-233 listed in Table A-1B, and either the CDR1 sequence or the CDR2 sequence is suitably chosen from the group consisting of the CDR1 and CDR2, respectively, listed in Table A-1B. Preferably, in this aspect, the remaining CDR sequence present is suitably chosen from the group of CDR sequences that have at least 80%, preferably at least 90%, more preferably at least 95%, even more preferably at least 99% sequence identity with at least one of the corresponding CDR sequences listed in Table A-1B; and/or from the group consisting of CDR sequences that have 3, 2 or only 1 amino acid difference(s) with the corresponding CDR sequences listed in Table A-1B.

Even more preferably, in the Nanobodies of the invention, all three CDR1, CDR2 and CDR3 present are suitably chosen from the group consisting of the CDR1, CDR2 and CDR3, respectively, listed in Table A-1B.

Also, generally, the combinations of CDR's listed in Table A-1B (i.e. those mentioned on the same line in Table A-1B) are preferred. Thus, it is generally preferred that, when a CDR in a Nanobody of the invention is a CDR sequence mentioned in Table A-1B or is suitably chosen from the group of CDR sequences that have at least 80%, preferably at least 90%, more preferably at least 95%, even more preferably at least 99% sequence identity with a CDR sequence listed in Table A-1B; and/or from the group consisting of CDR sequences that have 3, 2 or only 1 amino acid difference(s) with a CDR sequence listed in Table A-1B, that at least one and preferably both of the other CDR's are suitably chosen from the CDR sequences that belong to the same combination in Table A-1B (i.e. mentioned on the same line in Table A-1B) or are suitably chosen from the group of CDR sequences that have at least 80%, preferably at least 90%, more preferably at least 95%, even more preferably at least 99% sequence identity with the CDR sequence(s) belonging to the same combination and/or from the group consisting of CDR sequences that have 3, 2 or only 1 amino acid difference(s) with the CDR sequence(s) belonging to the same combination. The other preferences indicated in the above paragraphs also apply to the combinations of CDR's mentioned in Table A-1B.

Thus, by means of non-limiting examples, a Nanobody of the invention can for example comprise a CDR1 sequence that has more than 80% sequence identity with one of the CDR1 mentioned in Table A-1B, a CDR2 sequence that has 3, 2 or 1 amino acid difference with one of the CDR2 mentioned in Table A-1B (but belonging to a different combination), and a CDR3 sequence.

Some preferred Nanobodies of the invention may for example comprise: (1) a CDR1 sequence that has more than 80% sequence identity with one of the CDR1 mentioned in Table A-1B; a CDR2 sequence that has 3, 2 or 1 amino acid difference with one of the CDR2 mentioned in Table A-1B (but belonging to a different combination); and a CDR3 sequence that has more than 80% sequence identity with one of the CDR3 mentioned in Table A-1B (but belonging to a different combination); or (2) a CDR1 sequence that has more than 80% sequence identity with one of the CDR1 mentioned in Table A-1B; a CDR2 sequence, and one of the CDR3 listed in Table A-1B; or (3) a CDR1 sequence; a CDR2 sequence that has more than 80% sequence identity with one of the CDR2 sequence listed in Table A-1B; and a CDR3 sequence that has 3, 2 or 1 amino acid differences with the CDR3 sequence mentioned in Table A-1B that belongs to the same combination as the CDR2 sequence.

Some particularly preferred Nanobodies of the invention may for example comprise: (1) a CDR1 sequence that has more than 80% sequence identity with one of the CDR1 mentioned in Table A-1B; a CDR2 sequence that has 3, 2 or 1 amino acid difference with the CDR2 sequence mentioned in Table A-1B that belongs to the same combination; and a CDR3 sequence that has more than 80% sequence identity with the CDR3 sequence mentioned in Table A-1B that belongs to the same combination; (2) a CDR1 sequence; a CDR 2 listed in Table A-1B and a CDR3 sequence listed in Table A-1B (in which the CDR2 sequence and CDR3 sequence may belong to different combinations).

Some even more preferred Nanobodies of the invention may for example comprise: (1) a CDR1 sequence that has more than 80% sequence identity with one of the CDR1 mentioned in Table A-1B; the CDR2 sequence listed in Table A-1B that belongs to the same combination; and a CDR3 sequence mentioned in Table A-1B that belongs to a different combination; or (2) a CDR1 sequence mentioned in Table A-1B; a CDR2 sequence that has 3, 2 or 1 amino acid differences with the CDR2 sequence mentioned in Table A-1B that belongs to the same combination; and a CDR3 sequence that has more than 80% sequence identity with the CDR3 sequence listed in Table A-1B that belongs to the same or a different combination.

Particularly preferred Nanobodies of the invention may for example comprise a CDR1 sequence mentioned in Table A-1B, a CDR2 sequence that has more than 80% sequence identity with the CDR2 sequence mentioned in Table A-1B that belongs to the same combination; and the CDR3 sequence mentioned in Table A-1B that belongs to the same combination.

In the most preferred Nanobodies of the invention, the CDR1, CDR2 and CDR3 present are suitably chosen from one of the combinations of CDR1, CDR2 and CDR3, respectively, listed in Table A-1B.

According to another preferred, but non-limiting aspect of the invention (a) CDR1 has a length of between 1 and 12 amino acid residues, and usually between 2 and 9 amino acid residues, such as 5, 6 or 7 amino acid residues; and/or (b) CDR2 has a length of between 13 and 24 amino acid residues, and usually between 15 and 21 amino acid residues, such as 16 and 17 amino acid residues; and/or (c) CDR3 has a length of between 2 and 35 amino acid residues, and usually between 3 and 30 amino acid residues, such as between 6 and 23 amino acid residues.

In another preferred, but non-limiting aspect, the invention relates to a Nanobody in which the CDR sequences (as defined herein) have more than 80%, preferably more than 90%, more preferably more than 95%, such as 99% or more sequence identity (as defined herein) with the CDR sequences of at least one of the single variable domains of SEQ ID NO's: [255-269].

Generally, Nanobodies with the above CDR sequences may be as further described herein, and preferably have framework sequences that are also as further described herein. Thus, for example and as mentioned herein, such Nanobodies may be naturally occurring Nanobodies (from any suitable species), naturally occurring VHH sequences (i.e. from a suitable species of Camelid) or synthetic or semi-synthetic single variable domains or Nanobodies, including but not limited to partially humanized Nanobodies or VHH sequences, fully humanized Nanobodies or VHH sequences, camelized heavy chain variable domain sequences, as well as Nanobodies that have been obtained by the techniques mentioned herein.

Thus, in one specific, but non-limiting aspect, the invention relates to a humanized Nanobody, which consists of 4 framework regions (FR1 to FR4 respectively) and 3 complementarity determining regions (CDR1 to CDR3 respectively), in which CDR1 to CDR3 are as defined herein and in which said humanized Nanobody comprises at least one humanizing substitution (as defined herein), and in particular at least one humanizing substitution in at least one of its framework sequences (as defined herein).

In another preferred, but non-limiting aspect, the invention relates to a Nanobody in which the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the single variable domains of SEQ ID NO's: [255-269]. This degree of amino acid identity can for example be determined by determining the degree of amino acid identity (in a manner described herein) between said Nanobody and one or more of the sequences of SEQ ID NO's: [255-269], in which the amino acid residues that form the framework regions are disregarded. Such Nanobodies can be as further described herein.

In another preferred, but non-limiting aspect, the invention relates to a Nanobody with an amino acid sequence that is chosen from the group consisting of SEQ ID NO's: [255-269] or from the group consisting of from single variable domains that have more than 80%, preferably more than 90%, more preferably more than 95%, such as 99% or more sequence identity (as defined herein) with at least one of the single variable domains of SEQ ID NO's: [255-269].

Another preferred, but non-limiting aspect of the invention relates to humanized variants of the Nanobodies of SEQ ID NO's: [255-269], that comprise, compared to the corresponding native $V_{HH}$ sequence, at least one humanizing substitution (as defined herein), and in particular at least one humanizing substitution in at least one of its framework sequences (as defined herein).

The single variable domains of the invention comprise or essentially consist of at least one Nanobody of the invention. Some preferred, but non-limiting examples of single variable domains of the invention are given in SEQ ID NO's: [255-269].

It will be clear to the skilled person that the Nanobodies that are mentioned herein as "preferred" (or "more preferred", "even more preferred", etc.) are also preferred (or more preferred, or even more preferred, etc.) for use in the single variable domains described herein. Thus, single variable domains that comprise or essentially consist of one or more "preferred" Nanobodies of the invention will generally be preferred, and single variable domains that comprise or essentially consist of one or more "more preferred" Nanobodies of the invention will generally be more preferred, etc.

Generally, proteins or single variable domains that comprise or essentially consist of a single Nanobody (such as a single Nanobody of the invention) will be referred to herein as "monovalent" proteins or single variable domains or as "monovalent constructs". Proteins and single variable domains that comprise or essentially consist of two or more Nanobodies (such as at least two Nanobodies of the invention or at least one Nanobody of the invention and at least one other Nanobody) will be referred to herein as "multivalent" proteins or single variable domains or as "multivalent constructs", and these may provide certain advantages compared to the corresponding monovalent Nanobodies of the invention. Some non-limiting examples of such multivalent constructs will become clear from the further description herein.

According to one specific, but non-limiting aspect, a polypeptide of the invention comprises or essentially consists of at least two Nanobodies of the invention, such as two or three Nanobodies of the invention. As further described herein, such multivalent constructs can provide certain advantages compared to a protein or polypeptide comprising or essentially consisting of a single Nanobody of the invention, such as a much improved avidity for members for the Notch signalling pathway. Such multivalent constructs will be clear to the skilled person based on the disclosure herein.

According to another specific, but non-limiting aspect, a polypeptide of the invention comprises or essentially consists of at least one Nanobody of the invention and at least one other binding unit (i.e. directed against another epitope, antigen, target, protein or polypeptide), which is preferably also a Nanobody. Such proteins or single variable domains are also referred to herein as "multispecific" proteins or single variable domains or as 'multispecific constructs", and these may provide certain advantages compared to the corresponding monovalent Nanobodies of the invention (as will become clear from the further discussion herein of some preferred, but-nonlimiting multispecific constructs). Such multispecific constructs will be clear to the skilled person based on the disclosure herein.

According to yet another specific, but non-limiting aspect, a polypeptide of the invention comprises or essentially consists of at least one Nanobody of the invention, optionally one or more further Nanobodies, and at least one other amino acid sequence (such as a protein or polypeptide) that confers at least one desired property to the Nanobody of the invention and/or to the resulting fusion protein. Again, such fusion proteins may provide certain advantages compared to the corresponding monovalent Nanobodies of the invention. Some non-limiting examples of such of such fusion constructs will become clear from the further description herein.

It is also possible to combine two or more of the above aspects, for example to provide a trivalent bispecific construct comprising two Nanobodies of the invention and one other Nanobody, and optionally one or more other amino acid sequences. Further non-limiting examples of such constructs, as well as some constructs that are particularly preferred within the context of the present invention, will become clear from the further description herein.

In the above constructs, the one or more Nanobodies and/or other single variable domains may be directly linked to each other and/or suitably linked to each other via one or more linker sequences. Some suitable but non-limiting examples of such linkers will become clear from the further description herein.

In one specific aspect of the invention, a Nanobody of the invention or a compound, construct or polypeptide of the invention comprising at least one Nanobody of the invention may have an increased half-life, compared to the corresponding amino acid sequence of the invention. Some preferred, but non-limiting examples of such Nanobodies, compounds and single variable domains will become clear to the skilled person based on the further disclosure herein, and for example comprise Nanobodies sequences or single variable domains of the invention that have been chemically modified to increase the half-life thereof (for example, by means of pegylation); single variable domains of the invention that comprise at least one additional binding site for binding to a serum protein (such as serum albumin, see for example EP 0 368 684 B1, page 4); or single variable domains of the invention that comprise at least one Nanobody of the invention that is linked to at least one moiety (and in particular at least one amino acid sequence) that increases the half-life of the Nanobody of the invention. Examples of single variable domains of the invention that comprise such half-life extending moieties or single variable domains will become clear to the skilled person based on the further disclosure herein; and for example include, without limitation, single variable domains in which the one or more Nanobodies of the invention are suitable linked to one or more serum proteins or fragments thereof (such as serum albumin or suitable fragments thereof) or to one or more binding units that can bind to serum proteins (such as, for example, Nanobodies or (single) domain antibodies that can bind to serum proteins such as serum albumin, serum immunoglobulins such as IgG, or transferrin); single variable domains in which a Nanobody of the invention is linked to an Fc portion (such as a human Fc) or a suitable part or fragment thereof; or single variable domains in which the one or more Nanobodies of the invention are suitable linked to one or more small proteins or peptides that can bind to serum proteins (such as, without limitation, the proteins and peptides described in WO 91/01743, WO 01/45746, WO 02/076489 and to the US provisional application of Ablynx N.V. entitled "Peptides capable of binding to serum proteins" of Ablynx N.V. filed on Dec. 5, 2006 (see also PCT/EP/2007/063348).

Again, as will be clear to the skilled person, such Nanobodies, compounds, constructs or single variable domains may contain one or more additional groups, residues, moieties or binding units, such as one or more further in particular one or more additional Nanobodies (i.e. not directed against members for the Notch signalling pathway), so as to provide a tri- of multispecific Nanobody construct.

Generally, the Nanobodies of the invention (or compounds, constructs or single variable domains comprising the same) with increased half-life preferably have a half-life that is at least 1.5 times, preferably at least 2 times, such as at least 5 times, for example at least 10 times or more than 20 times, greater than the half-life of the corresponding amino acid sequence of the invention per se. For example, the Nanobodies, compounds, constructs or single variable domains of the invention with increased half-life may have a half-life that is increased with more than 1 hours, preferably more than 2 hours, more preferably more than 6 hours, such as more than 12 hours, or even more than 24, 48 or 72 hours, compared to the corresponding amino acid sequence of the invention per se.

In a preferred, but non-limiting aspect of the invention, such Nanobodies, compound, constructs or single variable domains of the invention exhibit a serum half-life in human of at least about 12 hours, preferably at least 24 hours, more preferably at least 48 hours, even more preferably at least 72 hours or more. For example, compounds or single variable domains of the invention may have a half-life of at least 5 days (such as about 5 to 10 days), preferably at least 9 days (such as about 9 to 14 days), more preferably at least about 10 days (such as about 10 to 15 days), or at least 11 days (such as about 11 to 16 days), more preferably at least 12 days (such as about 12 to 18 days or more), or more than 14 days (such as about 14 to 19 days).

In another one aspect of the invention, a polypeptide of the invention comprises one or more (such as two or preferably one) Nanobodies of the invention linked (optionally via one or more suitable linker sequences) to one or more (such as two and preferably one) single variable domains that allow the resulting polypeptide of the invention to cross the blood brain barrier. In particular, said one or more single variable domains that allow the resulting single variable domains of the invention to cross the blood brain barrier may be one or more (such as two and preferably one) Nanobodies, such as the Nanobodies described in WO 02/057445, of which FC44 (SEQ ID NO: 189 of WO 06/040153) and FC5 (SEQ ID NO: 190 of WO 06/040154) are preferred examples.

In particular, single variable domains comprising one or more Nanobodies of the invention are preferably such that they:

bind to members of the Notch signalling pathway with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles);

and/or such that they:

bind to members of the Notch signalling pathway with a $k_{on}$-rate of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$;

and/or such that they:

bind to members of the Notch signalling pathway with a $k_{off}$ rate between 1 $s^{-1}$ ($t_{1/2}$=0.69 s) and $10^{-6}$ $s^{-1}$ (providing a near irreversible complex with a $t_{1/2}$ of multiple days), preferably between $10^{-2}$ $s^{-1}$ and $10^{-6}$ $s^{-1}$, more preferably between $10^{-3}$ $s^{-1}$ and $10^{-6}$ $s^{-1}$, such as between $10^4$ $s^{-1}$ and $10^{-6}$ $s^{-1}$.

Preferably, a polypeptide that contains only one amino acid sequence of the invention is preferably such that it will bind to members of the Notch signalling pathway with an affinity less than 500 nM, preferably less than 200 nM, more preferably less than 10 nM, such as less than 500 pM. In this respect, it will be clear to the skilled person that a polypeptide that contains two or more Nanobodies of the invention may bind to members of the Notch signalling pathway with an increased avidity, compared to a polypeptide that contains only one amino acid sequence of the invention.

Some preferred $IC_{50}$ values for binding of the single variable domains or single variable domains of the invention to members of the Notch signalling pathway will become clear from the further description and examples herein.

Other single variable domains according to this preferred aspect of the invention may for example be chosen from the group consisting of single variable domains that have more than 80%, preferably more than 90%, more preferably more than 95%, such as 99% or more "sequence identity" (as defined herein) with one or more of the single variable domains of SEQ ID NO's: [255-269], in which the Nanobodies comprised within said single variable domains are preferably as further defined herein.

Another aspect of this invention relates to a nucleic acid that encodes an amino acid sequence of the invention (such as a Nanobody of the invention) or a polypeptide of the invention comprising the same. Again, as generally described herein for the nucleic acids of the invention, such a nucleic acid may be in the form of a genetic construct, as defined herein.

In another aspect, the invention relates to host or host cell that expresses or that is capable of expressing an amino acid sequence (such as a Nanobody) of the invention and/or a polypeptide of the invention comprising the same; and/or that contains a nucleic acid of the invention. Some preferred but non-limiting examples of such hosts or host cells will become clear from the further description herein.

Another aspect of the invention relates to a product or composition containing or comprising at least one amino acid sequence of the invention, at least one polypeptide of the invention and/or at least one nucleic acid of the invention, and optionally one or more further components of such compositions known per se, i.e. depending on the intended use of the composition. Such a product or composition may for example be a pharmaceutical composition (as described herein), a veterinary composition or a product or composition for diagnostic use (as also described herein). Some preferred but non-limiting examples of such products or compositions will become clear from the further description herein.

The invention further relates to methods for preparing or generating the amino acid sequences, compounds, constructs, single variable domains, nucleic acids, host cells, products and compositions described herein. Some preferred but non-limiting examples of such methods will become clear from the further description herein.

The invention further relates to applications and uses of the amino acid sequences, compounds, constructs, single variable domains, nucleic acids, host cells, products and compositions described herein, as well as to methods for the prevention and/or treatment for diseases and disorders associated with members for the Notch signalling pathway. Some preferred but non-limiting applications and uses will become clear from the further description herein.

Other aspects, embodiments, advantages and applications of the invention will also become clear from the further description hereinbelow.

Generally, it should be noted that the term Nanobody as used herein in its broadest sense is not limited to a specific biological source or to a specific method of preparation. For example, as will be discussed in more detail below, the Nanobodies of the invention can generally be obtained: (1) by isolating the $V_{HH}$ domain of a naturally occurring heavy chain antibody; (2) by expression of a nucleotide sequence encoding a naturally occurring $V_{HH}$ domain; (3) by "humanization" (as described herein) of a naturally occurring $V_{HH}$ domain or by expression of a nucleic acid encoding a such humanized $V_{HH}$ domain; (4) by "camelization" (as described herein) of a naturally occurring $V_H$ domain from any animal species, and in particular a from species of mammal, such as from a human being, or by expression of a nucleic acid encoding such a camelized $V_H$ domain; (5) by "camelisation" of a "domain antibody" or "Dab" as described by Ward et al (supra), or by expression of a nucleic acid encoding such a camelized $V_H$ domain; (6) by using synthetic or semi-synthetic techniques for preparing proteins, single variable domains or other single variable domains known per se; (7) by preparing a nucleic acid encoding a Nanobody using techniques for nucleic acid synthesis known per se, followed by expression of the nucleic acid thus obtained; and/or (8) by any combination of one or more of the foregoing. Suitable methods and techniques for performing the foregoing will be clear to the skilled person based on the disclosure herein and for example include the methods and techniques described in more detail herein.

One preferred class of Nanobodies corresponds to the $V_{HH}$ domains of naturally occurring heavy chain antibodies directed against members for the Notch signalling pathway. As further described herein, such VHH sequences can generally be generated or obtained by suitably immunizing a species of Camelid with members of the Notch signalling pathway (i.e. so as to raise an immune response and/or heavy chain antibodies directed against members for the Notch signalling pathway), by obtaining a suitable biological sample from said Camelid (such as a blood sample, serum sample or sample of B-cells), and by generating VHH sequences directed against members for the Notch signalling pathway, starting from said sample, using any suitable technique known per se. Such techniques will be clear to the skilled person and/or are further described herein.

Alternatively, such naturally occurring $V_{HH}$ domains against members for the Notch signalling pathway, can be obtained from naïve libraries of Camelid VHH sequences, for example by screening such a library using members for the Notch signalling pathway, or at least one part, fragment, antigenic determinant or epitope thereof using one or more screening techniques known per se. Such libraries and techniques are for example described in WO 99/37681, WO 01/90190, WO 03/025020 and WO 03/035694. Alternatively, improved synthetic or semi-synthetic libraries derived from naïve $V_{HH}$ libraries may be used, such as $V_{HH}$ libraries obtained from naïve $V_{HH}$ libraries by techniques such as random mutagenesis and/or CDR shuffling, as for example described in WO 00/43507.

Thus, in another aspect, the invention relates to a method for generating Nanobodies, that are directed against members for the Notch signalling pathway. In one aspect, said method at least comprises the steps of:

a) providing a set, collection or library of Nanobody sequences; and b) screening said set, collection or library of Nanobody sequences for Nanobody sequences that can bind to and/or have affinity for members for the Notch signalling pathway;

and c) isolating the amino acid sequence(s) that can bind to and/or have affinity for members for the Notch signalling pathway.

In such a method, the set, collection or library of Nanobody sequences may be a naïve set, collection or library of Nanobody sequences; a synthetic or semi-synthetic set, collection or library of Nanobody sequences; and/or a set, collection or library of Nanobody sequences that have been subjected to affinity maturation.

In a preferred aspect of this method, the set, collection or library of Nanobody sequences may be an immune set, collection or library of Nanobody sequences, and in particular an immune set, collection or library of VHH sequences, that have been derived from a species of Camelid that has been suitably immunized with members of the Notch signalling pathway or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

In the above methods, the set, collection or library of Nanobody or VHH sequences may be displayed on a phage, phagemid, ribosome or suitable micro-organism (such as yeast), such as to facilitate screening. Suitable methods, techniques and host organisms for displaying and screening (a set, collection or library of) Nanobody sequences will be clear to the person skilled in the art, for example on the basis of the further disclosure herein. Reference is also made to WO 03/054016 and to the review by Hoogenboom in Nature Biotechnology, 23, 9, 1105-1116 (2005).

In another aspect, the method for generating Nanobody sequences comprises at least the steps of:

a) providing a collection or sample of cells derived from a species of Camelid that express immunoglobulin sequences;

b) screening said collection or sample of cells for (i) cells that express an immunoglobulin sequence that can bind to and/or have affinity for members for the Notch signalling pathway; and (ii) cells that express heavy chain antibodies, in which substeps (i) and (ii) can be performed essentially as a single screening step or in any suitable order as two separate screening steps, so as to provide at least one cell that expresses a heavy chain antibody that can bind to and/or has affinity for members for the Notch signalling pathway;

and c) either (i) isolating from said cell the $V_{HH}$ sequence present in said heavy chain antibody; or (ii) isolating from said cell a nucleic acid sequence that encodes the $V_{HH}$ sequence present in said heavy chain antibody, followed by expressing said $V_{HH}$ domain.

In the method according to this aspect, the collection or sample of cells may for example be a collection or sample of B-cells. Also, in this method, the sample of cells may be derived from a Camelid that has been suitably immunized with members of the Notch signalling pathway or a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

The above method may be performed in any suitable manner, as will be clear to the skilled person. Reference is for example made to EP 0 542 810, WO 05/19824, WO 04/051268 and WO 04/106377. The screening of step b) is preferably performed using a flow cytometry technique such as FACS. For this, reference is for example made to Lieby et al., Blood, Vol. 97, No. 12, 3820. Particular reference is made to the so-called "Nanoclone™" technique described in International application WO 06/079372 by Ablynx N.V.

In another aspect, the method for generating an amino acid sequence directed against members of the Notch signalling pathway may comprise at least the steps of:
a) providing a set, collection or library of nucleic acid sequences encoding heavy chain antibodies or Nanobody sequences;
b) screening said set, collection or library of nucleic acid sequences for nucleic acid sequences that encode a heavy chain antibody or a Nanobody sequence that can bind to and/or has affinity for members for the Notch signalling pathway;
and
c) isolating said nucleic acid sequence, followed by expressing the $V_{HH}$ sequence present in said heavy chain antibody or by expressing said Nanobody sequence, respectively.

In such a method, the set, collection or library of nucleic acid sequences encoding heavy chain antibodies or Nanobody sequences may for example be a set, collection or library of nucleic acid sequences encoding a naïve set, collection or library of heavy chain antibodies or VHH sequences; a set, collection or library of nucleic acid sequences encoding a synthetic or semi-synthetic set, collection or library of Nanobody sequences; and/or a set, collection or library of nucleic acid sequences encoding a set, collection or library of Nanobody sequences that have been subjected to affinity maturation.

In a preferred aspect of this method, the set, collection or library of single variable domains may be an immune set, collection or library of nucleic acid sequences encoding heavy chain antibodies or VHH sequences derived from a Camelid that has been suitably immunized with members of the Notch signalling pathway or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

In the above methods, the set, collection or library of nucleotide sequences may be displayed on a phage, phagemid, ribosome or suitable micro-organism (such as yeast), such as to facilitate screening. Suitable methods, techniques and host organisms for displaying and screening (a set, collection or library of) nucleotide sequences encoding single variable domains will be clear to the person skilled in the art, for example on the basis of the further disclosure herein. Reference is also made to WO 03/054016 and to the review by Hoogenboom in Nature Biotechnology, 23, 9, 1105-1116 (2005).

As will be clear to the skilled person, the screening step of the methods described herein can also be performed as a selection step. Accordingly the term "screening" as used in the present description can comprise selection, screening or any suitable combination of selection and/or screening techniques. Also, when a set, collection or library of sequences is used, it may contain any suitable number of sequences, such as 1, 2, 3 or about 5, 10, 50, 100, 500, 1000, 5000, $10^4$, $10^5$, $10^6$, $10^7$, $10^8$ or more sequences.

Also, one or more or all of the sequences in the above set, collection or library of single variable domains may be obtained or defined by rational, or semi-empirical approaches such as computer modelling techniques or biostatics or data-mining techniques.

Furthermore, such a set, collection or library can comprise one, two or more sequences that are variants from one another (e.g. with designed point mutations or with randomized positions), compromise multiple sequences derived from a diverse set of naturally diversified sequences (e.g. an immune library)), or any other source of diverse sequences (as described for example in Hoogenboom et al, Nat Biotechnol 23:1105, 2005 and Binz et al, Nat Biotechnol 2005, 23:1247). Such set, collection or library of sequences can be displayed on the surface of a phage particle, a ribosome, a bacterium, a yeast cell, a mammalian cell, and linked to the nucleotide sequence encoding the amino acid sequence within these carriers. This makes such set, collection or library amenable to selection procedures to isolate the desired single variable domains of the invention. More generally, when a sequence is displayed on a suitable host or host cell, it is also possible (and customary) to first isolate from said host or host cell a nucleotide sequence that encodes the desired sequence, and then to obtain the desired sequence by suitably expressing said nucleotide sequence in a suitable host organism. Again, this can be performed in any suitable manner known per se, as will be clear to the skilled person.

Yet another technique for obtaining VHH sequences or Nanobody sequences directed against members of the Notch signalling pathway involves suitably immunizing a transgenic mammal that is capable of expressing heavy chain antibodies (i.e. so as to raise an immune response and/or heavy chain antibodies directed against members for the Notch signalling pathway), obtaining a suitable biological sample from said transgenic mammal that contains (nucleic acid sequences encoding) said VHH sequences or Nanobody sequences (such as a blood sample, serum sample or sample of B-cells), and then generating VHH sequences directed against members for the Notch signalling pathway, starting from said sample, using any suitable technique known per se (such as any of the methods described herein or a hybridoma technique). For example, for this purpose, the heavy chain antibody-expressing mice and the further methods and techniques described in WO 02/085945, WO 04/049794 and WO 06/008548 and Janssens et al., Proc. Natl. Acad. Sci. USA. 2006 Oct. 10; 103(41):15130-5 can be used. For example, such heavy chain antibody expressing mice can express heavy chain antibodies with any suitable (single) variable domain, such as (single) variable domains from natural sources (e.g. human (single) variable domains, Camelid (single) variable domains or shark (single) variable domains), as well as for example synthetic or semi-synthetic (single) variable domains.

The invention also relates to the VHH sequences or Nanobody sequences that are obtained by the above methods, or alternatively by a method that comprises the one of the above methods and in addition at least the steps of determining the nucleotide sequence or amino acid sequence of said $V_{HH}$ sequence or Nanobody sequence; and of expressing or synthesizing said $V_{HH}$ sequence or Nanobody sequence in a manner known per se, such as by expression in a suitable host cell or host organism or by chemical synthesis.

As mentioned herein, a particularly preferred class of Nanobodies of the invention comprises Nanobodies with an amino acid sequence that corresponds to the amino acid sequence of a naturally occurring $V_{HH}$ domain, but that has been "humanized", i.e. by replacing one or more amino acid residues in the amino acid sequence of said naturally occurring $V_{HH}$ sequence (and in particular in the framework sequences) by one or more of the amino acid residues that occur at the corresponding position(s) in a $V_H$ domain from a conventional 4-chain antibody from a human being (e.g. indicated above). This can be performed in a manner known per se, which will be clear to the skilled person, for example on the basis of the further description herein and the prior art on humanization referred to herein. Again, it should be noted that such humanized Nanobodies of the invention can be obtained in any suitable manner known per se (i.e. as indicated under points (1)-(8) above) and thus are not strictly limited to single variable domains that have been obtained using a polypeptide that comprises a naturally occurring $V_{HH}$ domain as a starting material.

Another particularly preferred class of Nanobodies of the invention comprises Nanobodies with an amino acid sequence that corresponds to the amino acid sequence of a naturally occurring $V_H$ domain, but that has been "camelized", i.e. by replacing one or more amino acid residues in the amino acid sequence of a naturally occurring $V_H$ domain from a conventional 4-chain antibody by one or more of the amino acid residues that occur at the corresponding position(s) in a $V_{HH}$ domain of a heavy chain antibody. This can be performed in a manner known per se, which will be clear to the skilled person, for example on the basis of the further description herein. Such "camelizing" substitutions are preferably inserted at amino acid positions that form and/or are present at the $V_H$-$V_L$ interface, and/or at the so-called Camelidae hallmark residues, as defined herein (see for example WO 94/04678 and Davies and Riechmann (1994 and 1996), supra). Preferably, the $V_H$ sequence that is used as a starting material or starting point for generating or designing the camelized Nanobody is preferably a $V_H$ sequence from a mammal, more preferably the $V_H$ sequence of a human being, such as a $V_H3$ sequence. However, it should be noted that such camelized Nanobodies of the invention can be obtained in any suitable manner known per se (i.e. as indicated under points (1)-(8) above) and thus are not strictly limited to single variable domains that have been obtained using a polypeptide that comprises a naturally occurring $V_H$ domain as a starting material.

For example, again as further described herein, both "humanization" and "camelization" can be performed by providing a nucleotide sequence that encodes a naturally occurring $V_{HH}$ domain or $V_H$ domain, respectively, and then changing, in a manner known per se, one or more codons in said nucleotide sequence in such a way that the new nucleotide sequence encodes a "humanized" or "camelized" Nanobody of the invention, respectively. This nucleic acid can then be expressed in a manner known per se, so as to provide the desired Nanobody of the invention. Alternatively, based on the amino acid sequence of a naturally occurring $V_{HH}$ domain or $V_H$ domain, respectively, the amino acid sequence of the desired humanized or camelized Nanobody of the invention, respectively, can be designed and then synthesized de novo using techniques for peptide synthesis known per se. Also, based on the amino acid sequence or nucleotide sequence of a naturally occurring $V_{HH}$ domain or $V_H$ domain, respectively, a nucleotide sequence encoding the desired humanized or camelized Nanobody of the invention, respectively, can be designed and then synthesized de novo using techniques for nucleic acid synthesis known per se, after which the nucleic acid thus obtained can be expressed in a manner known per se, so as to provide the desired Nanobody of the invention.

Other suitable methods and techniques for obtaining the Nanobodies of the invention and/or nucleic acids encoding the same, starting from naturally occurring $V_H$ sequences or preferably VHH sequences, will be clear from the skilled person, and may for example comprise combining one or more parts of one or more naturally occurring $V_H$ sequences (such as one or more FR sequences and/or CDR sequences), one or more parts of one or more naturally occurring VHH sequences (such as one or more FR sequences or CDR sequences), and/or one or more synthetic or semi-synthetic sequences, in a suitable manner, so as to provide a Nanobody of the invention or a nucleotide sequence or nucleic acid encoding the same (which may then be suitably expressed). Nucleotide sequences encoding framework sequences of VHH sequences or Nanobodies will be clear to the skilled person based on the disclosure herein and/or the further prior art cited herein (and/or may alternatively be obtained by PCR starting from the nucleotide sequences obtained using the methods described herein) and may be suitably combined with nucleotide sequences that encode the desired CDR's (for example, by PCR assembly using overlapping primers), so as to provide a nucleic acid encoding a Nanobody of the invention.

As mentioned herein, Nanobodies may in particular be characterized by the presence of one or more "Hallmark residues" (as described herein) in one or more of the framework sequences.

Thus, according to one preferred, but non-limiting aspect of the invention, a Nanobody in its broadest sense can be generally defined as a polypeptide comprising:

a) an amino acid sequence that is comprised of four framework regions/sequences interrupted by three complementarity determining regions/sequences, in which the amino acid residue at position 108 according to the Kabat numbering is Q;

and/or:

b) an amino acid sequence that is comprised of four framework regions/sequences interrupted by three complementarity determining regions/sequences, in which the amino acid residue at position 45 according to the Kabat numbering is a charged amino acid (as defined herein) or a cysteine residue, and position 44 is preferably an E;

and/or:

c) an amino acid sequence that is comprised of four framework regions/sequences interrupted by three complementarity determining regions/sequences, in which the amino acid residue at position 103 according to the Kabat numbering is chosen from the group consisting of P, R and S, and is in particular chosen from the group consisting of R and S.

Thus, in a first preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which a) the amino acid residue at position 108 according to the Kabat numbering is Q; and/or in which:

b) the amino acid residue at position 45 according to the Kabat numbering is a charged amino acid or a cysteine and the amino acid residue at position 44 according to the Kabat numbering is preferably E;

and/or in which:

c) the amino acid residue at position 103 according to the Kabat numbering is chosen from the group consisting of P, R and S, and is in particular chosen from the group consisting of R and S;

and in which:
d) CDR1, CDR2 and CDR3 are as defined herein, and are preferably as defined according to one of the preferred aspects herein, and are more preferably as defined according to one of the more preferred aspects herein.

In particular, a Nanobody in its broadest sense can be generally defined as a polypeptide comprising:

a) an amino acid sequence that is comprised of four framework regions/sequences interrupted by three complementarity determining regions/sequences, in which the amino acid residue at position 108 according to the Kabat numbering is Q;

and/or:

b) an amino acid sequence that is comprised of four framework regions/sequences interrupted by three complementarity determining regions/sequences, in which the amino acid residue at position 44 according to the Kabat numbering is E and in which the amino acid residue at position 45 according to the Kabat numbering is an R;

and/or:

c) an amino acid sequence that is comprised of four framework regions/sequences interrupted by three complementarity determining regions/sequences, in which the amino acid residue at position 103 according to the Kabat numbering is chosen from the group consisting of P, R and S, and is in particular chosen from the group consisting of R and S.

Thus, according to a preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which a) the amino acid residue at position 108 according to the Kabat numbering is Q;

and/or in which:

b) the amino acid residue at position 44 according to the Kabat numbering is E and in which the amino acid residue at position 45 according to the Kabat numbering is an R;

and/or in which:

c) the amino acid residue at position 103 according to the Kabat numbering is chosen from the group consisting of P, R and S, and is in particular chosen from the group consisting of R and S;

and in which:

d) CDR1, CDR2 and CDR3 are as defined herein, and are preferably as defined according to one of the preferred aspects herein, and are more preferably as defined according to one of the more preferred aspects herein.

In particular, a Nanobody against members of the Notch signalling pathway according to the invention may have the structure:

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which a) the amino acid residue at position 108 according to the Kabat numbering is Q;

and/or in which:

b) the amino acid residue at position 44 according to the Kabat numbering is E and in which the amino acid residue at position 45 according to the Kabat numbering is an R;

and/or in which:

c) the amino acid residue at position 103 according to the Kabat numbering is chosen from the group consisting of P, R and S, and is in particular chosen from the group consisting of R and S;

and in which:

d) CDR1, CDR2 and CDR3 are as defined herein, and are preferably as defined according to one of the preferred aspects herein, and are more preferably as defined according to one of the more preferred aspects herein.

In particular, according to one preferred, but non-limiting aspect of the invention, a Nanobody can generally be defined as a polypeptide comprising an amino acid sequence that is comprised of four framework regions/sequences interrupted by three complementarity determining regions/sequences, in which;

a-1) the amino acid residue at position 44 according to the Kabat numbering is chosen from the group consisting of A, G, E, D, G, Q, R, S, L; and is preferably chosen from the group consisting of G, E or Q; and a-2) the amino acid residue at position 45 according to the Kabat numbering is chosen from the group consisting of L, R or C; and is preferably chosen from the group consisting of L or R; and a-3) the amino acid residue at position 103 according to the Kabat numbering is chosen from the group consisting of W, R or S; and is preferably W or R, and is most preferably W;

a-4) the amino acid residue at position 108 according to the Kabat numbering is Q; or in which:

b-1) the amino acid residue at position 44 according to the Kabat numbering is chosen from the group consisting of E and Q; and b-2) the amino acid residue at position 45 according to the Kabat numbering is R; and b-3) the amino acid residue at position 103 according to the Kabat numbering is chosen from the group consisting of W, R and S; and is preferably W;

b-4) the amino acid residue at position 108 according to the Kabat numbering is chosen from the group consisting of Q and L; and is preferably Q;

or in which:

c-1) the amino acid residue at position 44 according to the Kabat numbering is chosen from the group consisting of A, G, E, D, Q, R, S and L; and is preferably chosen from the group consisting of G, E and Q; and c-2) the amino acid residue at position 45 according to the Kabat numbering is chosen from the group consisting of L, R and C; and is preferably chosen from the group consisting of L and R; and c-3) the amino acid residue at position 103 according to the Kabat numbering is chosen from the group consisting of P, R and S; and is in particular chosen from the group consisting of R and S; and c-4) the amino acid residue at position 108 according to the Kabat numbering is chosen from the group consisting of Q and L; is preferably Q;

and in which d) CDR1, CDR2 and CDR3 are as defined herein, and are preferably as defined according to one of the preferred aspects herein, and are more preferably as defined according to one of the more preferred aspects herein.

Thus, in another preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

a-1) the amino acid residue at position 44 according to the Kabat numbering is chosen from the group consisting of A, G, E, D, G, Q, R, S, L; and is preferably chosen from the group consisting of G, E or Q;

and in which:

a-2) the amino acid residue at position 45 according to the Kabat numbering is chosen from the group consisting of L, R or C; and is preferably chosen from the group consisting of L or R;

and in which:

a-3) the amino acid residue at position 103 according to the Kabat numbering is chosen from the group consisting of W, R or S; and is preferably W or R, and is most preferably W;

and in which a-4) the amino acid residue at position 108 according to the Kabat numbering is Q; and in which:

d) CDR1, CDR2 and CDR3 are as defined herein, and are preferably as defined according to one of the preferred aspects herein, and are more preferably as defined according to one of the more preferred aspects herein.

In another preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

b-1) the amino acid residue at position 44 according to the Kabat numbering is chosen from the group consisting of E and Q;

and in which:

b-2) the amino acid residue at position 45 according to the Kabat numbering is R;

and in which:

b-3) the amino acid residue at position 103 according to the Kabat numbering is chosen from the group consisting of W, R and S; and is preferably W;

and in which:

b-4) the amino acid residue at position 108 according to the Kabat numbering is chosen from the group consisting of Q and L; and is preferably Q;

and in which:

d) CDR1, CDR2 and CDR3 are as defined herein, and are preferably as defined according to one of the preferred aspects herein, and are more preferably as defined according to one of the more preferred aspects herein.

In another preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

c-1) the amino acid residue at position 44 according to the Kabat numbering is chosen from the group consisting of A, G, E, D, Q, R, S and L; and is preferably chosen from the group consisting of G, E and Q;

and in which:

c-2) the amino acid residue at position 45 according to the Kabat numbering is chosen from the group consisting of L, R and C; and is preferably chosen from the group consisting of L and R;

and in which:

c-3) the amino acid residue at position 103 according to the Kabat numbering is chosen from the group consisting of P, R and S; and is in particular chosen from the group consisting of R and S;

and in which:

c-4) the amino acid residue at position 108 according to the Kabat numbering is chosen from the group consisting of Q and L; is preferably Q;

and in which:

d) CDR1, CDR2 and CDR3 are as defined herein, and are preferably as defined according to one of the preferred aspects herein, and are more preferably as defined according to one of the more preferred aspects herein.

Two particularly preferred, but non-limiting groups of the Nanobodies of the invention are those according to a) above; according to (a-1) to (a-4) above; according to b) above; according to (b-1) to (b-4) above; according to (c) above; and/or according to (c-1) to (c-4) above, in which either:

i) the amino acid residues at positions 44-47 according to the Kabat numbering form the sequence GLEW (or a GLEW-like sequence as described herein) and the amino acid residue at position 108 is Q;

or in which:

ii) the amino acid residues at positions 43-46 according to the Kabat numbering form the sequence KERE or KQRE (or a KERE-like sequence as described) and the amino acid residue at position 108 is Q or L, and is preferably Q.

Thus, in another preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

i) the amino acid residues at positions 44-47 according to the Kabat numbering form the sequence GLEW (or a GLEW-like sequence as defined herein) and the amino acid residue at position 108 is Q;

and in which:

ii) CDR1, CDR2 and CDR3 are as defined herein, and are preferably as defined according to one of the preferred aspects herein, and are more preferably as defined according to one of the more preferred aspects herein.

In another preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

i) the amino acid residues at positions 43-46 according to the Kabat numbering form the sequence KERE or KQRE (or a KERE-like sequence) and the amino acid residue at position 108 is Q or L, and is preferably Q;

and in which:

ii) CDR1, CDR2 and CDR3 are as defined herein, and are preferably as defined according to one of the preferred aspects herein, and are more preferably as defined according to one of the more preferred aspects herein.

In the Nanobodies of the invention in which the amino acid residues at positions 43-46 according to the Kabat numbering form the sequence KERE or KQRE, the amino acid residue at position 37 is most preferably F. In the Nanobodies of the invention in which the amino acid residues at positions 44-47 according to the Kabat numbering form the sequence GLEW, the amino acid residue at position 37 is chosen from the group consisting of Y, H, I, L, V or F, and is most preferably V.

Thus, without being limited hereto in any way, on the basis of the amino acid residues present on the positions mentioned above, the Nanobodies of the invention can generally be classified on the basis of the following three groups:

i) The "GLEW-group": Nanobodies with the amino acid sequence GLEW at positions 44-47 according to the Kabat numbering and Q at position 108 according to the Kabat numbering. As further described herein, Nanobodies within this group usually have a V at position 37, and can have a W, P, R or S at position 103, and preferably have a W at position 103. The GLEW group also comprises some GLEW-like sequences such as those mentioned in Table A-3 below. More generally, and without limitation, Nanobodies belonging to the GLEW-group can be defined as Nanobodies with a G at position 44 and/or with a W at position 47, in which position 46 is usually E and in which preferably position 45 is not a charged amino acid residue and not cysteine;

ii) The "KERE-group": Nanobodies with the amino acid sequence KERE or KQRE (or another KERE-like sequence) at positions 43-46 according to the Kabat numbering and Q or L at position 108 according to the Kabat numbering. As further described herein, Nanobodies within this group usually have a F at position 37, an L or F at position 47; and can have a W, P, R or S at position 103, and preferably have a W at position 103. More generally, and without limitation, Nanobodies belonging to the KERE-group can be defined as Nanobodies with a K, Q or R at position 44 (usually K) in which position 45 is a charged amino acid residue or cysteine, and position 47 is as further defined herein;

iii) The "103 P, R, S-group": Nanobodies with a P, R or S at position 103. These Nanobodies can have either the amino acid sequence GLEW at positions 44-47 according to the Kabat numbering or the amino acid sequence KERE or KQRE at positions 43-46 according to the Kabat numbering, the latter most preferably in combination with an F at position 37 and an L or an F at position 47 (as defined for the KERE-group); and can have Q or L at position 108 according to the Kabat numbering, and preferably have Q.

Also, where appropriate, Nanobodies may belong to (i.e. have characteristics of) two or more of these classes. For example, one specifically preferred group of Nanobodies has GLEW or a GLEW-like sequence at positions 44-47; P, R or S (and in particular R) at position 103; and Q at position 108 (which may be humanized to L).

More generally, it should be noted that the definitions referred to above describe and apply to Nanobodies in the form of a native (i.e. non-humanized) $V_{HH}$ sequence, and that humanized variants of these Nanobodies may contain other amino acid residues than those indicated above (i.e. one or more humanizing substitutions as defined herein). For example, and without limitation, in some humanized Nanobodies of the GLEW-group or the 103 P, R, S-group, Q at position 108 may be humanized to 108L. As already mentioned herein, other humanizing substitutions (and suitable combinations thereof) will become clear to the skilled person based on the disclosure herein. In addition, or alternatively, other potentially useful humanizing substitutions can be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined can be introduced into said $V_{HH}$ sequence (in any manner known per se, as further described herein) and the resulting humanized $V_{HH}$ sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person based on the disclosure herein. Also, based on the foregoing, (the framework regions of) a Nanobody may be partially humanized or fully humanized.

Thus, in another preferred, but non-limiting aspect, a Nanobody of the invention may be a Nanobody belonging to the GLEW-group (as defined herein), and in which CDR1, CDR2 and CDR3 are as defined herein, and are preferably as defined according to one of the preferred aspects herein, and are more preferably as defined according to one of the more preferred aspects herein.

In another preferred, but non-limiting aspect, a Nanobody of the invention may be a Nanobody belonging to the KERE-group (as defined herein), and CDR1, CDR2 and CDR3 are as defined herein, and are preferably as defined according to one of the preferred aspects herein, and are more preferably as defined according to one of the more preferred aspects herein.

Thus, in another preferred, but non-limiting aspect, a Nanobody of the invention may be a Nanobody belonging to the 103 P, R, S-group (as defined herein), and in which CDR1, CDR2 and CDR3 are as defined herein, and are preferably as defined according to one of the preferred aspects herein, and are more preferably as defined according to one of the more preferred aspects herein.

Also, more generally and in addition to the 108Q, 43E/44R and 103 P,R,S residues mentioned above, the Nanobodies of the invention can contain, at one or more positions that in a conventional $V_H$ domain would form (part of) the $V_H/V_L$ interface, one or more amino acid residues that are more highly charged than the amino acid residues that naturally occur at the same position(s) in the corresponding naturally occurring $V_H$ sequence, and in particular one or more charged amino acid residues (as mentioned in Table A-2). Such substitutions include, but are not limited to, the GLEW-like sequences mentioned in Table A-3 below; as well as the substitutions that are described in the International Application WO 00/29004 for so-called "microbodies", e.g. so as to obtain a Nanobody with Q at position 108 in combination with KLEW at positions 44-47. Other possible substitutions at these positions will be clear to the skilled person based upon the disclosure herein.

In one aspect of the Nanobodies of the invention, the amino acid residue at position 83 is chosen from the group consisting of L, M, S, V and W; and is preferably L.

Also, in one aspect of the Nanobodies of the invention, the amino acid residue at position 83 is chosen from the group consisting of R, K, N, E, G, I, T and Q; and is most preferably either K or E (for Nanobodies corresponding to naturally occurring $V_{HH}$ domains) or R (for "humanized" Nanobodies, as described herein). The amino acid residue at position 84 is chosen from the group consisting of P, A, R, S, D T, and V in one aspect, and is most preferably P (for Nanobodies corresponding to naturally occurring $V_{HH}$ domains) or R (for "humanized" Nanobodies, as described herein).

Furthermore, in one aspect of the Nanobodies of the invention, the amino acid residue at position 104 is chosen from the group consisting of G and D; and is most preferably G.

Collectively, the amino acid residues at positions 11, 37, 44, 45, 47, 83, 84, 103, 104 and 108, which in the Nanobodies are as mentioned above, will also be referred to herein as the "Hallmark Residues". The Hallmark Residues and the amino acid residues at the corresponding positions of the most closely related human $V_H$ domain, $V_H3$, are summarized in Table A-3.

Some especially preferred but non-limiting combinations of these Hallmark Residues as occur in naturally occurring $V_{HH}$ domains are mentioned in Table A-4. For comparison, the corresponding amino acid residues of the human $V_H3$ called DP-47 have been indicated in italics.

TABLE A-3

Hallmark Residues in Nanobodies

| Position | Human $V_H3$ | Hallmark Residues |
|---|---|---|
| 11 | L, V; predominantly L | L, M, S, V, W; preferably L |
| 37 | V, I, F; usually V | F[1], Y, H, I, L or V, preferably F[1] or Y |
| 44[8] | G | G[2], E[3], A, D, Q, R, S, L; preferably G[2], E[3] or Q; most preferably G[2] or E[3]. |
| 45[8] | L | L[2], R[3], C, I, L, P, Q, V; preferably L[2] or R[3] |
| 47[8] | W, Y | W[2], L[1] or F[1], A, G, I, M, R, S, V or Y; preferably W[2], L[1], F[1] or R |
| 83 | R or K; usually R | R, K[5], N, E[5], G, I, M, Q or T; preferably K or R; most preferably K |
| 84 | A, T, D; predominantly A | P[5], A, L, R, S, T, D, V; preferably P |
| 103 | W | W[4], P[6], R[6], S; preferably W |
| 104 | G | G or D; preferably G |
| 108 | L, M or T; predominantly L | Q, L[7] or R; preferably Q or L[7] |

Notes:
[1] In particular, but not exclusively, in combination with KERE or KQRE at positions 43-46.
[2] Usually as GLEW at positions 44-47.
[3] Usually as KERE or KQRE at positions 43-46, e.g. as KEREL, KEREF, KQREL, KQREF or KEREG at positions 43-47. Alternatively, also sequences such as TERE (for example TEREL), KECE (for example KECEL or KECER), RERE (for example REREG), QERE (for example QEREG), KGRE (for example KGREG), KDRE (for example KDREV) are possible. Some other possible, but less preferred sequences include for example DECKL and NVCEL.
[4] With both GLEW at positions 44-47 and KERE or KQRE at positions 43-46.
[5] Often as KP or EP at positions 83-84 of naturally occurring $V_{HH}$ domains.
[6] In particular, but not exclusively, in combination with GLEW at positions 44-47.
[7] With the proviso that when positions 44-47 are GLEW, position 108 is always Q in (non-humanized) $V_{HH}$ sequences that also contain a W at position 103.
The GLEW group also contains GLEW-like sequences at positions 44-47, such as for example GVEW, EPEW, GLER, DQEW, DLEW, GIEW, ELEW, GPEW, EWLP, GPER, GLER and ELEW.

TABLE A-4

Some preferred but non-limiting combinations of Hallmark Residues in naturally occurring Nanobodies. For humanization of these combinations, reference is made to the specification.

| | 11 | 37 | 44 | 45 | 47 | 83 | 84 | 103 | 104 | 108 |
|---|---|---|---|---|---|---|---|---|---|---|
| DP-47 (human) | M | V | G | L | W | R | A | W | G | L |
| "KERE" group | L | F | E | R | L | K | P | W | G | Q |
| | L | F | E | R | F | E | P | W | G | Q |
| | L | F | E | R | F | K | P | W | G | Q |
| | L | Y | Q | R | L | K | P | W | G | Q |
| | L | F | L | R | V | K | P | Q | G | Q |
| | L | F | Q | R | L | K | P | W | G | Q |
| | L | F | E | R | F | K | P | W | G | Q |
| "GLEW" group | L | V | G | L | W | K | S | W | G | Q |
| | M | V | G | L | W | K | P | R | G | Q |

In the Nanobodies, each amino acid residue at any other position than the Hallmark Residues can be any amino acid residue that naturally occurs at the corresponding position (according to the Kabat numbering) of a naturally occurring $V_{HH}$ domain.

Such amino acid residues will be clear to the skilled person. Tables A-5 to A-8 mention some non-limiting residues that can be present at each position (according to the Kabat numbering) of the FR1, FR2, FR3 and FR4 of naturally occurring $V_{HH}$ domains. For each position, the amino acid residue that most frequently occurs at each position of a naturally occurring $V_{HH}$ domain (and which is the most preferred amino acid residue for said position in a Nanobody) is indicated in bold; and other preferred amino acid residues for each position have been underlined (note: the number of amino acid residues that are found at positions 26-30 of naturally occurring $V_{HH}$ domains supports the hypothesis underlying the numbering by Chothia (supra) that the residues at these positions already form part of CDR1.)

In Tables A-5-A-8, some of the non-limiting residues that can be present at each position of a human $V_H3$ domain have also been mentioned. Again, for each position, the amino acid residue that most frequently occurs at each position of a naturally occurring human $V_H3$ domain is indicated in bold; and other preferred amino acid residues have been underlined.

For reference only, Tables A-5-A-8 also contain data on the $V_{HH}$ entropy ("$V_{HH}$ Ent.") and $V_{HH}$ variability ("$V_{HH}$ Var.") at each amino acid position for a representative sample of 1118 $V_{HH}$ sequences (data kindly provided by David Lutje Hulsing and Prof. Theo Verrips of Utrecht University). The values for the $V_{HH}$ entropy and the $V_{HH}$ variability provide a measure for the variability and degree of conservation of amino acid residues between the 1118 $V_{HH}$ sequences analyzed: low values (i.e. <1, such as <0.5) indicate that an amino acid residue is highly conserved between the $V_{HH}$ sequences (i.e. little variability). For example, the G at position 8 and the G at position 9 have values for the $V_{HH}$ entropy of 0.1 and 0 respectively, indicating that these residues are highly conserved and have little variability (and in case of position 9 is G in all 1118 sequences analysed), whereas for residues that form part of the CDR's generally values of 1.5 or more are found (data not shown). Note that (1) the amino acid residues listed in the second column of Tables A-5-A-8 are based on a bigger sample than the 1118 $V_{HH}$ sequences that were analysed for determining the $V_{HH}$ entropy and $V_{HH}$ variability referred to in the last two columns; and (2) the data represented below support the hypothesis that the amino acid residues at positions 27-30 and maybe even also at positions 93 and 94 already form part of the CDR's (although the invention is not limited to any specific hypothesis or explanation, and as mentioned above, herein the numbering according to Kabat is used). For a general explanation of sequence entropy, sequence variability and the methodology for determining the same, see Oliveira et al., PROTEINS: Structure, Function and Genetics, 52: 544-552 (2003).

TABLE A-5

Non-limiting examples of amino acid residues in FR1
(for the footnotes, see the footnotes to Table A-3)

| | Amino acid residue(s): | | $V_{HH}$ | $V_{HH}$ |
|---|---|---|---|---|
| Pos. | Human $V_H3$ | Camelid $V_{HH}$'s | Ent. | Var. |
| 1 | E, Q | Q, A, E | — | — |
| 2 | V | V | 0.2 | 1 |
| 3 | Q | Q, K | 0.3 | 2 |
| 4 | L | L | 0.1 | 1 |

TABLE A-5-continued

Non-limiting examples of amino acid residues in FR1
(for the footnotes, see the footnotes to Table A-3)

| Pos. | Human V$_H$3 | Camelid V$_{HH}$'s | V$_{HH}$ Ent. | V$_{HH}$ Var. |
|---|---|---|---|---|
| 5 | V, L | Q, E, L, V | 0.8 | 3 |
| 6 | E | E, D, Q, A | 0.8 | 4 |
| 7 | S, T | S, F | 0.3 | 2 |
| 8 | G, R | G | 0.1 | 1 |
| 9 | G | G | 0 | 1 |
| 10 | G, V | G, D, R | 0.3 | 2 |
| 11 | Hallmark residue: L, M, S, V, W; preferably L | | 0.8 | 2 |
| 12 | V, I | V, A | 0.2 | 2 |
| 13 | Q, K, R | Q, E, K, P, R | 0.4 | 4 |
| 14 | P | A, Q, A, G, P, S, T, V | 1 | 5 |
| 15 | G | G | 0 | 1 |
| 16 | G, R | G, A, E, D | 0.4 | 3 |
| 17 | S | S, F | 0.5 | 2 |
| 18 | L | L, V | 0.1 | 1 |
| 19 | R, K | R, K, L, N, S, T | 0.6 | 4 |
| 20 | L | L, F, I, V | 0.5 | 4 |
| 21 | S | S, A, F, T | 0.2 | 3 |
| 22 | C | C | 0 | 1 |
| 23 | A, T | A, D, E, P, S, T, V | 1.3 | 5 |
| 24 | A | A, I, L, S, T, V | 1 | 6 |
| 25 | S | S, A, F, P, T | 0.5 | 5 |
| 26 | G | G, A, D, E, R, S, T, V | 0.7 | 7 |
| 27 | F | S, F, R, L, P, G, N, | 2.3 | 13 |
| 28 | T | N, T, E, D, S, I, R, A, G, R, F, Y | 1.7 | 11 |
| 29 | F, V | F, L, D, S, I, G, V, A | 1.9 | 11 |
| 30 | S, D, G | N, S, E, G, A, D, M, T | 1.8 | 11 |

TABLE A-6

Non-limiting examples of amino acid residues in FR2
(for the footnotes, see the footnotes to Table A-3)

| Pos. | Human V$_H$3 | Camelid V$_{HH}$'s | V$_{HH}$ Ent. | V$_{HH}$ Var. |
|---|---|---|---|---|
| 36 | W | W | 0.1 | 1 |
| 37 | Hallmark residue: F$^{(1)}$, H, I, L, Y or V, preferably F$^{(1)}$ or Y | | 1.1 | 6 |
| 38 | R | R | 0.2 | 1 |
| 39 | Q | Q, H, P, R | 0.3 | 2 |
| 40 | A | A, F, G, L, P, T, V | 0.9 | 7 |
| 41 | P, S, T | P, A, L, S | 0.4 | 3 |
| 42 | G | G, E | 0.2 | 2 |
| 43 | K | K, D, E, N, Q, R, T, V | 0.7 | 6 |
| 44 | Hallmark residue: G$^{(2)}$, E$^{(3)}$, A, D, Q, R, S, L; preferably G$^{(2)}$, E$^{(3)}$ or Q; most preferably G$^{(2)}$ or E$^{(3)}$. | | 1.3 | 5 |
| 45 | Hallmark residue: L$^{(2)}$, R$^{(3)}$, C, I, L, P, Q, V; preferably L$^{(2)}$ or R$^{(3)}$ | | 0.6 | 4 |
| 46 | E, V | E, D, K, Q, V | 0.4 | 2 |
| 47 | Hallmark residue: W$^{(2)}$, L$^{(1)}$ or F$^{(1)}$, A, G, I, M, R, S, V or Y; preferably W$^{(2)}$, L$^{(1)}$, F$^{(1)}$ or R | | 1.9 | 9 |
| 48 | V | V, I, L | 0.4 | 3 |
| 49 | S, A, G | A, S, G, T, V | 0.8 | 3 |

TABLE A-7

Non-limiting examples of amino acid residues in FR3
(for the footnotes, see the footnotes to Table A-3)

| Pos. | Human V$_H$3 | Camelid V$_{HH}$'s | V$_{HH}$ Ent. | V$_{HH}$ Var. |
|---|---|---|---|---|
| 66 | R | R | 0.1 | 1 |
| 67 | F | F, L, V | 0.1 | 1 |
| 68 | T | T, A, N, S | 0.5 | 4 |
| 69 | I | I, L, M, V | 0.4 | 4 |
| 70 | S | S, A, F, T | 0.3 | 4 |
| 71 | R | R, G, H, I, L, K, Q, S, T, W | 1.2 | 8 |
| 72 | D, E | D, E, G, N, V | 0.5 | 4 |
| 73 | N, D, G | N, A, D, F, I, K, L, R, S, T, V, Y | 1.2 | 9 |
| 74 | A, S | A, D, G, N, P, S, T, V | 1 | 7 |
| 75 | K | K, A, E, K, L, N, Q, R | 0.9 | 6 |
| 76 | N, S | N, D, K, R, S, T, Y | 0.9 | 6 |
| 77 | S, T, I | T, A, E, I, M, P, S | 0.8 | 5 |
| 78 | L, A | V, L, A, F, G, I, M | 1.2 | 5 |
| 79 | Y, H | Y, A, D, F, H, N, S, T | 1 | 7 |
| 80 | L | L, F, V | 0.1 | 1 |
| 81 | Q | Q, E, I, L, R, T | 0.6 | 5 |
| 82 | M | M, I, L, V | 0.2 | 2 |
| 82a | N, G | N, D, G, H, S, T | 0.8 | 4 |
| 82b | S | S, N, D, G, R, T | 1 | 6 |
| 82c | L | L, P, V | 0.1 | 2 |
| 83 | Hallmark residue: R, K$^{(5)}$, N, E$^{(5)}$, G, I, M, Q or T; preferably K or R; most preferably K | | 0.9 | 7 |
| 84 | Hallmark residue: P$^{(5)}$, A, D, L, R, S, T, V; preferably P | | 0.7 | 6 |
| 85 | E, G | E, D, G, Q | 0.5 | 3 |
| 86 | D | D | 0 | 1 |
| 87 | T, M | T, A, S | 0.2 | 3 |
| 88 | A | A, G, S | 0.3 | 2 |
| 89 | V, L | V, A, D, I, L, M, N, R, T | 1.4 | 6 |
| 90 | Y | Y, F | 0 | 1 |
| 91 | Y, H | Y, D, F, H, L, S, T, V | 0.6 | 4 |
| 92 | C | C | 0 | 1 |
| 93 | A, K, T | A, N, G, H, K, N, R, S, T, V, Y | 1.4 | 10 |
| 94 | K, R, T | A, V, C, F, G, I, K, L, R, S or T | 1.6 | 9 |

TABLE A-8

Non-limiting examples of amino acid residues in FR4
(for the footnotes, see the footnotes to Table A-3)

| Pos. | Human V$_H$3 | Camelid V$_{HH}$'s | V$_{HH}$ Ent. | V$_{HH}$ Var. |
|---|---|---|---|---|
| 103 | Hallmark residue: W$^{(4)}$, P$^{(6)}$, R$^{(6)}$, S; preferably W | | 0.4 | 2 |
| 104 | Hallmark residue: G or D; preferably G | | 0.1 | 1 |
| 105 | Q, R | Q, E, K, P, R | 0.6 | 4 |
| 106 | G | G | 0.1 | 1 |
| 107 | T | T, A, I | 0.3 | 2 |
| 108 | Hallmark residue: Q, L$^{(7)}$ or R: preferably Q or L$^{(7)}$ | | 0.4 | 3 |
| 109 | V | V | 0.1 | 1 |
| 110 | T | T, I, A | 0.2 | 1 |
| 111 | V | V, A, I | 0.3 | 2 |
| 112 | S | S, F | 0.3 | 1 |
| 113 | S | S, A, L, P, T | 0.4 | 3 |

Thus, in another preferred, but not limiting aspect, a Nanobody of the invention can be defined as an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

i) one or more of the amino acid residues at positions 11, 37, 44, 45, 47, 83, 84, 103, 104 and 108 according to the Kabat numbering are chosen from the Hallmark residues mentioned in Table A-3;

and in which:

ii) CDR1, CDR2 and CDR3 are as defined herein, and are preferably as defined according to one of the preferred aspects herein, and are more preferably as defined according to one of the more preferred aspects herein.

The above Nanobodies may for example be $V_{HH}$ sequences or may be humanized Nanobodies. When the above Nanobody sequences are $V_{HH}$ sequences, they may be suitably humanized, as further described herein. When the Nanobodies are partially humanized Nanobodies, they may optionally be further suitably humanized, again as described herein.

In particular, a Nanobody of the invention can be an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

i) (preferably) one or more of the amino acid residues at positions 11, 37, 44, 45, 47, 83, 84, 103, 104 and 108 according to the Kabat numbering are chosen from the Hallmark residues mentioned in Table A-3 (it being understood that $V_{HH}$ sequences will contain one or more Hallmark residues; and that partially humanized Nanobodies will usually, and preferably, [still] contain one or more Hallmark residues [although it is also within the scope of the invention to provide—where suitable in accordance with the invention—partially humanized Nanobodies in which all Hallmark residues, but not one or more of the other amino acid residues, have been humanized]; and that in fully humanized Nanobodies, where suitable in accordance with the invention, all amino acid residues at the positions of the Hallmark residues will be amino acid residues that occur in a human $V_H3$ sequence. As will be clear to the skilled person based on the disclosure herein that such $V_{HH}$ sequences, such partially humanized Nanobodies with at least one Hallmark residue, such partially humanized Nanobodies without Hallmark residues and such fully humanized Nanobodies all form aspects of this invention);

and in which:

ii) said amino acid sequence has at least 80% amino acid identity with at least one of the single variable domains of SEQ ID NO's: 1 to 22, in which for the purposes of determining the degree of amino acid identity, the amino acid residues that form the CDR sequences (indicated with X in the sequences of SEQ ID NO's: 1 to 22) are disregarded;

and in which:

iii) CDR1, CDR2 and CDR3 are as defined herein, and are preferably as defined according to one of the preferred aspects herein, and are more preferably as defined according to one of the more preferred aspects herein.

The above Nanobodies may for example be $V_{HH}$ or may be humanized Nanobodies. When the above Nanobody sequences are $V_{HH}$ sequences, they may be suitably humanized, as further described herein. When the Nanobodies are partially humanized Nanobodies, they may optionally be further suitably humanized, again as described herein.

TABLE A-9

Representative single variable domains for Nanobodies of the KERE, GLEW and P, R, S 103 group. The CDR's are indicated with XXXX

| | | |
|---|---|---|
| KERE sequence no. 1 | SEQ ID NO: 1 | EVQLVESGGGLVQPGGSLRLSCAASGIPFSXXXXXWFRQAPGKQRDSVAXXXXXXRFTISRDN AKNTVYLQMNSLKPEDTAVYRCYFXXXXXWGQGTQVTVSS |
| KERE sequence no. 2 | SEQ ID NO: 2 | QVKLEESGGGLVQAGGSLRLSCVGSGRTFSXXXXXWFRLAPGKEREFVAXXXXXXRFTISRDTA SNRGYLHMNNLTPEDTAVYYCAAXXXXXWGQGTQVTVSS |
| KERE sequence no. 3 | SEQ ID NO: 3 | AVQLVDSGGGLVQAGDSLKLSCALTGGAFTXXXXXWFRQTPGREREFVAXXXXXXRFTI SRDNAKNMVYLRMNSLIPEDAAVYSCAAXXXXXWGQGTLVTVSS |
| KERE sequence no. 4 | SEQ ID NO: 4 | QVQLVESGGGLVEAGGSLRLSCTASESPFRXXXXXWFRQTSGQEREFVAXXXXXXRFTI SRDDAKNTVWLHGSTLKPEDTAVYYCAAXXXXXWGQGTQVTVSS |
| KERE sequence no. 5 | SEQ ID NO: 5 | AVQLVESGGGLVQGGGSLRLACAASERIFDXXXXXWYRQGPGNERELVAXXXXXXRFTI SMDYTKQTVYLHMNSLRPEDTGLYYCKIXXXXXWGQGTQVTVSS |
| KERE sequence no. 6 | SEQ ID NO: 6 | DVKFVESGGGLVQAGGSLRLSCVASGFNFDXXXXXWFRQAPGKEREEVAXXXXXXRFT ISSEKDKNSVYLQMNSLKPEDTALYICAGXXXXXWGRGTQVTVSS |
| KERE sequence no. 7 | SEQ ID NO: 7 | QVRLAESGGGLVQSGGSLRLSCVASGSTYTXXXXXWYRQYPGKQRALVAXXXXXXRFT IARDSTKDTFCLQMNNLKPEDTAVYYCYAXXXXXWGQGTQVTVSS |
| KERE sequence no. 8 | SEQ ID NO: 8 | EVQLVESGGGLVQAGGSLRLSCAASGFTSDXXXXXWFRQAPGKPREGVSXXXXXXRFT ISTDNAKNTVHLLMNRVNAEDTALYYCAVXXXXXWGRGTRVTVSS |
| KERE sequence no. 9 | SEQ ID NO: 9 | QVQLVESGGGLVQPGGSLRLSCQASGDISTXXXXXWYRQVPGKLREFVAXXXXXXRFTI SGDNAKRAIYLQMNNLKPDDTAVYYCNRXXXXXWGQGTQVTVSP |
| KERE sequence no. 10 | SEQ ID NO: 10 | QVPVVESGGGLVQAGDSLRLFCAVPSFTSTXXXXXWFRQAPGKEREFVAXXXXXXRFTI SRNATKNTLTLRMDSLKPEDTAVYYCAAXXXXXWGQGTQVTVSS |
| KERE sequence no. 11 | SEQ ID NO: 11 | EVQLVESGGGLVQAGDSLRLFCTVSGGTASXXXXXWFRQAPGEKREFVAXXXXXXRFTI ARENAGNMVYLQMNNLKPDDTALYTCAAXXXXXWGRGTQVTVSS |
| KERE sequence no. 12 | SEQ ID NO: 12 | AVQLVESGGDSVQPGDSQTLSCAASGRTNSXXXXXWFRQAPGKERVFLAXXXXXXRFT ISRDSAKNMMYLQMNNLKPQDTAVYYCAAXXXXXWGQGTQVTVSS |
| KERE sequence no. 13 | SEQ ID NO: 13 | AVQLVESGGGLVQAGGSLRLSCVVSGLTSSXXXXXWFRQTPWQERDFVAXXXXXXRFT ISRDNYKDTVLLEMNFLKPEDTAIYYCAAXXXXXWGQGTQVTVSS |
| KERE sequence no. 14 | SEQ ID NO: 14 | AVQLVESGGGLVQAGASLRLSCATSTRTLDXXXXXWFRQAPGRDREFVAXXXXXXRFT VSRDSAENTVALQMNSLKPEDTAVYYCAAXXXXXWGQGTRVTVSS |

TABLE A-9-continued

Representative single variable domains for Nanobodies of the KERE, GLEW and P, R, S 103 group.
The CDR's are indicated with XXXX

| | | |
|---|---|---|
| KERE sequence no. 15 | SEQ ID NO: 15 | QVQLVESGGGLVQPGGSLRLSCTVSRLTAHXXXXXWFRQAPGKEREAVSXXXXXRFTISRDYAGNTAFLQMDSLKPEDTGVYYCATXXXXXWGQGTQVTVSS |
| KERE sequence no. 16 | SEQ ID NO: 16 | EVQLVESGGELVQAGGSLKLSCTASGRNFVXXXXXWFRRAPGKEREFVAXXXXXRFTVSRDNGKNTAYLRMNSLKPEDTADYYCAVXXXXXLGSGTQVTVSS |
| GLEW sequence no. 1 | SEQ ID NO: 17 | AVQLVESGGGLVQPGGSLRLSCAASGFTFSXXXXXWVRQAPGKVLEWVSXXXXXRFTISRDNAKNTLYLQMNSLKPEDTAVYYCVKXXXXXGSQGTQVTVSS |
| GLEW sequence no. 2 | SEQ ID NO: 18 | EVQLVESGGGLVQPGGSLRLSCVCVSSGCTXXXXXWVRQAPGKAEEWVSXXXXXRFKISRDNAKKTLYLQMNSLGPEDTAMYYCQRXXXXXRGQGTQVTVSS |
| GLEW sequence no. 3 | SEQ ID NO: 19 | EVQLVESGGGLALPGGSLTLSCVFSGSTFSXXXXXWVRHTPGKAEEWVSXXXXXRFTISRDNAKNTLYLEMNSLSPEDTAMYYCGRXXXXXRSKGIQVTVSS |
| P, R, S 103 sequence no. 1 | SEQ ID NO: 20 | AVQLVESGGGLVQAGGSLRLSCAASGRTFSXXXXXWFRQAPGKEREFVAXXXXXRFTISRDNAKNTVYLQMNSLKPEDTAVYYCAAXXXXXRGQGTQVTVSS |
| P, R, S 103 sequence no. 2 | SEQ ID NO: 21 | DVQLVESGGDLVQPGGSLRLSCAASGFSFDXXXXXWLRQTPGKGLEWVGXXXXXRFTISRDNAKNMLYLHLNNLKSEDTAVYYCRRXXXXXLGQGTQVTVSS |
| P, R, S 103 sequence no. 3 | SEQ ID NO: 22 | EVQLVESGGGLVQPGGSLRLSCVCVSSGCTXXXXXWVRQAPGKAEEWVSXXXXXRFKISRDNAKKTLYLQMNSLGPEDTAMYYCQRXXXXXRGQGTQVTVSS |

In particular, a Nanobody of the invention of the KERE group can be an amino acid sequence with the (general) structure

FR1-CDR1-FR2-CDR2-FR3-CDR3-FR4 in which:
i) the amino acid residue at position 45 according to the Kabat numbering is a charged amino acid (as defined herein) or a cysteine residue, and position 44 is preferably an E; and in which:
ii) FR1 is an amino acid sequence that has at least 80% amino acid identity with at least one of the following amino acid sequences:

and in which:
iii) FR2 is an amino acid sequence that has at least 80% amino acid identity with at least one of the following amino acid sequences:

TABLE A-11

Representative FW2 sequences for Nanobodies of the KERE-group.

| | | |
|---|---|---|
| KERE FW2 sequence no. 1 | SEQ ID NO: 41 | WFRQAPGKEREFVA |

TABLE A-10

Representative FW1 sequences for Nanobodies of the KERE-group.

| | | |
|---|---|---|
| KERE FW1 sequence no. 1 | SEQ ID NO: 23 | QVQRVESGGGLVQAGGSLRLSCAASGRTSS |
| KERE FW1 sequence no. 2 | SEQ ID NO: 24 | QVQLVESGGGLVQTGDSLSLSCSASGRTFS |
| KERE FW1 sequence no. 3 | SEQ ID NO: 25 | QVKLEESGGGLVQAGDSLRLSCAATGRAFG |
| KERE FW1 sequence no. 4 | SEQ ID NO: 26 | AVQLVESGGGLVQPGESLGLSCVASGRDFV |
| KERE FW1 sequence no. 5 | SEQ ID NO: 27 | EVQLVESGGGLVQAGGSLRLSCEVLGRTAG |
| KERE FW1 sequence no. 6 | SEQ ID NO: 28 | QVQLVESGGGWVQPGGSLRLSCAASETILS |
| KERE FW1 sequence no. 7 | SEQ ID NO: 29 | QVQLVESGGGTVQPGGSLNLSCVASGNTFN |
| KERE FW1 sequence no. 8 | SEQ ID NO: 30 | EVQLVESGGGLAQPGGSLQLSCSAPGFTLD |
| KERE FW1 sequence no. 9 | SEQ ID NO: 31 | AQELEESGGGLVQAGGSLRLSCAASGRTFN |

TABLE A-11-continued

Representative FW2 sequences for Nanobodies of the KERE-group.

| | | |
|---|---|---|
| KERE FW2 sequence no. 2 | SEQ ID NO: 42 | WFRQTPGREREFVA |
| KERE FW2 sequence no. 3 | SEQ ID NO: 43 | WYRQAPGKQREMVA |
| KERE FW2 sequence no. 4 | SEQ ID NO: 44 | WYRQGPGKQRELVA |
| KERE FW2 sequence no. 5 | SEQ ID NO: 45 | WIRQAPGKEREGVS |
| KERE FW2 sequence no. 6 | SEQ ID NO: 46 | WFREAPGKEREGIS |
| KERE FW2 sequence no. 7 | SEQ ID NO: 47 | WYRQAPGKERDLVA |
| KERE FW2 sequence no. 8 | SEQ ID NO: 48 | WFRQAPGKQREEVS |
| KERE FW2 sequence no. 9 | SEQ ID NO: 49 | WFRQPPGKVREFVG | and in which:
iv) FR3 is an amino acid sequence that has at least 80% amino acid identity with at least one of the following amino acid sequences:

TABLE A-12

Representative FW3 sequences for Nanobodies of the KERE-group.

| | | |
|---|---|---|
| KERE FW3 sequence no. 1 | SEQ ID NO: 50 | RFTISRDNAKNTVYLQMNSLKPEDTAVYRCYF |
| KERE FW3 sequence no. 2 | SEQ ID NO: 51 | RFAISRDNNKNTGYLQMNSLEPEDTAVYYCAA |
| KERE FW3 sequence no. 3 | SEQ ID NO: 52 | RFTVARNNAKNTVNLEMNSLKPEDTAVYYCAA |
| KERE FW3 sequence no. 4 | SEQ ID NO: 53 | RFTISRDIAKNTVDLLMNNLEPEDTAVYYCAA |
| KERE FW3 sequence no. 5 | SEQ ID NO: 54 | RLTISRDNAVDTMYLQMNSLKPEDTAVYYCAA |
| KERE FW3 sequence no. 6 | SEQ ID NO: 55 | RFTISRDNAKNTVYLQMDNVKPEDTAIYYCAA |
| KERE FW3 sequence no. 7 | SEQ ID NO: 56 | RFTISKDSGKNTVYLQMTSLKPEDTAVYYCAT |
| KERE FW3 sequence no. 8 | SEQ ID NO: 57 | RFTISRDSAKNMMYLQMNNLKPQDTAVYYCAA |
| KERE FW3 sequence no. 9 | SEQ ID NO: 58 | RFTISRENDKSTVYLQLNSLKPEDTAVYYCAA |
| KERE FW3 sequence no. 10 | SEQ ID NO: 59 | RFTISRDYAGNTAYLQMNSLKPEDTGVYYCAT | and in which:
v) FR4 is an amino acid sequence that has at least 80% amino acid identity with at least one of the following amino acid sequences:

TABLE A-13

Representative FW4 sequences for Nanobodies of the KERE-group.

| | | |
|---|---|---|
| KERE FW4 sequence no. 1 | SEQ ID NO: 60 | WGQGTQVTVSS |
| KERE FW4 sequence no. 2 | SEQ ID NO: 61 | WGKGTLVTVSS |
| KERE FW4 sequence no. 3 | SEQ ID NO: 62 | RGQGTRVTVSS |
| KERE FW4 sequence no. 4 | SEQ ID NO: 63 | WGLGTQVTISS | and in which:
vi) CDR1, CDR2 and CDR3 are as defined herein, and are preferably as defined according to one of the preferred aspects herein, and are more preferably as defined according to one of the more preferred aspects herein.

In the above Nanobodies, one or more of the further Hallmark residues are preferably as described herein (for example, when they are VHH sequences or partially humanized Nanobodies).

Also, the above Nanobodies may for example be VHH sequences or may be humanized Nanobodies. When the above Nanobody sequences are VHH sequences, they may be suitably humanized, as further described herein. When the Nanobodies are partially humanized Nanobodies, they may optionally be further suitably humanized, again as described herein.

With regard to framework 1, it will be clear to the skilled person that, when an amino acid sequence as outlined above is generated by expression of a nucleotide sequence, the first four single variable domains (i.e. amino acid residues 1-4 according to the Kabat numbering) may often be determined by the primer(s) that have been used to generate said nucleic acid. Thus, for determining the degree of amino acid identity, the first four amino acid residues are preferably disregarded.

Also, with regard to framework 1, and although amino acid positions 27 to 30 are according to the Kabat numbering considered to be part of the framework regions (and not the CDR's), it has been found by analysis of a database of more than 1000 VHH sequences that the positions 27 to 30 have a variability (expressed in terms of $V_{HH}$ entropy and $V_{HH}$ variability—see Tables A-5 to A-8) that is much greater than the variability on positions 1 to 26. Because of this, for determining the degree of amino acid identity, the amino acid residues at positions 27 to 30 are preferably also disregarded.

In view of this, a Nanobody of the KERE class may be an amino acid sequence that is comprised of four framework regions/sequences interrupted by three complementarity determining regions/sequences, in which:
i) the amino acid residue at position 45 according to the Kabat numbering is a charged amino acid (as defined herein) or a cysteine residue, and position 44 is preferably an E;
and in which:
ii) FR1 is an amino acid sequence that, on positions 5 to 26 of the Kabat numbering, has at least 80% amino acid identity with at least one of the following amino acid sequences:

TABLE A-14

Representative FW1 sequences (amino acid residues 5 to 26) for Nanobodies of the KERE-group.

| | | |
|---|---|---|
| KERE FW1 sequence no. 10 | SEQ ID NO: 32 | VESGGGLVQPGGSLRLSCAASG |
| KERE FW1 sequence no. 11 | SEQ ID NO: 33 | VDSGGGLVQAGDSLKLSCALTG |
| KERE FW1 sequence no. 12 | SEQ ID NO: 34 | VDSGGGLVQAGDSLRLSCAASG |
| KERE FW1 sequence no. 13 | SEQ ID NO: 35 | VDSGGGLVEAGGSLRLSCQVSE |
| KERE FW1 sequence no. 14 | SEQ ID NO: 36 | QDSGGGSVQAGGSLKLSCAASG |
| KERE FW1 sequence no. 15 | SEQ ID NO: 37 | VQSGGRLVQAGDSLRLSCAASE |
| KERE FW1 sequence no. 16 | SEQ ID NO: 38 | VESGGTLVQSGDSLKLSCASST |
| KERE FW1 sequence no. 17 | SEQ ID NO: 39 | MESGGDSVQSGGSLTLSCVASG |
| KERE FW1 sequence no. 18 | SEQ ID NO: 40 | QASGGGLVQAGGSLRLSCSASV | and in which:
iii) FR2, FR3 and FR4 are as mentioned herein for FR2, FR3 and FR4 of Nanobodies of the KERE-class;
and in which:
iv) CDR1, CDR2 and CDR3 are as defined herein, and are preferably as defined according to one of the preferred aspects herein, and are more preferably as defined according to one of the more preferred aspects herein.

The above Nanobodies may for example be VHH sequences or may be humanized Nanobodies. When the above Nanobody sequences are VHH sequences, they may be suitably humanized, as further described herein. When the Nanobodies are partially humanized Nanobodies, they may optionally be further suitably humanized, again as described herein.

A Nanobody of the GLEW class may be an amino acid sequence that is comprised of four framework regions/sequences interrupted by three complementarity determining regions/sequences, in which
i) preferably, when the Nanobody of the GLEW-class is a non-humanized Nanobody, the amino acid residue in position 108 is Q;
ii) FR1 is an amino acid sequence that has at least 80% amino acid identity with at least one of the following amino acid sequences:

TABLE A-15

Representative FW1 sequences for Nanobodies of the GLEW-group.

| | | |
|---|---|---|
| GLEW FW1 sequence no. 1 | SEQ ID NO: 64 | QVQLVESGGGLVQPGGSLRLSCAASGFTFS |
| GLEW FW1 sequence no. 2 | SEQ ID NO: 65 | EVHLVESGGGLVRPGGSLRLSCAAFGFIFK |
| GLEW FW1 sequence no. 3 | SEQ ID NO: 66 | QVKLEESGGGLAQPGGSLRLSCVASGFTFS |
| GLEW FW1 sequence no. 4 | SEQ ID NO: 67 | EVQLVESGGGLVQPGGSLRLSCVCVSSGCT |
| GLEW FW1 sequence no. 5 | SEQ ID NO: 68 | EVQLVESGGGLALPGGSLTLSCVFSGSTFS |

TABLE A-16

Representative FW2 sequences for Nanobodies of the GLEW-group.

| | | |
|---|---|---|
| GLEW FW2 sequence no. 1 | SEQ ID NO: 72 | WVRQAPGKVLEWVS |
| GLEW FW2 sequence no. 2 | SEQ ID NO: 73 | WVRRPPGKGLEWVS |
| GLEW FW2 sequence no. 3 | SEQ ID NO: 74 | WVRQAPGMGLEWVS |
| GLEW FW2 sequence no. 4 | SEQ ID NO: 75 | WVRQAPGKEPEWVS |
| GLEW FW2 sequence no. 5 | SEQ ID NO: 76 | WVRQAPGKDQEWVS |
| GLEW FW2 sequence no. 6 | SEQ ID NO: 77 | WVRQAPGKAEEWVS |
| GLEW FW2 sequence no. 7 | SEQ ID NO: 78 | WVRQAPGKGLEWVA |
| GLEW FW2 sequence no. 8 | SEQ ID NO: 79 | WVRQAPGRATEWVS | and in which:
iii) FR2 is an amino acid sequence that has at least 80% amino acid identity with at least one of the following amino acid sequences:

and in which:
iv) FR3 is an amino acid sequence that has at least 80% amino acid identity with at least one of the following amino acid sequences:

TABLE A-17

Representative FW3 sequences for Nanobodies of the GLEW-group.

| | | |
|---|---|---|
| GLEW FW3 sequence no. 1 | SEQ ID NO: 80 | RFTISRDNAKNTLYLQMNSLKPEDTAVYYCVK |
| GLEW FW3 sequence no. 2 | SEQ ID NO: 81 | RFTISRDNARNTLYLQMDSLIPEDTALYYCAR |
| GLEW FW3 sequence no. 3 | SEQ ID NO: 82 | RFTSSRDNAKSTLYLQMNDLKPEDTALYYCAR |
| GLEW FW3 sequence no. 4 | SEQ ID NO: 83 | RFIISRDNAKNTLYLQMNSLGPEDTAMYYCQR |
| GLEW FW3 sequence no. 5 | SEQ ID NO: 84 | RFTASRDNAKNTLYLQMNSLKSEDTARYYCAR |
| GLEW FW3 sequence no. 6 | SEQ ID NO: 85 | RFTISRDNAKNTLYLQMDDLQSEDTAMYYCGR | and in which:

v) FR4 is an amino acid sequence that has at least 80% amino acid identity with at least one of the following amino acid sequences:

TABLE A-18

Representative FW4 sequences for Nanobodies of the GLEW-group.

| | | |
|---|---|---|
| GLEW FW4 sequence no. 1 | SEQ ID NO: 86 | GSQGTQVTVSS |
| GLEW FW4 sequence no. 2 | SEQ ID NO: 87 | LRGGTQVTVSS |
| GLEW FW4 sequence no. 3 | SEQ ID NO: 88 | RGQGTLVTVSS |
| GLEW FW4 sequence no. 4 | SEQ ID NO: 89 | RSRGIQVTVSS |
| GLEW FW4 sequence no. 5 | SEQ ID NO: 90 | WGKGTQVTVSS |
| GLEW FW4 sequence no. 6 | SEQ ID NO: 91 | WGQGTQVTVSS | and in which:

vi) CDR1, CDR2 and CDR3 are as defined herein, and are preferably as defined according to one of the preferred aspects herein, and are more preferably as defined according to one of the more preferred aspects herein.

In the above Nanobodies, one or more of the further Hallmark residues are preferably as described herein (for example, when they are VHH sequences or partially humanized Nanobodies).

With regard to framework 1, it will again be clear to the skilled person that, for determining the degree of amino acid identity, the amino acid residues on positions 1 to 4 and 27 to 30 are preferably disregarded.

In view of this, a Nanobody of the GLEW class may be an amino acid sequence that is comprised of four framework regions/sequences interrupted by three complementarity determining regions/sequences, in which:

i) preferably, when the Nanobody of the GLEW-class is a non-humanized Nanobody, the amino acid residue in position 108 is Q;

and in which:

ii) FR1 is an amino acid sequence that, on positions 5 to 26 of the Kabat numbering, has at least 80% amino acid identity with at least one of the following amino acid sequences:

TABLE A-19

Representative FW1 sequences (amino acid residues 5 to 26) for Nanobodies of the KERE-group.

| | | |
|---|---|---|
| GLEW FW1 sequence no. 6 | SEQ ID NO: 69 | VESGGGLVQPGGSLRLSCAASG |

TABLE A-19-continued

Representative FW1 sequences (amino acid residues 5 to 26) for Nanobodies of the KERE-group.

| | | |
|---|---|---|
| GLEW FW1 sequence no. 7 | SEQ ID NO: 70 | EESGGGLAQPGGSLRLSCVASG |
| GLEW FW1 sequence no. 8 | SEQ ID NO: 71 | VESGGGLALPGGSLTLSCVFSG | and in which:

iii) FR2, FR3 and FR4 are as mentioned herein for FR2, FR3 and FR4 of Nanobodies of the GLEW-class;

and in which:

iv) CDR1, CDR2 and CDR3 are as defined herein, and are preferably as defined according to one of the preferred aspects herein, and are more preferably as defined according to one of the more preferred aspects herein.

The above Nanobodies may for example be VHH sequences or may be humanized Nanobodies. When the above Nanobody sequences are VHH sequences, they may be suitably humanized, as further described herein. When the Nanobodies are partially humanized Nanobodies, they may optionally be further suitably humanized, again as described herein. In the above Nanobodies, one or more of the further Hallmark residues are preferably as described herein (for example, when they are VHH sequences or partially humanized Nanobodies).

A Nanobody of the P, R, S 103 class may be an amino acid sequence that is comprised of four framework regions/sequences interrupted by three complementarity determining regions/sequences, in which i) the amino acid residue at position 103 according to the Kabat numbering is different from W;

and in which:

ii) preferably the amino acid residue at position 103 according to the Kabat numbering is P, R or S, and more preferably R;

and in which:

iii) FR1 is an amino acid sequence that has at least 80% amino acid identity with at least one of the following amino acid sequences:

TABLE A-20

Representative FW1 sequences for Nanobodies of the P, R, S 103-group.

| | |
|---|---|
| P, R, S 103 FW1 sequence no. 1 SEQ ID NO: 92 | AVQLVESGGGLVQAGGSLRLSCAASGRTFS |
| P, R, S 103 FW1 sequence no. 2 SEQ ID NO: 93 | QVQLQESGGGMVQPGGSLRLSCAASGFDFG |
| P, R, S 103 FW1 sequence no. 3 SEQ ID NO: 94 | EVHLVESGGGLVRPGGSLRLSCAAFGFIFK |
| P, R, S 103 FW1 sequence no. 4 SEQ ID NO: 95 | QVQLAESGGGLVQPGGSLKLSCAASRTIVS |
| P, R, S 103 FW1 sequence no. 5 SEQ ID NO: 96 | QEHLVESGGGLVDIGGSLRLSCAASERIFS |
| P, R, S 103 FW1 sequence no. 6 SEQ ID NO: 97 | QVKLEESGGGLAQPGGSLRLSCVASGFTFS |
| P, R, S 103 FW1 sequence no. 7 SEQ ID NO: 98 | EVQLVESGGGLVQPGGSLRLSCVCVSSGCT |
| P, R, S 103 FW1 sequence no. 8 SEQ ID NO: 99 | EVQLVESGGGLALPGGSLTLSCVFSGSTFS | and in which
iv) FR2 is an amino acid sequence that has at least 80% amino acid identity with at least one of the following amino acid sequences:

TABLE A-21

Representative FW2 sequences for Nanobodies of the P, R, S 103-group.

| | |
|---|---|
| P, R, S 103 FW2 sequence no. 1 SEQ ID NO: 102 | WFRQAPGKEREFVA |
| P, R, S 103 FW2 sequence no. 2 SEQ ID NO: 103 | WVRQAPGKVLEWVS |
| P, R, S 103 FW2 sequence no. 3 SEQ ID NO: 104 | WVRRPPGKGLEWVS |
| P, R, S 103 FW2 sequence no. 4 SEQ ID NO: 105 | WIRQAPGKEREGVS |
| P, R, S 103 FW2 sequence no. 5 SEQ ID NO: 106 | WVRQYPGKEPEWVS |
| P, R, S 103 FW2 sequence no. 6 SEQ ID NO: 107 | WFRQPPGKEHEFVA |
| P, R, S 103 FW2 sequence no. 7 SEQ ID NO: 108 | WYRQAPGKRTELVA |
| P, R, S 103 FW2 sequence no. 8 SEQ ID NO: 109 | WLRQAPGQGLEWVS |
| P, R, S 103 FW2 sequence no. 9 SEQ ID NO: 110 | WLRQTPGKGLEWVG |
| P, R, S 103 FW2 sequence no. 10 SEQ ID NO: 111 | WVRQAPGKAEEFVS | and in which:
v) FR3 is an amino acid sequence that has at least 80% amino acid identity with at least one of the following amino acid sequences:

TABLE A-22

Representative FW3 sequences for Nanobodies of the P, R, S 103-group.

| | |
|---|---|
| P, R, S 103 FW3 sequence no. 1 SEQ ID NO: 112 | RFTISRDNAKNTVYLQMNSLKPEDTAVYYCAA |
| P, R, S 103 FW3 sequence no. 2 SEQ ID NO: 113 | RFTISRDNARNTLYLQMDSLIPEDTALYYCAR |
| P, R, S 103 FW3 sequence no. 3 SEQ ID NO: 114 | RFTISRDNAKNEMYLQMNNLKTEDTGVYWCGA |
| P, R, S 103 FW3 sequence no. 4 SEQ ID NO: 115 | RFTISSDSNRNMIYLQMNNLKPEDTAVYYCAA |
| P, R, S 103 FW3 sequence no. 5 SEQ ID NO: 116 | RFTISRDNAKNMLYLHLNNLKSEDTAVYYCRR |
| P, R, S 103 FW3 sequence no. 6 SEQ ID NO: 117 | RFTISRDNAKKTVYLRLNSLNPEDTAVYSCNL |
| P, R, S 103 FW3 sequence no. 7 SEQ ID NO: 118 | RFKISRDNAKKTLYLQMNSLGPEDTAMYYCQR |
| P, R, S 103 FW3 sequence no. 8 SEQ ID NO: 119 | RFTVSRDNGKNTAYLRMNSLKPEDTADYYCAV | and in which:

vi) FR4 is an amino acid sequence that has at least 80% amino acid identity with at least one of the following amino acid sequences:

TABLE A-23

Representative FW4 sequences for Nanobodies of the P, R, S 103-group.

| | | |
|---|---|---|
| P, R, S 103 FW4 sequence no. 1 | SEQ ID NO: 120 | RGQGTQVTVSS |
| P, R, S 103 FW4 sequence no. 2 | SEQ ID NO: 121 | LRGGTQVTVSS |
| P, R, S 103 FW4 sequence no. 3 | SEQ ID NO: 122 | GNKGTLVTVSS |
| P, R, S 103 FW4 sequence no. 4 | SEQ ID NO: 123 | SSPGTQVTVSS |
| P, R, S 103 FW4 sequence no. 5 | SEQ ID NO: 124 | SSQGTLVTVSS |
| P, R, S 103 FW4 sequence no. 6 | SEQ ID NO: 125 | RSRGIQVTVSS | and in which:

vii) CDR1, CDR2 and CDR3 are as defined herein, and are preferably as defined according to one of the preferred aspects herein, and are more preferably as defined according to one of the more preferred aspects herein.

In the above Nanobodies, one or more of the further Hallmark residues are preferably as described herein (for example, when they are VHH sequences or partially humanized Nanobodies).

With regard to framework 1, it will again be clear to the skilled person that, for determining the degree of amino acid identity, the amino acid residues on positions 1 to 4 and 27 to 30 are preferably disregarded.

In view of this, a Nanobody of the P,R,S 103 class may be an amino acid sequence that is comprised of four framework regions/sequences interrupted by three complementarity determining regions/sequences, in which:

i) the amino acid residue at position 103 according to the Kabat numbering is different from W;

and in which:

ii) preferably the amino acid residue at position 103 according to the Kabat numbering is P, R or S, and more preferably R;

and in which:

iii) FR1 is an amino acid sequence that, on positions 5 to 26 of the Kabat numbering, has at least 80% amino acid identity with at least one of the following amino acid sequences:

TABLE A-24

Representative FW1 sequences (amino acid residues 5 to 26) for Nanobodies of the P, R, S 103-group.

| | | |
|---|---|---|
| P, R, S 103 FW1 sequence no. 9 | SEQ ID NO: 100 | VESGGGLVQAGGSLRLSCAASG |
| P, R, S 103 FW1 sequence no. 10 | SEQ ID NO: 101 | AESGGGLVQPGGSLKLSCAASR | and in which:

iv) FR2, FR3 and FR4 are as mentioned herein for FR2, FR3 and FR4 of Nanobodies of the P,R,S 103 class;

and in which:

v) CDR1, CDR2 and CDR3 are as defined herein, and are preferably as defined according to one of the preferred aspects herein, and are more preferably as defined according to one of the more preferred aspects herein.

The above Nanobodies may for example be VHH sequences or may be humanized Nanobodies. When the above Nanobody sequences are VHH sequences, they may be suitably humanized, as further described herein. When the Nanobodies are partially humanized Nanobodies, they may optionally be further suitably humanized, again as described herein.

In the above Nanobodies, one or more of the further Hallmark residues are preferably as described herein (for example, when they are VHH sequences or partially humanized Nanobodies).

In another preferred, but non-limiting aspect, the invention relates to a Nanobody as described above, in which the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the single variable domains of SEQ ID NO's: [255-269]. This degree of amino acid identity can for example be determined by determining the degree of amino acid identity (in a manner described herein) between said Nanobody and one or more of the sequences of SEQ ID NO's: [255-269], in which the amino acid residues that form the framework regions are disregarded. Such Nanobodies can be as further described herein.

As already mentioned herein, another preferred but non-limiting aspect of the invention relates to a Nanobody with an amino acid sequence that is chosen from the group consisting of SEQ ID NO's: [255-269] or from the group consisting of from single variable domains that have more than 80%, preferably more than 90%, more preferably more than 95%, such as 99% or more sequence identity (as defined herein) with at least one of the single variable domains of SEQ ID NO's: [255-269].

Also, in the above Nanobodies:

i) any amino acid substitution (when it is not a humanizing substitution as defined herein) is preferably, and compared to the corresponding amino acid sequence of SEQ ID NO's: [255-269], a conservative amino acid substitution, (as defined herein);

and/or:

ii) its amino acid sequence preferably contains either only amino acid substitutions, or otherwise preferably no more than 5, preferably no more than 3, and more preferably only 1 or 2 amino acid deletions or insertions, compared to the corresponding amino acid sequence of SEQ ID NO's: [255-269];

and/or iii) the CDR's may be CDR's that are derived by means of affinity maturation, for example starting from the CDR's of to the corresponding amino acid sequence of SEQ ID NO's: [255-269].

Preferably, the CDR sequences and FR sequences in the Nanobodies of the invention are such that the Nanobodies of the invention (and single variable domains of the invention comprising the same):

bind to members of the Notch signalling pathway with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles);

and/or such that they:

bind to members of the Notch signalling pathway with a $k_{on}$-rate of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$;

and/or such that they:

bind to members of the Notch signalling pathway with a $k_{off}$-rate between 1 $s^{-1}$ ($t_{1/2}$=0.69 s) and $10^{-6}$ $s^{-1}$ (providing a near irreversible complex with a $t_{1/2}$ of multiple days), preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

Preferably, CDR sequences and FR sequences present in the Nanobodies of the invention are such that the Nanobodies of the invention will bind to members of the Notch signalling pathway with an affinity less than 500 nM, preferably less than 200 nM, more preferably less than 10 nM, such as less than 500 pM.

According to one non-limiting aspect of the invention, a Nanobody may be as defined herein, but with the proviso that it has at least "one amino acid difference" (as defined herein) in at least one of the framework regions compared to the corresponding framework region of a naturally occurring human $V_H$ domain, and in particular compared to the corresponding framework region of DP-47. More specifically, according to one non-limiting aspect of the invention, a Nanobody may be as defined herein, but with the proviso that it has at least "one amino acid difference" (as defined herein) at least one of the Hallmark residues (including those at positions 108, 103 and/or 45) compared to the corresponding framework region of a naturally occurring human $V_H$ domain, and in particular compared to the corresponding framework region of DP-47. Usually, a Nanobody will have at least one such amino acid difference with a naturally occurring $V_H$ domain in at least one of FR2 and/or FR4, and in particular at least one of the Hallmark residues in FR2 and/or FR4 (again, including those at positions 108, 103 and/or 45).

Also, a humanized Nanobody of the invention may be as defined herein, but with the proviso that it has at least "one amino acid difference" (as defined herein) in at least one of the framework regions compared to the corresponding framework region of a naturally occurring $V_{HH}$ domain. More specifically, according to one non-limiting aspect of the invention, a humanized Nanobody may be as defined herein, but with the proviso that it has at least "one amino acid difference" (as defined herein) at least one of the Hallmark residues (including those at positions 108, 103 and/or 45) compared to the corresponding framework region of a naturally occurring $V_{HH}$ domain. Usually, a humanized Nanobody will have at least one such amino acid difference with a naturally occurring $V_{HH}$ domain in at least one of FR2 and/or FR4, and in particular at least one of the Hallmark residues in FR2 and/or FR4 (again, including those at positions 108, 103 and/or 45).

As will be clear from the disclosure herein, it is also within the scope of the invention to use natural or synthetic analogs, mutants, variants, alleles, homologs and orthologs (herein collectively referred to as "analogs") of the Nanobodies of the invention as defined herein, and in particular analogs of the Nanobodies of SEQ ID NO's [255-269]. Thus, according to one aspect of the invention, the term "Nanobody of the invention" in its broadest sense also covers such analogs.

Generally, in such analogs, one or more amino acid residues may have been replaced, deleted and/or added, compared to the Nanobodies of the invention as defined herein. Such substitutions, insertions or deletions may be made in one or more of the framework regions and/or in one or more of the CDR's. When such substitutions, insertions or deletions are made in one or more of the framework regions, they may be made at one or more of the Hallmark residues and/or at one or more of the other positions in the framework residues, although substitutions, insertions or deletions at the Hallmark residues are generally less preferred (unless these are suitable humanizing substitutions as described herein).

By means of non-limiting examples, a substitution may for example be a conservative substitution (as described herein) and/or an amino acid residue may be replaced by another amino acid residue that naturally occurs at the same position in another $V_{HH}$ domain (see Tables A-5 to A-8 for some non-limiting examples of such substitutions), although the invention is generally not limited thereto. Thus, any one or more substitutions, deletions or insertions, or any combination thereof, that either improve the properties of the Nanobody of the invention or that at least do not detract too much from the desired properties or from the balance or combination of desired properties of the Nanobody of the invention (i.e. to the extent that the Nanobody is no longer suited for its intended use) are included within the scope of the invention. A skilled person will generally be able to determine and select suitable substitutions, deletions or insertions, or suitable combinations of thereof, based on the disclosure herein and optionally after a limited degree of routine experimentation, which may for example involve introducing a limited number of possible substitutions and determining their influence on the properties of the Nanobodies thus obtained.

For example, and depending on the host organism used to express the Nanobody or polypeptide of the invention, such deletions and/or substitutions may be designed in such a way that one or more sites for post-translational modification (such as one or more glycosylation sites) are removed, as will be within the ability of the person skilled in the art. Alternatively, substitutions or insertions may be designed so as to introduce one or more sites for attachment of functional groups (as described herein), for example to allow site-specific pegylation (again as described herein).

As can be seen from the data on the $V_{HH}$ entropy and $V_{HH}$ variability given in Tables A-5 to A-8 above, some amino acid residues in the framework regions are more conserved than others. Generally, although the invention in its broadest sense is not limited thereto, any substitutions, deletions or insertions are preferably made at positions that are less conserved. Also, generally, amino acid substitutions are preferred over amino acid deletions or insertions.

The analogs are preferably such that they can bind to members of the Notch signalling pathway with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein for the Nanobodies of the invention.

The analogs are preferably also such that they retain the favourable properties the Nanobodies, as described herein.

Also, according to one preferred aspect, the analogs have a degree of sequence identity of at least 70%, preferably at least 80%, more preferably at least 90%, such as at least 95% or 99% or more; and/or preferably have at most 20, preferably at most 10, even more preferably at most 5, such as 4, 3, 2 or only 1 amino acid difference (as defined herein), with one of the Nanobodies of SEQ ID NOs: [255-269].

Also, the framework sequences and CDR's of the analogs are preferably such that they are in accordance with the preferred aspects defined herein. More generally, as described herein, the analogs will have (a) a Q at position 108; and/or (b) a charged amino acid or a cysteine residue at position 45 and preferably an E at position 44, and more preferably E at position 44 and R at position 45; and/or (c) P, R or S at position 103.

One preferred class of analogs of the Nanobodies of the invention comprise Nanobodies that have been humanized (i.e. compared to the sequence of a naturally occurring Nanobody of the invention). As mentioned in the background art cited herein, such humanization generally involves replacing one or more amino acid residues in the sequence of a naturally occurring $V_{HH}$ with the amino acid residues that occur at the same position in a human $V_H$ domain, such as a human $V_H3$ domain. Examples of possible humanizing substitutions or combinations of humanizing substitutions will be clear to the skilled person, for example from the Tables herein, from the possible humanizing substitutions mentioned in the background art cited herein, and/or from a comparison between the sequence of a Nanobody and the sequence of a naturally occurring human $V_H$ domain.

The humanizing substitutions should be chosen such that the resulting humanized Nanobodies still retain the favourable properties of Nanobodies as defined herein, and more preferably such that they are as described for analogs in the preceding paragraphs. A skilled person will generally be able to determine and select suitable humanizing substitutions or suitable combinations of humanizing substitutions, based on the disclosure herein and optionally after a limited degree of routine experimentation, which may for example involve introducing a limited number of possible humanizing substitutions and determining their influence on the properties of the Nanobodies thus obtained.

Generally, as a result of humanization, the Nanobodies of the invention may become more "human-like", while still retaining the favorable properties of the Nanobodies of the invention as described herein. As a result, such humanized Nanobodies may have several advantages, such as a reduced immunogenicity, compared to the corresponding naturally occurring $V_{HH}$ domains. Again, based on the disclosure herein and optionally after a limited degree of routine experimentation, the skilled person will be able to select humanizing substitutions or suitable combinations of humanizing substitutions which optimize or achieve a desired or suitable balance between the favourable properties provided by the humanizing substitutions on the one hand and the favourable properties of naturally occurring $V_{HH}$ domains on the other hand.

The Nanobodies of the invention may be suitably humanized at any framework residue(s), such as at one or more Hallmark residues (as defined herein) or at one or more other framework residues (i.e. non-Hallmark residues) or any suitable combination thereof. One preferred humanizing substitution for Nanobodies of the "P,R,S-103 group" or the "KERE group" is Q108 into L108. Nanobodies of the "GLEW class" may also be humanized by a Q108 into L108 substitution, provided at least one of the other Hallmark residues contains a camelid (camelizing) substitution (as defined herein). For example, as mentioned above, one particularly preferred class of humanized Nanobodies has GLEW or a GLEW-like sequence at positions 44-47; P, R or S (and in particular R) at position 103, and an L at position 108.

The humanized and other analogs, and nucleic acid sequences encoding the same, can be provided in any manner known per se. For example, the analogs can be obtained by providing a nucleic acid that encodes a naturally occurring $V_{HH}$ domain, changing the codons for the one or more amino acid residues that are to be substituted into the codons for the corresponding desired amino acid residues (e.g. by site-directed mutagenesis or by PCR using suitable mismatch primers), expressing the nucleic acid/nucleotide sequence thus obtained in a suitable host or expression system; and optionally isolating and/or purifying the analog thus obtained to provide said analog in essentially isolated form (e.g. as further described herein). This can generally be performed using methods and techniques known per se, which will be clear to the skilled person, for example from the handbooks and references cited herein, the background art cited herein and/or from the further description herein. Alternatively, a nucleic acid encoding the desired analog can be synthesized in a manner known per se (for example using an automated apparatus for synthesizing nucleic acid sequences with a predefined amino acid sequence) and can then be expressed as described herein. Yet another technique may involve combining one or more naturally occurring and/or synthetic nucleic acid sequences each encoding a part of the desired analog, and then expressing the combined nucleic acid sequence as described herein. Also, the analogs can be provided using chemical synthesis of the pertinent amino acid sequence using techniques for peptide synthesis known per se, such as those mentioned herein.

In this respect, it will be also be clear to the skilled person that the Nanobodies of the invention (including their analogs) can be designed and/or prepared starting from human $V_H$ sequences (i.e. single variable domains or the corresponding nucleotide sequences), such as for example from human $V_H3$ sequences such as DP-47, DP-51 or DP-29, i.e. by introducing one or more camelizing substitutions (i.e. changing one or more amino acid residues in the amino acid sequence of said human $V_H$ domain into the amino acid residues that occur at the corresponding position in a $V_{HH}$ domain), so as to provide the sequence of a Nanobody of the invention and/or so as to confer the favourable properties of a Nanobody to the sequence thus obtained. Again, this can generally be performed using the various methods and techniques referred to in the previous paragraph, using an amino acid sequence and/or nucleotide sequence for a human $V_H$ domain as a starting point.

Some preferred, but non-limiting camelizing substitutions can be derived from Tables A-5-A-8. It will also be clear that camelizing substitutions at one or more of the Hallmark residues will generally have a greater influence on the desired properties than substitutions at one or more of the other amino acid positions, although both and any suitable combination thereof are included within the scope of the invention. For example, it is possible to introduce one or more camelizing substitutions that already confer at least some the desired properties, and then to introduce further camelizing substitutions that either further improve said properties and/or confer additional favourable properties. Again, the skilled person will generally be able to determine and select suitable camelizing substitutions or suitable combinations of camelizing substitutions, based on the disclosure herein and optionally after a limited degree of routine experimentation, which may for example involve introducing a limited number of possible camelizing substitutions and determining whether the favourable properties of Nanobodies are obtained or improved (i.e. compared to the original $V_H$ domain). Generally, however, such camelizing substitutions are preferably such that the resulting an amino acid sequence at least contains (a) a Q at position 108; and/or (b) a charged amino acid or a cysteine residue at position 45 and preferably also an E at position 44, and more preferably E at position 44 and R at position 45; and/or (c) P, R or S at position 103; and optionally one or more further camelizing substitutions. More preferably, the camelizing substitutions are such that they result in a Nanobody of the invention and/or in an analog thereof (as defined herein), such as in a humanized analog and/or preferably in an analog that is as defined in the preceding paragraphs.

As will also be clear from the disclosure herein, it is also within the scope of the invention to use parts or fragments, or combinations of two or more parts or fragments, of the Nanobodies of the invention as defined herein, and in particular parts or fragments of the Nanobodies of SEQ ID NO's: [255-269]. Thus, according to one aspect of the invention, the term "Nanobody of the invention" in its broadest sense also covers such parts or fragments.

Generally, such parts or fragments of the Nanobodies of the invention (including analogs thereof) have single variable domains in which, compared to the amino acid sequence of the corresponding full length Nanobody of the invention (or analog thereof), one or more of the amino acid residues at the N-terminal end, one or more amino acid residues at the C-terminal end, one or more contiguous internal amino acid residues, or any combination thereof, have been deleted and/or removed.

The parts or fragments are preferably such that they can bind to members of the Notch signalling pathway with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein for the Nanobodies of the invention.

Any part or fragment is preferably such that it comprises at least 10 contiguous amino acid residues, preferably at least 20 contiguous amino acid residues, more preferably at least 30 contiguous amino acid residues, such as at least 40 contiguous amino acid residues, of the amino acid sequence of the corresponding full length Nanobody of the invention.

Also, any part or fragment is such preferably that it comprises at least one of CDR1, CDR2 and/or CDR3 or at least part thereof (and in particular at least CDR3 or at least part thereof). More preferably, any part or fragment is such that it comprises at least one of the CDR's (and preferably at least CDR3 or part thereof) and at least one other CDR (i.e. CDR1 or CDR2) or at least part thereof, preferably connected by suitable framework sequence(s) or at least part thereof. More preferably, any part or fragment is such that it comprises at least one of the CDR's (and preferably at least CDR3 or part thereof) and at least part of the two remaining CDR's, again preferably connected by suitable framework sequence(s) or at least part thereof.

According to another particularly preferred, but non-limiting aspect, such a part or fragment comprises at least CDR3, such as FR3, CDR3 and FR4 of the corresponding full length Nanobody of the invention, i.e. as for example described in the International application WO 03/050531 (Lasters et al.).

As already mentioned above, it is also possible to combine two or more of such parts or fragments (i.e. from the same or different Nanobodies of the invention), i.e. to provide an analog (as defined herein) and/or to provide further parts or fragments (as defined herein) of a Nanobody of the invention. It is for example also possible to combine one or more parts or fragments of a Nanobody of the invention with one or more parts or fragments of a human $V_H$ domain.

According to one preferred aspect, the parts or fragments have a degree of sequence identity of at least 50%, preferably at least 60%, more preferably at least 70%, even more preferably at least 80%, such as at least 90%, 95% or 99% or more with one of the Nanobodies of SEQ ID NOs [255-269].

The parts and fragments, and nucleic acid sequences encoding the same, can be provided and optionally combined in any manner known per se. For example, such parts or fragments can be obtained by inserting a stop codon in a nucleic acid that encodes a full-sized Nanobody of the invention, and then expressing the nucleic acid thus obtained in a manner known per se (e.g. as described herein). Alternatively, nucleic acids encoding such parts or fragments can be obtained by suitably restricting a nucleic acid that encodes a full-sized Nanobody of the invention or by synthesizing such a nucleic acid in a manner known per se. Parts or fragments may also be provided using techniques for peptide synthesis known per se.

The invention in its broadest sense also comprises derivatives of the Nanobodies of the invention. Such derivatives can generally be obtained by modification, and in particular by chemical and/or biological (e.g. enzymatical) modification, of the Nanobodies of the invention and/or of one or more of the amino acid residues that form the Nanobodies of the invention.

Examples of such modifications, as well as examples of amino acid residues within the Nanobody sequence that can be modified in such a manner (i.e. either on the protein backbone but preferably on a side chain), methods and techniques that can be used to introduce such modifications and the potential uses and advantages of such modifications will be clear to the skilled person.

For example, such a modification may involve the introduction (e.g. by covalent linking or in an other suitable manner) of one or more functional groups, residues or moieties into or onto the Nanobody of the invention, and in particular of one or more functional groups, residues or moieties that confer one or more desired properties or functionalities to the Nanobody of the invention. Example of such functional groups will be clear to the skilled person.

For example, such modification may comprise the introduction (e.g. by covalent binding or in any other suitable manner) of one or more functional groups that increase the half-life, the solubility and/or the absorption of the Nanobody of the invention, that reduce the immunogenicity and/or the toxicity of the Nanobody of the invention, that eliminate or attenuate any undesirable side effects of the Nanobody of the invention, and/or that confer other advantageous properties to and/or reduce the undesired properties of the Nanobodies and/or single variable domains of the invention; or any combination of two or more of the foregoing. Examples of such functional groups and of techniques for introducing them will be clear to the skilled person, and can generally comprise all functional groups and techniques mentioned in the general background art cited hereinabove as well as the functional groups and techniques known per se for the modification of pharmaceutical proteins, and in particular for the modification of antibodies or antibody fragments (including ScFv's and single domain antibodies), for which reference is for example made to Remington's Pharmaceutical Sciences, 16th ed., Mack Publishing Co., Easton, Pa. (1980). Such functional groups may for example be linked directly (for example covalently) to a Nanobody of the invention, or optionally via a suitable linker or spacer, as will again be clear to the skilled person.

One of the most widely used techniques for increasing the half-life and/or reducing the immunogenicity of pharmaceutical proteins comprises attachment of a suitable pharmacologically acceptable polymer, such as poly(ethyleneglycol) (PEG) or derivatives thereof (such as methoxypoly(ethyleneglycol) or mPEG). Generally, any suitable form of pegylation can be used, such as the pegylation used in the art for antibodies and antibody fragments (including but not limited to (single) domain antibodies and ScFv's); reference is made to for example Chapman, Nat. Biotechnol., 54, 531-545 (2002); by Veronese and Harris, Adv. Drug Deliv. Rev. 54, 453-456 (2003), by Harris and Chess, Nat. Rev. Drug. Discov., 2, (2003) and in WO 04/060965. Various reagents for pegylation of proteins are also commercially available, for example from Nektar Therapeutics, USA.

Preferably, site-directed pegylation is used, in particular via a cysteine-residue (see for example Yang et al., Protein Engineering, 16, 10, 761-770 (2003). For example, for this purpose, PEG may be attached to a cysteine residue that naturally occurs in a Nanobody of the invention, a Nanobody of the invention may be modified so as to suitably introduce one or more cysteine residues for attachment of PEG, or an amino acid sequence comprising one or more cysteine residues for attachment of PEG may be fused to the N- and/or C-terminus of a Nanobody of the invention, all using techniques of protein engineering known per se to the skilled person.

Preferably, for the Nanobodies and proteins of the invention, a PEG is used with a molecular weight of more than 5000, such as more than 10,000 and less than 200,000, such as less than 100,000; for example in the range of 20,000-80,000.

Another, usually less preferred modification comprises N-linked or O-linked glycosylation, usually as part of co-translational and/or post-translational modification, depending on the host cell used for expressing the Nanobody or polypeptide of the invention.

Yet another modification may comprise the introduction of one or more detectable labels or other signal-generating groups or moieties, depending on the intended use of the labelled Nanobody. Suitable labels and techniques for attaching, using and detecting them will be clear to the skilled person, and for example include, but are not limited to, fluorescent labels (such as fluorescein, isothiocyanate, rhodamine, phycoerythrin, phycocyanin, allophycocyanin, o-phthaldehyde, and fluorescamine and fluorescent metals such as $^{152}$Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes (such as $^{3}$H, $^{125}$I, $^{32}$P, $^{35}$S, $^{14}$C, $^{51}$Cr, $^{36}$Cl, $^{57}$Co, $^{58}$Co, $^{59}$Fe, and $^{75}$Se), metals, metal chelates or metallic cations (for example metallic cations such as $^{99m}$Tc, $^{123}$I, $^{111}$In, $^{131}$I, $^{97}$Ru, $^{67}$Cu, $^{67}$Ga, and $^{68}$Ga or other metals or metallic cations that are particularly suited for use in in vivo, in vitro or in situ diagnosis and imaging, such as ($^{157}$Gd, $^{55}$Mn, $^{162}$Dy, $^{52}$Cr, and $^{56}$Fe), as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotin-avidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase). Other suitable labels will be clear to the skilled person, and for example include moieties that can be detected using NMR or ESR spectroscopy.

Such labelled Nanobodies and single variable domains of the invention may for example be used for in vitro, in vivo or in situ assays (including immunoassays known per se such as ELISA, RIA, EIA and other "sandwich assays", etc.) as well as in vivo diagnostic and imaging purposes, depending on the choice of the specific label.

As will be clear to the skilled person, another modification may involve the introduction of a chelating group, for example to chelate one of the metals or metallic cations referred to above. Suitable chelating groups for example include, without limitation, diethylenetriaminepentaacetic acid (DTPA) or ethylenediaminetetraacetic acid (EDTA).

Yet another modification may comprise the introduction of a functional group that is one part of a specific binding pair, such as the biotin-(strept)avidin binding pair. Such a functional group may be used to link the Nanobody of the invention to another protein, polypeptide or chemical compound that is bound to the other half of the binding pair, i.e. through formation of the binding pair. For example, a Nanobody of the invention may be conjugated to biotin, and linked to another protein, polypeptide, compound or carrier conjugated to avidin or streptavidin. For example, such a conjugated Nanobody may be used as a reporter, for example in a diagnostic system where a detectable signal-producing agent is conjugated to avidin or streptavidin. Such binding pairs may for example also be used to bind the Nanobody of the invention to a carrier, including carriers suitable for pharmaceutical purposes. One non-limiting example are the liposomal formulations described by Cao and Suresh, Journal of Drug Targetting, 8, 4, 257 (2000). Such binding pairs may also be used to link a therapeutically active agent to the Nanobody of the invention.

For some applications, in particular for those applications in which it is intended to kill a cell that expresses the target against which the Nanobodies of the invention are directed (e.g. in the treatment of cancer), or to reduce or slow the growth and/or proliferation such a cell, the Nanobodies of the invention may also be linked to a toxin or to a toxic residue or moiety. Examples of toxic moieties, compounds or residues which can be linked to a Nanobody of the invention to provide—for example—a cytotoxic compound will be clear to the skilled person and can for example be found in the prior art cited above and/or in the further description herein. One example is the so-called ADEPT™ technology described in WO 03/055527.

Other potential chemical and enzymatical modifications will be clear to the skilled person. Such modifications may also be introduced for research purposes (e.g. to study function-activity relationships). Reference is for example made to Lundblad and Bradshaw, Biotechnol. Appl. Biochem., 26, 143-151 (1997).

Preferably, the derivatives are such that they bind to members of the Notch signalling pathway with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein for the Nanobodies of the invention.

As mentioned above, the invention also relates to proteins or single variable domains that essentially consist of or comprise at least one Nanobody of the invention. By "essentially consist of" is meant that the amino acid sequence of the polypeptide of the invention either is exactly the same as the amino acid sequence of a Nanobody of the invention or corresponds to the amino acid sequence of a Nanobody of the invention which has a limited number of amino acid residues, such as 1-20 amino acid residues, for example 1-10 amino acid residues and preferably 1-6 amino acid residues, such as 1, 2, 3, 4, 5 or 6 amino acid residues, added at the amino terminal end, at the carboxy terminal end, or at both the amino terminal end and the carboxy terminal end of the amino acid sequence of the Nanobody.

Said amino acid residues may or may not change, alter or otherwise influence the (biological) properties of the Nanobody and may or may not add further functionality to the Nanobody. For example, such amino acid residues:

can comprise an N-terminal Met residue, for example as result of expression in a heterologous host cell or host organism.

may form a signal sequence or leader sequence that directs secretion of the Nanobody from a host cell upon synthesis. Suitable secretory leader peptides will be clear to the skilled person, and may be as further described herein. Usually, such a leader sequence will be linked to the N-terminus of the Nanobody, although the invention in its broadest sense is not limited thereto;

may form a sequence or signal that allows the Nanobody to be directed towards and/or to penetrate or enter into specific organs, tissues, cells, or parts or compartments of cells, and/or that allows the Nanobody to penetrate or cross a biological barrier such as a cell membrane, a cell layer such as a layer of epithelial cells, a tumor including solid tumors, or the blood-brain-barrier. Examples of such single variable domains will be clear to the skilled person. Some non-limiting examples are the small peptide vectors ("Pep-trans vectors") described in WO 03/026700 and in Temsamani et al., Expert Opin. Biol. Ther., 1, 773 (2001); Temsamani and Vidal, Drug Discov. Today, 9, 1012 (004) and Rousselle, J. Pharmacol. Exp. Ther., 296, 124-131 (2001), and the membrane translocator sequence described by Zhao et al., Apoptosis, 8, 631-637 (2003). C-terminal and N-terminal single variable domains for intracellular targeting of antibody fragments are for example described by Cardinale et al., Methods, 34, 171 (2004). Other suitable techniques for intracellular targeting involve the expression and/or use of so-called "intrabodies" comprising a Nanobody of the invention, as mentioned below;

may form a "tag", for example an amino acid sequence or residue that allows or facilitates the purification of the Nanobody, for example using affinity techniques directed against said sequence or residue. Thereafter, said sequence or residue may be removed (e.g. by chemical or enzymatical cleavage) to provide the Nanobody sequence (for this purpose, the tag may optionally be linked to the Nanobody sequence via a cleavable linker sequence or contain a cleavable motif). Some preferred, but non-limiting examples of such residues are multiple histidine residues, glutathione residues and a myc-tag (see for example SEQ ID NO:31 of WO 06/12282).

may be one or more amino acid residues that have been functionalized and/or that can serve as a site for attachment of functional groups. Suitable amino acid residues and functional groups will be clear to the skilled person and include, but are not limited to, the amino acid residues and functional groups mentioned herein for the derivatives of the Nanobodies of the invention.

According to another aspect, a polypeptide of the invention comprises a Nanobody of the invention, which is fused at its amino terminal end, at its carboxy terminal end, or both at its amino terminal end and at its carboxy terminal end to at least one further amino acid sequence, i.e. so as to provide a fusion protein comprising said Nanobody of the invention and the one or more further amino acid sequences. Such a fusion will also be referred to herein as a "Nanobody fusion".

The one or more further amino acid sequence may be any suitable and/or desired amino acid sequences. The further single variable domains may or may not change, alter or otherwise influence the (biological) properties of the Nanobody, and may or may not add further functionality to the Nanobody or the polypeptide of the invention. Preferably, the further amino acid sequence is such that it confers one or more desired properties or functionalities to the Nanobody or the polypeptide of the invention.

For example, the further amino acid sequence may also provide a second binding site, which binding site may be directed against any desired protein, polypeptide, antigen, antigenic determinant or epitope (including but not limited to the same protein, polypeptide, antigen, antigenic determinant or epitope against which the Nanobody of the invention is directed, or a different protein, polypeptide, antigen, antigenic determinant or epitope).

Example of such single variable domains will be clear to the skilled person, and may generally comprise all single variable domains that are used in peptide fusions based on conventional antibodies and fragments thereof (including but not limited to ScFv's and single domain antibodies). Reference is for example made to the review by Holliger and Hudson, Nature Biotechnology, 23, 9, 1126-1136 (2005).

For example, such an amino acid sequence may be an amino acid sequence that increases the half-life, the solubility, or the absorption, reduces the immunogenicity or the toxicity, eliminates or attenuates undesirable side effects, and/or confers other advantageous properties to and/or reduces the undesired properties of the single variable domains of the invention, compared to the Nanobody of the invention per se. Some non-limiting examples of such single variable domains are serum proteins, such as human serum albumin (see for example WO 00/27435) or haptenic molecules (for example haptens that are recognized by circulating antibodies, see for example WO 98/22141).

In particular, it has been described in the art that linking fragments of immunoglobulins (such as $V_H$ domains) to serum albumin or to fragments thereof can be used to increase the half-life. Reference is for made to WO 00/27435 and WO 01/077137). According to the invention, the Nanobody of the invention is preferably either directly linked to serum albumin (or to a suitable fragment thereof) or via a suitable linker, and in particular via a suitable peptide linked so that the polypeptide of the invention can be expressed as a genetic fusion (protein). According to one specific aspect, the Nanobody of the invention may be linked to a fragment of serum albumin that at least comprises the domain III of serum albumin or part thereof. Reference is for example made to the U.S. provisional application 60/788,256 of Ablynx N.V. entitled "Albumin derived amino acid sequence, use thereof for increasing the half-life of therapeutic proteins and of other therapeutic proteins and entities, and constructs comprising the same" filed on Mar. 31, 2006 (see also PCT/EP2007/002817).

Alternatively, the further amino acid sequence may provide a second binding site or binding unit that is directed against a serum protein (such as, for example, human serum albumin or another serum protein such as IgG), so as to provide increased half-life in serum. Such single variable domains for example include the Nanobodies described below, as well as the small peptides and binding proteins described in WO 91/01743, WO 01/45746 and WO 02/076489 and the dAb's described in WO 03/002609 and WO 04/003019. Reference is also made to Harmsen et al., Vaccine, 23 (41); 4926-42, 2005, as well as to EP 0 368 684, as well as to the following the U.S. provisional applications 60/843,349 (see also PCT/EP2007/059475), 60/850,774 (see also PCT/EP2007/060849), 60/850,775 (see also PCT/EP2007/060850) by Ablynx N.V. mentioned herein and US provisional application of Ablynx N.V. entitled "Peptides capable of binding to serum proteins" filed on Dec. 5, 2006 ((see also PCT/EP2007/063348).

Such single variable domains may in particular be directed against serum albumin (and more in particular human serum albumin) and/or against IgG (and more in particular human IgG). For example, such single variable domains may be single variable domains that are directed against (human) serum albumin and single variable domains that can bind to amino acid residues on (human) serum albumin that are not involved in binding of serum albumin to FcRn (see for example WO 06/0122787) and/or single variable domains that are capable of binding to amino acid residues on serum albumin that do not form part of domain III of serum albumin (see again for example WO 06/0122787); single variable domains that have or can provide an increased half-life (see for example the U.S. provisional application 60/843,349 by Ablynx N.V. entitled "Serum albumin binding proteins with long half-lives" filed on Sep. 8, 2006; see also PCT/EP2007/059475); single variable domains against human serum albumin that are cross-reactive with serum albumin from at least one species of mammal, and in particular with at least one species of primate (such as, without limitation, monkeys from the genus *Macaca* (such as, and in particular, cynomolgus monkeys (*Macaca fascicularis*) and/or rhesus monkeys (*Macaca mulatta*)) and baboon (*Papio ursinus*), reference is again made to the U.S. provisional application 60/843,349 and PCT/EP2007/059475); single variable domains that can bind to serum albumin in a pH independent manner (see for example the U.S. provisional application 60/850,774 by Ablynx N.V. entitled "Single variable domains that bind to serum proteins in a manner that is essentially independent of the pH, compounds comprising the same, and uses thereof", filed on Oct. 11, 2006; see also and PCT/EP2007/059475) and/or single variable domains that are conditional binders (see for example the U.S. provisional application 60/850,775 by Ablynx N.V. entitled "Single variable domains that bind to a desired molecule in a conditional manner", filed on Oct. 11, 2006; see also PCT/EP2007/060850).

According to another aspect, the one or more further single variable domains may comprise one or more parts, fragments or domains of conventional 4-chain antibodies (and in particular human antibodies) and/or of heavy chain antibodies. For example, although usually less preferred, a Nanobody of the invention may be linked to a conventional (preferably human) $V_H$ or $V_L$ domain or to a natural or synthetic analog of a $V_H$ or $V_L$ domain, again optionally via a linker sequence (including but not limited to other (single) domain antibodies, such as the dAb's described by Ward et al.).

The at least one Nanobody may also be linked to one or more (preferably human) $C_H1$, $C_H2$ and/or $C_H3$ domains, optionally via a linker sequence. For instance, a Nanobody linked to a suitable $C_H1$ domain could for example be used—together with suitable light chains—to generate antibody fragments/structures analogous to conventional Fab fragments or F(ab')$_2$ fragments, but in which one or (in case of an F(ab')$_2$ fragment) one or both of the conventional $V_H$ domains have been replaced by a Nanobody of the invention. Also, two Nanobodies could be linked to a $C_H3$ domain (optionally via a linker) to provide a construct with increased half-life in vivo.

According to one specific aspect of a polypeptide of the invention, one or more Nanobodies of the invention may be linked (optionally via a suitable linker or hinge region) to one or more constant domains (for example, 2 or 3 constant domains that can be used as part of/to form an Fc portion), to an Fc portion and/or to one or more antibody parts, fragments or domains that confer one or more effector functions to the polypeptide of the invention and/or may confer the ability to bind to one or more Fc receptors. For example, for this purpose, and without being limited thereto, the one or more further single variable domains may comprise one or more $C_H2$ and/or $C_H3$ domains of an antibody, such as from a heavy chain antibody (as described herein) and more preferably from a conventional human 4-chain antibody; and/or may form (part of) and Fc region, for example from IgG (e.g. from IgG1, IgG2, IgG3 or IgG4), from IgE or from another human Ig such as IgA, IgD or IgM. For example, WO 94/04678 describes heavy chain antibodies comprising a Camelid $V_{HH}$ domain or a humanized derivative thereof (i.e. a Nanobody), in which the Camelidae $C_H2$ and/or $C_H3$ domain have been replaced by human $C_H2$ and $C_H3$ domains, so as to provide an immunoglobulin that consists of 2 heavy chains each comprising a Nanobody and human $C_H2$ and $C_H3$ domains (but no $C_H1$ domain), which immunoglobulin has the effector function provided by the $C_H2$ and $C_H3$ domains and which immunoglobulin can function without the presence of any light chains. Other single variable domains that can be suitably linked to the Nanobodies of the invention so as to provide an effector function will be clear to the skilled person, and may be chosen on the basis of the desired effector function(s). Reference is for example made to WO 04/058820, WO 99/42077, WO 02/056910 and WO 05/017148, as well as the review by Holliger and Hudson, supra; and to the non-prepublished US provisional application by Ablynx N.V. entitled "Constructs comprising single variable domains and an Fc portion derived from IgE" which has a filing date of Dec. 4, 2007. Coupling of a Nanobody of the invention to an Fc portion may also lead to an increased half-life, compared to the corresponding Nanobody of the invention. For some applications, the use of an Fc portion and/or of constant domains (i.e. $C_H2$ and/or $C_H3$ domains) that confer increased half-life without any biologically significant effector function may also be suitable or even preferred. Other suitable constructs comprising one or more Nanobodies and one or more constant domains with increased half-life in vivo will be clear to the skilled person, and may for example comprise two Nanobodies linked to a $C_H3$ domain, optionally via a linker sequence. Generally, any fusion protein or derivatives with increased half-life will preferably have a molecular weight of more than 50 kD, the cut-off value for renal absorption.

In another one specific, but non-limiting, aspect, in order to form a polypeptide of the invention, one or more single variable domains of the invention may be linked (optionally via a suitable linker or hinge region) to naturally occurring, synthetic or semisynthetic constant domains (or analogs, variants, mutants, parts or fragments thereof) that have a reduced (or essentially no) tendency to self-associate into dimers (i.e. compared to constant domains that naturally occur in conventional 4-chain antibodies). Such monomeric (i.e. not self-associating) Fc chain variants, or fragments thereof, will be clear to the skilled person. For example, Helm et al., J Biol Chem 1996 271 7494, describe monomeric Fcε chain variants that can be used in the polypeptide chains of the invention.

Also, such monomeric Fc chain variants are preferably such that they are still capable of binding to the complement or the relevant Fc receptor(s) (depending on the Fc portion from which they are derived), and/or such that they still have some or all of the effector functions of the Fc portion from which they are derived (or at a reduced level still suitable for the intended use). Alternatively, in such a polypeptide chain of the invention, the monomeric Fc chain may be used to confer increased half-life upon the polypeptide chain, in which case the monomeric Fc chain may also have no or essentially no effector functions.

Bivalent/multivalent, bispecific/multispecific or biparatopic/multiparatopic single variable domains of the invention may also be linked to Fc portions, in order to provide polypeptide constructs of the type that is described in the non-prepublished US provisional application entitled "immunoglobulin constructs" filed on Dec. 4, 2007.

The further single variable domains may also form a signal sequence or leader sequence that directs secretion of the Nanobody or the polypeptide of the invention from a host cell upon synthesis (for example to provide a pre-, pro- or prepro-form of the polypeptide of the invention, depending on the host cell used to express the polypeptide of the invention).

The further amino acid sequence may also form a sequence or signal that allows the Nanobody or polypeptide of the invention to be directed towards and/or to penetrate or enter into specific organs, tissues, cells, or parts or compartments of cells, and/or that allows the Nanobody or polypeptide of the invention to penetrate or cross a biological barrier such as a cell membrane, a cell layer such as a layer of epithelial cells, a tumor including solid tumors, or the blood-brain-barrier. Suitable examples of such single variable domains will be clear to the skilled person, and for example include, but are not limited to, the "Peptrans" vectors mentioned above, the sequences described by Cardinale et al. and the antibody fragments known per se that can be used to express or produce the Nanobodies and single variable domains of the invention as so-called "intrabodies", for example as described in WO 94/02610, WO 95/22618, U.S. Pat. No. 7,004,940, WO 03/014960, WO 99/07414; WO 05/01690; EP 1 512 696; and in Cattaneo, A. & Biocca, S. (1997) Intracellular Antibodies: Development and Applications. Landes and Springer-Verlag; and in Kontermann, Methods 34, (2004), 163-170, and the further references described therein.

For some applications, in particular for those applications in which it is intended to kill a cell that expresses the target against which the Nanobodies of the invention are directed (e.g. in the treatment of cancer), or to reduce or slow the growth and/or proliferation of such a cell, the Nanobodies of the invention may also be linked to a (cyto)toxic protein or polypeptide. Examples of such toxic proteins and single variable domains which can be linked to a Nanobody of the invention to provide—for example—a cytotoxic polypeptide of the invention will be clear to the skilled person and can for example be found in the prior art cited above and/or in the further description herein. One example is the so-called ADEPT™ technology described in WO 03/055527.

According to one preferred, but non-limiting aspect, said one or more further single variable domains comprise at least one further Nanobody, so as to provide a polypeptide of the invention that comprises at least two, such as three, four, five or more Nanobodies, in which said Nanobodies may optionally be linked via one or more linker sequences (as defined herein). Single variable domains of the invention that comprise two or more Nanobodies, of which at least one is a Nanobody of the invention, will also be referred to herein as "multivalent" single variable domains of the invention, and the Nanobodies present in such single variable domains will also be referred to herein as being in a "multivalent format". For example a "bivalent" polypeptide of the invention comprises two Nanobodies, optionally linked via a linker sequence, whereas a "trivalent" polypeptide of the invention comprises three Nanobodies, optionally linked via two linker sequences; etc.; in which at least one of the Nanobodies present in the polypeptide, and up to all of the Nanobodies present in the polypeptide, is/are a Nanobody of the invention.

In a multivalent polypeptide of the invention, the two or more Nanobodies may be the same or different, and may be directed against the same antigen or antigenic determinant (for example against the same part(s) or epitope(s) or against different parts or epitopes) or may alternatively be directed against different antigens or antigenic determinants; or any suitable combination thereof. For example, a bivalent polypeptide of the invention may comprise (a) two identical Nanobodies; (b) a first Nanobody directed against a first antigenic determinant of a protein or antigen and a second Nanobody directed against the same antigenic determinant of said protein or antigen which is different from the first Nanobody; (c) a first Nanobody directed against a first antigenic determinant of a protein or antigen and a second Nanobody directed against another antigenic determinant of said protein or antigen; or (d) a first Nanobody directed against a first protein or antigen and a second Nanobody directed against a second protein or antigen (i.e. different from said first antigen). Similarly, a trivalent polypeptide of the invention may, for example and without being limited thereto. comprise (a) three identical Nanobodies; (b) two identical Nanobody against a first antigenic determinant of an antigen and a third Nanobody directed against a different antigenic determinant of the same antigen; (c) two identical Nanobody against a first antigenic determinant of an antigen and a third Nanobody directed against a second antigen different from said first antigen; (d) a first Nanobody directed against a first antigenic determinant of a first antigen, a second Nanobody directed against a second antigenic determinant of said first antigen and a third Nanobody directed against a second antigen different from said first antigen; or (e) a first Nanobody directed against a first antigen, a second Nanobody directed against a second antigen different from said first antigen, and a third Nanobody directed against a third antigen different from said first and second antigen.

Single variable domains of the invention that contain at least two Nanobodies, in which at least one Nanobody is directed against a first antigen (i.e. against members for the Notch signalling pathway,) and at least one Nanobody is directed against a second antigen (i.e. different from members for the Notch signalling pathway,), will also be referred to as "multispecific" single variable domains of the invention, and the Nanobodies present in such single variable domains will also be referred to herein as being in a "multispecific format". Thus, for example, a "bispecific" polypeptide of the invention is a polypeptide that comprises at least one Nanobody directed against a first antigen (i.e. members for the Notch signalling pathway,) and at least one further Nanobody directed against a second antigen (i.e. different from members for the Notch signalling pathway,), whereas a "trispecific" polypeptide of the invention is a polypeptide that comprises at least one Nanobody directed against a first antigen (i.e. members for the Notch signalling pathway,), at least one further Nanobody directed against a second antigen (i.e. different from members for the Notch signalling pathway,) and at least one further Nanobody directed against a third antigen (i.e. different from both members for the Notch signalling pathway, and the second antigen); etc.

Accordingly, in its simplest form, a bispecific polypeptide of the invention is a bivalent polypeptide of the invention (as defined herein), comprising a first Nanobody directed against members for the Notch signalling pathway, and a second Nanobody directed against a second antigen, in which said first and second Nanobody may optionally be linked via a linker sequence (as defined herein); whereas a trispecific polypeptide of the invention in its simplest form is a trivalent polypeptide of the invention (as defined herein), comprising a first Nanobody directed against members for the Notch signalling pathway, a second Nanobody directed against a second antigen and a third Nanobody directed against a third antigen, in which said first, second and third Nanobody may optionally be linked via one or more, and in particular one and more, in particular two, linker sequences.

However, as will be clear from the description hereinabove, the invention is not limited thereto, in the sense that a multispecific polypeptide of the invention may comprise at least one Nanobody against members for the Notch signalling pathway, and any number of Nanobodies directed against one or more antigens different from members for the Notch signalling pathway.

Furthermore, although it is encompassed within the scope of the invention that the specific order or arrangement of the various Nanobodies in the single variable domains of the invention may have some influence on the properties of the final polypeptide of the invention (including but not limited to the affinity, specificity or avidity for members for the Notch signalling pathway, or against the one or more other antigens), said order or arrangement is usually not critical and may be suitably chosen by the skilled person, optionally after some limited routine experiments based on the disclosure herein. Thus, when reference is made to a specific multivalent or multispecific polypeptide of the invention, it should be noted that this encompasses any order or arrangements of the relevant Nanobodies, unless explicitly indicated otherwise.

Finally, it is also within the scope of the invention that the single variable domains of the invention contain two or more Nanobodies and one or more further single variable domains (as mentioned herein).

For multivalent and multispecific single variable domains containing one or more $V_{HH}$ domains and their preparation, reference is also made to Conrath et al., J. Biol. Chem., Vol. 276, 10. 7346-7350, 2001; Muyldermans, Reviews in Molecular Biotechnology 74 (2001), 277-302; as well as to for example WO 96/34103 and WO 99/23221. Some other examples of some specific multispecific and/or multivalent polypeptide of the invention can be found in the applications by Ablynx N.V. referred to herein.

One preferred, but non-limiting example of a multispecific polypeptide of the invention comprises at least one Nanobody of the invention and at least one Nanobody that provides for an increased half-life. Such Nanobodies may for example be Nanobodies that are directed against a serum protein, and in particular a human serum protein, such as human serum albumin, thyroxine-binding protein, (human) transferrin, fibrinogen, an immunoglobulin such as IgG, IgE or IgM, or against one of the serum proteins listed in WO 04/003019. Of these, Nanobodies that can bind to serum albumin (and in particular human serum albumin) or to IgG (and in particular human IgG, see for example Nanobody VH-1 described in the review by Muyldermans, supra) are particularly preferred (although for example, for experiments in mice or primates, Nanobodies against or cross-reactive with mouse serum albumin (MSA) or serum albumin from said primate, respectively, can be used. However, for pharmaceutical use, Nanobodies against human serum albumin or human IgG will usually be preferred). Nanobodies that provide for increased half-life and that can be used in the single variable domains of the invention include the Nanobodies directed against serum albumin that are described in WO 04/041865, in WO 06/122787 and in the further patent applications by Ablynx N.V., such as those mentioned above.

For example, the some preferred Nanobodies that provide for increased half-life for use in the present invention include Nanobodies that can bind to amino acid residues on (human) serum albumin that are not involved in binding of serum albumin to FcRn (see for example WO 06/0122787); Nanobodies that are capable of binding to amino acid residues on serum albumin that do not form part of domain III of serum albumin (see for example WO 06/0122787); Nanobodies that have or can provide an increased half-life (see for example the U.S. provisional application 60/843,349 by Ablynx N.V mentioned herein; see also PCT/EP2007/059475); Nanobodies against human serum albumin that are cross-reactive with serum albumin from at least one species of mammal, and in particular with at least one species of primate (such as, without limitation, monkeys from the genus *Macaca* (such as, and in particular, cynomolgus monkeys (*Macaca fascicularis*) and/or rhesus monkeys (*Macaca mulatta*)) and baboon (*Papio ursinus*)) (see for example the U.S. provisional application 60/843,349 by Ablynx N.V; see also PCT/EP2007/ 059475)); Nanobodies that can bind to serum albumin in a pH independent manner (see for example the U.S. provisional application 60/850,774 by Ablynx N.V. mentioned herein) and/or Nanobodies that are conditional binders (see for example the U.S. provisional application 60/850,775 by Ablynx N.V.; see also PCT/EP2007/060850).

Some particularly preferred Nanobodies that provide for increased half-life and that can be used in the single variable domains of the invention include the Nanobodies ALB-1 to ALB-10 disclosed in WO 06/122787 (see Tables II and III) of which ALB-8 (SEQ ID NO: 62 in WO 06/122787) is particularly preferred.

According to a specific, but non-limiting aspect of the invention, the single variable domains of the invention contain, besides the one or more Nanobodies of the invention, at least one Nanobody against human serum albumin.

Generally, any single variable domains of the invention with increased half-life that contain one or more Nanobodies of the invention, and any derivatives of Nanobodies of the invention or of such single variable domains that have an increased half-life, preferably have a half-life that is at least 1.5 times, preferably at least 2 times, such as at least 5 times, for example at least 10 times or more than 20 times, greater than the half-life of the corresponding Nanobody of the invention per se. For example, such a derivative or single variable domains with increased half-life may have a half-life that is increased with more than 1 hours, preferably more than 2 hours, more preferably more than 6 hours, such as more than 12 hours, or even more than 24, 48 or 72 hours, compared to the corresponding Nanobody of the invention per se.

In a preferred, but non-limiting aspect of the invention, such derivatives or single variable domains may exhibit a serum half-life in human of at least about 12 hours, preferably at least 24 hours, more preferably at least 48 hours, even more preferably at least 72 hours or more. For example, such derivatives or single variable domains may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

According to one aspect of the invention the single variable domains are capable of binding to one or more molecules which can increase the half-life of the polypeptide in vivo.

The single variable domains of the invention are stabilised in vivo and their half-life increased by binding to molecules which resist degradation and/or clearance or sequestration. Typically, such molecules are naturally occurring proteins which themselves have a long half-life in vivo.

Another preferred, but non-limiting example of a multispecific polypeptide of the invention comprises at least one Nanobody of the invention and at least one Nanobody that directs the polypeptide of the invention towards, and/or that allows the polypeptide of the invention to penetrate or to enter into specific organs, tissues, cells, or parts or compartments of cells, and/or that allows the Nanobody to penetrate or cross a biological barrier such as a cell membrane, a cell layer such as a layer of epithelial cells, a tumor including solid tumors, or the blood-brain-barrier. Examples of such Nanobodies include Nanobodies that are directed towards specific cell-surface proteins, markers or epitopes of the desired organ, tissue or cell (for example cell-surface markers associated with tumor cells), and the single-domain brain targeting antibody fragments described in WO 02/057445 and WO 06/040153, of which FC44 (SEQ ID NO: 189 of WO 06/040153) and FC5 (SEQ ID NO: 190 of WO 06/040154) are preferred examples.

In the single variable domains of the invention, the one or more Nanobodies and the one or more single variable domains may be directly linked to each other (as for example described in WO 99/23221) and/or may be linked to each other via one or more suitable spacers or linkers, or any combination thereof.

Suitable spacers or linkers for use in multivalent and multispecific single variable domains will be clear to the skilled person, and may generally be any linker or spacer used in the art to link amino acid sequences. Preferably, said linker or spacer is suitable for use in constructing proteins or single variable domains that are intended for pharmaceutical use.

Some particularly preferred spacers include the spacers and linkers that are used in the art to link antibody fragments or antibody domains. These include the linkers mentioned in the general background art cited above, as well as for example linkers that are used in the art to construct diabodies or ScFv fragments (in this respect, however, its should be noted that, whereas in diabodies and in ScFv fragments, the linker sequence used should have a length, a degree of flexibility and other properties that allow the pertinent $V_H$ and $V_L$ domains to come together to form the complete antigen-binding site, there is no particular limitation on the length or the flexibility of the linker used in the polypeptide of the invention, since each Nanobody by itself forms a complete antigen-binding site).

For example, a linker may be a suitable amino acid sequence, and in particular single variable domains of between 1 and 50, preferably between 1 and 30, such as between 1 and 10 amino acid residues. Some preferred examples of such single variable domains include gly-ser linkers, for example of the type $(gly_xser_y)_z$, such as (for example $(gly_4ser)_3$ or $(gly_3ser_2)_3$, as described in WO 99/42077 and the GS30, GS15, GS9 and GS7 linkers described in the applications by Ablynx mentioned herein (see for example WO 06/040153 and WO 06/122825), as well as hinge-like regions, such as the hinge regions of naturally occurring heavy chain antibodies or similar sequences (such as described in WO 94/04678).

Some other particularly preferred linkers are poly-alanine (such as AAA), as well as the linkers GS30 (SEQ ID NO: 85 in WO 06/122825) and GS9 (SEQ ID NO: 84 in WO 06/122825).

Other suitable linkers generally comprise organic compounds or polymers, in particular those suitable for use in proteins for pharmaceutical use. For instance, poly(ethyleneglycol) moieties have been used to link antibody domains, see for example WO 04/081026.

It is encompassed within the scope of the invention that the length, the degree of flexibility and/or other properties of the linker(s) used (although not critical, as it usually is for linkers used in ScFv fragments) may have some influence on the properties of the final polypeptide of the invention, including but not limited to the affinity, specificity or avidity for members for the Notch signalling pathway, or for one or more of the other antigens. Based on the disclosure herein, the skilled person will be able to determine the optimal linker(s) for use in a specific polypeptide of the invention, optionally after some limited routine experiments.

For example, in multivalent single variable domains of the invention that comprise Nanobodies directed against a multimeric antigen (such as a multimeric receptor or other protein), the length and flexibility of the linker are preferably such that it allows each Nanobody of the invention present in the polypeptide to bind to the antigenic determinant on each of the subunits of the multimer. Similarly, in a multispecific polypeptide of the invention that comprises Nanobodies directed against two or more different antigenic determinants on the same antigen (for example against different epitopes of an antigen and/or against different subunits of a multimeric receptor, channel or protein), the length and flexibility of the linker are preferably such that it allows each Nanobody to bind to its intended antigenic determinant. Again, based on the disclosure herein, the skilled person will be able to determine the optimal linker(s) for use in a specific polypeptide of the invention, optionally after some limited routine experiments.

It is also within the scope of the invention that the linker(s) used confer one or more other favourable properties or functionality to the single variable domains of the invention, and/or provide one or more sites for the formation of derivatives and/or for the attachment of functional groups (e.g. as described herein for the derivatives of the Nanobodies of the invention). For example, linkers containing one or more charged amino acid residues (see Table A-2 above) can provide improved hydrophilic properties, whereas linkers that form or contain small epitopes or tags can be used for the purposes of detection, identification and/or purification. Again, based on the disclosure herein, the skilled person will be able to determine the optimal linkers for use in a specific polypeptide of the invention, optionally after some limited routine experiments.

Finally, when two or more linkers are used in the single variable domains of the invention, these linkers may be the same or different. Again, based on the disclosure herein, the skilled person will be able to determine the optimal linkers for use in a specific polypeptide of the invention, optionally after some limited routine experiments.

Usually, for easy of expression and production, a polypeptide of the invention will be a linear polypeptide. However, the invention in its broadest sense is not limited thereto. For example, when a polypeptide of the invention comprises three of more Nanobodies, it is possible to link them by use of a linker with three or more "arms", which each "arm" being linked to a Nanobody, so as to provide a "star-shaped" construct. It is also possible, although usually less preferred, to use circular constructs.

The invention also comprises derivatives of the single variable domains of the invention, which may be essentially analogous to the derivatives of the Nanobodies of the invention, i.e. as described herein.

The invention also comprises proteins or single variable domains that "essentially consist" of a polypeptide of the invention (in which the wording "essentially consist of" has essentially the same meaning as indicated hereinabove).

According to one aspect of the invention, the polypeptide of the invention is in essentially isolated from, as defined herein.

The amino acid sequences, Nanobodies, single variable domains and nucleic acids of the invention can be prepared in a manner known per se, as will be clear to the skilled person from the further description herein. For example, the Nanobodies and polypeptides of the invention can be prepared in any manner known per se for the preparation of antibodies and in particular for the preparation of antibody fragments (including but not limited to (single) domain antibodies and ScFv fragments). Some preferred, but non-limiting methods for preparing the amino acid sequences, Nanobodies, single variable domains and nucleic acids include the methods and techniques described herein.

As will be clear to the skilled person, one particularly useful method for preparing an amino acid sequence, Nanobody and/or a polypeptide of the invention generally comprises the steps of:

i) the expression, in a suitable host cell or host organism (also referred to herein as a "host of the invention") or in another suitable expression system of a nucleic acid that encodes said amino acid sequence, Nanobody or polypeptide of the invention (also referred to herein as a "nucleic acid of the invention"), optionally followed by:

ii) isolating and/or purifying the amino acid sequence, Nanobody or polypeptide of the invention thus obtained.

In particular, such a method may comprise the steps of:

i) cultivating and/or maintaining a host of the invention under conditions that are such that said host of the invention expresses and/or produces at least one amino acid sequence, Nanobody and/or polypeptide of the invention; optionally followed by:

ii) isolating and/or purifying the amino acid sequence, Nanobody or polypeptide of the invention thus obtained.

A nucleic acid of the invention can be in the form of single or double stranded DNA or RNA, and is preferably in the form of double stranded DNA. For example, the nucleotide sequences of the invention may be genomic DNA, cDNA or synthetic DNA (such as DNA with a codon usage that has been specifically adapted for expression in the intended host cell or host organism).

According to one aspect of the invention, the nucleic acid of the invention is in essentially isolated from, as defined herein.

The nucleic acid of the invention may also be in the form of, be present in and/or be part of a vector, such as for example a plasmid, cosmid or YAC, which again may be in essentially isolated form.

The nucleic acids of the invention can be prepared or obtained in a manner known per se, based on the information on the single variable domains for the single variable domains of the invention given herein, and/or can be isolated from a suitable natural source. To provide analogs, nucleotide sequences encoding naturally occurring $V_{HH}$ domains can for example be subjected to site-directed mutagenesis, so at to provide a nucleic acid of the invention encoding said analog. Also, as will be clear to the skilled person, to prepare a nucleic acid of the invention, also several nucleotide sequences, such as at least one nucleotide sequence encoding a Nanobody and for example nucleic acids encoding one or more linkers can be linked together in a suitable manner.

Techniques for generating the nucleic acids of the invention will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers, using for example a sequence of a naturally occurring form of members of the Notch signalling pathway as a template. These and other techniques will be clear to the skilled person, and reference is again made to the standard handbooks, such as Sambrook et al. and Ausubel et al., mentioned above, as well as the Examples below.

The nucleic acid of the invention may also be in the form of, be present in and/or be part of a genetic construct, as will be clear to the person skilled in the art. Such genetic constructs generally comprise at least one nucleic acid of the invention that is optionally linked to one or more elements of genetic constructs known per se, such as for example one or more suitable regulatory elements (such as a suitable promoter(s), enhancer(s), terminator(s), etc.) and the further elements of genetic constructs referred to herein. Such genetic constructs comprising at least one nucleic acid of the invention will also be referred to herein as "genetic constructs of the invention".

The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In a preferred but non-limiting aspect, a genetic construct of the invention comprises i) at least one nucleic acid of the invention; operably connected to ii) one or more regulatory elements, such as a promoter and optionally a suitable terminator;

and optionally also iii) one or more further elements of genetic constructs known per se;

in which the terms "regulatory element", "promoter", "terminator" and "operably connected" have their usual meaning in the art (as further described herein); and in which said "further elements" present in the genetic constructs may for example be 3'- or 5'-UTR sequences, leader sequences, selection markers, expression markers/reporter genes, and/or elements that may facilitate or increase (the efficiency of) transformation or integration. These and other suitable elements for such genetic constructs will be clear to the skilled person, and may for instance depend upon the type of construct used, the intended host cell or host organism; the manner in which the nucleotide sequences of the invention of interest are to be expressed (e.g. via constitutive, transient or inducible expression); and/or the transformation technique to be used. For example, regulatory sequences, promoters and terminators known per se for the expression and production of antibodies and antibody fragments (including but not limited to (single) domain antibodies and ScFv fragments) may be used in an essentially analogous manner.

Preferably, in the genetic constructs of the invention, said at least one nucleic acid of the invention and said regulatory elements, and optionally said one or more further elements, are "operably linked" to each other, by which is generally meant that they are in a functional relationship with each other. For instance, a promoter is considered "operably linked" to a coding sequence if said promoter is able to initiate or otherwise control/regulate the transcription and/or the expression of a coding sequence (in which said coding sequence should be understood as being "under the control of" said promoter). Generally, when two nucleotide sequences are operably linked, they will be in the same orientation and usually also in the same reading frame. They will usually also be essentially contiguous, although this may also not be required.

Preferably, the regulatory and further elements of the genetic constructs of the invention are such that they are capable of providing their intended biological function in the intended host cell or host organism.

For instance, a promoter, enhancer or terminator should be "operable" in the intended host cell or host organism, by which is meant that (for example) said promoter should be capable of initiating or otherwise controlling/regulating the transcription and/or the expression of a nucleotide sequence—e.g. a coding sequence—to which it is operably linked (as defined herein).

Some particularly preferred promoters include, but are not limited to, promoters known per se for the expression in the host cells mentioned herein; and in particular promoters for the expression in the bacterial cells, such as those mentioned herein and/or those used in the Examples.

A selection marker should be such that it allows—i.e. under appropriate selection conditions—host cells and/or host organisms that have been (successfully) transformed with the nucleotide sequence of the invention to be distinguished from host cells/organisms that have not been (successfully) transformed. Some preferred, but non-limiting examples of such markers are genes that provide resistance against antibiotics (such as kanamycin or ampicillin), genes that provide for temperature resistance, or genes that allow the host cell or host organism to be maintained in the absence of certain factors, compounds and/or (food) components in the medium that are essential for survival of the non-transformed cells or organisms.

A leader sequence should be such that—in the intended host cell or host organism—it allows for the desired post-translational modifications and/or such that it directs the transcribed mRNA to a desired part or organelle of a cell. A leader sequence may also allow for secretion of the expression product from said cell. As such, the leader sequence may be any pro-, pre-, or prepro-sequence operable in the host cell or host organism. Leader sequences may not be required for expression in a bacterial cell. For example, leader sequences known per se for the expression and production of antibodies and antibody fragments (including but not limited to single domain antibodies and ScFv fragments) may be used in an essentially analogous manner.

An expression marker or reporter gene should be such that—in the host cell or host organism—it allows for detection of the expression of (a gene or nucleotide sequence present on) the genetic construct. An expression marker may optionally also allow for the localisation of the expressed product, e.g. in a specific part or organelle of a cell and/or in (a) specific cell(s), tissue(s), organ(s) or part(s) of a multicellular organism. Such reporter genes may also be expressed as a protein fusion with the amino acid sequence of the invention. Some preferred, but non-limiting examples include fluorescent proteins such as GFP.

Some preferred, but non-limiting examples of suitable promoters, terminator and further elements include those that can be used for the expression in the host cells mentioned herein; and in particular those that are suitable for expression in bacterial cells, such as those mentioned herein and/or those used in the Examples below. For some (further) non-limiting examples of the promoters, selection markers, leader sequences, expression markers and further elements that may be present/used in the genetic constructs of the invention—such as terminators, transcriptional and/or translational enhancers and/or integration factors—reference is made to the general handbooks such as Sambrook et al. and Ausubel et al. mentioned above, as well as to the examples that are given in WO 95/07463, WO 96/23810, WO 95/07463, WO 95/21191, WO 97/11094, WO 97/42320, WO 98/06737, WO 98/21355, U.S. Pat. Nos. 7,207,410, 5,693,492 and EP 1 085 089. Other examples will be clear to the skilled person. Reference is also made to the general background art cited above and the further references cited herein.

The genetic constructs of the invention may generally be provided by suitably linking the nucleotide sequence(s) of the invention to the one or more further elements described above, for example using the techniques described in the general handbooks such as Sambrook et al. and Ausubel et al., mentioned above.

Often, the genetic constructs of the invention will be obtained by inserting a nucleotide sequence of the invention in a suitable (expression) vector known per se. Some preferred, but non-limiting examples of suitable expression vectors are those used in the Examples below, as well as those mentioned herein.

The nucleic acids of the invention and/or the genetic constructs of the invention may be used to transform a host cell or host organism, i.e. for expression and/or production of the amino acid sequence, Nanobody or polypeptide of the invention. Suitable hosts or host cells will be clear to the skilled person, and may for example be any suitable fungal, prokaryotic or eukaryotic cell or cell line or any suitable fungal, prokaryotic or eukaryotic organism, for example:

a bacterial strain, including but not limited to gram-negative strains such as strains of *Escherichia coli*; of *Proteus*, for example of *Proteus mirabilis*; of *Pseudomonas*, for example of *Pseudomonas fluorescens*; and gram-positive strains such as strains of *Bacillus*, for example of *Bacillus subtilis* or of *Bacillus brevis*; of *Streptomyces*, for example of *Streptomyces lividans*; of *Staphylococcus*, for example of *Staphylococcus carnosus*; and of *Lactococcus*, for example of *Lactococcus lactis*;
 a fungal cell, including but not limited to cells from species of *Trichoderma*, for example from *Trichoderma reesei*; of *Neurospora*, for example from *Neurospora crassa*; of *Sordaria*, for example from *Sordaria macrospora*; of *Aspergillus*, for example from *Aspergillus niger* or from *Aspergillus sojae*; or from other filamentous fungi;
 a yeast cell, including but not limited to cells from species of *Saccharomyces*, for example of *Saccharomyces cerevisiae*; of *Schizosaccharomyces*, for example of *Schizosaccharomyces pombe*; of *Pichia*, for example of *Pichia pastoris* or of *Pichia methanolica*; of *Hansenula*, for example of *Hansenula polymorpha*; of *Kluyveromyces*, for example of *Kluyveromyces lactis*; of *Arxula*, for example of *Arxula adeninivorans*; of *Yarrowia*, for example of *Yarrowia lipolytica;*
 an amphibian cell or cell line, such as *Xenopus* oocytes;
 an insect-derived cell or cell line, such as cells/cell lines derived from lepidoptera, including but not limited to *Spodoptera* SF9 and Sf21 cells or cells/cell lines derived from *Drosophila*, such as Schneider and Kc cells;
 a plant or plant cell, for example in tobacco plants; and/or
 a mammalian cell or cell line, for example a cell or cell line derived from a human, a cell or a cell line from mammals including but not limited to CHO-cells, BHK-cells (for example BHK-21 cells) and human cells or cell lines such as HeLa, COS (for example COS-7) and PER.C6 cells;

as well as all other hosts or host cells known per se for the expression and production of antibodies and antibody fragments (including but not limited to (single) domain antibodies and ScFv fragments), which will be clear to the skilled person. Reference is also made to the general background art cited hereinabove, as well as to for example WO 94/29457; WO 96/34103; WO 99/42077; Frenken et al., (1998), supra; Riechmann and Muyldermans, (1999), supra; van der Linden, (2000), supra; Thomassen et al., (2002), supra; Joosten et al., (2003), supra; Joosten et al., (2005), supra; and the further references cited herein.

The amino acid sequences, Nanobodies and single variable domains of the invention can also be introduced and expressed in one or more cells, tissues or organs of a multicellular organism, for example for prophylactic and/or therapeutic purposes (e.g. as a gene therapy). For this purpose, the nucleotide sequences of the invention may be introduced into the cells or tissues in any suitable way, for example as such (e.g. using liposomes) or after they have been inserted into a suitable gene therapy vector (for example derived from retroviruses such as adenovirus, or parvoviruses such as adeno-associated virus). As will also be clear to the skilled person, such gene therapy may be performed in vivo and/or in situ in the body of a patient by administering a nucleic acid of the invention or a suitable gene therapy vector encoding the same to the patient or to specific cells or a specific tissue or organ of the patient; or suitable cells (often taken from the body of the patient to be treated, such as explanted lymphocytes, bone marrow aspirates or tissue biopsies) may be treated in vitro with a nucleotide sequence of the invention and then be suitably (re-)introduced into the body of the patient. All this can be performed using gene therapy vectors, techniques and delivery systems which are well known to the skilled person, and for example described in Culver, K. W., "Gene Therapy", 1994, p. xii, Mary Ann Liebert, Inc., Publishers, New York, N.Y.); Giordano, Nature F Medicine 2 (1996), 534-539; Schaper, Circ. Res. 79 (1996), 911-919; Anderson, Science 256 (1992), 808-813; Verma, Nature 389 (1994), 239; Isner, Lancet 348 (1996), 370-374; Muhlhauser, Circ. Res. 77 (1995), 1077-1086; Onodera, Blood 91; (1998), 30-36; Verma, Gene Ther. 5 (1998), 692-699; Nabel, Ann. N.Y. Acad. Sci.: 811 (1997), 289-292; Verzeletti, Hum. Gene Ther. 9 (1998), 2243-51; Wang, Nature Medicine 2 (1996), 714-716; WO 94/29469; WO 97/00957, U.S. Pat. No. 5,580,859; US 5,5895466; or Schaper, Current Opinion in Biotechnology 7 (1996), 635-640. For example, in situ expression of ScFv fragments (Afanasieva et al., Gene Ther., 10, 1850-1859 (2003)) and of diabodies (Blanco et al., J. Immunol, 171, 1070-1077 (2003)) has been described in the art.

For expression of the Nanobodies in a cell, they may also be expressed as so-called "intrabodies", as for example described in WO 94/02610, WO 95/22618 and U.S. Pat. No. 7,004,940; WO 03/014960; in Cattaneo, A. & Biocca, S. (1997) Intracellular Antibodies: Development and Applications. Landes and Springer-Verlag; and in Kontermann, Methods 34, (2004), 163-170.

The amino acid sequences, Nanobodies and single variable domains of the invention can for example also be produced in the milk of transgenic mammals, for example in the milk of rabbits, cows, goats or sheep (see for example U.S. Pat. Nos. 6,741,957, 6,304,489 and 6,849,992 for general techniques for introducing transgenes into mammals), in plants or parts of plants including but not limited to their leaves, flowers, fruits, seed, roots or tubers (for example in tobacco, maize, soybean or alfalfa) or in for example pupae of the silkworm *Bombix mori*.

Furthermore, the amino acid sequences, Nanobodies and single variable domains of the invention can also be expressed and/or produced in cell-free expression systems, and suitable examples of such systems will be clear to the skilled person. Some preferred, but non-limiting examples include expression in the wheat germ system; in rabbit reticulocyte lysates; or in the *E. coli* Zubay system.

As mentioned above, one of the advantages of the use of Nanobodies is that the single variable domains based thereon can be prepared through expression in a suitable bacterial system, and suitable bacterial expression systems, vectors, host cells, regulatory elements, etc., will be clear to the skilled person, for example from the references cited above. It should however be noted that the invention in its broadest sense is not limited to expression in bacterial systems.

Preferably, in the invention, an (in vivo or in vitro) expression system, such as a bacterial expression system, is used that provides the single variable domains of the invention in a form that is suitable for pharmaceutical use, and such expression systems will again be clear to the skilled person. As also will be clear to the skilled person, single variable domains of the invention suitable for pharmaceutical use can be prepared using techniques for peptide synthesis.

For production on industrial scale, preferred heterologous hosts for the (industrial) production of Nanobodies or Nanobody-containing protein therapeutics include strains of *E. coli, Pichia pastoris, S. cerevisiae* that are suitable for large scale expression/production/fermentation, and in particular for large scale pharmaceutical (i.e. GMP grade) expression/production/fermentation. Suitable examples of such strains will be clear to the skilled person. Such strains and production/expression systems are also made available by companies such as Biovitrum (Uppsala, Sweden).

Alternatively, mammalian cell lines, in particular Chinese hamster ovary (CHO) cells, can be used for large scale expression/production/fermentation, and in particular for large scale pharmaceutical expression/production/fermentation. Again, such expression/production systems are also made available by some of the companies mentioned above.

The choice of the specific expression system would depend in part on the requirement for certain post-translational modifications, more specifically glycosylation. The production of a Nanobody-containing recombinant protein for which glycosylation is desired or required would necessitate the use of mammalian expression hosts that have the ability to glycosylate the expressed protein. In this respect, it will be clear to the skilled person that the glycosylation pattern obtained (i.e. the kind, number and position of residues attached) will depend on the cell or cell line that is used for the expression. Preferably, either a human cell or cell line is used (i.e. leading to a protein that essentially has a human glycosylation pattern) or another mammalian cell line is used that can provide a glycosylation pattern that is essentially and/or functionally the same as human glycosylation or at least mimics human glycosylation. Generally, prokaryotic hosts such as *E. coli* do not have the ability to glycosylate proteins, and the use of lower eukaryotes such as yeast usually leads to a glycosylation pattern that differs from human glycosylation. Nevertheless, it should be understood that all the foregoing host cells and expression systems can be used in the invention, depending on the desired amino acid sequence, Nanobody or polypeptide to be obtained.

Thus, according to one non-limiting aspect of the invention, the amino acid sequence, Nanobody or polypeptide of the invention is glycosylated. According to another non-limiting aspect of the invention, the amino acid sequence, Nanobody or polypeptide of the invention is non-glycosylated.

According to one preferred, but non-limiting aspect of the invention, the amino acid sequence, Nanobody or polypeptide of the invention is produced in a bacterial cell, in particular a bacterial cell suitable for large scale pharmaceutical production, such as cells of the strains mentioned above.

According to another preferred, but non-limiting aspect of the invention, the amino acid sequence, Nanobody or polypeptide of the invention is produced in a yeast cell, in particular a yeast cell suitable for large scale pharmaceutical production, such as cells of the species mentioned above.

According to yet another preferred, but non-limiting aspect of the invention, the amino acid sequence, Nanobody or polypeptide of the invention is produced in a mammalian cell, in particular in a human cell or in a cell of a human cell line, and more in particular in a human cell or in a cell of a human cell line that is suitable for large scale pharmaceutical production, such as the cell lines mentioned hereinabove.

When expression in a host cell is used to produce the amino acid sequences, Nanobodies and the single variable domains of the invention, the amino acid sequences, Nanobodies and single variable domains of the invention can be produced either intracellullarly (e.g. in the cytosol, in the periplasma or in inclusion bodies) and then isolated from the host cells and optionally further purified; or can be produced extracellularly (e.g. in the medium in which the host cells are cultured) and then isolated from the culture medium and optionally further purified. When eukaryotic host cells are used, extracellular production is usually preferred since this considerably facilitates the further isolation and downstream processing of the Nanobodies and proteins obtained. Bacterial cells such as the strains of E. coli mentioned above normally do not secrete proteins extracellularly, except for a few classes of proteins such as toxins and hemolysin, and secretory production in E. coli refers to the translocation of proteins across the inner membrane to the periplasmic space. Periplasmic production provides several advantages over cytosolic production. For example, the N-terminal amino acid sequence of the secreted product can be identical to the natural gene product after cleavage of the secretion signal sequence by a specific signal peptidase. Also, there appears to be much less protease activity in the periplasm than in the cytoplasm. In addition, protein purification is simpler due to fewer contaminating proteins in the periplasm. Another advantage is that correct disulfide bonds may form because the periplasm provides a more oxidative environment than the cytoplasm. Proteins overexpressed in E. coli are often found in insoluble aggregates, so-called inclusion bodies. These inclusion bodies may be located in the cytosol or in the periplasm; the recovery of biologically active proteins from these inclusion bodies requires a denaturation/refolding process. Many recombinant proteins, including therapeutic proteins, are recovered from inclusion bodies. Alternatively, as will be clear to the skilled person, recombinant strains of bacteria that have been genetically modified so as to secrete a desired protein, and in particular an amino acid sequence, Nanobody or a polypeptide of the invention, can be used.

Thus, according to one non-limiting aspect of the invention, the amino acid sequence, Nanobody or polypeptide of the invention is an amino acid sequence, Nanobody or polypeptide that has been produced intracellularly and that has been isolated from the host cell, and in particular from a bacterial cell or from an inclusion body in a bacterial cell. According to another non-limiting aspect of the invention, the amino acid sequence, Nanobody or polypeptide of the invention is an amino acid sequence, Nanobody or polypeptide that has been produced extracellularly, and that has been isolated from the medium in which the host cell is cultivated.

Some preferred, but non-limiting promoters for use with these host cells include, for expression in E. coli: lac promoter (and derivatives thereof such as the lacUV5 promoter); arabinose promoter; left—(PL) and rightward (PR) promoter of phage lambda; promoter of the trp operon; hybrid lac/trp promoters (tac and trc); T7 promoter (more specifically that of T7-phage gene 10) and other T-phage promoters; promoter of the Tn10 tetracycline resistance gene; engineered variants of the above promoters that include one or more copies of an extraneous regulatory operator sequence;

for expression in S. cerevisiae: constitutive: ADH1 (alcohol dehydrogenase 1), ENO (enolase), CYC1 (cytochrome c iso-1), GAPDH (glyceraldehydes-3-phosphate dehydrogenase), PGK1 (phosphoglycerate kinase), PYK1 (pyruvate kinase); regulated: GAL1,10,7 (galactose metabolic enzymes), ADH2 (alcohol dehydrogenase 2), PHO5 (acid phosphatase), CUP1 (copper metallothionein); heterologous: CaMV (cauliflower mosaic virus 35S promoter);

for expression in Pichia pastoris: the AOX1 promoter (alcohol oxidase I);

for expression in mammalian cells: human cytomegalovirus (hCMV) immediate early enhancer/promoter; human cytomegalovirus (hCMV) immediate early promoter variant that contains two tetracycline operator sequences such that the promoter can be regulated by the Tet repressor; Herpes Simplex Virus thymidine kinase (TK) promoter; Rous Sarcoma Virus long terminal repeat (RSV LTR) enhancer/promoter; elongation factor 1α (hEF-1α) promoter from human, chimpanzee, mouse or rat; the SV40 early promoter; HIV-1 long terminal repeat promoter; β-actin promoter;

Some preferred, but non-limiting vectors for use with these host cells include:

vectors for expression in mammalian cells: pMAMneo (Clontech), pcDNA3 (Invitrogen), pMC1neo (Stratagene), pSG5 (Stratagene), EBO-pSV2-neo (ATCC 37593), pBPV-1 (8-2) (ATCC 37110), pdBPV-MMTneo (342-12) (ATCC 37224), pRSVgpt (ATCC37199), pRSVneo (ATCC37198), pSV2-dhfr (ATCC 37146), pUC-Tag (ATCC 37460) and 1ZD35 (ATCC 37565), as well as viral-based expression systems, such as those based on adenovirus;

vectors for expression in bacterial cells: pET vectors (Novagen) and pQE vectors (Qiagen);

vectors for expression in yeast or other fungal cells: pYES2 (Invitrogen) and Pichia expression vectors (Invitrogen);

vectors for expression in insect cells: pBlueBacII (Invitrogen) and other baculovirus vectors vectors for expression in plants or plant cells: for example vectors based on cauliflower mosaic virus or tobacco mosaic virus, suitable strains of Agrobacterium, or Ti-plasmid based vectors.

Some preferred, but non-limiting secretory sequences for use with these host cells include:

for use in bacterial cells such as E. coli: PelB, Bla, OmpA, OmpC, OmpF, OmpT, StII, PhoA, PhoE, MalE, Lpp, LamB, and the like; TAT signal peptide, hemolysin C-terminal secretion signal;

for use in yeast: α-mating factor prepro-sequence, phosphatase (pho1), invertase (Suc), etc., for use in mammalian cells: indigenous signal in case the target protein is of eukaryotic origin; murine Ig η-chain V-J2-C signal peptide; etc.

Suitable techniques for transforming a host or host cell of the invention will be clear to the skilled person and may depend on the intended host cell/host organism and the genetic construct to be used. Reference is again made to the handbooks and patent applications mentioned above.

After transformation, a step for detecting and selecting those host cells or host organisms that have been successfully transformed with the nucleotide sequence/genetic construct of the invention may be performed. This may for instance be a selection step based on a selectable marker present in the genetic construct of the invention or a step involving the detection of the amino acid sequence of the invention, e.g. using specific antibodies.

The transformed host cell (which may be in the form or a stable cell line) or host organisms (which may be in the form of a stable mutant line or strain) form further aspects of the present invention.

Preferably, these host cells or host organisms are such that they express, or are (at least) capable of expressing (e.g. under suitable conditions), an amino acid sequence, Nanobody or polypeptide of the invention (and in case of a host organism: in at least one cell, part, tissue or organ thereof). The invention also includes further generations, progeny and/or offspring of the host cell or host organism of the invention, that may for instance be obtained by cell division or by sexual or asexual reproduction.

To produce/obtain expression of the single variable domains of the invention, the transformed host cell or transformed host organism may generally be kept, maintained and/or cultured under conditions such that the (desired) amino acid sequence, Nanobody or polypeptide of the invention is expressed/produced. Suitable conditions will be clear to the skilled person and will usually depend upon the host cell/host organism used, as well as on the regulatory elements that control the expression of the (relevant) nucleotide sequence of the invention. Again, reference is made to the handbooks and patent applications mentioned above in the paragraphs on the genetic constructs of the invention.

Generally, suitable conditions may include the use of a suitable medium, the presence of a suitable source of food and/or suitable nutrients, the use of a suitable temperature, and optionally the presence of a suitable inducing factor or compound (e.g. when the nucleotide sequences of the invention are under the control of an inducible promoter); all of which may be selected by the skilled person. Again, under such conditions, the single variable domains of the invention may be expressed in a constitutive manner, in a transient manner, or only when suitably induced.

It will also be clear to the skilled person that the amino acid sequence, Nanobody or polypeptide of the invention may (first) be generated in an immature form (as mentioned above), which may then be subjected to post-translational modification, depending on the host cell/host organism used. Also, the amino acid sequence, Nanobody or polypeptide of the invention may be glycosylated, again depending on the host cell/host organism used.

The amino acid sequence, Nanobody or polypeptide of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g. using a specific, cleavable amino acid sequence fused with the amino acid sequence, Nanobody or polypeptide of the invention) and/or preparative immunological techniques (i.e. using antibodies against the amino acid sequence to be isolated).

Generally, for pharmaceutical use, the single variable domains of the invention may be formulated as a pharmaceutical preparation or compositions comprising at least one polypeptide of the invention and at least one pharmaceutically acceptable carrier, diluent or excipient and/or adjuvant, and optionally one or more further pharmaceutically active single variable domains and/or compounds. By means of non-limiting examples, such a formulation may be in a form suitable for oral administration, for parenteral administration (such as by intravenous, intramuscular or subcutaneous injection or intravenous infusion), for topical administration, for administration by inhalation, by a skin patch, by an implant, by a suppository, etc. Such suitable administration forms—which may be solid, semi-solid or liquid, depending on the manner of administration—as well as methods and carriers for use in the preparation thereof, will be clear to the skilled person, and are further described herein.

Thus, in a further aspect, the invention relates to a pharmaceutical composition that contains at least one amino acid of the invention, at least one Nanobody of the invention or at least one polypeptide of the invention and at least one suitable carrier, diluent or excipient (i.e. suitable for pharmaceutical use), and optionally one or more further active substances.

Generally, the amino acid sequences, Nanobodies and single variable domains of the invention can be formulated and administered in any suitable manner known per se, for which reference is for example made to the general background art cited above (and in particular to WO 04/041862, WO 04/041863, WO 04/041865 and WO 04/041867) as well as to the standard handbooks, such as Remington's Pharmaceutical Sciences, $18^{th}$ Ed., Mack Publishing Company, USA (1990) or Remington, the Science and Practice of Pharmacy, 21st Edition, Lippincott Williams and Wilkins (2005).

For example, the amino acid sequences, Nanobodies and single variable domains of the invention may be formulated and administered in any manner known per se for conventional antibodies and antibody fragments (including ScFv's and diabodies) and other pharmaceutically active proteins. Such formulations and methods for preparing the same will be clear to the skilled person, and for example include preparations suitable for parenteral administration (for example intravenous, intraperitoneal, subcutaneous, intramuscular, intraluminal, intra-arterial or intrathecal administration) or for topical (i.e. transdermal or intradermal) administration.

Preparations for parenteral administration may for example be sterile solutions, suspensions, dispersions or emulsions that are suitable for infusion or injection. Suitable carriers or diluents for such preparations for example include, without limitation, sterile water and aqueous buffers and solutions such as physiological phosphate-buffered saline, Ringer's solutions, dextrose solution, and Hank's solution; water oils; glycerol; ethanol; glycols such as propylene glycol or as well as mineral oils, animal oils and vegetable oils, for example peanut oil, soybean oil, as well as suitable mixtures thereof. Usually, aqueous solutions or suspensions will be preferred.

The amino acid sequences, Nanobodies and single variable domains of the invention can also be administered using gene therapy methods of delivery. See, e.g., U.S. Pat. No. 5,399,346, which is incorporated by reference in its entirety. Using a gene therapy method of delivery, primary cells transfected with the gene encoding an amino acid sequence, Nanobody or polypeptide of the invention can additionally be transfected with tissue specific promoters to target specific organs, tissue, grafts, tumors, or cells and can additionally be transfected with signal and stabilization sequences for subcellularly localized expression.

Thus, the amino acid sequences, Nanobodies and single variable domains of the invention may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the amino acid sequences, Nanobodies and single variable domains of the invention may be combined with one or more excipients and used in the form of ingestible tablets, buccal tablets, troches, capsules, elixirs, suspensions, syrups, wafers, and the like. Such compositions and preparations should contain at least 0.1% of the amino acid sequence, Nanobody or polypeptide of the invention. Their percentage in the compositions and preparations may, of course, be varied and may conveniently be between about 2 to about 60% of the weight of a given unit dosage form. The amount of the amino acid sequence, Nanobody or polypeptide of the invention in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the amino acid sequences, Nanobodies and single variable domains of the invention, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the amino acid sequences, Nanobodies and single variable domains of the invention may be incorporated into sustained-release preparations and devices.

Preparations and formulations for oral administration may also be provided with an enteric coating that will allow the constructs of the invention to resist the gastric environment and pass into the intestines. More generally, preparations and formulations for oral administration may be suitably formulated for delivery into any desired part of the gastrointestinal tract. In addition, suitable suppositories may be used for delivery into the gastrointestinal tract.

The amino acid sequences, Nanobodies and single variable domains of the invention may also be administered intravenously or intraperitoneally by infusion or injection. Solutions of the amino acid sequences, Nanobodies and single variable domains of the invention or their salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the amino acid sequences, Nanobodies and single variable domains of the invention in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the amino acid sequences, Nanobodies and single variable domains of the invention may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, hydroxyalkyls or glycols or water-alcohol/glycol blends, in which the amino acid sequences, Nanobodies and single variable domains of the invention can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the amino acid sequences, Nanobodies and single variable domains of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820, 508).

Useful dosages of the amino acid sequences, Nanobodies and single variable domains of the invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the amino acid sequences, Nanobodies and single variable domains of the invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the amino acid sequences, Nanobodies and single variable domains of the invention required for use in treatment will vary not only with the particular amino acid sequence, Nanobody or polypeptide selected but also with the route of administration, the nature of the condition being treated and the age and condition of the patient and will be ultimately at the discretion of the attendant physician or clinician. Also the dosage of the amino acid sequences, Nanobodies and single variable domains of the invention varies depending on the target cell, tumor, tissue, graft, or organ.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

An administration regimen could include long-term, daily treatment. By "long-term" is meant at least two weeks and preferably, several weeks, months, or years of duration. Necessary modifications in this dosage range may be determined by one of ordinary skill in the art using only routine experimentation given the teachings herein. See Remington's Pharmaceutical Sciences (Martin, E. W., ed. 4), Mack Publishing Co., Easton, Pa. The dosage can also be adjusted by the individual physician in the event of any complication.

In another aspect, the invention relates to a method for the prevention and/or treatment of at least one cancer, neurodegenerative diseases and immunomodulatory diseases, said method comprising administering, to a subject in need thereof, a pharmaceutically active amount of an amino acid sequence of the invention, of a Nanobody of the invention, of a polypeptide of the invention, and/or of a pharmaceutical composition comprising the same.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The subject to be treated may be any warm-blooded animal, but is in particular a mammal, and more in particular a human being. As will be clear to the skilled person, the subject to be treated will in particular be a person suffering from, or at risk of, the diseases and disorders mentioned herein.

The invention relates to a method for the prevention and/or treatment of at least one disease or disorder that is associated with members for the Notch signalling pathway, with its biological or pharmacological activity, and/or with the biological pathways or signalling in which members of the Notch signalling pathway is involved, said method comprising administering, to a subject in need thereof, a pharmaceutically active amount of an amino acid sequence of the invention, of a Nanobody of the invention, of a polypeptide of the invention, and/or of a pharmaceutical composition comprising the same. In particular, the invention relates to a method for the prevention and/or treatment of at least one disease or disorder that can be treated by modulating members for the Notch signalling pathway, its biological or pharmacological activity, and/or the biological pathways or signalling in which members of the Notch signalling pathway is involved, said method comprising administering, to a subject in need thereof, a pharmaceutically active amount of an amino acid sequence of the invention, of a Nanobody of the invention, of a polypeptide of the invention, and/or of a pharmaceutical composition comprising the same. In particular, said pharmaceutically effective amount may be an amount that is sufficient to modulate members for the Notch signalling pathway, its biological or pharmacological activity, and/or the biological pathways or signalling in which members of the Notch signalling pathway is involved; and/or an amount that provides a level of the amino acid sequence of the invention, of a Nanobody of the invention, of a polypeptide of the invention in the circulation that is sufficient to modulate members for the Notch signalling pathway, its biological or pharmacological activity, and/or the biological pathways or signalling in which members of the Notch signalling pathway is involved.

The invention furthermore relates to a method for the prevention and/or treatment of at least one disease or disorder that can be prevented and/or treated by administering an amino acid sequence of the invention, a Nanobody of the invention or a polypeptide of the invention to a patient, said method comprising administering, to a subject in need thereof, a pharmaceutically active amount of an amino acid sequence of the invention, of a Nanobody of the invention, of a polypeptide of the invention, and/or of a pharmaceutical composition comprising the same.

More in particular, the invention relates to a method for the prevention and/or treatment of at least one disease or disorder chosen from the group consisting of the diseases and disorders listed herein, said method comprising administering, to a subject in need thereof, a pharmaceutically active amount of an amino acid sequence of the invention, of a Nanobody of the invention, of a polypeptide of the invention, and/or of a pharmaceutical composition comprising the same.

In another aspect, the invention relates to a method for immunotherapy, and in particular for passive immunotherapy, which method comprises administering, to a subject suffering from or at risk of the diseases and disorders mentioned herein, a pharmaceutically active amount of an amino acid sequence of the invention, of a Nanobody of the invention, of a polypeptide of the invention, and/or of a pharmaceutical composition comprising the same.

In the above methods, the amino acid sequences, Nanobodies and/or single variable domains of the invention and/or the compositions comprising the same can be administered in any suitable manner, depending on the specific pharmaceutical formulation or composition to be used. Thus, the amino acid sequences, Nanobodies and/or single variable domains of the invention and/or the compositions comprising the same can for example be administered orally, intraperitoneally (e.g. intravenously, subcutaneously, intramuscularly, or via any other route of administration that circumvents the gastrointestinal tract), intranasally, transdermally, topically, by means of a suppository, by inhalation, again depending on the specific pharmaceutical formulation or composition to be used. The clinician will be able to select a suitable route of administration and a suitable pharmaceutical formulation or composition to be used in such administration, depending on the disease or disorder to be prevented or treated and other factors well known to the clinician.

The amino acid sequences, Nanobodies and/or single variable domains of the invention and/or the compositions comprising the same are administered according to a regime of treatment that is suitable for preventing and/or treating the disease or disorder to be prevented or treated. The clinician will generally be able to determine a suitable treatment regimen, depending on factors such as the disease or disorder to be prevented or treated, the severity of the disease to be treated and/or the severity of the symptoms thereof, the specific amino acid sequence, Nanobody or polypeptide of the invention to be used, the specific route of administration and pharmaceutical formulation or composition to be used, the age, gender, weight, diet, general condition of the patient, and similar factors well known to the clinician.

Generally, the treatment regimen will comprise the administration of one or more amino acid sequences, Nanobodies and/or single variable domains of the invention, or of one or more compositions comprising the same, in one or more pharmaceutically effective amounts or doses. The specific amount(s) or doses to be administered can be determined by the clinician, again based on the factors cited above.

Generally, for the prevention and/or treatment of the diseases and disorders mentioned herein and depending on the specific disease or disorder to be treated, the potency of the specific amino acid sequence, Nanobody and polypeptide of the invention to be used, the specific route of administration and the specific pharmaceutical formulation or composition used, the amino acid sequences, Nanobodies and single variable domains of the invention will generally be administered in an amount between 1 gram and 0.01 microgram per kg body weight per day, preferably between 0.1 gram and 0.1 microgram per kg body weight per day, such as about 1, 10, 100 or 1000 microgram per kg body weight per day, either continuously (e.g. by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment. Generally, some guidance on the amounts to be administered can be obtained from the amounts usually administered for comparable conventional antibodies or antibody fragments against the same target administered via essentially the same route, taking into account however differences in affinity/avidity, efficacy, biodistribution, half-life and similar factors well known to the skilled person.

Usually, in the above method, a single amino acid sequence, Nanobody or polypeptide of the invention will be used. It is however within the scope of the invention to use two or more amino acid sequences, Nanobodies and/or single variable domains of the invention in combination.

The Nanobodies, single variable domains of the invention may also be used in combination with one or more further pharmaceutically active compounds or principles, i.e. as a combined treatment regimen, which may or may not lead to a synergistic effect. Again, the clinician will be able to select such further compounds or principles, as well as a suitable combined treatment regimen, based on the factors cited above and his expert judgement.

In particular, the amino acid sequences, Nanobodies and single variable domains of the invention may be used in combination with other pharmaceutically active compounds or principles that are or can be used for the prevention and/or treatment of the diseases and disorders cited herein, as a result of which a synergistic effect may or may not be obtained. Examples of such compounds and principles, as well as routes, methods and pharmaceutical formulations or compositions for administering them will be clear to the clinician.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmaceutical or therapeutic effect.

The effectiveness of the treatment regimen used according to the invention may be determined and/or followed in any manner known per se for the disease or disorder involved, as will be clear to the clinician. The clinician will also be able, where appropriate and on a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

In another aspect, the invention relates to the use of an amino acid sequence, Nanobody or polypeptide of the invention in the preparation of a pharmaceutical composition for prevention and/or treatment of at least one cancer, neurodegenerative diseases and immunomodulatory diseases; and/or for use in one or more of the methods of treatment mentioned herein.

The subject to be treated may be any warm-blooded animal, but is in particular a mammal, and more in particular a human being. As will be clear to the skilled person, the subject to be treated will in particular be a person suffering from, or at risk of, the diseases and disorders mentioned herein.

The invention also relates to the use of an amino acid sequence, Nanobody or polypeptide of the invention in the preparation of a pharmaceutical composition for the prevention and/or treatment of at least one disease or disorder that can be prevented and/or treated by administering an amino acid sequence, Nanobody or polypeptide of the invention to a patient.

More in particular, the invention relates to the use of an amino acid sequence, Nanobody or polypeptide of the invention in the preparation of a pharmaceutical composition for the prevention and/or treatment of cancer, neurodegenerative diseases and immunomodulatory diseases, and in particular for the prevention and treatment of one or more of the diseases and disorders listed herein.

Again, in such a pharmaceutical composition, the one or more amino acid sequences, Nanobodies or single variable domains of the invention may also be suitably combined with one or more other active principles, such as those mentioned herein.

Finally, although the use of the Nanobodies of the invention (as defined herein) and of the single variable domains of the invention is much preferred, it will be clear that on the basis of the description herein, the skilled person will also be able to design and/or generate, in an analogous manner, other in particular (single) domain antibodies against members for the Notch signalling pathway, as well as single variable domains comprising such (single) domain antibodies.

For example, it will also be clear to the skilled person that it may be possible to "graft" one or more of the CDR's mentioned above for the Nanobodies of the invention onto such (single) domain antibodies or other protein scaffolds, including but not limited to human scaffolds or non-immunoglobulin scaffolds. Suitable scaffolds and techniques for such CDR grafting will be clear to the skilled person and are well known in the art, see for example U.S. Pat. No. 7,180, 370, WO 01/27160, EP 0 605 522, EP 0 460 167, U.S. Pat. No. 7,054,297, Nicaise et al., Protein Science (2004), 13:1882-1891; Ewert et al., Methods, 2004 October; 34(2):184-199; Kettleborough et al., Protein Eng. 1991 October; 4(7): 773-783; O'Brien and Jones, Methods Mol. Biol. 2003:207:81-100; Skerra, J. Mol. Recognit. 2000:13:167-187, and Saerens et al., J. Mol. Biol. 2005 Sep. 23; 352 (3):597-607, and the further references cited therein. For example, techniques known per se for grafting mouse or rat CDR's onto human frameworks and scaffolds can be used in an analogous manner to provide chimeric proteins comprising one or more of the CDR's of the Nanobodies of the invention and one or more human framework regions or sequences.

It should also be noted that, when the Nanobodies of the inventions contain one or more other CDR sequences than the preferred CDR sequences mentioned above, these CDR sequences can be obtained in any manner known per se, for example from Nanobodies (preferred), $V_H$ domains from conventional antibodies (and in particular from human antibodies), heavy chain antibodies, conventional 4-chain antibodies (such as conventional human 4-chain antibodies) or other immunoglobulin sequences directed against members for the Notch signalling pathway. Such immunoglobulin sequences directed against members of the Notch signalling pathway can be generated in any manner known per se, as will be clear to the skilled person, i.e. by immunization with members of the Notch signalling pathway or by screening a suitable library of immunoglobulin sequences with members for the Notch signalling pathway, or any suitable combination thereof. Optionally, this may be followed by techniques such as random or site-directed mutagenesis and/or other techniques for affinity maturation known per se. Suitable techniques for generating such immunoglobulin sequences will be clear to the skilled person, and for example include the screening techniques reviewed by Hoogenboom, Nature Biotechnology, 23, 9, 1105-1116 (2005) Other techniques for generating immunoglobulins against a specified target include for example the Nanoclone technology (as for example described in the published US patent application 2006-0211088), so-called SLAM technology (as for example described in the European patent application 0 542 810), the use of transgenic mice expressing human immunoglobulins or the well-known hybridoma techniques (see for example Larrick et al, Biotechnology, Vol. 7, 1989, p. 934). All these techniques can be used to generate immunoglobulins against members for the Notch signalling pathway, and the CDR's of such immunoglobulins can be used in the Nanobodies of the invention, i.e. as outlined above. For example, the sequence of such a CDR can be determined, synthesized and/or isolated, and inserted into the sequence of a Nanobody of the invention (e.g. so as to replace the corresponding native CDR), all using techniques known per se such as those described herein, or Nanobodies of the invention containing such CDR's (or nucleic acids encoding the same) can be synthesized de novo, again using the techniques mentioned herein.

Further uses of the amino acid sequences, Nanobodies, single variable domains, nucleic acids, genetic constructs and hosts and host cells of the invention will be clear to the skilled person based on the disclosure herein. For example, and without limitation, the single variable domains of the invention can be linked to a suitable carrier or solid support so as to provide a medium than can be used in a manner known per se to purify members of the Notch signalling pathway from compositions and preparations comprising the same. Derivatives of the single variable domains of the invention that comprise a suitable detectable label can also be used as markers to determine (qualitatively or quantitatively) the presence of members of the Notch signalling pathway in a composition or preparation or as a marker to selectively detect the presence of members of the Notch signalling pathway on the surface of a cell or tissue (for example, in combination with suitable cell sorting techniques).

The invention will now be further described by means of the following non-limiting examples and figures:

Figures:

FIG. 1: The results in FIG. 1 show that most Nanobodies of Table B-1 were able to bind to human Notch-1 in a concentration dependent manner.

Figure 2:
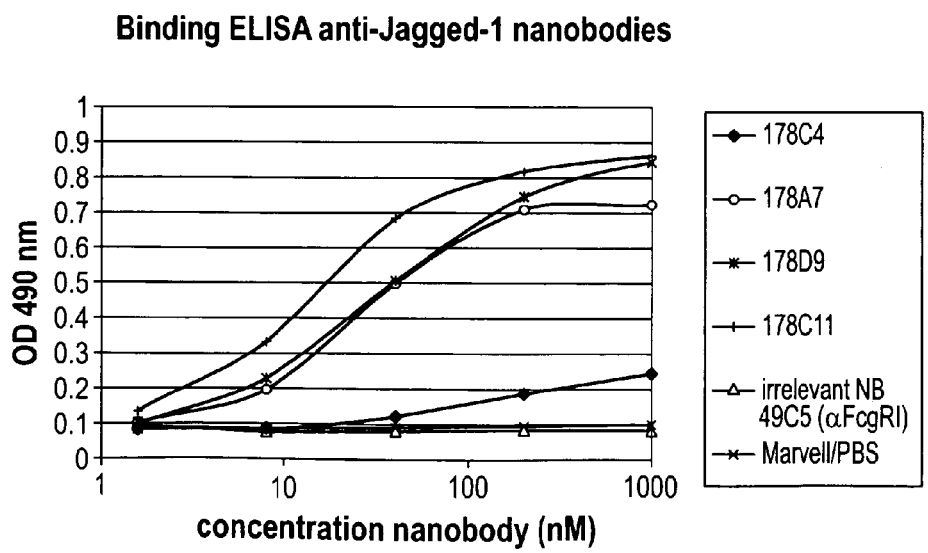

FIG. 2: Binding assay of Nanobodies selected for Jagged-1. All Nanobodies were able to bind in a concentration dependent matter. An irrelevant Nanobody is not able to bind to Jagged-1.

Figure 3:
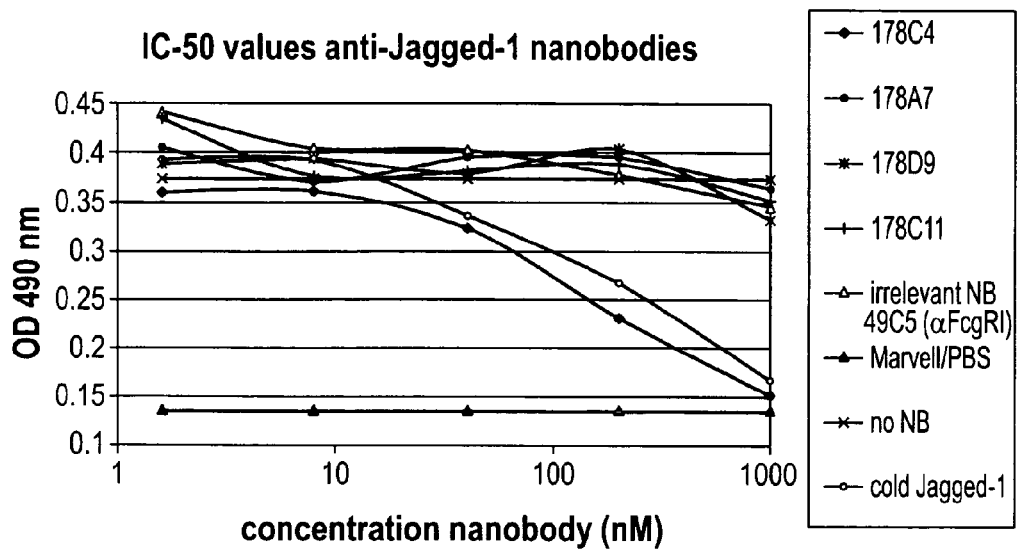

FIG. 3: Competition assay of Nanobodies selected for Jagged-1. Nanobody 178C4 is able to compete for Jagged-1 binding to Notch-1 in a concentration dependent matter. An irrelevant Nanobody is not able to compete for Jagged-1 binding to Notch-1. Non-biotinylated Jagged-1 is also able to compete for biot-Jagged-1 binding to Notch-1.

Figure 4:
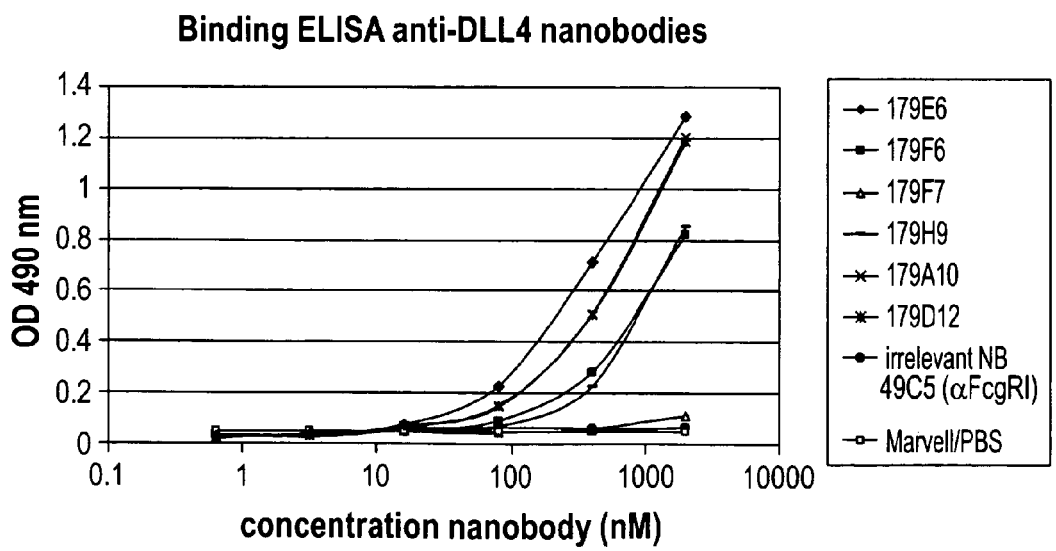

FIG. 4: Binding assay of Nanobodies selected for DLL4. All Nanobodies are able to bind in a concentration dependent matter. An irrelevant Nanobody is not able to bind to DLL4.

Figure 5:
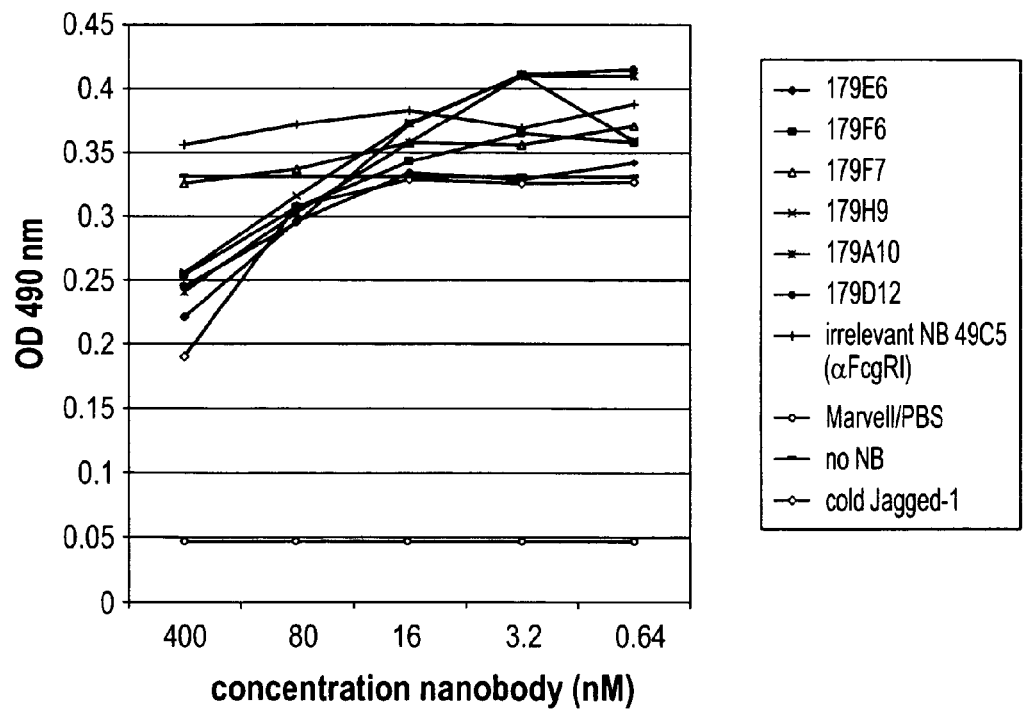

FIG. 5: Competition assay of Nanobodies selected for DLL4. Some Nanobodies are able to compete for DLL4 to Notch-1 in a concentration dependent matter. An irrelevant Nanobody is not able to compete for DLL4 binding to Notch-1.

Figure 6B:
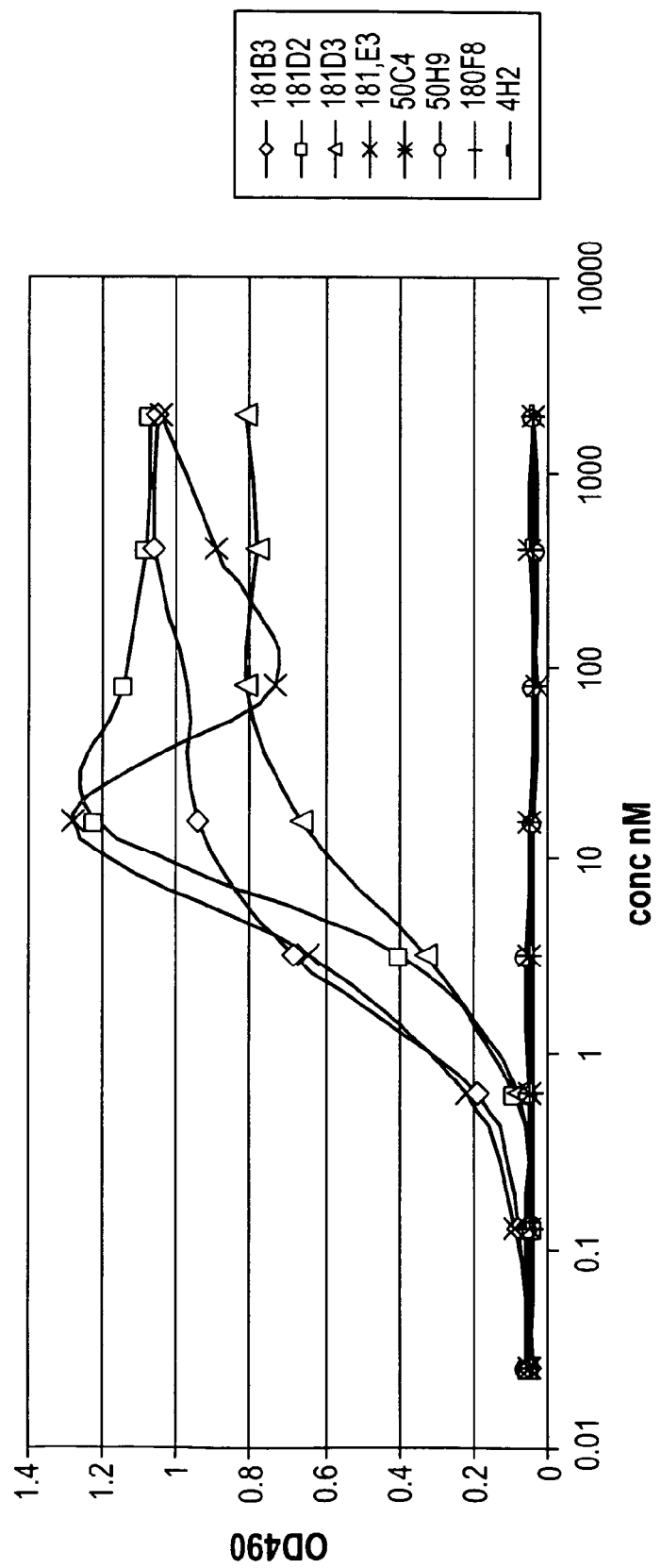
Figure 6C:
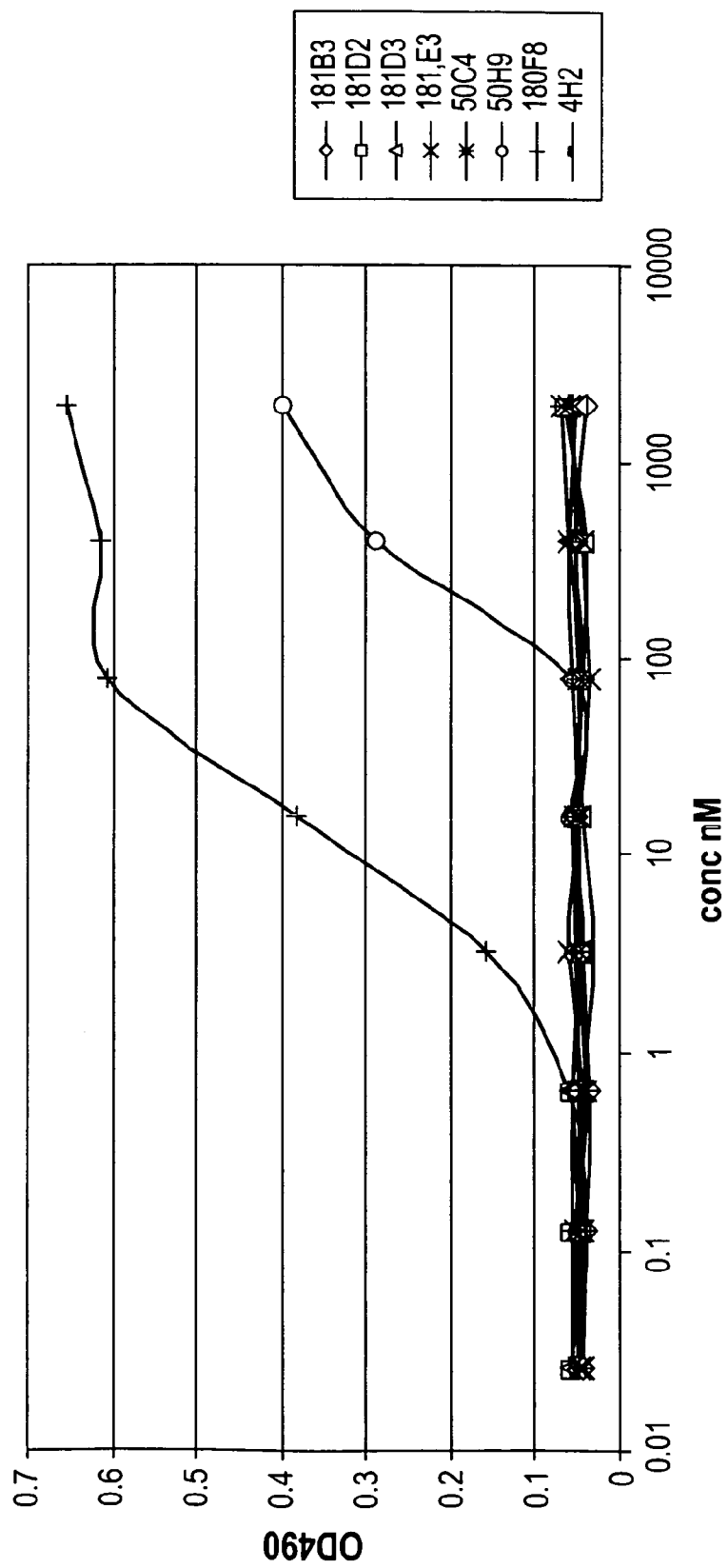

FIG. 6: Binding assay to CD36-Fc (FIG. 6a), human Notch-2 (FIG. 6b), human Notch-1 (FIG. 6c), and human Notch-3 (FIG. 6d).

EXPERIMENTAL PART

Example 1

Generation of Nanobodies Specifically Binding to Human Notch-1

1.1. Animal Immunizations

Two llamas—*lama glama* (designated "Llama 161" and "Llama 166") were immunized by intramuscular injection in the neck at 2 different spots with 2 boosts of antigen cocktail preparations comprising 40 microgram of recombinant human Notch-1/Fc Chimera (R&D Systems Cat No 3647-TK) at day 0 and day 7 and 4 boosts of the same cocktail comprising 20 microgram of recombinant human Notch-1/Fc Chimera at day 14, 21, 28 and 35. The antigen cocktail was prepared by a) mixing above amounts of recombinant human Notch-1/Fc Chimera in a total of 2 ml PBS; and b) adding this mixture very slowly to 2.5 ml of the adjuvants Stimune (Stimune, previously known as Specol; Cedi-diagnostics, Lelystad, The Netherlands); and c) mixing vigorously for 1 minute. Blood is collected from these animals 4 and 8 days after boost 6. In addition, approximately 1 g of lymph node is collected from each animal 5 days after boost 6.

1.2. Library Construction

The library was prepared according to a standard protocol known to the skilled person in the art. In short, peripheral blood mononuclear cells are prepared from blood samples using Ficoll-Hypaque according to the manufacturer's instructions. Next, total RNA was extracted from these cells and lymph node tissue and used as starting material for RT-PCR to amplify VHH fragments encoding gene fragments. Then, a ligation was prepared between VHH fragments prepared from an immunized animal (330 ng cDNA per library) and pAX50 vector digested with BstEII/SfiI/XhoI (pAX50, an expression vector, is used that is derived from pUC119 which contains the LacZ promoter, a coliphage pIII protein coding sequence, a resistance gene for ampicillin or carbenicillin, a multicloning site and the gen3 leader sequence. In frame with the Nanobody coding sequence, the vector codes for a C-terminal c-myc tag and a His6x tag). Then, electrocompetent *E. coli* TG1 cells were transformed with ligated vectors containing the various VHH sequences by electroporation, grown at suitable conditions, prepared for storage. So obtained libraries comprising phage particles were stored at −80 degrees Celsius.

1.3. Selections of Human Notch-1 Binding Nanobodies

1$^{st}$ Round of Selection:

The above prepared library was rescued, i.e. the above prepared phage particles containing the VHH sequences were released upon maturation of the TG1 *E. coli* cells by infection with helper phage VCSM13 (Stratagene) with a multiplicity of infection of 10 (i.e. each bacterial cell is infected with no more than 10 helper phage particles. Rescued phage libraries designated as "library 161" (derived from "Llama 161") and "library 166" (derived from "Llama 166") were used for selections on recombinant human Notch-1/Fc Chimera (R&D Systems Cat No 3647-TK)—hereinafter "Notch-1/Fc". Notch-1/Fc was immobilized directly on Maxisorp 96 well microtiter plates (Nunc) at 5 microgram/ml and 0.5 microgram/ml. In addition, a control without Notch-1/Fc was treated in parallel to the Notch/Fc incubated wells. To minimize the number of phage binding to the Fc portion of Notch-1/Fc the phage was pre-incubated with 150 microgram/ml of human IgG for 1 h at room temperature (hereinafter "RT"). Following incubation with the rescued phage libraries 161 and 166 (100 microliter of 10 microliter library in 2% marvel PBS for 2 h at RT), extensive washing (PBS in 0.05% Tween 20), bound phage was eluted aspecific with 1 mg/ml freshly prepared trypsin in PBS. The eluted phages of library 161 and 166 were amplified and the 5 microgram/ml Notch-1/Fc fractions of both libraries pooled and applied to a second round of selection on 5 microgram/ml, 0.5 microgram/ml, 0 microgram/ml (control) immobilized Notch-1/Fc. To minimize the number of phage binding to the Fc-portion of Notch-1/Fc the phage is pre-incubated with 150 microgram/ml human IgG. Individual colonies obtained from the eluted phage pools (obtained from all 4 conditions, i.e. both libraries and both concentrations of Notch-1/Fc) were grown and induced with IPTG for Nanobodies-expression and extraction (periplasmic extracts) according to standard methods.

1.4. Screening for Human Notch-1 Binding Nanobodies

In order to identify Nanobodies with binding specificity to human Notch-1, individual clones picked from above selected Nanobodies are further tested in an ELISA binding assay setup. In short, 2 microgram/ml of human Notch-1/Fc was immobilized on Maxisorp ELISA plates (Nunc) in PBS over night (O/N) at 4 degrees Celsius (4° C.). After washing the plate was blocked using 4% Marvel skimmed milk in PBS for 30 minutes on shaker. A concentration series of Nanobody (1 to 1000 nM) was added in 100 microliter 2% Marvell/PBS and incubated for 1 h on shaker. After washing human Notch-1 binding Nanobodies were detected with 100 microliter 1:5000 Mouse-anti-MycTag in 2% Marvell/PBS and 100 microliter 1:5000 DAMPO in 2% Marvell/PBS for 1 h on shaker. PO was detected with 100 microliter OPD and stopped with 50 microliter H2SO4. Quantification was performed at 490 nm in a plate reader. The results in FIG. 1 show that most Nanobodies of Table B-1 were able to bind to human Notch-1 in a concentration dependent manner.

TABLE B-1

Selected Nanobodies against human Notch-1.

| Name | SEQ ID NO: | Sequence |
|---|---|---|
| >180A4 | 339 | EVQLVESGGGLVQPGGSLRLSCAASGRTSSPIAMGWFRQAPGKEREFVSGI TWSGAYTHYANSVKGRFTISRDSAKNTVYLQMNSLKPEDTAVYYCTTATNST TGYDYWGQGTQVTVSS |
| >180B1 | 340 | EVQLVESGGDLVQPGGSLRLSCAASGTVFSNNDMGWSRQAPGKERELVAS FTSGGNTVYADAAKGRFTISRDNSKNTVYLEMNSLKPDDTAVYYCRVVDLLR GKLYWGQGTQVTVSS |
| >180B3 | 341 | EVQLVESGGDLVQPGGSLRLSCAASGTVFSNNDMGWSRQAPGKERELVAS FTSGGNTVYADAAKGRFTISRDNSKNTVYLEMNSLKPDDTAVYYCRVVDLLR GKLYWGQGTQVTVSS |

TABLE B-1-continued

Selected Nanobodies against human Notch-1.

| Name | SEQ ID NO: | Sequence |
|---|---|---|
| >180C1 | 342 | EVQLVESGGDLVQPGGSLRLSCAASRTVFSISDMGWSRQAPGKERELVASI SSDNYTVYADAAKGRFTISRDNSKNTVYLEMNSLKPDDTAVYYCRVVDPLR GKLYWGQGTQVTVSS |
| >180C7 | 343 | EVQLVESGGGLVQAGGSLRLSCAASGGIFGINAVAWYRQAPGKERDWVALI VGEAITRYTDSVSGRFTISRDNAKNTVYLEMNSLKPDDTAVYYCRVVDPLRG KLYWGQGTQVTVSS |
| >180F8 | 344 | EVQLVESGGDLVQPGGSLRLSCTTSGTVFSINDMGWSRQAPGKGRELVASI SSEGTTIYADAAKGRFTISRDNSKNTVYLEMNSLKPDDTAVYYCRVVDPLRG KLYWGQGTQVTVSS |
| >180F4 | 345 | EVQLVESGGGLVQAGDSLRLSCAVSGGSFSSYTMGWVRQAPGKEREAVAS IWRSGGNTYYADSVKGRFTVSRDNAKHTVYLQMNSLKPEDTAVYYCAAASF APGSRGYDYWGQGTQVTVSS |
| >180F5 | 346 | EVQLVESGGGLVQPGGSLRLSCAASGRTSSPIAMGWFRQAPGKEREFVSGI TWSGAYTHYANSVKGRFTISRDSAKNTVYLQMNSLKPEDTAVYYCTTATNST TGYDYWGQGTQVTVSS |

Above set of selected single variable domains (Nanobodies™) consists of 5 families:
Family 1: 180B1, 180B3, 180F10
Family 2: 180A4
Family 3: 180F4
Family 4: 180C11
Family 5: 180C1, 180F8, 18007

1.5. Selection for Notch-1 Specific Binders

In order to select for Notch-1 binders that do not cross-react with Notch-2 and Notch-3 second round selections were performed with counterselection in solution with Notch-2 and Notch-3. Binding assays were performed. In short: Maxisorp plate was coated with 100 ul 2 ug/ml of rhNotch-1 or Notch-2 (R&D systems) in PBS O/N at 4° C. After washing the plate was blocked with 4% MPBS for 30 minutes hour on shaker. Ten ul of Nanobody from the periplasmic extract was added in 100 ul 2% Marvell/PBS and incubate for 1 hour on shaker. After washing Nanobodies were detected with 100 ul 1:5000 Mouse-anti-MycTag in 2% Marvell/PBS and 100 ul 1:5000 DAMPO in 2% Marvell/PBS for 1 hour on shaker. PO was detected with 100 ul OPD and stopped with 50 ul H2SO4. Quantification was performed at 490 nm in a plate reader. The results showed that from the 96 clones tested 85% was able to bind to Notch-1 and only 2% was cross-reactive for Notch-2, indicating that most selected clones were specific for Notch-1.

Example 2

Generation of Nanobodies Specifically Binding to Human Notch-2

2.1. Immunizations

Two llamas were immunized with 6 boosts of R&D Systems Cat #3735-NT-050, which is the ectodomain of human Notch-2, according to standard protocols, e.g. as above.

2.2. Library Construction

Peripheral blood mononuclear cells were prepared from blood samples using Ficoll-Hypaque according to the manufacturer's instructions. Next, total RNA extracted was extracted from these cells and used as starting material for RT-PCR to amplify Nanobody encoding gene fragments. These fragments were cloned into phagemid vector pAX50. Phage was prepared according to standard methods (see for example the prior art and applications filed by applicant cited herein) and stored after filter sterilization at 4° C. for further use.

2.3. Selection

Two rounds of phage display selection were performed according to standard protocols, see above. Binding assays (screening) were performed as above. In short: Maxisorp plate was coated with 100 ul 2 ug/ml of Notch-2 (R&D systems) or with total human IgG in PBS O/N at 4° C. After washing the plate 4× with PBS the plate was blocked with 4% Marvel in PBS for 30 minutes on shaker. 10 ul of periplasmic extract of Nanobody was added in 100 ul 2% Marvell/PBS and incubate for 1 hour on shaker. After washing the plate 4× with PBS the Nanobodies were detected with 100 ul 1:5000 Mouse-anti-MycTag in 2% Marvell/PBS for 1 hour and 100 ul 1:5000 DAMPO in 2% Marvell/PBS for 1 hour. After washing the DAMPO was detected with 100 ul OPD, stopped with 50 ul H2SO4 and quantification was performed at 490 nm in a plate reader. Results showed that the 90% of the Nanobodies bind to the Notch-2-Fc fusion (see below Table). Two of the clones were shown to bind to IgG as well. 181C10, 181C11 and 181D11 belong to one family

TABLE B-2

Selected Nanobodies against human Notch-2.

| Name | SEQ ID NO: | Sequence |
|---|---|---|
| >181G4 | 348 | EVQLVESGGGLVQAGGSLRLSCAASGSIFSITEMDWYRQAPGKQREWVAGET SDGSTNYADSVKGRFTISRDNANNAVYLQMNRLKPEDTAVYHCAASLRNSGS NVEGRYWGQGTQVTVSS |

TABLE B-2-continued

Selected Nanobodies against human Notch-2.

| Name | SEQ ID NO: | Sequence |
|---|---|---|
| >181B4 | 349 | EVQLVESGGGLVQPGGSLRLSCAASGRINSMNWYHQAPGKEREWVASITSSG<br>TAIYADSVKGRITISRDNAKNTVYLQMNSLKTEDTGVYYCAANLQNARGSYYGQ<br>GTQVTVSS |
| >181D4 | 350 | EVQLVESGGGLVQPGGSLRLSCAASGFTFGDYAMNWVRQAPGKGLEWVSSI<br>SAGGYSTTYADSVKGRFTISRDNAKNTLYLQMNSLNPEDTAVYYCARGDWRY<br>GSRGQGTQVTVSS |
| >181E4 | 351 | EVQLVESGGGLVQAGGSLRLSCAASGSMSSINAMRWYRQASGKQREPVAEIT<br>SEGTIIYADSVKGRFTTSRDNAKNTVYLQMNSLKPEDTGVYYCAADDGARGSY<br>YGQGTQVTVSS |
| >181F4 | 352 | EVQLVESGGALVQAGGSLRLSCVASGSSFSINDMDWYRQAPGKTREWVAGIN<br>EYGGRNYANSVKDRFTISTDNAKNTVYLQMNSLKPEDTGVYYCAATLAKGGG<br>RYWGQGTPVTVSS |
| >181H4 | 353 | EVKLVESGGGLVQPGGSLRLSCAASGSIFRFNGVDWYRQAPGAEREWVAGF<br>GSGGTTNYADSVKGRFIVSRDNAENTVFLQMNSLKPEDSAVYFCAASIEGVSG<br>RYYGQGTQVTVSS |
| >181A5 | 354 | EVQLVESGGGLVQAGGSLRLSCVVSGSILSINTMDWYRQAPGNEREWVGGIT<br>DGGRSNYADSVKDRFTIYRANAKNTVYLQMNSLKPEDTAVYYCAADLRGGIAT<br>TGRYWGQGTQVTVSS |
| >181C10 | 355 | EVQLVESGGGLVQAGGSLRLSCAASGMTTIGPMGWYRQGPGKQRELVARITG<br>GGSTNYVDSAKGRFTISRDNAKNAVYLQMNNLKLDDTAVYYCNAYGSGSDYL<br>PIDYWGQGTQVTVSS |
| >181C11 | 356 | EVQLVESGGGLVQAGGSLRLSCAASGMTTIGPMGWYRQGPGKQRELVARITG<br>GGSTNYVDSAKGRFTISRDNAKNMGYLQMNNLKLDDTAIYYCYAYGSGSDYLP<br>TDYWGQGTQVTVSS |
| >181D11 | 357 | EVQLVESGGGLVQAGGSLRLSCAASGMTTIGPMGWYRQGPGKQRELVARITG<br>GGSTNYVDSAKGRFTISRHNAKNMVYLQMNNLKLDDTAVYYCNAYGSGSDYL<br>PMDYWGQGTQVTVSS |

Example 3

Generation of Nanobodies Specifically Binding to Jagged-1

3.1. Immunizations

Two llamas were immunized with 6 boosts of R&D Systems Cat #599-JG, which is the ectodomain of rat Jagged-1, according to standard protocols.

3.2. Library Construction

Peripheral blood mononuclear cells were prepared from blood samples using Ficoll-Hypaque according to the manufacturer's instructions. Next, total RNA extracted was extracted from these cells and used as starting material for RT-PCR to amplify Nanobody encoding gene fragments. These fragments were cloned into phagemid vector pAX50. Phage was prepared according to standard methods (see for example the prior art and applications filed by applicant cited herein) and stored after filter sterilization at 4° C. for further use.

3.3. Selection

Two rounds of phage display selection were performed similarly as described above. Binding assays were performed. In short: Maxisorp plate was coated with 100 ul 2 ug/ml of rrJagged-1 (R&D systems) in PBS O/N at 4 C. After washing the plate 4x with PBS the plate was blocked with 4% Marvel in PBS for 30 minutes on shaker. A concentration series of Nanobody (1-1000 nM) was added in 100 ul 2% Marvell/PBS and incubate for 1 hour on shaker. After washing the plate 4x with PBS the Nanobodies were detected with 100 ul 1:5000 Mouse-anti-MycTag in 2% Marvell/PBS for 1 hour and 100 ul 1:5000 DAMPO in 2% Marvell/PBS for 1 hour. After washing the DAMPO was detected with 100 ul OPD, stopped with 50 ul H2SO4 and quantification was performed at 490 nm in a plate reader. Results are shown in FIG. 2 and show that four Nanobodies (Table B-3) bind to rat Jagged-1, where 178C4 seems to have a lower affinity for Jagged-1 compared to the others.

TABLE B-3

Selected Nanobodies against rat Jagged-1.

| Name | SEQ ID NO: | Sequence |
|---|---|---|
| >178C4 | 335 | EVQLVESGGGLVQAGGSLRLSCAASGFTFDDYAIGWFRQAPGKEREGVSCMR<br>GRDGSTYYADSVNGRFTISSDNAKNTVYLQMNSLKPEDTAVYYCAAHTDFACY<br>IGYYSDYDPHDYWGQGTQVTVSS |

TABLE B-3-continued

Selected Nanobodies against rat Jagged-1.

| Name | SEQ ID NO: | Sequence |
|---|---|---|
| >178A7 | 336 | EVQLVESGGGLVQPGGSLRLSCATSGVIFSTAAMGWYRQAPGKSRVLVARMF SDGRTIYAESVKRRFTISRDNAKNTVYLQMNSLEPEDTAVYYCNALQFGAVYW GQGTQVTVSS |
| >178D9 | 337 | EVQLVKSGGGLVQPGGSLRLSCAASGSIVSANLIGWYRQAPGKQREGVAFITS GGAINYADSVKGRFTISRDDAKNTVYLQMNSLKPEDTAIYYCNLRQLGNVYWA QGTQVTVSS |
| >178C11 | 338 | EVQLVESGGGLVQPGGSLRLSCATSGVIFSTAAMGWYRQAPGKSRVLVARMF SDGRTIYAESVKRRFTISRDNAKNTVYLQMNSLEPEDTAVYYCNALQFGAVYW GQGTQVTVSS |

Above selected single variable domains (Nanobodies™) consists of 3 families:
3 Families:
Family 1: 1 competitive binder: 178C4
Family 2: 1 binder: 178D9
Family 3: 2 binders: 178A7 and 178C11
3.4. Competition Assay Competition ELISA assay was performed to check the competition of Jagged-1 binding to human Notch-1 by the Nanobodies. In short: Maxisorp plate was coated with 100 ul 5 ug/ml of rhNotch-1/hFc (R&D systems) in PBS O/N at 4° C. After washing the plate 4× with PBS the plate was blocked with 4% Marvel PBS for 30 minutes hour on shaker. A concentration series of Nanobody (1-1000 nM) and 0.3 ug/ml biotinylated rrJagged-1 (R&D systems, biotinylated in-house) was added in 100 ul 2% Marvell/PBS and incubated for 1 hour on shaker. (0.3 ug/ml biotinylated rrJagged-1~2.1 nM). After washing the biotin was detected with 100 ul 1:5000 streptavidin-PO in 2% Marvell/PBS for 1 hour on shaker. PO was detected with 100 ul OPD and stopped with 50 ul H2SO4. Quantification was performed at 490 nm in a plate reader. The results are shown in FIG. 3 and show that 178C4 is able to compete for Jagged-1 binding to Notch-1 in a concentration dependent matter. The competition of 178C4 is comparable to the competition by adding non-biotinylated Jagged-1 (cold-jagged1).

Example 4

Generation of Nanobodies Specifically Binding to Human DLL4

4.1. Immunizations

Two llamas were immunized with 6 boosts of R&D Systems Cat #1506-D4-050, which is the ectodomain of human DLL4, according to standard protocols.

4.2. Library Construction

Peripheral blood mononuclear cells were prepared from blood samples using Ficoll-Hypaque according to the manufacturer's instructions. Next, total RNA extracted was extracted from these cells and used as starting material for RT-PCR to amplify Nanobody encoding gene fragments. These fragments were cloned into phagemid vector pAX50. Phage was prepared according to standard methods (see for example the prior art and applications filed by applicant cited herein) and stored after filter sterilization at 4° C. for further use.

4.3. Selection

Two rounds of phage display selection were performed similarly as described above. Binding assays were performed. In short: Maxisorp plate was coated with 100 ul 5 ug/ml of rhDLL4 (R&D systems) in PBS O/N at 4° C. After washing the plate was blocked with 4% MPBS for 30 minutes hour on shaker. A concentration series of Nanobody (1-1000 nM) was added in 100 ul 2% Marvell/PBS and incubate for 1 hour on shaker. Nanobody was detected with 100 ul 1:5000 Mouse-anti-MycTag (9E10) in 2% Marvell/PBS and with 100 ul 1:5000 DAMPO in 2% Marvell/PBS for 1 hour on shaker. After washing PO was detected with 100 ul OPD and stopped with 50 ul H2SO4. Quantification was performed at 490 nm in a plate reader. Results show in FIG. 4 that all Nanobodies show a concentration dependent binding to DLL4, where 179F7 shows only little binding at the highest concentration.

TABLE B-4

Selected Nanobodies against human DLL4.

| Name | SEQ ID NO: | Sequence |
|---|---|---|
| >179E6 | 329 | EVQLVESGGGLVQAGGSLRLSCIASGDTSEIYDMGWFRQAPGKEREFVSSIH WRGRGTNYTDSVEGRFTISKDNAKNMVYLQMNSLKPEDTAVYYCAATRLIVYT PTGFRQYFDWGQGAQVTVSS |
| >179H9 | 330 | EVQLVESGGGLVQAGGSLRLSCAASG??F?SDVMGWFRRAPGKEREFVASITT TGNEYYEDSLKGRFTVSRDIAENTMYLEMTNLKPEDTAEYSCAGRLLGSTIRSH EYRYWGQGTQVTVSS |
| >179A10 | 331 | EVQLVESGGGLVQAGGSLRLSCVASGDTSEIYDMGWFRQAPGKEREFVSSIH WGGRGTNYTDSVKGRFTISKDNAKNMVHLQMNSLKPEDTAVYYCAATRLIVYT PTGFRQYFDWGQGTQVTVSS |

TABLE B-4-continued

Selected Nanobodies against human DLL4.

| Name | SEQ ID NO: | Sequence |
|---|---|---|
| >179D12 | 332 | EVQLVESGGGLVQAGGSLRLSCVASGDTSEIYDMGWFRQAPGKEREFVSSIH WGGRGTNYTDSVKGRFTISKDNAKNMVYLQMNSLKPEDTAVYYCAATRLIVYT PTGFRQYFDWGQGTQVTVSS |
| >179F6 | 333 | EVQLVESGGGLVQAGGSLRLSCAASGSDFSGFLLGWYRQPPGKQRELIAQTT DGGRTNYGDSVKGRFTISRDNAKNTWYLQMDSLKPEDTGVYYCNTFPLTSWG QGTQVTVSS |
| >179F7 | 334 | EVQLVESGGGLVQSGGSLSLSCAASGSVLRINDMGWYRQAPGKTREMVATIT RSGVLNYTDSVKGRFTVSRDDAKNTVYLQMSSLKPEDTAVYSCFANIVIRSSGY FNRYWGQGTLVTVSS |

Above selected single variable domains (Nanobodies™) consists of 4 families:

4 Families
Family 1: competitive binders: 179A10, 179D12, 179E6
Family 2: competitive binder: 179H9
Family 3: competitive binder: 179F6
Family 4: binder: 179F7

4.4. Competition

Competition ELISA assay was performed to check the competition of DLL4 binding to human Notch-1 by the Nanobodies. In short: Maxisorp plate was coated with 100 ul 5 ug/ml of rhDLL4 (R&D systems) in PBS O/N at 4° C. After washing the plate 4× with PBS the plate was blocked with 4% Marvel PBS for 30 minutes hour on shaker. A concentration series of Nanobody (1-1000 nM) and 0.2 ug/ml rhNotch-1/hFc (R&D systems) was added in 100 ul 2% Marvell/PBS and incubated for 1 hour on shaker. After washing the Notch-Fc binding was detected with 100 ul 1:5000 anti-hFc-HRP (Jackson) in 2% Marvell/PBS for 1 hour on shaker. PO was detected with 100 ul OPD and stopped with 50 ul H2SO4. Quantification was performed at 490 nm in a plate reader. The results show in FIG. 5 that all Nanobodies, except for 179F7, are able to compete for DLL4 binding to Notch-1 in a concentration dependent matter. The competition of the Nanobodies is comparable to the competition by adding non-biotinylated Jagged-1 (cold-jagged1).

Example 5

Most Nanobodies Bind Only to One Member of the Notch Family

Various Nanobodies were generated as above against human Notch-1, Notch-2, and Notch-3 (see Table B-5).

TABLE B-5

Selected Nanobodies against human Notch-1, Notch-2, and Notch-3

| SEQ ID NO: | Target | Name of Nanobody | Amino acid sequence |
|---|---|---|---|
| 358 | Human Notch-2 | 181B3 | EVQLVESGGGLVQAGGSLRLSCVVSGSILSINTMD WYRQAPGKQREWFAGLSDGGRANYADSVKDRFT IARDNAKNTVYLQMNSLKPGDTAIYYCAADLWD RGATTGRYWGQGTQVTVSS |
| 359 | Human Notch-2 | 181D2 | EVQLVESGGGLVQPGGSLRLSCAASGRINSMNWY RQAPGKEREWVASITSSGTTIYADSVKGRITISEDN AKNTVYLQMNSLKTEDTGVYYCAANLRNARGSY YGQGTQVTVSS |
| 360 | Human Notch-2 | 181D3 | EVQLVESGGGLVQAGGSLRLSCAASTNVSSFNTM SWYRQSPRKQREWVATITDGDNTHYADSVKGRFT TSRDNAKNLLYLQMNSLKPEDTAVYYCTGWRAT SGGSYGQGTQVTVSS |
| 361 | Human Notch-2 | 181E3 | EVQLVESGGGLVQPGGSLRLSCAASGFTFGDYAM NWVRQAPGKGLEWVSSISAGGYSTTYADSVKGRF TISRDNAKNTLYLQMNSLNPEDTAVYYCARGDW RYGSRGQGTQVTVSS |
| 362 | Human Notch-3 | 50C4 | EVQLVESGGDLVQPGGSLRLSCAASGFTFSTYYMS WVRQAPGKGLEWVSGIYSDGSNTYYADSVKGRF TISRDNAKNTLYLQMNSLKSEDTAVYYCTRPVVV AGSPVSYEYDYIGQGTQVTVSS |
| 363 | Human Notch-3 | 50H9 | EVQLVESGGDLVQPGGSLRLSCAASGFTFSTYYMS WVRQAPGKGLEWVSGIYSDGSNTYYADSVKGRF TISRDNAKNTLYLQMNSLKSEDTAVYYCTRPVVV AGSPVSYEYDYIGQGTQVTVSS |

TABLE B-5-continued

Selected Nanobodies against human Notch-1, Notch-2, and Notch-3

| SEQ ID NO: | Target | Name of Nanobody | Amino acid sequence |
|---|---|---|---|
| 364 | Human Notch-1 | 180F8 | EVQLVESGGDLVQPGGSLRLSCTTSGTVFSINDMG WSRQAPGKGRELVASISSEGTTIYADAAKGRFTISR DNSKNTVYLEMNSLKPDDTAVYYCRVVDPLRGK LYWGQGTQVTVSS |
| 365 | Negative control | 4H2 | EVQLVESGGGLVQAGGSLRLSCATSGFTFSRFDMS WFRQAPGKQREFIATIFSGGDTDYIDSVKGRFTISR DNAKNTVYLQMNSLKPEDTAVYYCCPLGIEYAW GQGTQVTVSS |

In order to test whether Nanobodies with binding specificity to human Notch-1, -2 or -3 have cross-reactivity to other members of the Notch family, individual clones picked from above selected Nanobodies are further tested in an ELISA binding assay setup. In short, 2 microgram/ml of human Notch-1, Notch-2, Notch-3 and CD36-Fc was immobilized on Maxisorp ELISA plates (Nunc) in marvell PBST for 1 h at 4 degrees Celsius (4° C.). After washing, the plate was blocked using 4% Marvel skimmed milk in PBS for 30 minutes on shaker. A concentration series of the Nanobodies in Table B-5 (25 pM to 2000 nM) was added in 100 microliter 2% Marvell/PBS and incubated for 1 h on shaker. After washing the Nanobodies were detected with 100 microliter 1:2500 R-anti-VHH (1:2500) in 2% Marvell/PBS and 100 microliter 1:5000 DAMPO in 2% Marvell/PBS for 1 h on shaker. PO was detected with 100 microliter OPD and stopped with 50 microliter H2SO4. Quantification was performed at 490 nm in a plate reader. The results in FIG. 6 show that:

- None of the Notch clones binds to Fc (FIG. 6a)
- 50H9 (Notch-3 binder) shows some crossreactivity with Notch-1 (FIGS. 6c and 6d)
- All other clones seem to be specific FIGS. 6b, 6c, 6d
- Binding (IC50) is in the low nanomolar range Example 6

List of General in vitro, Cell-based or in vivo Assays

In vitro binding assays: ELISA, Biacore
In vivo binding assay: Flow cytometry
In vivo functional assay: Mouse models for several diseases where Notch is involved have been developed (Gridley T., 2003, Human Molecular Genetics, Vol 12, Review Issue 1, R9-R13)

Example 7

List of Target Proteins of the Invention (Links to Nucleic and Amino Acid Sequence)

| Sequence of human members of the Notch signalling pathway | Sequences from various species found e.g. on www.ncbi.nlm.nih.gov/sites/entrez |
|---|---|
| Human Notch-1 | AAG33848 |
| Human Notch-2 | AAA36377 |
| Human Notch-3 | CAA55955 |
| Human Notch-4 | Q99466 |
| Human Jagged-1 | AAC52020 |
| Human Jagged-2 | AAB61285 |
| Human DLL1 | AAQ89251 |
| Human DLL3 | AAF62542 |
| Human DLL4 | AAQ89253 |

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

Preferred Aspects

1. A single variable domain that specifically binds to at least one member of the Notch pathway.

2. The single variable domain according to aspect 1, wherein the member of the Notch pathway is selected from the group consisting of the human members of the Notch pathway.

3. The single variable domain according to aspect 1, wherein the member of the Notch pathway is selected from the group consisting of the Notch receptors and Notch ligands.

4. The single variable domain according to aspect 1, wherein the member of the Notch pathway is selected from the group consisting of the human Notch receptors and human Notch ligands.

5. The single variable domain according to aspect 1, wherein the member of the Notch pathway is selected from the group consisting of Jagged-1, Jagged-2, DLL1, DLL3, DLL4, Notch-1, Notch-2, Notch-3, and Notch-4.

6. The single variable domain according to aspect 1, wherein the member of the Notch pathway is selected from the group consisting of human Jagged-1, human Jagged-2, human DLL1, human DLL3, human DLL4, human Notch-1, human Notch-2, human Notch-3, and human Notch-4.

7. The single variable domain according to aspect 1, wherein the member of the Notch pathway is selected from the group consisting of human Jagged-1, human DLL4, human Notch-1 and human Notch-2.

8. The single variable domain according to aspect 1, wherein the single variable domain additionally blocks the interaction between at least one member of the Notch ligands with at least one other member of the Notch receptors.

9. The single variable domain according to aspect 1, wherein the single variable domain additionally blocks the interaction between at least one member of the group consisting of Notch ligands and Notch receptors with at least one single variable domain with sequences having SEQ ID NO: 329 to 364.

10. The single variable domain according to aspect 1, wherein the single variable domain is selected from the group consisting of a) single variable domains with sequences having SEQ ID NO: 329 to 364; and b) single variable domains with 80% sequence identity to at least one sequence selected from the group consisting of single variable domains with sequences having SEQ ID NO: 329 to 364.

11. The single variable domain according to aspect 1, wherein the single variable domain is selected from the group consisting of a) single variable domains with sequences having SEQ ID NO: 329 to 364; and b) single variable domains with sequences having SEQ ID NO: 329 to 364, wherein up to 10 amino acid residues are replaced by naturally occurring amino acids and wherein said replaced amino acids are located within the framework regions.

12. The single variable domain according to aspect 1, wherein the single variable domain is selected from the group consisting of a) single variable domains with sequences having SEQ ID NO: 329 to 364; and b) single variable domains with sequences having SEQ ID NO: 329 to 364, wherein up to 8 amino acid residues are replaced by naturally occurring amino acids and wherein said replaced amino acids are located within the framework regions.

13. The single variable domain according to aspect 1, wherein the single variable domain is selected from the group consisting of a) single variable domains with sequences having SEQ ID NO: 329 to 364; and b) single variable domains with sequences having SEQ ID NO: 329 to 364, wherein up to 5 amino acid residues are replaced by naturally occurring amino acids and wherein said replaced amino acids are located within the framework regions.

14. The single variable domain according to aspect 1, wherein the single variable domain is selected from the group consisting of a) single variable domains with sequences having SEQ ID NO: 329 to 364; and b) single variable domains with sequences having SEQ ID NO: 329 to 364, wherein up to 3 amino acid residues are replaced by naturally occurring amino acids and wherein said replaced amino acids are located within the framework regions.

15. The single variable domain according to aspect 1, wherein the single variable domain is selected from the group consisting of a) single variable domains with sequences having SEQ ID NO: 329 to 364; and b) single variable domains with 80% sequence identity to at least one sequences selected from the group consisting of sequences having SEQ ID NO: 329 to 364; and wherein said selected single variable domain from group a) and b) binds to at least one member of the Notch signalling pathway with a dissociation constant ($K_D$) of $10^{-7}$ to $10^{-12}$ moles/liter or less.

16. The single variable domain according to aspect 1, wherein the single variable domain is selected from the group consisting of a) single variable domains with sequences having SEQ ID NO: 329 to 364; and b) single variable domains with sequences having SEQ ID NO: 329 to 364, wherein up to 10 amino acid residues are replaced by naturally occurring amino acids and wherein said replaced amino acids are located within the framework regions; and wherein said selected single variable domain from group a) and b) binds to at least one member of the Notch signalling pathway with a dissociation constant ($K_D$) of $10^{-7}$ to $10^{-12}$ moles/liter or less.

17. The single variable domain according to aspect 1, wherein the single variable domain is selected from the group consisting of a) single variable domains with sequences having SEQ ID NO: 329 to 364; and b) single variable domains with sequences having SEQ ID NO: 329 to 364, wherein up to 8 amino acid residues are replaced by naturally occurring amino acids and wherein said replaced amino acids are located within the framework regions; and wherein said selected single variable domain from group a) and b) binds to at least one member of the Notch signalling pathway with a dissociation constant ($K_D$) of $10^{-7}$ to $10^{-12}$ moles/liter or less.

18. The single variable domain according to aspect 1, wherein the single variable domain is selected from the group consisting of a) single variable domains with sequences having SEQ ID NO: 329 to 364; and b) single variable domains with sequences having SEQ ID NO: 329 to 364, wherein up to 5 amino acid residues are replaced by naturally occurring amino acids and wherein said replaced amino acids are located within the framework regions; and wherein said selected single variable domain from group a) and b) binds to at least one member of the Notch signalling pathway with a dissociation constant ($K_D$) of $10^{-7}$ to $10^{-12}$ moles/liter or less.

19. The single variable domain according to aspect 1, wherein the single variable domain is selected from the group consisting of a) single variable domains with sequences having SEQ ID NO: 329 to 364; and b) single variable domains with sequences having SEQ ID NO: 329 to 364, wherein up to 3 amino acid residues are replaced by naturally occurring amino acids and wherein said replaced amino acids are located within the framework regions; and wherein said selected single variable domain from group a) and b) binds to at least one member of the Notch signalling pathway with a dissociation constant ($K_D$) of $10^{-7}$ to $10^{-12}$ moles/liter or less.

20. The single variable domain according to aspect 1, wherein the single variable domain is selected from the group consisting of a) single variable domains with sequences having SEQ ID NO: 329 to 364; and b) single variable domains with 80% sequence identity to at least one sequences selected from the group consisting of sequences having SEQ ID NO: 329 to 364; and wherein said selected single variable domain from group a) and b) binds to at least one member of the Notch signalling pathway with a dissociation constant ($K_D$) of $10^{-8}$ to $10^{-12}$ moles/liter or less.

21. The single variable domain according to aspect 1, wherein the single variable domain is selected from the group consisting of a) single variable domains with sequences having SEQ ID NO: 329 to 364; and b) single variable domains with sequences having SEQ ID NO: 329 to 364, wherein up to 10 amino acid residues are replaced by naturally occurring amino acids and wherein said replaced amino acids are located within the framework regions; and wherein said selected single variable domain from group a) and b) binds to at least one member of the Notch signalling pathway with a dissociation constant ($K_D$) of $10^{-8}$ to $10^{-12}$ moles/liter or less.

22. The single variable domain according to aspect 1, wherein the single variable domain is selected from the group consisting of a) single variable domains with sequences having SEQ ID NO: 329 to 364; and b) single variable domains with sequences SEQ ID NO: 329 to 364 wherein up to 8 amino acid residues are replaced by naturally occurring amino acids and wherein said replaced amino acids are located within the framework regions; and wherein said selected single variable domain from group a) and b) binds to at least one member of the Notch signalling pathway with a dissociation constant ($K_D$) of $10^{-8}$ to $10^{-12}$ moles/liter or less.

23. The single variable domain according to aspect 1, wherein the single variable domain is selected from the group consisting of a) single variable domains with sequences having SEQ ID NO: 329 to 364; and b) single variable domains with sequences having SEQ ID NO: 329 to 364, wherein up to 5 amino acid residues are replaced by naturally occurring amino acids and wherein said replaced amino acids are located within the framework regions; and wherein said selected single variable domain from group a) and b) binds to at least one member of the Notch signalling pathway with a dissociation constant ($K_D$) of $10^{-8}$ to $10^{-12}$ moles/liter or less.

24. The single variable domain according to aspect 1, wherein the single variable domain is selected from the group consisting of a) single variable domains with sequences having SEQ ID NO: 329 to 364; and b) single variable domains with sequences having SEQ ID NO: 329 to 364, wherein up to 3 amino acid residues are replaced by naturally occurring amino acids and wherein said replaced amino acids are located within the framework regions; and wherein said selected single variable domain from group a) and b) binds to at least one member of the Notch signalling pathway with a dissociation constant ($K_D$) of $10^{-8}$ to $10^{-12}$ moles/liter or less.

25. A single variable domain that specifically binds to at least one member of the Notch receptors.

26. The single variable domain according to aspect 25, wherein the member of the Notch receptors is selected from the group consisting of the human members of the Notch receptors.

27. The single variable domain according to aspect 25 wherein the member of the Notch receptors is selected from the group consisting of Notch-1, Notch-2, Notch-3, and Notch-4.

28. The single variable domain according to aspect 25 wherein the member of the Notch receptors is selected from the group consisting of human Notch-1, human Notch-2, human Notch-3, and human Notch-4.

29. The single variable domain according to aspect 25 wherein the member of the Notch receptors is selected from the group consisting of human Notch-1 and human Notch-2.

30. The single variable domain according to aspect 25, wherein the single variable domain additionally blocks the interaction between at least one member of the Notch ligands with at least one other member of the Notch receptors.

31. The single variable domain according to aspect 25, wherein the single variable domain additionally blocks the interaction between at least one member of the group consisting of Notch receptors with at least one single variable domain with sequences having SEQ ID NO: 339 to 364.

32. The single variable domain according to aspect 25, wherein the single variable domain is selected from the group consisting of a) single variable domains with sequences having SEQ ID NO: 339 to 364; and b) single variable domains with 80% sequence identity to at least one sequence selected from the group consisting of single variable domains with sequences having SEQ ID NO: 339 to 364.

33. The single variable domain according to aspect 25, wherein the single variable domain is selected from the group consisting of a) single variable domains with sequences having SEQ ID NO: 339 to 364; and b) single variable domains with sequences having SEQ ID NO: 339 to 364, wherein up to 10 amino acid residues are replaced by naturally occurring amino acids and wherein said replaced amino acids are located within the framework regions.

34. The single variable domain according to aspect 25, wherein the single variable domain is selected from the group consisting of a) single variable domains with sequences having SEQ ID NO: 339 to 364; and b) single variable domains with sequences having SEQ ID NO: 339 to 364, wherein up to 8 amino acid residues are replaced by naturally occurring amino acids and wherein said replaced amino acids are located within the framework regions.

35. The single variable domain according to aspect 25, wherein the single variable domain is selected from the group consisting of a) single variable domains with sequences having SEQ ID NO: 339 to 364; and b) single variable domains with sequences having SEQ ID NO: 339 to 364, wherein up to 5 amino acid residues are replaced by naturally occurring amino acids and wherein said replaced amino acids are located within the framework regions.

36. The single variable domain according to aspect 25, wherein the single variable domain is selected from the group consisting of a) single variable domains with sequences having SEQ ID NO: 339 to 364; and b) single variable domains with sequences having SEQ ID NO: 339 to 364, wherein up to 3 amino acid residues are replaced by naturally occurring amino acids and wherein said replaced amino acids are located within the framework regions.

37. The single variable domain according to aspect 25, wherein the single variable domain is selected from the group consisting of a) single variable domains with sequences having SEQ ID NO: 339 to 364; and b) single variable domains with 80% sequence identity to at least one sequences selected from the group consisting of sequences having SEQ ID NO: 339 to 364; and wherein said selected single variable domain from group a) and b) binds to at least one member of the Notch receptors with a dissociation constant ($K_D$) of $10^{-7}$ to $10^{-12}$ moles/liter or less.

38. The single variable domain according to aspect 25, wherein the single variable domain is selected from the group consisting of a) single variable domains with sequences having SEQ ID NO: 339 to 364; and b) single variable domains with sequences having SEQ ID NO: 339 to 364, wherein up to 10 amino acid residues are replaced by naturally occurring amino acids and wherein said replaced amino acids are located within the framework regions; and wherein said selected single variable domain from group a) and b) binds to at least one member of the Notch receptors with a dissociation constant ($K_D$) of $10^{-7}$ to $10^{-12}$ moles/liter or less.

39. The single variable domain according to aspect 25, wherein the single variable domain is selected from the group consisting of a) single variable domains with sequences having SEQ ID NO: 339 to 364; and b) single variable domains with sequences having SEQ ID NO: 339 to 364, wherein up to 8 amino acid residues are replaced by naturally occurring amino acids and wherein said replaced amino acids are located within the framework regions; and wherein said selected single variable domain from group a) and b) binds to at least one member of the Notch receptors with a dissociation constant ($K_D$) of $10^{-7}$ to $10^{-12}$ moles/liter or less.

40. The single variable domain according to aspect 25, wherein the single variable domain is selected from the group consisting of a) single variable domains with sequences having SEQ ID NO: 339 to 364; and b) single variable domains with sequences having SEQ ID NO: 339 to 364, wherein up to 5 amino acid residues are replaced by naturally occurring amino acids and wherein said replaced amino acids are located within the framework regions; and wherein said selected single variable domain from group a) and b) binds to at least one member of the Notch receptors with a dissociation constant ($K_D$) of $10^{-7}$ to $10^{-12}$ moles/liter or less.

41. The single variable domain according to aspect 25, wherein the single variable domain is selected from the group consisting of a) single variable domains with sequences having SEQ ID NO: 339 to 364; and b) single variable domains with sequences having SEQ ID NO: 339 to 364, wherein up to 3 amino acid residues are replaced by naturally occurring amino acids and wherein said replaced amino acids are located within the framework regions; and wherein said selected single variable domain from group a) and b) binds to at least one member of the Notch receptors with a dissociation constant ($K_D$) of $10^{-7}$ to $10^{-12}$ moles/liter or less.

42. The single variable domain according to aspect 25, wherein the single variable domain is selected from the group consisting of a) single variable domains with sequences having SEQ ID NO: 339 to 364; and b) single variable domains with 80% sequence identity to at least one sequences selected from the group consisting of sequences having SEQ ID NO: 339 to 364; and wherein said selected single variable domain from group a) and b) binds to members of the Notch signalling pathway with a dissociation constant ($K_D$) of $10^{-8}$ to $10^{-12}$ moles/liter or less.

43. The single variable domain according to aspect 25, wherein the single variable domain is selected from the group consisting of a) single variable domains with sequences having SEQ ID NO: 339 to 364; and b) single variable domains with sequences having SEQ ID NO: 339 to 364, wherein up to 10 amino acid residues are replaced by naturally occurring amino acids and wherein said replaced amino acids are located within the framework regions; and wherein said selected single variable domain from group a) and b) binds to at least one member of the Notch receptors with a dissociation constant ($K_D$) of $10^{-8}$ to $10^{-12}$ moles/liter or less.

44. The single variable domain according to aspect 25, wherein the single variable domain is selected from the group consisting of a) single variable domains with sequences having SEQ ID NO: 339 to 364; and b) single variable domains with sequences having SEQ ID NO: 339 to 364, wherein up to 8 amino acid residues are replaced by naturally occurring amino acids and wherein said replaced amino acids are located within the framework regions; and wherein said selected single variable domain from group a) and b) binds to at least one member of the Notch receptors with a dissociation constant ($K_D$) of $10^{-8}$ to $10^{-12}$ moles/liter or less.

45. The single variable domain according to aspect 25, wherein the single variable domain is selected from the group consisting of a) single variable domains with sequences having SEQ ID NO: 339 to 364; and b) single variable domains with sequences having SEQ ID NO: 339 to 364, wherein up to 5 amino acid residues are replaced by naturally occurring amino acids and wherein said replaced amino acids are located within the framework regions; and wherein said selected single variable domain from group a) and b) binds to at least one member of the Notch receptors with a dissociation constant ($K_D$) of $10^{-8}$ to $10^{-12}$ moles/liter or less.

46. The single variable domain according to aspect 25, wherein the single variable domain is selected from the group consisting of a) single variable domains with sequences having SEQ ID NO: 339 to 364; and b) single variable domains with sequences having SEQ ID NO: 339 to 364, wherein up to 3 amino acid residues are replaced by naturally occurring amino acids and wherein said replaced amino acids are located within the framework regions; and wherein said selected single variable domain from group a) and b) binds to at least one member of the Notch receptors with a dissociation constant ($K_D$) of $10^{-8}$ to $10^{-12}$ moles/liter or less.

47. A single variable domain that specifically binds to at least one member of the Notch ligands.

48. The single variable domain according to aspect 47, wherein the member of the Notch ligands is selected from the group consisting of the human members of the Notch ligands.

49. The single variable domain according to aspect 47, wherein the member of the Notch receptors is selected from the group consisting of Jagged-1, Jagged-2, DLL1, DLL3, DLL4.

50. The single variable domain according to aspect 47, wherein the member of the Notch receptors is selected from the group consisting of human Jagged-1, human Jagged-2, human DLL1, human DLL3, and human DLL4.

51. The single variable domain according to aspect 47, wherein the member of the Notch receptors is selected from the group consisting of human Jagged-1 and human DLL4.

52. The single variable domain according to aspect 47, wherein the single variable domain additionally blocks the interaction between at least one member of the Notch ligands with at least one other member of the Notch receptors.

53. The single variable domain according to aspect 47, wherein the single variable domain additionally blocks the interaction between at least one member of the group consisting of Notch ligands with at least one single variable domain with sequences having SEQ ID NO: 329 to 338.

54. The single variable domain according to aspect 47, wherein the single variable domain is selected from the group consisting of a) single variable domains with sequences having SEQ ID NO: 329 to 338; and b) single variable domains with 80% sequence identity to at least one sequence selected from the group consisting of single variable domains with sequences having SEQ ID NO: 329 to 338.

55. The single variable domain according to aspect 47, wherein the single variable domain is selected from the group consisting of a) single variable domains with sequences having SEQ ID NO: 329 to 338; and b) single variable domains with sequences having SEQ ID NO: 329 to 338, wherein up to 10 amino acid residues are replaced by naturally occurring amino acids and wherein said replaced amino acids are located within the framework regions.

56. The single variable domain according to aspect 47, wherein the single variable domain is selected from the group consisting of a) single variable domains with sequences having SEQ ID NO: 329 to 338; and b) single variable domains with sequences having SEQ ID NO: 329 to 338, wherein up to 8 amino acid residues are replaced by naturally occurring amino acids and wherein said replaced amino acids are located within the framework regions.

57. The single variable domain according to aspect 47, wherein the single variable domain is selected from the group consisting of a) single variable domains with sequences having SEQ ID NO: 329 to 338; and b) single variable domains with sequences having SEQ ID NO: 329 to 338, wherein up to 5 amino acid residues are replaced by naturally occurring amino acids and wherein said replaced amino acids are located within the framework regions.

58. The single variable domain according to aspect 47, wherein the single variable domain is selected from the group consisting of a) single variable domains with sequences having SEQ ID NO: 329 to 338; and b) single variable domains with sequences having SEQ ID NO: 329 to 338, wherein up to 3 amino acid residues are replaced by naturally occurring amino acids and wherein said replaced amino acids are located within the framework regions.

59. The single variable domain according to aspect 47, wherein the single variable domain is selected from the group consisting of a) single variable domains with sequences having SEQ ID NO: 329 to 338; and b) single variable domains with 80% sequence identity to at least one sequences selected from the group consisting of sequences having SEQ ID NO: 329 to 338; and wherein said selected single variable domain from group a) and b) binds to at least one member of the Notch ligands with a dissociation constant ($K_D$) of $10^{-7}$ to $10^{-12}$ moles/liter or less.

60. The single variable domain according to aspect 47, wherein the single variable domain is selected from the group consisting of a) single variable domains with sequences having SEQ ID NO: 329 to 338; and b) single variable domains with sequences having SEQ ID NO: 329 to 338, wherein up to 10 amino acid residues are replaced by naturally occurring amino acids and wherein said replaced amino acids are located within the framework regions; and wherein said selected single variable domain from group a) and b) binds to at least one member of the Notch ligands with a dissociation constant ($K_D$) of $10^{-7}$ to $10^{-12}$ moles/liter or less.

61. The single variable domain according to aspect 47, wherein the single variable domain is selected from the group consisting of a) single variable domains with sequences having SEQ ID NO: 329 to 338; and b) single variable domains with sequences having SEQ ID NO: 329 to 338, wherein up to 8 amino acid residues are replaced by naturally occurring amino acids and wherein said replaced amino acids are located within the framework regions; and wherein said selected single variable domain from group a) and b) binds to at least one member of the Notch ligands with a dissociation constant ($K_D$) of $10^{-7}$ to $10^{-12}$ moles/liter or less.

62. The single variable domain according to aspect 47, wherein the single variable domain is selected from the group consisting of a) single variable domains with sequences having SEQ ID NO: 329 to 338; and b) single variable domains with sequences having SEQ ID NO: 329 to 338, wherein up to 5 amino acid residues are replaced by naturally occurring amino acids and wherein said replaced amino acids are located within the framework regions; and wherein said selected single variable domain from group a) and b) binds to at least one member of the Notch ligands with a dissociation constant ($K_D$) of $10^{-7}$ to $10^{-12}$ moles/liter or less.

63. The single variable domain according to aspect 47, wherein the single variable domain is selected from the group consisting of a) single variable domains with sequences having SEQ ID NO: 329 to 338; and b) single variable domains with sequences having SEQ ID NO: 329 to 338, wherein up to 3 amino acid residues are replaced by naturally occurring amino acids and wherein said replaced amino acids are located within the framework regions; and wherein said selected single variable domain from group a) and b) binds to at least one member of the Notch ligands with a dissociation constant ($K_D$) of $10^{-7}$ to $10^{-12}$ moles/liter or less.

64. The single variable domain according to aspect 47, wherein the single variable domain is selected from the group consisting of a) single variable domains with sequences having SEQ ID NO: 329 to 338; and b) single variable domains with 80% sequence identity to at least one sequences selected from the group consisting of sequences having SEQ ID NO: 329 to 338; and wherein said selected single variable domain from group a) and b) binds to at least one member of the Notch ligands with a dissociation constant ($K_D$) of $10^{-8}$ to $10^{-12}$ moles/liter or less.

65. The single variable domain according to aspect 47, wherein the single variable domain is selected from the group consisting of a) single variable domains with sequences having SEQ ID NO: 329 to 338; and b) single variable domains with sequences having SEQ ID NO: 329 to 338, wherein up to 10 amino acid residues are replaced by naturally occurring amino acids and wherein said replaced amino acids are located within the framework regions; and wherein said selected single variable domain from group a) and b) binds to at least one member of the Notch ligands with a dissociation constant ($K_D$) of $10^{-8}$ to $10^{-12}$ moles/liter or less.

66. The single variable domain according to aspect 47, wherein the single variable domain is selected from the group consisting of a) single variable domains with sequences having SEQ ID NO: 329 to 338; and b) single variable domains with sequences having SEQ ID NO: 329 to 338, wherein up to 8 amino acid residues are replaced by naturally occurring amino acids and wherein said replaced amino acids are located within the framework regions; and wherein said selected single variable domain from group a) and b) binds to at least one member of the Notch ligands with a dissociation constant ($K_D$) of $10^{-8}$ to $10^{-12}$ moles/liter or less.

67. The single variable domain according to aspect 47, wherein the single variable domain is selected from the group consisting of a) single variable domains with sequences having SEQ ID NO: 329 to 338; and b) single variable domains with sequences having SEQ ID NO: 329 to 338, wherein up to 5 amino acid residues are replaced by naturally occurring amino acids and wherein said replaced amino acids are located within the framework regions; and wherein said selected single variable domain from group a) and b) binds to at least one member of the Notch ligands with a dissociation constant ($K_D$) of $10^{-8}$ to $10^{-12}$ moles/liter or less.

68. The single variable domain according to aspect 47, wherein the single variable domain is selected from the group consisting of a) single variable domains with sequences having SEQ ID NO: 329 to 338; and b) single variable domains with sequences having SEQ ID NO: 329 to 338, wherein up to 3 amino acid residues are replaced by naturally occurring amino acids and wherein said replaced amino acids are located within the framework regions; and wherein said selected single variable domain from group a) and b) binds to at least one member of the Notch ligands with a dissociation constant ($K_D$) of $10^{-8}$ to $10^{-12}$ moles/liter or less.

69. A single variable domain that specifically binds to at least one member of the DLL4 family.

70. The single variable domain according to aspect 69, wherein the member of the DLL4 family is selected from human DLL4.

71. The single variable domain according to aspect 69, wherein the single variable domain additionally blocks the interaction between human DLL4 with at least one other member of the DLL4 family.

72. The single variable domain according to aspect 69, wherein the single variable domain additionally blocks the interaction between human DLL4 with at least one single variable domain with sequences having SEQ ID NO: 329 to 334.

73. The single variable domain according to aspect 69, wherein the single variable domain is selected from the group consisting of a) single variable domains with sequences having SEQ ID NO: 329 to 334; and b) single variable domains with 80% sequence identity to at least one sequence selected from the group consisting of single variable domains with sequences having SEQ ID NO: 329 to 334.

74. The single variable domain according to aspect 69, wherein the single variable domain is selected from the group consisting of a) single variable domains with sequences having SEQ ID NO: 329 to 334; and b) single variable domains with sequences having SEQ ID NO: 329 to 334, wherein up to 10 amino acid residues are replaced by naturally occurring amino acids and wherein said replaced amino acids are located within the framework regions.

75. The single variable domain according to aspect 69, wherein the single variable domain is selected from the group consisting of a) single variable domains with sequences having SEQ ID NO: 329 to 334; and b) single variable domains with sequences having SEQ ID NO: 329 to 334, wherein up to 8 amino acid residues are replaced by naturally occurring amino acids and wherein said replaced amino acids are located within the framework regions.

76. The single variable domain according to aspect 69, wherein the single variable domain is selected from the group consisting of a) single variable domains with sequences having SEQ ID NO: 329 to 334; and b) single variable domains with sequences having SEQ ID NO: 329 to 334, wherein up to 5 amino acid residues are replaced by naturally occurring amino acids and wherein said replaced amino acids are located within the framework regions.

77. The single variable domain according to aspect 69, wherein the single variable domain is selected from the group consisting of a) single variable domains with sequences having SEQ ID NO: 329 to 334; and b) single variable domains with sequences having SEQ ID NO: 329 to 334, wherein up to 3 amino acid residues are replaced by naturally occurring amino acids and wherein said replaced amino acids are located within the framework regions.

78. The single variable domain according to aspect 69, wherein the single variable domain is selected from the group consisting of a) single variable domains with sequences having SEQ ID NO: 329 to 334; and b) single variable domains with 80% sequence identity to at least one sequences selected from the group consisting of sequences having SEQ ID NO: 329 to 334; and wherein said selected single variable domain from group a) and b) binds to human DLL4 with a dissociation constant ($K_D$) of $10^{-7}$ to $10^{-12}$ moles/liter or less.

79. The single variable domain according to aspect 69, wherein the single variable domain is selected from the group consisting of a) single variable domains with sequences having SEQ ID NO: 329 to 334; and b) single variable domains with sequences having SEQ ID NO: 329 to 334, wherein up to 10 amino acid residues are replaced by naturally occurring amino acids and wherein said replaced amino acids are located within the framework regions; and wherein said selected single variable domain from group a) and b) binds to human DLL4 with a dissociation constant ($K_D$) of $10^{-7}$ to $10^{-12}$ moles/liter or less.

80. The single variable domain according to aspect 69, wherein the single variable domain is selected from the group consisting of a) single variable domains with sequences having SEQ ID NO: 329 to 334; and b) single variable domains with sequences having SEQ ID NO: 329 to 334, wherein up to 8 amino acid residues are replaced by naturally occurring amino acids and wherein said replaced amino acids are located within the framework regions; and wherein said selected single variable domain from group a) and b) binds to human DLL4 with a dissociation constant ($K_D$) of $10^{-7}$ to $10^{-12}$ moles/liter or less.

81. The single variable domain according to aspect 69, wherein the single variable domain is selected from the group consisting of a) single variable domains with sequences having SEQ ID NO: 329 to 334; and b) single variable domains with sequences having SEQ ID NO: 329 to 334, wherein up to 5 amino acid residues are replaced by naturally occurring amino acids and wherein said replaced amino acids are located within the framework regions; and wherein said selected single variable domain from group a) and b) binds to human DLL4 with a dissociation constant ($K_D$) of $10^{-7}$ to $10^{-12}$ moles/liter or less.

82. The single variable domain according to aspect 69, wherein the single variable domain is selected from the group consisting of a) single variable domains with sequences having SEQ ID NO: 329 to 334; and b) single variable domains with sequences having SEQ ID NO: 329 to 334, wherein up to 3 amino acid residues are replaced by naturally occurring amino acids and wherein said replaced amino acids are located within the framework regions; and wherein said selected single variable domain from group a) and b) binds to human DLL4 with a dissociation constant ($K_D$) of $10^{-7}$ to $10^{-12}$ moles/liter or less.

83. The single variable domain according to aspect 69, wherein the single variable domain is selected from the group consisting of a) single variable domains with sequences having SEQ ID NO: 329 to 334; and b) single variable domains with 80% sequence identity to at least one sequences selected from the group consisting of sequences having SEQ ID NO: 329 to 334; and wherein said selected single variable domain from group a) and b) binds to human DLL4 with a dissociation constant ($K_D$) of $10^{-8}$ to $10^{-12}$ moles/liter or less.

84. The single variable domain according to aspect 69, wherein the single variable domain is selected from the group consisting of a) single variable domains with sequences having SEQ ID NO: 329 to 334; and b) single variable domains with sequences having SEQ ID NO: 329 to 334, wherein up to 10 amino acid residues are replaced by naturally occurring amino acids and wherein said replaced amino acids are located within the framework regions; and wherein said selected single variable domain from group a) and b) binds to human DLL4 with a dissociation constant ($K_D$) of $10^{-8}$ to $10^{-12}$ moles/liter or less.

85. The single variable domain according to aspect 69, wherein the single variable domain is selected from the group consisting of a) single variable domains with sequences having SEQ ID NO: 329 to 334; and b) single variable domains with sequences having SEQ ID NO: 329 to 334, wherein up to 8 amino acid residues are replaced by naturally occurring amino acids and wherein said replaced amino acids are located within the framework regions; and wherein said selected single variable domain from group a) and b) binds to human DLL4 with a dissociation constant ($K_D$) of $10^{-8}$ to $10^{-12}$ moles/liter or less.

86. The single variable domain according to aspect 69, wherein the single variable domain is selected from the group consisting of a) single variable domains with sequences having SEQ ID NO: 329 to 334; and b) single variable domains with sequences having SEQ ID NO: 329 to 334, wherein up to 5 amino acid residues are replaced by naturally occurring amino acids and wherein said replaced amino acids are located within the framework regions; and wherein said selected single variable domain from group a) and b) binds to human DLL4 with a dissociation constant ($K_D$) of $10^{-8}$ to $10^{-12}$ moles/liter or less.

87. The single variable domain according to aspect 69, wherein the single variable domain is selected from the group consisting of a) single variable domains with sequences having SEQ ID NO: 329 to 334; and b) single variable domains with sequences having SEQ ID NO: 329 to 334, wherein up to 3 amino acid residues are replaced by naturally occurring amino acids and wherein said replaced amino acids are located within the framework regions; and wherein said selected single variable domain from group a) and b) binds to human DLL4 with a dissociation constant ($K_D$) of $10^{-8}$ to $10^{-12}$ moles/liter or less.

88. A single variable domain that specifically binds to at least one member of the Jagged-1 family.

89. The single variable domain according to aspect 88, wherein the member of the Jagged-1 family is selected from human Jagged-1.

90. The single variable domain according to aspect 88, wherein the single variable domain additionally blocks the interaction between human Jagged-1 with at least one other member of the Jagged-1 family.

91. The single variable domain according to aspect 88, wherein the single variable domain additionally blocks the interaction between human Jagged-1 with at least one single variable domain with sequences having SEQ ID NO: 335 to 338.

92. The single variable domain according to aspect 88, wherein the single variable domain is selected from the group consisting of a) single variable domains with sequences having SEQ ID NO: 335 to 338; and b) single variable domains with 80% sequence identity to at least one sequence selected from the group consisting of single variable domains with sequences having SEQ ID NO: 335 to 338.

93. The single variable domain according to aspect 88, wherein the single variable domain is selected from the group consisting of a) single variable domains with sequences having SEQ ID NO: 335 to 338; and b) single variable domains with sequences having SEQ ID NO: 335 to 338, wherein up to 10 amino acid residues are replaced by naturally occurring amino acids and wherein said replaced amino acids are located within the framework regions.

94. The single variable domain according to aspect 88, wherein the single variable domain is selected from the group consisting of a) single variable domains with sequences having SEQ ID NO: 335 to 338; and b) single variable domains with sequences having SEQ ID NO: 335 to 338, wherein up to 8 amino acid residues are replaced by naturally occurring amino acids and wherein said replaced amino acids are located within the framework regions.

95. The single variable domain according to aspect 88, wherein the single variable domain is selected from the group consisting of a) single variable domains with sequences having SEQ ID NO: 335 to 338; and b) single variable domains with sequences having SEQ ID NO: 335 to 338, wherein up to 5 amino acid residues are replaced by naturally occurring amino acids and wherein said replaced amino acids are located within the framework regions.

96. The single variable domain according to aspect 88, wherein the single variable domain is selected from the group consisting of a) single variable domains with sequences having SEQ ID NO: 335 to 338; and b) single variable domains with sequences having SEQ ID NO: 335 to 338, wherein up to 3 amino acid residues are replaced by naturally occurring amino acids and wherein said replaced amino acids are located within the framework regions.

97. The single variable domain according to aspect 88, wherein the single variable domain is selected from the group consisting of a) single variable domains with sequences having SEQ ID NO: 335 to 338; and b) single variable domains with 80% sequence identity to at least one sequences selected from the group consisting of sequences having SEQ ID NO: 335 to 338; and wherein said selected single variable domain from group a) and b) binds to human Jagged-1 with a dissociation constant ($K_D$) of $10^{-7}$ to $10^{-12}$ moles/liter or less.

98. The single variable domain according to aspect 88, wherein the single variable domain is selected from the group consisting of a) single variable domains with sequences having SEQ ID NO: 335 to 338; and b) single variable domains with sequences having SEQ ID NO: 335 to 338, wherein up to 10 amino acid residues are replaced by naturally occurring amino acids and wherein said replaced amino acids are located within the framework regions; and wherein said selected single variable domain from group a) and b) binds to human Jagged-1 with a dissociation constant ($K_D$) of $10^{-7}$ to $10^{-12}$ moles/liter or less.

99. The single variable domain according to aspect 88, wherein the single variable domain is selected from the group consisting of a) single variable domains with sequences having SEQ ID NO: 335 to 338; and b) single variable domains with sequences having SEQ ID NO: 335 to 338, wherein up to 8 amino acid residues are replaced by naturally occurring amino acids and wherein said replaced amino acids are located within the framework regions; and wherein said selected single variable domain from group a) and b) binds to human Jagged-1 with a dissociation constant ($K_D$) of $10^{-7}$ to $10^{-12}$ moles/liter or less.

100. The single variable domain according to aspect 88, wherein the single variable domain is selected from the group consisting of a) single variable domains with sequences having SEQ ID NO: 335 to 338; and b) single variable domains with sequences having SEQ ID NO: 335 to 338, wherein up to 5 amino acid residues are replaced by naturally occurring amino acids and wherein said replaced amino acids are located within the framework regions; and wherein said selected single variable domain from group a) and b) binds to human Jagged-1 with a dissociation constant ($K_D$) of $10^{-7}$ to $10^{-12}$ moles/liter or less.

101. The single variable domain according to aspect 88, wherein the single variable domain is selected from the group consisting of a) single variable domains with sequences having SEQ ID NO: 335 to 338; and b) single variable domains with sequences having SEQ ID NO: 335 to 338, wherein up to 3 amino acid residues are replaced by naturally occurring amino acids and wherein said replaced amino acids are located within the framework regions; and wherein said selected single variable domain from group a) and b) binds to human Jagged-1 with a dissociation constant ($K_D$) of $10^{-7}$ to $10^{-12}$ moles/liter or less.

102. The single variable domain according to aspect 88, wherein the single variable domain is selected from the group consisting of a) single variable domains with sequences having SEQ ID NO: 335 to 338; and b) single variable domains with 80% sequence identity to at least one sequences selected from the group consisting of sequences having SEQ ID NO: 335 to 338; and wherein said selected single variable domain from group a) and b) binds to human Jagged-1 with a dissociation constant ($K_D$) of $10^{-8}$ to $10^{-12}$ moles/liter or less.

103. The single variable domain according to aspect 88, wherein the single variable domain is selected from the group consisting of a) single variable domains with sequences having SEQ ID NO: 335 to 338; and b) single variable domains with sequences having SEQ ID NO: 335 to 338, wherein up to 10 amino acid residues are replaced by naturally occurring amino acids and wherein said replaced amino acids are located within the framework regions; and wherein said selected single variable domain from group a) and b) binds to human Jagged-1 with a dissociation constant ($K_D$) of $10^{-8}$ to $10^{-12}$ moles/liter or less.

104. The single variable domain according to aspect 88, wherein the single variable domain is selected from the group consisting of a) single variable domains with sequences having SEQ ID NO: 335 to 338; and b) single variable domains with sequences having SEQ ID NO: 335 to 338, wherein up to 8 amino acid residues are replaced by naturally occurring amino acids and wherein said replaced amino acids are located within the framework regions; and wherein said selected single variable domain from group a) and b) binds to human Jagged-1 with a dissociation constant ($K_D$) of $10^{-8}$ to $10^{-12}$ moles/liter or less.

105. The single variable domain according to aspect 88, wherein the single variable domain is selected from the group consisting of a) single variable domains with sequences having SEQ ID NO: 335 to 338; and b) single variable domains with sequences having SEQ ID NO: 335 to 338, wherein up to 5 amino acid residues are replaced by naturally occurring amino acids and wherein said replaced amino acids are located within the framework regions; and wherein said selected single variable domain from group a) and b) binds to human Jagged-1 with a dissociation constant ($K_D$) of $10^{-8}$ to $10^{-12}$ moles/liter or less.

106. The single variable domain according to aspect 88, wherein the single variable domain is selected from the group consisting of a) single variable domains with sequences having SEQ ID NO: 335 to 338; and b) single variable domains with sequences having SEQ ID NO: 335 to 338, wherein up to 3 amino acid residues are replaced by naturally occurring amino acids and wherein said replaced amino acids are located within the framework regions; and wherein said selected single variable domain from group a) and b) binds to human Jagged-1 with a dissociation constant ($K_D$) of $10^{-8}$ to $10^{-12}$ moles/liter or less.

107. A single variable domain that specifically binds to at least one member of the Notch-1 family.

108. The single variable domain according to aspect 107, wherein the member of the Notch-1 family is selected from human Notch-1.

109. The single variable domain according to aspect 107, wherein the single variable domain additionally blocks the interaction between human Notch-1 with at least one other member of the Notch ligands.

110. The single variable domain according to aspect 107, wherein the single variable domain additionally blocks the interaction between human Notch-1 with at least one single variable domain with sequences having SEQ ID NO: 339 to 347 and SEQ ID NO: 364.

111. The single variable domain according to aspect 107, wherein the single variable domain is selected from the group consisting of a) single variable domains with sequences having SEQ ID NO: 339 to 347 and SEQ ID NO: 364; and b) single variable domains with 80% sequence identity to at least one sequence selected from the group consisting of single variable domains with sequences having SEQ ID NO: 339 to 347 and SEQ ID NO: 364.

112. The single variable domain according to aspect 107, wherein the single variable domain is selected from the group consisting of a) single variable domains with sequences having SEQ ID NO: 339 to 347 and SEQ ID NO: 364; and b) single variable domains with sequences having SEQ ID NO: 339 to 347 and SEQ ID NO: 364, wherein up to 10 amino acid residues are replaced by naturally occurring amino acids and wherein said replaced amino acids are located within the framework regions.

113. The single variable domain according to aspect 107, wherein the single variable domain is selected from the group consisting of a) single variable domains with sequences having SEQ ID NO: 339 to 347 and SEQ ID NO: 364; and b) single variable domains with sequences having SEQ ID NO: 339 to 347 and SEQ ID NO: 364, wherein up to 8 amino acid residues are replaced by naturally occurring amino acids and wherein said replaced amino acids are located within the framework regions.

114. The single variable domain according to aspect 107, wherein the single variable domain is selected from the group consisting of a) single variable domains with sequences having SEQ ID NO: 339 to 347 and SEQ ID NO: 364; and b) single variable domains with sequences having SEQ ID NO: 339 to 347 and SEQ ID NO: 364, wherein up to 5 amino acid residues are replaced by naturally occurring amino acids and wherein said replaced amino acids are located within the framework regions.

115. The single variable domain according to aspect 107, wherein the single variable domain is selected from the group consisting of a) single variable domains with sequences having SEQ ID NO: 339 to 347 and SEQ ID NO: 364; and b) single variable domains with sequences having SEQ ID NO: 339 to 347 and SEQ ID NO: 364, wherein up to 3 amino acid residues are replaced by naturally occurring amino acids and wherein said replaced amino acids are located within the framework regions.

116. The single variable domain according to aspect 107, wherein the single variable domain is selected from the group consisting of a) single variable domains with sequences having SEQ ID NO: 339 to 347 and SEQ ID NO: 364; and b) single variable domains with 80% sequence identity to at least one sequences selected from the group consisting of sequences having SEQ ID NO: 339 to 347 and SEQ ID NO: 364; and wherein said selected single variable domain from group a) and b) binds to human Notch-1 with a dissociation constant ($K_D$) of $10^{-7}$ to $10^{-12}$ moles/liter or less.

117. The single variable domain according to aspect 107, wherein the single variable domain is selected from the group consisting of a) single variable domains with sequences having SEQ ID NO: 339 to 347 and SEQ ID NO: 364; and b) single variable domains with sequences having SEQ ID NO: 339 to 347 and SEQ ID NO: 364, wherein up to 10 amino acid residues are replaced by naturally occurring amino acids and wherein said replaced amino acids are located within the framework regions; and wherein said selected single variable domain from group a) and b) binds to human Notch-1 with a dissociation constant ($K_D$) of $10^{-7}$ to $10^{-12}$ moles/liter or less.

118. The single variable domain according to aspect 107, wherein the single variable domain is selected from the group consisting of a) single variable domains with sequences having SEQ ID NO: 339 to 347 and SEQ ID NO: 364; and b) single variable domains with sequences having SEQ ID NO: 339 to 347 and SEQ ID NO: 364, wherein up to 8 amino acid residues are replaced by naturally occurring amino acids and wherein said replaced amino acids are located within the framework regions; and wherein said selected single variable domain from group a) and b) binds to human Notch-1 with a dissociation constant ($K_D$) of $10^{-7}$ to $10^{-12}$ moles/liter or less.

119. The single variable domain according to aspect 107, wherein the single variable domain is selected from the group consisting of a) single variable domains with sequences having SEQ ID NO: 339 to 347 and SEQ ID NO: 364; and b) single variable domains sequences having SEQ ID NO: 339 to 347 and SEQ ID NO: 364, wherein up to 5 amino acid residues are replaced by naturally occurring amino acids and wherein said replaced amino acids are located within the framework regions; and wherein said selected single variable domain from group a) and b) binds to human Notch-1 with a dissociation constant ($K_D$) of $10^{-7}$ to $10^{-12}$ moles/liter or less.

120. The single variable domain according to aspect 107, wherein the single variable domain is selected from the group consisting of a) single variable domains with sequences having SEQ ID NO: 339 to 347 and SEQ ID NO: 364; and b) single variable domains with sequences having SEQ ID NO: 339 to 347 and SEQ ID NO: 364, wherein up to 3 amino acid residues are replaced by naturally occurring amino acids and wherein said replaced amino acids are located within the framework regions; and wherein said selected single variable domain from group a) and b) binds to human Notch-1 with a dissociation constant ($K_D$) of $10^{-7}$ to $10^{-12}$ moles/liter or less.

121. The single variable domain according to aspect 107, wherein the single variable domain is selected from the group consisting of a) single variable domains with sequences having SEQ ID NO: 339 to 347 and SEQ ID NO: 364; and b) single variable domains with 80% sequence identity to at least one sequences selected from the group consisting of sequences having SEQ ID NO: 339 to 347 and SEQ ID NO: 364; and wherein said selected single variable domain from group a) and b) binds to human Notch-1 with a dissociation constant ($K_D$) of $10^{-8}$ to $10^{-12}$ moles/liter or less.

122. The single variable domain according to aspect 107, wherein the single variable domain is selected from the group consisting of a) single variable domains with sequences having SEQ ID NO: 339 to 347 and SEQ ID NO: 364; and b) single variable domains with sequences having SEQ ID NO: 339 to 347 and SEQ ID NO: 364, wherein up to 10 amino acid residues are replaced by naturally occurring amino acids and wherein said replaced amino acids are located within the framework regions; and wherein said selected single variable domain from group a) and b) binds to human Notch-1 with a dissociation constant ($K_D$) of $10^{-8}$ to $10^{-12}$ moles/liter or less.

123. The single variable domain according to aspect 107, wherein the single variable domain is selected from the group consisting of a) single variable domains with sequences having SEQ ID NO: 339 to 347 and SEQ ID NO: 364; and b) single variable domains with sequences having SEQ ID NO: 339 to 347 and SEQ ID NO: 364, wherein up to 8 amino acid residues are replaced by naturally occurring amino acids and wherein said replaced amino acids are located within the framework regions; and wherein said selected single variable domain from group a) and b) binds to human Notch-1 with a dissociation constant ($K_D$) of $10^{-8}$ to $10^{-12}$ moles/liter or less.

124. The single variable domain according to aspect 107, wherein the single variable domain is selected from the group consisting of a) single variable domains with sequences having SEQ ID NO: 339 to 347 and SEQ ID NO: 364; and b) single variable domains with sequences having SEQ ID NO: 339 to 347 and SEQ ID NO: 364, wherein up to 5 amino acid residues are replaced by naturally occurring amino acids and wherein said replaced amino acids are located within the framework regions; and wherein said selected single variable domain from group a) and b) binds to human Notch-1 with a dissociation constant ($K_D$) of $10^{-8}$ to $10^{-12}$ moles/liter or less.

125. The single variable domain according to aspect 107, wherein the single variable domain is selected from the group consisting of a) single variable domains with sequences having SEQ ID NO: 339 to 347 and SEQ ID NO: 364; and b) single variable domains with sequences having SEQ ID NO: 339 to 347 and SEQ ID NO: 364, wherein up to 3 amino acid residues are replaced by naturally occurring amino acids and wherein said replaced amino acids are located within the framework regions; and wherein said selected single variable domain from group a) and b) binds to human Notch-1 with a dissociation constant ($K_D$) of $10^{-8}$ to $10^{-12}$ moles/liter or less.

126. A single variable domain that specifically binds to at least one member of the Notch-2 family.

127. The single variable domain according to aspect 126, wherein the member of the Notch-2 family is selected from human Notch-2.

128. The single variable domain according to aspect 126, wherein the single variable domain additionally blocks the interaction between human Notch-2 with at least one other member of the Notch ligands.

129. The single variable domain according to aspect 126, wherein the single variable domain additionally blocks the interaction between human Notch-2 with at least one single variable domain with sequences having SEQ ID NO: 348 to 361.

130. The single variable domain according to aspect 126, wherein the single variable domain is selected from the group consisting of a) single variable domains with sequences having SEQ ID NO: 348 to 361; and b) single variable domains with 80% sequence identity to at least one sequence selected from the group consisting of single variable domains with sequences having SEQ ID NO: 348 to 361.

131. The single variable domain according to aspect 126, wherein the single variable domain is selected from the group consisting of a) single variable domains with sequences having SEQ ID NO: 348 to 361; and b) single variable domains with sequences having SEQ ID NO: 348 to 361, wherein up to 10 amino acid residues are replaced by naturally occurring amino acids and wherein said replaced amino acids are located within the framework regions.

132. The single variable domain according to aspect 126, wherein the single variable domain is selected from the group consisting of a) single variable domains with sequences having SEQ ID NO: 348 to 361; and b) single variable domains with sequences having SEQ ID NO: 348 to 361, wherein up to 8 amino acid residues are replaced by naturally occurring amino acids and wherein said replaced amino acids are located within the framework regions.

133. The single variable domain according to aspect 126, wherein the single variable domain is selected from the group consisting of a) single variable domains with sequences having SEQ ID NO: 348 to 361; and b) single variable domains with sequences having SEQ ID NO: 348 to 361, wherein up to 5 amino acid residues are replaced by naturally occurring amino acids and wherein said replaced amino acids are located within the framework regions.

134. The single variable domain according to aspect 126, wherein the single variable domain is selected from the group consisting of a) single variable domains with sequences having SEQ ID NO: 348 to 361; and b) single variable domains with sequences having SEQ ID NO: 348 to 361, wherein up to 3 amino acid residues are replaced by naturally occurring amino acids and wherein said replaced amino acids are located within the framework regions.

135. The single variable domain according to aspect 126, wherein the single variable domain is selected from the group consisting of a) single variable domains with sequences having SEQ ID NO: 348 to 361; and b) single variable domains with 80% sequence identity to at least one sequences selected from the group consisting of sequences having SEQ ID NO: 348 to 361; and wherein said selected single variable domain from group a) and b) binds to human Notch-2 with a dissociation constant ($K_D$) of $10^{-7}$ to $10^{-12}$ moles/liter or less.

136. The single variable domain according to aspect 126, wherein the single variable domain is selected from the group consisting of a) single variable domains with sequences having SEQ ID NO: 348 to 361; and b) single variable domains with sequences having SEQ ID NO: 348 to 361, wherein up to 10 amino acid residues are replaced by naturally occurring amino acids and wherein said replaced amino acids are located within the framework regions; and wherein said selected single variable domain from group a) and b) binds to human Notch-2 with a dissociation constant ($K_D$) of $10^{-7}$ to $10^{-12}$ moles/liter or less.

137. The single variable domain according to aspect 126, wherein the single variable domain is selected from the group consisting of a) single variable domains with sequences having SEQ ID NO: 348 to 361; and b) single variable domains with sequences having SEQ ID NO: 348 to 361, wherein up to 8 amino acid residues are replaced by naturally occurring amino acids and wherein said replaced amino acids are located within the framework regions; and wherein said selected single variable domain from group a) and b) binds to human Notch-2 with a dissociation constant ($K_D$) of $10^{-7}$ to $10^{-12}$ moles/liter or less.

138. The single variable domain according to aspect 126, wherein the single variable domain is selected from the group consisting of a) single variable domains with sequences having SEQ ID NO: 348 to 361; and b) single variable domains with sequences having SEQ ID NO: 348 to 361, wherein up to 5 amino acid residues are replaced by naturally occurring amino acids and wherein said replaced amino acids are located within the framework regions; and wherein said selected single variable domain from group a) and b) binds to human Notch-2 with a dissociation constant ($K_D$) of $10^{-7}$ to $10^{-12}$ moles/liter or less.

139. The single variable domain according to aspect 126, wherein the single variable domain is selected from the group consisting of a) single variable domains with sequences having SEQ ID NO: 348 to 361; and b) single variable domains with sequences having SEQ ID NO: 348 to 361, wherein up to 3 amino acid residues are replaced by naturally occurring amino acids and wherein said replaced amino acids are located within the framework regions; and wherein said selected single variable domain from group a) and b) binds to human Notch-2 with a dissociation constant ($K_D$) of $10^{-7}$ to $10^{-12}$ moles/liter or less.

140. The single variable domain according to aspect 126, wherein the single variable domain is selected from the group consisting of a) single variable domains with sequences having SEQ ID NO: 348 to 361; and b) single variable domains with 80% sequence identity to at least one sequences selected from the group consisting of sequences having SEQ ID NO: 348 to 361; and wherein said selected single variable domain from group a) and b) binds to human Notch-2 with a dissociation constant ($K_D$) of $10^{-8}$ to $10^{-12}$ moles/liter or less.

141. The single variable domain according to aspect 126, wherein the single variable domain is selected from the group consisting of a) single variable domains with sequences having SEQ ID NO: 348 to 361; and b) single variable domains with sequences having SEQ ID NO: 348 to 361, wherein up to 10 amino acid residues are replaced by naturally occurring amino acids and wherein said replaced amino acids are located within the framework regions; and wherein said selected single variable domain from group a) and b) binds to human Notch-2 with a dissociation constant ($K_D$) of $10^{-8}$ to $10^{-12}$ moles/liter or less.

142. The single variable domain according to aspect 126, wherein the single variable domain is selected from the group consisting of a) single variable domains with sequences having SEQ ID NO: 348 to 361; and b) single variable domains with sequences having SEQ ID NO: 348 to 361, wherein up to 8 amino acid residues are replaced by naturally occurring amino acids and wherein said replaced amino acids are located within the framework regions; and wherein said selected single variable domain from group a) and b) binds to human Notch-2 with a dissociation constant ($K_D$) of $10^{-8}$ to $10^{-12}$ moles/liter or less.

143. The single variable domain according to aspect 126, wherein the single variable domain is selected from the group consisting of a) single variable domains with sequences having SEQ ID NO: 348 to 361; and b) single variable domains with sequences having SEQ ID NO: 348 to 361, wherein up to 5 amino acid residues are replaced by naturally occurring amino acids and wherein said replaced amino acids are located within the framework regions; and wherein said selected single variable domain from group a) and b) binds to human Notch-2 with a dissociation constant ($K_D$) of $10^{-8}$ to $10^{-12}$ moles/liter or less.

144. The single variable domain according to aspect 126, wherein the single variable domain is selected from the group consisting of a) single variable domains with sequences having SEQ ID NO: 348 to 361; and b) single variable domains with sequences having SEQ ID NO: 348 to 361, wherein up to 3 amino acid residues are replaced by naturally occurring amino acids and wherein said replaced amino acids are located within the framework regions; and wherein said selected single variable domain from group a) and b) binds to human Notch-2 with a dissociation constant ($K_D$) of $10^{-8}$ to $10^{-12}$ moles/liter or less.

145. A single variable domain that specifically binds to Jagged-2.

146. The single variable domain according to aspect 145, wherein the member of the Jagged-2 family is selected from the group consisting of the human Jagged-2.

147. The single variable domain according to aspect 145, wherein the single variable domain additionally blocks the interaction between human Jagged-2 with at least one other member of the Notch receptors.

148. A single variable domain that specifically binds to DLL1.

149. The single variable domain according to aspect 148, wherein the member of the DLL1 family is selected from the group consisting of the human DLL1.

150. The single variable domain according to aspect 148, wherein the single variable domain additionally blocks the interaction between human DLL1 with at least one other member of the Notch receptors.

151. A single variable domain that specifically binds to DLL3.

152. The single variable domain according to aspect 151, wherein the member of the DLL3 family is selected from the group consisting of the human DLL3.

153. The single variable domain according to aspect 151, wherein the single variable domain additionally blocks the interaction between human DLL3 with at least one other member of the Notch receptors.

154. A single variable domain that specifically binds to at least one member of the Notch-3 family.

155. The single variable domain according to aspect 154, wherein the member of the Notch-2 family is selected from human Notch-3.

156. The single variable domain according to aspect 154, wherein the single variable domain additionally blocks the interaction between human Notch-3 with at least one other member of the Notch ligands.

157. The single variable domain according to aspect 154, wherein the single variable domain additionally blocks the interaction between human Notch-3 with at least one single variable domain with sequences having SEQ ID NO: 362 to 363.

158. The single variable domain according to aspect 154, wherein the single variable domain is selected from the group consisting of a) single variable domains with sequences having SEQ ID NO: 362 to 363; and b) single variable domains with 80% sequence identity to at least one sequence selected from the group consisting of single variable domains with sequences having SEQ ID NO: 362 to 363.

159. The single variable domain according to aspect 154, wherein the single variable domain is selected from the group consisting of a) single variable domains with sequences having SEQ ID NO: 362 to 363; and b) single variable domains with sequences having SEQ ID NO: 362 to 363, wherein up to 10 amino acid residues are replaced by naturally occurring amino acids and wherein said replaced amino acids are located within the framework regions.

160. The single variable domain according to aspect 154, wherein the single variable domain is selected from the group consisting of a) single variable domains with sequences having SEQ ID NO: 362 to 363; and b) single variable domains with sequences having SEQ ID NO: 362 to 363, wherein up to 8 amino acid residues are replaced by naturally occurring amino acids and wherein said replaced amino acids are located within the framework regions.

161. The single variable domain according to aspect 154, wherein the single variable domain is selected from the group consisting of a) single variable domains with sequences having SEQ ID NO: 362 to 363; and b) single variable domains with sequences having SEQ ID NO: 362 to 363, wherein up to 5 amino acid residues are replaced by naturally occurring amino acids and wherein said replaced amino acids are located within the framework regions.

162. The single variable domain according to aspect 154, wherein the single variable domain is selected from the group consisting of a) single variable domains with sequences having SEQ ID NO: 362 to 363; and b) single variable domains with sequences having SEQ ID NO: 348 to 361, wherein up to 3 amino acid residues are replaced by naturally occurring amino acids and wherein said replaced amino acids are located within the framework regions.

163. The single variable domain according to aspect 154, wherein the single variable domain is selected from the group consisting of a) single variable domains with sequences having SEQ ID NO: 362 to 363; and b) single variable domains with 80% sequence identity to at least one sequences selected from the group consisting of sequences having SEQ ID NO: 362 to 363; and wherein said selected single variable domain from group a) and b) binds to human Notch-3 with a dissociation constant ($K_D$) of $10^{-7}$ to $10^{-12}$ moles/liter or less.

164. The single variable domain according to aspect 154, wherein the single variable domain is selected from the group consisting of a) single variable domains with sequences having SEQ ID NO: 362 to 363; and b) single variable domains with sequences having SEQ ID NO: 348 to 361, wherein up to 10 amino acid residues are replaced by naturally occurring amino acids and wherein said replaced amino acids are located within the framework regions; and wherein said selected single variable domain from group a) and b) binds to human Notch-3 with a dissociation constant ($K_D$) of $10^{-7}$ to $10^{-12}$ moles/liter or less.

165. The single variable domain according to aspect 154, wherein the single variable domain is selected from the group consisting of a) single variable domains with sequences having SEQ ID NO: 362 to 363; and b) single variable domains with sequences having SEQ ID NO: 362 to 363, wherein up to 8 amino acid residues are replaced by naturally occurring amino acids and wherein said replaced amino acids are located within the framework regions; and wherein said selected single variable domain from group a) and b) binds to human Notch-3 with a dissociation constant ($K_D$) of $10^{-7}$ to $10^{-12}$ moles/liter or less.

166. The single variable domain according to aspect 154, wherein the single variable domain is selected from the group consisting of a) single variable domains with sequences having SEQ ID NO: 362 to 363; and b) single variable domains with sequences having SEQ ID NO: 362 to 363, wherein up to 5 amino acid residues are replaced by naturally occurring amino acids and wherein said replaced amino acids are located within the framework regions; and wherein said selected single variable domain from group a) and b) binds to human Notch-3 with a dissociation constant ($K_D$) of $10^{-7}$ to $10^{-12}$ moles/liter or less.

167. The single variable domain according to aspect 154, wherein the single variable domain is selected from the group consisting of a) single variable domains with sequences having SEQ ID NO: 362 to 363; and b) single variable domains with sequences having SEQ ID NO: 362 to 363, wherein up to 3 amino acid residues are replaced by naturally occurring amino acids and wherein said replaced amino acids are located within the framework regions; and wherein said selected single variable domain from group a) and b) binds to human Notch-3 with a dissociation constant ($K_D$) of $10^{-7}$ to $10^{-12}$ moles/liter or less.

168. The single variable domain according to aspect 154, wherein the single variable domain is selected from the group consisting of a) single variable domains with sequences having SEQ ID NO: 362 to 363; and b) single variable domains with 80% sequence identity to at least one sequences selected from the group consisting of sequences having SEQ ID NO: 362 to 363; and wherein said selected single variable domain from group a) and b) binds to human Notch-3 with a dissociation constant ($K_D$) of $10^{-8}$ to $10^{-12}$ moles/liter or less.

169. The single variable domain according to aspect 154, wherein the single variable domain is selected from the group consisting of a) single variable domains with sequences having SEQ ID NO: 362 to 363; and b) single variable domains with sequences having SEQ ID NO: 362 to 363, wherein up to 10 amino acid residues are replaced by naturally occurring amino acids and wherein said replaced amino acids are located within the framework regions; and wherein said selected single variable domain from group a) and b) binds to human Notch-2 with a dissociation constant ($K_D$) of $10^{-8}$ to $10^{-12}$ moles/liter or less.

170. The single variable domain according to aspect 154, wherein the single variable domain is selected from the group consisting of a) single variable domains with sequences having SEQ ID NO: 362 to 363; and b) single variable domains with sequences having SEQ ID NO: 362 to 363, wherein up to 8 amino acid residues are replaced by naturally occurring amino acids and wherein said replaced amino acids are located within the framework regions; and wherein said selected single variable domain from group a) and b) binds to human Notch-3 with a dissociation constant ($K_D$) of $10^{-8}$ to $10^{-12}$ moles/liter or less.

171. The single variable domain according to aspect 126, wherein the single variable domain is selected from the group consisting of a) single variable domains with sequences having SEQ ID NO: 362 to 363; and b) single variable domains with sequences having SEQ ID NO: 362 to 363, wherein up to 5 amino acid residues are replaced by naturally occurring amino acids and wherein said replaced amino acids are located within the framework regions; and wherein said selected single variable domain from group a) and b) binds to human Notch-3 with a dissociation constant ($K_D$) of $10^{-8}$ to $10^{-12}$ moles/liter or less.

172. The single variable domain according to aspect 154, wherein the single variable domain is selected from the group consisting of a) single variable domains with sequences having SEQ ID NO: 362 to 363; and b) single variable domains with sequences having SEQ ID NO: 362 to 363, wherein up to 3 amino acid residues are replaced by naturally occurring amino acids and wherein said replaced amino acids are located within the framework regions; and wherein said selected single variable domain from group a) and b) binds to human Notch-3 with a dissociation constant ($K_D$) of $10^{-8}$ to $10^{-12}$ moles/liter or less.

173. A single variable domain that specifically binds to Notch-4.

174. The single variable domain according to aspect 173, wherein the member of the Notch-3 family is selected from the group consisting of the human Notch-4.

175. The single variable domain according to aspect 173, wherein the single variable domain additionally blocks the interaction between human Notch-4 with at least one other member of the Notch ligands.

176. Single variable domain with sequence having SEQ ID NO: 329.
177. Single variable domain with sequence having SEQ ID NO: 330.
178. Single variable domain with sequence having SEQ ID NO: 331.
179. Single variable domain with sequence having SEQ ID NO: 332.
180. Single variable domain with sequence having SEQ ID NO: 333.
181. Single variable domain with sequence having SEQ ID NO: 334.
182. Single variable domain with sequence having SEQ ID NO: 335.
183. Single variable domain with sequence having SEQ ID NO: 336.
184. Single variable domain with sequence having SEQ ID NO: 337.
185. Single variable domain with sequence having SEQ ID NO: 338.
186. Single variable domain with sequence having SEQ ID NO: 339.
187. Single variable domain with sequence having SEQ ID NO: 340.
188. Single variable domain with sequence having SEQ ID NO: 341.
189. Single variable domain with sequence having SEQ ID NO: 342.
190. Single variable domain with sequence having SEQ ID NO: 343.
191. Single variable domain with sequence having SEQ ID NO: 344.
192. Single variable domain with sequence having SEQ ID NO: 345.
193. Single variable domain with sequence having SEQ ID NO: 346.
194. Single variable domain with sequence having SEQ ID NO: 347.
195. Single variable domain with sequence having SEQ ID NO: 348.
196. Single variable domain with sequence having SEQ ID NO: 349.
197. Single variable domain with sequence having SEQ ID NO: 350.
198. Single variable domain with sequence having SEQ ID NO: 351.
199. Single variable domain with sequence having SEQ ID NO: 352.
200. Single variable domain with sequence having SEQ ID NO: 353.
201. Single variable domain with sequence having SEQ ID NO: 354.
202. Single variable domain with sequence having SEQ ID NO: 355.
203. Single variable domain with sequence having SEQ ID NO: 356.
204. Single variable domain with sequence having SEQ ID NO: 356.
205. Single variable domain with sequence having SEQ ID NO: 357.
206. Single variable domain with sequence having SEQ ID NO: 358.
207. Single variable domain with sequence having SEQ ID NO: 359.
208. Single variable domain with sequence having SEQ ID NO: 360.
209. Single variable domain with sequence having SEQ ID NO: 361.
210. Single variable domain with sequence having SEQ ID NO: 362.
211. Single variable domain with sequence having SEQ ID NO: 363.
212. Single variable domain with sequence having SEQ ID NO: 364.
213. Single variable domain with sequence having SEQ ID NO: 365.
214. A construct comprising at least one single variable domain of aspects 1 to 24.
215. A construct comprising at least one single variable domain according to aspects 25 to 46.
216. A construct comprising at least one single variable domain of aspects 47 to 68.
217. A construct comprising at least one single variable domain of aspects 69 to 87.
218. A construct comprising at least one single variable domain of aspects 88 to 106.
219. A construct comprising at least one single variable domain of aspects 107 to 125.
220. A construct comprising at least one single variable domain of aspects 126 to 144.
221. A construct comprising at least one single variable domain of aspects 145 to 147.
222. A construct comprising at least one single variable domain of aspects 148 to 150.
223. A construct comprising at least one single variable domain of aspects 151 to 153.
224. A construct comprising at least one single variable domain of aspects 154 to 172.
225. A construct comprising at least one single variable domain of aspects 173 to 175.
226. A construct comprising at least one single variable domain of aspects 107 to 125.
227. A construct comprising at least one single variable domain of aspect 176.
228. A construct comprising at least one single variable domain of aspect 177.
229. A construct comprising at least one single variable domain of aspect 178.
230. A construct comprising at least one single variable domain of aspect 179.
231. A construct comprising at least one single variable domain of aspect 180.
232. A construct comprising at least one single variable domain of aspect 181.
233. A construct comprising at least one single variable domain of aspect 182.
234. A construct comprising at least one single variable domain of aspect 183.
235. A construct comprising at least one single variable domain of aspect 184.
236. A construct comprising at least one single variable domain of aspect 185.
237. A construct comprising at least one single variable domain of aspect 186.
238. A construct comprising at least one single variable domain of aspect 187.
239. A construct comprising at least one single variable domain of aspect 188.
240. A construct comprising at least one single variable domain of aspect 189.
241. A construct comprising at least one single variable domain of aspect 190.

242. A construct comprising at least one single variable domain of aspect 191.

243. A construct comprising at least one single variable domain of aspect 192.

244. A construct comprising at least one single variable domain of aspect 193.

245. A construct comprising at least one single variable domain of aspect 194.

246. A construct comprising at least one single variable domain of aspect 195.

247. A construct comprising at least one single variable domain of aspect 196.

248. A construct comprising at least one single variable domain of aspect 197.

249. A construct comprising at least one single variable domain of aspect 198.

250. A construct comprising at least one single variable domain of aspect 199.

251. A construct comprising at least one single variable domain of aspect 200.

252. A construct comprising at least one single variable domain of aspect 201.

253. A construct comprising at least one single variable domain of aspect 202.

254. A construct comprising at least one single variable domain of aspect 203.

255. A construct comprising at least one single variable domain of aspect 204.

256. A construct comprising at least one single variable domain of aspect 205.

257. A construct comprising at least one single variable domain of aspect 206.

258. A construct comprising at least one single variable domain of aspect 207.

259. A construct comprising at least one single variable domain of aspect 208.

260. A construct comprising at least one single variable domain of aspect 209.

261. A construct comprising at least one single variable domain of aspect 210.

262. A construct comprising at least one single variable domain of aspect 211.

263. A construct comprising at least one single variable domain of aspect 212.

264. A construct comprising at least one single variable domain of aspect 213.

265. A pharmaceutical composition comprising a single variable domain of aspects 1 to 213 and/or a construct of aspects 214 to 264.

266. A nucleotide sequence encoding for a single variable domain of aspects 1 to 213 and/or a construct of aspects 214 to 264.

267. A host cell able to express and/or comprising a single variable domain of aspects 1 to 213 and/or a construct of aspects 214 to 264, and/or a nucleotide sequence of aspect 234.

268. Method of making a single variable domain of any aspects 1 to 213, method of making a construct of aspects 214 to 264; method of making a pharmaceutical composition of aspect 265; method of making a nucleotide sequence of aspect 266; and/or making a host cell of 267.

269. Method of screening a molecule specifically binding to a member of the Notch pathway using a single variable domain of aspects 1 to 213 or a construct of aspects 214 to 264, a pharmaceutical composition of aspect 265, a nucleotide sequence of aspect 266, and/or a host cell of aspects 267.

270. Method for the prevention and/or treatment of at least one disease or disorder in which a member selected from the group consisting of the Notch pathway plays a role or is implicated, said method comprising administering, to a subject in need thereof, a pharmaceutically active amount of at least one single variable domain of aspects 1 to 213, one construct of aspects 214 to 264, or one pharmaceutical composition of aspect 265.

271. Method for the prevention and/or treatment of at least one disease or disorder selected from the group of diseases consisting of cancers, an autoimmune diseases or neurodegenerative diseases, said method comprising administering, to a subject in need thereof, a pharmaceutically active amount of at least one single variable domain of aspects 1 to 213, one construct of aspects 214 to 264, or one pharmaceutical composition of aspect 265.

272. Use of a pharmaceutically active amount of at least one single variable domain of aspects 1 to 213, one construct of aspects 214 to 264, or one pharmaceutical composition of aspect 265 for the prevention and/or treatment of at least one disease or disorder in which a member selected from the group consisting of the Notch pathway plays a role or is implicated.

273. Use of a pharmaceutically active amount of at least one single variable domain of aspects 1 to 213, one construct of aspects 214 to 264, or one pharmaceutical composition of aspect 265 for the prevention and/or treatment of at least one disease or disorder selected from the group of diseases consisting of cancers, an autoimmune diseases or neurodegenerative diseases.

274. Use of a pharmaceutically active amount of at least one single variable domain of aspects 1 to 213, one construct of aspects 214 to 264, or one pharmaceutical composition of aspect 265 for the manufacture of a medicament for the prevention and/or treatment of at least one disease or disorder in which a member selected from the group consisting of the Notch pathway plays a role or is implicated.

275. Use of a pharmaceutically active amount of at least one single variable domain of aspects 1 to 213, one construct of aspects 214 to 264, or one pharmaceutical composition of aspect 265 for the manufacture of a medicament for the prevention and/or treatment of at least one disease or disorder selected from the group of diseases consisting of cancers, an autoimmune diseases or neurodegenerative diseases.

The invention claimed is:

1. An isolated immunoglobulin single variable domain that specifically binds to at least one member of the Notch pathway, wherein the immunoglobulin single variable domain is selected from the group consisting of a) immunoglobulin single variable domains with sequences having SEQ ID NOs: 329 to 333 and SEQ ID NOs: 335 to 364; and b) immunoglobulin single variable domains with at least 90% sequence identity to at least one sequence selected from the group consisting of immunoglobulin single variable domains with sequences having SEQ ID NO: 329 to 333 and SEQ ID NOs: 335 to 364, in which for the purposes of determining the degree of amino acid identity, the amino acid residues that form the CDR sequences are disregarded.

2. The isolated immunoglobulin single variable domain according to claim 1, wherein the member of the Notch pathway is selected from the group consisting of the human members of the Notch pathway.

3. The isolated immunoglobulin single variable domain according to claim 1, wherein the member of the Notch pathway is selected from the group consisting of the Notch receptors and Notch ligands.

4. The isolated immunoglobulin single variable domain according to claim 1, wherein the member of the Notch pathway is selected from the group consisting of the human Notch receptors and human Notch ligands.

5. The isolated immunoglobulin single variable domain according to claim 1, wherein the member of the Notch pathway is selected from the group consisting of Jagged-1, Delta-like ligand 4 (DLL4), Notch-1, Notch-2, and Notch 3.

6. The isolated immunoglobulin single variable domain according to claim 1, wherein the member of the Notch pathway is selected from the group consisting of human Jagged-1, human Delta-like ligand 4 (DLL4), human Notch-1, human Notch-2, and human Notch 3.

7. The isolated immunoglobulin single variable domain according to claim 1, wherein the immunoglobulin single variable domain additionally blocks the interaction between at least one member of the Notch ligands with at least one other member of the Notch receptors.

8. The isolated immunoglobulin single variable domain according to claim 1, wherein the immunoglobulin single variable domain is selected from the group consisting of immunoglobulin single variable domains with sequences having SEQ ID NO: 329 to 333 and SEQ ID NOs: 335 to 364, wherein up to 10 amino acid residues are replaced by naturally occurring amino acids and wherein said replaced amino acids are located within the framework regions.

9. The isolated polypeptide comprising an immunoglobulin single variable domain according to claim 1, wherein the immunoglobulin single variable domain is selected from the group consisting of immunoglobulin single variable domains with sequences having SEQ ID NO: 329 to 333 and SEQ ID NOs: 335 to 364, wherein up to 8 amino acid residues are replaced by naturally occurring amino acids and wherein said replaced amino acids are located within the framework regions.

10. The isolated immunoglobulin single variable domain according to claim 1, wherein the immunoglobulin single variable domain is selected from the group consisting of immunoglobulin single variable domains with sequences having SEQ ID NO: 329 to 333 and SEQ ID NOs: 335 to 364, wherein up to 5 amino acid residues are replaced by naturally occurring amino acids and wherein said replaced amino acids are located within the framework regions.

11. The isolated immunoglobulin single variable domain according to claim 1, wherein the immunoglobulin single variable domain is selected from the group consisting of immunoglobulin single variable domains with sequences having SEQ ID NO: 329 to 333 and SEQ ID NOs: 335 to 364, wherein up to 3 amino acid residues are replaced by naturally occurring amino acids and wherein said replaced amino acids are located within the framework regions.

12. The isolated immunoglobulin single variable domain according to claim 1, wherein said selected immunoglobulin single variable domain from group a) and b) binds to at least one member of the Notch signalling pathway with a dissociation constant ($K_D$) of $10^{-7}$ to $10^{-12}$ moles/liter or less.

13. An isolated polypeptide comprising the immunoglobulin single variable domain of claim 1.

* * * * *

UNITED STATES PATENT AND TRADEMARK OFFICE
CERTIFICATE OF CORRECTION

| | | |
|---|---|---|
| PATENT NO. | : 8,557,965 B2 | Page 1 of 1 |
| APPLICATION NO. | : 12/934766 | |
| DATED | : October 15, 2013 | |
| INVENTOR(S) | : Saunders et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 231 days.

Signed and Sealed this
Twenty-sixth Day of May, 2015

Michelle K. Lee
*Director of the United States Patent and Trademark Office*

SEQUENCE LISTING

<160> NUMBER OF SEQ ID NOS: 365

<210> SEQ ID NO 1
<211> LENGTH: 102
<212> TYPE: PRT
<213> ORGANISM: Artificial
<220> FEATURE:

```
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Pro Phe Ser Xaa Xaa
            20                  25                  30

Xaa Xaa Xaa Trp Phe Arg Gln Ala Pro Gly Lys Gln Arg Asp Ser Val
        35                  40                  45

Ala Xaa Xaa Xaa Xaa Xaa Arg Phe Thr Ile Ser Arg Asp Asn Ala Lys
    50                  55                  60

Asn Thr Val Tyr Leu Gln Met Asn Ser Leu Lys Pro Glu Asp Thr Ala
65                  70                  75                  80

Val Tyr Arg Cys Tyr Phe Xaa Xaa Xaa Xaa Xaa Trp Gly Gln Gly Thr
                85                  90                  95

Gln Val Thr Val Ser Ser
            100

<210> SEQ ID NO 2
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 2

Gln Val Lys Leu Glu Glu Ser Gly Gly Gly Leu Val Gln Ala Gly Gly
1               5                   10                  15

Ser Leu Arg Leu Ser Cys Val Gly Ser Gly Arg Thr Phe Ser Xaa Xaa
            20                  25                  30

Xaa Xaa Xaa Trp Phe Arg Leu Ala Pro Gly Lys Glu Arg Glu Phe Val
        35                  40                  45

Ala Xaa Xaa Xaa Xaa Xaa Arg Phe Thr Ile Ser Arg Asp Thr Ala Ser
    50                  55                  60

Asn Arg Gly Tyr Leu His Met Asn Asn Leu Thr Pro Glu Asp Thr Ala
65                  70                  75                  80

Val Tyr Tyr Cys Ala Ala Xaa Xaa Xaa Xaa Xaa Trp Gly Gln Gly Thr
                85                  90                  95

Gln Val Thr Val Ser Ser
            100
```

<210> SEQ ID NO 3
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 3

Ala Val Gln Leu Val Asp Ser Gly Gly Gly Leu Val Gln Ala Gly Asp
1               5                   10                  15

Ser Leu Lys Leu Ser Cys Ala Leu Thr Gly Gly Ala Phe Thr Xaa Xaa
            20                  25                  30

Xaa Xaa Xaa Trp Phe Arg Gln Thr Pro Gly Arg Glu Arg Glu Phe Val
        35                  40                  45

Ala Xaa Xaa Xaa Xaa Xaa Arg Phe Thr Ile Ser Arg Asp Asn Ala Lys
50                  55                  60

Asn Met Val Tyr Leu Arg Met Asn Ser Leu Ile Pro Glu Asp Ala Ala
65                  70                  75                  80

Val Tyr Ser Cys Ala Ala Xaa Xaa Xaa Xaa Xaa Trp Gly Gln Gly Thr
            85                  90                  95

Leu Val Thr Val Ser Ser
            100

<210> SEQ ID NO 4
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 4

Gln Val Gln Leu Val Glu Ser Gly Gly Gly Leu Val Glu Ala Gly Gly
1               5                   10                  15

Ser Leu Arg Leu Ser Cys Thr Ala Ser Glu Ser Pro Phe Arg Xaa Xaa
            20                  25                  30

Xaa Xaa Xaa Trp Phe Arg Gln Thr Ser Gly Gln Glu Arg Glu Phe Val
        35                  40                  45

Ala Xaa Xaa Xaa Xaa Xaa Arg Phe Thr Ile Ser Arg Asp Asp Ala Lys
50                  55                  60

Asn Thr Val Trp Leu His Gly Ser Thr Leu Lys Pro Glu Asp Thr Ala
65                  70                  75                  80

```
Val Tyr Tyr Cys Ala Ala Xaa Xaa Xaa Xaa Trp Gly Gln Gly Thr
                85                  90                  95

Gln Val Thr Val Ser Ser
            100

<210> SEQ ID NO 5
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 5

Ala Val Gln Leu Val Glu Ser Gly Gly Gly Leu Val Gln Gly Gly
1               5                   10                  15

Ser Leu Arg Leu Ala Cys Ala Ala Ser Glu Arg Ile Phe Asp Xaa Xaa
            20                  25                  30

Xaa Xaa Xaa Trp Tyr Arg Gln Gly Pro Gly Asn Glu Arg Glu Leu Val
        35                  40                  45

Ala Xaa Xaa Xaa Xaa Xaa Arg Phe Thr Ile Ser Met Asp Tyr Thr Lys
    50                  55                  60

Gln Thr Val Tyr Leu His Met Asn Ser Leu Arg Pro Glu Asp Thr Gly
65                  70                  75                  80

Leu Tyr Tyr Cys Lys Ile Xaa Xaa Xaa Xaa Xaa Trp Gly Gln Gly Thr
                85                  90                  95

Gln Val Thr Val Ser Ser
            100

<210> SEQ ID NO 6
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 6

Asp Val Lys Phe Val Glu Ser Gly Gly Gly Leu Val Gln Ala Gly Gly
1               5                   10                  15

Ser Leu Arg Leu Ser Cys Val Ala Ser Gly Phe Asn Phe Asp Xaa Xaa
            20                  25                  30

Xaa Xaa Xaa Trp Phe Arg Gln Ala Pro Gly Lys Glu Arg Glu Val
        35                  40                  45
```

```
Ala Xaa Xaa Xaa Xaa Xaa Arg Phe Thr Ile Ser Ser Glu Lys Asp Lys
        50                  55                  60

Asn Ser Val Tyr Leu Gln Met Asn Ser Leu Lys Pro Glu Asp Thr Ala
 65                  70                  75                  80

Leu Tyr Ile Cys Ala Gly Xaa Xaa Xaa Xaa Trp Gly Arg Gly Thr
                 85                  90                  95

Gln Val Thr Val Ser Ser
            100
```

<210> SEQ ID NO 7
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 7

```
Gln Val Arg Leu Ala Glu Ser Gly Gly Gly Leu Val Gln Ser Gly Gly
 1               5                  10                  15

Ser Leu Arg Leu Ser Cys Val Ala Ser Gly Ser Thr Tyr Thr Xaa Xaa
             20                  25                  30

Xaa Xaa Xaa Trp Tyr Arg Gln Tyr Pro Gly Lys Gln Arg Ala Leu Val
        35                  40                  45

Ala Xaa Xaa Xaa Xaa Xaa Arg Phe Thr Ile Ala Arg Asp Ser Thr Lys
        50                  55                  60

Asp Thr Phe Cys Leu Gln Met Asn Asn Leu Lys Pro Glu Asp Thr Ala
 65                  70                  75                  80

Val Tyr Tyr Cys Tyr Ala Xaa Xaa Xaa Xaa Xaa Trp Gly Gln Gly Thr
                 85                  90                  95

Gln Val Thr Val Ser Ser
            100
```

<210> SEQ ID NO 8
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 8

```
Glu Val Gln Leu Val Glu Ser Gly Gly Gly Leu Val Gln Ala Gly Gly
 1               5                  10                  15
```

Ser Leu Arg Leu Ser Cys Ala Ala Ser Gly Phe Thr Ser Asp Xaa Xaa
            20                  25                  30

Xaa Xaa Xaa Trp Phe Arg Gln Ala Pro Gly Lys Pro Arg Glu Gly Val
        35                  40                  45

Ser Xaa Xaa Xaa Xaa Xaa Arg Phe Thr Ile Ser Thr Asp Asn Ala Lys
 50                  55                  60

Asn Thr Val His Leu Leu Met Asn Arg Val Asn Ala Glu Asp Thr Ala
 65                  70                  75                  80

Leu Tyr Tyr Cys Ala Val Xaa Xaa Xaa Xaa Trp Gly Arg Gly Thr
                 85                  90                  95

Arg Val Thr Val Ser Ser
            100

<210> SEQ ID NO 9
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 9

Gln Val Gln Leu Val Glu Ser Gly Gly Gly Leu Val Gln Pro Gly Gly
 1               5                  10                  15

Ser Leu Arg Leu Ser Cys Gln Ala Ser Gly Asp Ile Ser Thr Xaa Xaa
            20                  25                  30

Xaa Xaa Xaa Trp Tyr Arg Gln Val Pro Gly Lys Leu Arg Glu Phe Val
        35                  40                  45

Ala Xaa Xaa Xaa Xaa Xaa Arg Phe Thr Ile Ser Gly Asp Asn Ala Lys
 50                  55                  60

Arg Ala Ile Tyr Leu Gln Met Asn Asn Leu Lys Pro Asp Asp Thr Ala
 65                  70                  75                  80

Val Tyr Tyr Cys Asn Arg Xaa Xaa Xaa Xaa Xaa Trp Gly Gln Gly Thr
                 85                  90                  95

Gln Val Thr Val Ser Pro
            100

<210> SEQ ID NO 10
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 10

```
Gln Val Pro Val Val Glu Ser Gly Gly Gly Leu Val Gln Ala Gly Asp
1               5                   10                  15

Ser Leu Arg Leu Phe Cys Ala Val Pro Ser Phe Thr Ser Thr Xaa Xaa
            20                  25                  30

Xaa Xaa Xaa Trp Phe Arg Gln Ala Pro Gly Lys Glu Arg Glu Phe Val
            35                  40                  45

Ala Xaa Xaa Xaa Xaa Xaa Arg Phe Thr Ile Ser Arg Asn Ala Thr Lys
    50                  55                  60

Asn Thr Leu Thr Leu Arg Met Asp Ser Leu Lys Pro Glu Asp Thr Ala
65                  70                  75                  80

Val Tyr Tyr Cys Ala Ala Xaa Xaa Xaa Xaa Xaa Trp Gly Gln Gly Thr
            85                  90                  95

Gln Val Thr Val Ser Ser
            100
```

<210> SEQ ID NO 11
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 11

```
Glu Val Gln Leu Val Glu Ser Gly Gly Gly Leu Val Gln Ala Gly Asp
1               5                   10                  15

Ser Leu Arg Leu Phe Cys Thr Val Ser Gly Gly Thr Ala Ser Xaa Xaa
            20                  25                  30

Xaa Xaa Xaa Trp Phe Arg Gln Ala Pro Gly Glu Lys Arg Glu Phe Val
            35                  40                  45

Ala Xaa Xaa Xaa Xaa Xaa Arg Phe Thr Ile Ala Arg Glu Asn Ala Gly
    50                  55                  60

Asn Met Val Tyr Leu Gln Met Asn Asn Leu Lys Pro Asp Asp Thr Ala
65                  70                  75                  80

Leu Tyr Thr Cys Ala Ala Xaa Xaa Xaa Xaa Xaa Trp Gly Arg Gly Thr
            85                  90                  95

Gln Val Thr Val Ser Ser
            100
```

<210> SEQ ID NO 12
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature

```
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 12

Ala Val Gln Leu Val Glu Ser Gly Gly Asp Ser Val Gln Pro Gly Asp
1               5                   10                  15

Ser Gln Thr Leu Ser Cys Ala Ala Ser Gly Arg Thr Asn Ser Xaa Xaa
            20                  25                  30

Xaa Xaa Xaa Trp Phe Arg Gln Ala Pro Gly Lys Glu Arg Val Phe Leu
        35                  40                  45

Ala Xaa Xaa Xaa Xaa Xaa Arg Phe Thr Ile Ser Arg Asp Ser Ala Lys
    50                  55                  60

Asn Met Met Tyr Leu Gln Met Asn Asn Leu Lys Pro Gln Asp Thr Ala
65                  70                  75                  80

Val Tyr Tyr Cys Ala Ala Xaa Xaa Xaa Xaa Xaa Trp Gly Gln Gly Thr
            85                  90                  95

Gln Val Thr Val Ser Ser
            100

<210> SEQ ID NO 13
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 13

Ala Val Gln Leu Val Glu Ser Gly Gly Gly Leu Val Gln Ala Gly Gly
1               5                   10                  15

Ser Leu Arg Leu Ser Cys Val Val Ser Gly Leu Thr Ser Ser Xaa Xaa
            20                  25                  30

Xaa Xaa Xaa Trp Phe Arg Gln Thr Pro Trp Gln Glu Arg Asp Phe Val
        35                  40                  45

Ala Xaa Xaa Xaa Xaa Xaa Arg Phe Thr Ile Ser Arg Asp Asn Tyr Lys
    50                  55                  60

Asp Thr Val Leu Leu Glu Met Asn Phe Leu Lys Pro Glu Asp Thr Ala
65                  70                  75                  80

Ile Tyr Tyr Cys Ala Ala Xaa Xaa Xaa Xaa Xaa Trp Gly Gln Gly Thr
            85                  90                  95

Gln Val Thr Val Ser Ser
            100

<210> SEQ ID NO 14
<211> LENGTH: 102
<212> TYPE: PRT
<213> ORGANISM: Artificial
<220> FEATURE:
<223> OTHER INFORMATION: KERE-class Nanobody
```

```
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 14

Ala Val Gln Leu Val Glu Ser Gly Gly Gly Leu Val Gln Ala Gly Ala
 1               5                  10                  15

Ser Leu Arg Leu Ser Cys Ala Thr Ser Thr Arg Thr Leu Asp Xaa Xaa
             20                  25                  30

Xaa Xaa Xaa Trp Phe Arg Gln Ala Pro Gly Arg Asp Arg Glu Phe Val
         35                  40                  45

Ala Xaa Xaa Xaa Xaa Xaa Arg Phe Thr Val Ser Arg Asp Ser Ala Glu
     50                  55                  60

Asn Thr Val Ala Leu Gln Met Asn Ser Leu Lys Pro Glu Asp Thr Ala
 65                  70                  75                  80

Val Tyr Tyr Cys Ala Ala Xaa Xaa Xaa Xaa Xaa Trp Gly Gln Gly Thr
                 85                  90                  95

Arg Val Thr Val Ser Ser
            100

<210> SEQ ID NO 15
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 15

Gln Val Gln Leu Val Glu Ser Gly Gly Gly Leu Val Gln Pro Gly Gly
 1               5                  10                  15

Ser Leu Arg Leu Ser Cys Thr Val Ser Arg Leu Thr Ala His Xaa Xaa
             20                  25                  30

Xaa Xaa Xaa Trp Phe Arg Gln Ala Pro Gly Lys Glu Arg Glu Ala Val
         35                  40                  45

Ser Xaa Xaa Xaa Xaa Xaa Arg Phe Thr Ile Ser Arg Asp Tyr Ala Gly
     50                  55                  60

Asn Thr Ala Phe Leu Gln Met Asp Ser Leu Lys Pro Glu Asp Thr Gly
 65                  70                  75                  80

Val Tyr Tyr Cys Ala Thr Xaa Xaa Xaa Xaa Xaa Trp Gly Gln Gly Thr
                 85                  90                  95

Gln Val Thr Val Ser Ser
            100
```

```
<210> SEQ ID NO 16
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 16

Glu Val Gln Leu Val Glu Ser Gly Gly Glu Leu Val Gln Ala Gly Gly
1               5                   10                  15

Ser Leu Lys Leu Ser Cys Thr Ala Ser Gly Arg Asn Phe Val Xaa Xaa
            20                  25                  30

Xaa Xaa Xaa Trp Phe Arg Arg Ala Pro Gly Lys Glu Arg Glu Phe Val
        35                  40                  45

Ala Xaa Xaa Xaa Xaa Xaa Arg Phe Thr Val Ser Arg Asp Asn Gly Lys
50                  55                  60

Asn Thr Ala Tyr Leu Arg Met Asn Ser Leu Lys Pro Glu Asp Thr Ala
65                  70                  75                  80

Asp Tyr Tyr Cys Ala Val Xaa Xaa Xaa Xaa Xaa Leu Gly Ser Gly Thr
                85                  90                  95

Gln Val Thr Val Ser Ser
            100

<210> SEQ ID NO 17
<211> LENGTH: 102
<212> TYPE: PRT
<213> ORGANISM: Artificial
<220> FEATURE:
<223> OTHER INFORMATION: GLEW-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 17

Ala Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Xaa Xaa
            20                  25                  30

Xaa Xaa Xaa Trp Val Arg Gln Ala Pro Gly Lys Val Leu Glu Trp Val
        35                  40                  45

Ser Xaa Xaa Xaa Xaa Xaa Arg Phe Thr Ile Ser Arg Asp Asn Ala Lys
        50                  55                  60

Asn Thr Leu Tyr Leu Gln Met Asn Ser Leu Lys Pro Glu Asp Thr Ala
65                  70                  75                  80

Val Tyr Tyr Cys Val Lys Xaa Xaa Xaa Xaa Xaa Xaa Gly Ser Gln Gly Thr
```

```
                85                  90                  95

Gln Val Thr Val Ser Ser
            100

<210> SEQ ID NO 18
<211> LENGTH: 102
<212> TYPE: PRT
<213> ORGANISM: Artificial
<220> FEATURE:
<223> OTHER INFORMATION: GLEW-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Val Cys Val Ser Ser Gly Cys Thr Xaa Xaa
            20                  25                  30

Xaa Xaa Xaa Trp Val Arg Gln Ala Pro Gly Lys Ala Glu Glu Trp Val
        35                  40                  45

Ser Xaa Xaa Xaa Xaa Xaa Arg Phe Lys Ile Ser Arg Asp Asn Ala Lys
    50                  55                  60

Lys Thr Leu Tyr Leu Gln Met Asn Ser Leu Gly Pro Glu Asp Thr Ala
65                  70                  75                  80

Met Tyr Tyr Cys Gln Arg Xaa Xaa Xaa Xaa Xaa Arg Gly Gln Gly Thr
                85                  90                  95

Gln Val Thr Val Ser Ser
            100

<210> SEQ ID NO 19
<211> LENGTH: 102
<212> TYPE: PRT
<213> ORGANISM: Artificial
<220> FEATURE:
<223> OTHER INFORMATION: GLEW-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 19

Glu Val Gln Leu Val Glu Ser Gly Gly Gly Leu Ala Leu Pro Gly Gly
1               5                   10                  15

Ser Leu Thr Leu Ser Cys Val Phe Ser Gly Ser Thr Phe Ser Xaa Xaa
            20                  25                  30

Xaa Xaa Xaa Trp Val Arg His Thr Pro Gly Lys Ala Glu Glu Trp Val
        35                  40                  45

Ser Xaa Xaa Xaa Xaa Xaa Arg Phe Thr Ile Ser Arg Asp Asn Ala Lys
```

```
                    50                  55                  60
Asn Thr Leu Tyr Leu Glu Met Asn Ser Leu Ser Pro Glu Asp Thr Ala
 65                  70                  75                  80

Met Tyr Tyr Cys Gly Arg Xaa Xaa Xaa Xaa Xaa Arg Ser Lys Gly Ile
                 85                  90                  95

Gln Val Thr Val Ser Ser
            100
```

<210> SEQ ID NO 20
<211> LENGTH: 102
<212> TYPE: PRT
<213> ORGANISM: Artificial
<220> FEATURE:
<223> OTHER INFORMATION: P,R,S 103-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 20

```
Ala Val Gln Leu Val Glu Ser Gly Gly Gly Leu Val Gln Ala Gly Gly
 1               5                  10                  15

Ser Leu Arg Leu Ser Cys Ala Ala Ser Gly Arg Thr Phe Ser Xaa Xaa
                 20                  25                  30

Xaa Xaa Xaa Trp Phe Arg Gln Ala Pro Gly Lys Glu Arg Glu Phe Val
             35                  40                  45

Ala Xaa Xaa Xaa Xaa Xaa Arg Phe Thr Ile Ser Arg Asp Asn Ala Lys
         50                  55                  60

Asn Thr Val Tyr Leu Gln Met Asn Ser Leu Lys Pro Glu Asp Thr Ala
 65                  70                  75                  80

Val Tyr Tyr Cys Ala Ala Xaa Xaa Xaa Xaa Xaa Xaa Arg Gly Gln Gly Thr
                 85                  90                  95

Gln Val Thr Val Ser Ser
            100
```

<210> SEQ ID NO 21
<211> LENGTH: 102
<212> TYPE: PRT
<213> ORGANISM: Artificial
<220> FEATURE:
<223> OTHER INFORMATION: P,R,S 103-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 21

```
Asp Val Gln Leu Val Glu Ser Gly Gly Asp Leu Val Gln Pro Gly Gly
 1               5                  10                  15

Ser Leu Arg Leu Ser Cys Ala Ala Ser Gly Phe Ser Phe Asp Xaa Xaa
```

```
                     20                  25                  30
Xaa Xaa Xaa Trp Leu Arg Gln Thr Pro Gly Lys Gly Leu Glu Trp Val
            35                  40                  45

Gly Xaa Xaa Xaa Xaa Xaa Arg Phe Thr Ile Ser Arg Asp Asn Ala Lys
    50                  55                  60

Asn Met Leu Tyr Leu His Leu Asn Asn Leu Lys Ser Glu Asp Thr Ala
 65                  70                  75                  80

Val Tyr Tyr Cys Arg Arg Xaa Xaa Xaa Xaa Xaa Leu Gly Gln Gly Thr
                85                  90                  95

Gln Val Thr Val Ser Ser
            100

<210> SEQ ID NO 22
<211> LENGTH: 102
<212> TYPE: PRT
<213> ORGANISM: Artificial
<220> FEATURE:
<223> OTHER INFORMATION: P,R,S 103-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 22

Glu Val Gln Leu Val Glu Ser Gly Gly Gly Leu Val Gln Pro Gly Gly
 1               5                  10                  15

Ser Leu Arg Leu Ser Cys Val Cys Val Ser Ser Gly Cys Thr Xaa Xaa
            20                  25                  30

Xaa Xaa Xaa Trp Val Arg Gln Ala Pro Gly Lys Ala Glu Glu Trp Val
            35                  40                  45

Ser Xaa Xaa Xaa Xaa Xaa Arg Phe Lys Ile Ser Arg Asp Asn Ala Lys
    50                  55                  60

Lys Thr Leu Tyr Leu Gln Met Asn Ser Leu Gly Pro Glu Asp Thr Ala
 65                  70                  75                  80

Met Tyr Tyr Cys Gln Arg Xaa Xaa Xaa Xaa Xaa Arg Gly Gln Gly Thr
                85                  90                  95

Gln Val Thr Val Ser Ser
            100

<210> SEQ ID NO 23
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 23

Gln Val Gln Arg Val Glu Ser Gly Gly Gly Leu Val Gln Ala Gly Gly
 1               5                  10                  15

Ser Leu Arg Leu Ser Cys Ala Ala Ser Gly Arg Thr Ser Ser
            20                  25                  30

<210> SEQ ID NO 24
<211> LENGTH: 30
<212> TYPE: PRT
```

```
<213> ORGANISM: Artificial
<220> FEATURE:
<223> OTHER INFORMATION: KERE-class Nanobody FW1 sequence

<400> SEQUENCE: 24

Gln Val Gln Leu Val Glu Ser Gly Gly Gly Leu Val Gln Thr Gly Asp
1               5                   10                  15

Ser Leu Ser Leu Ser Cys Ser Ala Ser Gly Arg Thr Phe Ser
            20                  25                  30

<210> SEQ ID NO 25
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 25

Gln Val Lys Leu Glu Glu Ser Gly Gly Gly Leu Val Gln Ala Gly Asp
1               5                   10                  15

Ser Leu Arg Leu Ser Cys Ala Ala Thr Gly Arg Ala Phe Gly
            20                  25                  30

<210> SEQ ID NO 26
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 26

Ala Val Gln Leu Val Glu Ser Gly Gly Gly Leu Val Gln Pro Gly Glu
1               5                   10                  15

Ser Leu Gly Leu Ser Cys Val Ala Ser Gly Arg Asp Phe Val
            20                  25                  30

<210> SEQ ID NO 27
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 27

Glu Val Gln Leu Val Glu Ser Gly Gly Gly Leu Val Gln Ala Gly Gly
1               5                   10                  15

Ser Leu Arg Leu Ser Cys Glu Val Leu Gly Arg Thr Ala Gly
            20                  25                  30

<210> SEQ ID NO 28
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 28

Gln Val Gln Leu Val Glu Ser Gly Gly Gly Trp Val Gln Pro Gly Gly
1               5                   10                  15

Ser Leu Arg Leu Ser Cys Ala Ala Ser Glu Thr Ile Leu Ser
            20                  25                  30

<210> SEQ ID NO 29
<211> LENGTH: 30
<212> TYPE: PRT
```

```
<213> ORGANISM: Artificial
<220> FEATURE:
<223> OTHER INFORMATION: KERE-class Nanobody FW1 sequence

<400> SEQUENCE: 29

Gln Val Gln Leu Val Glu Ser Gly Gly Gly Thr Val Gln Pro Gly Gly
1               5                   10                  15

Ser Leu Asn Leu Ser Cys Val Ala Ser Gly Asn Thr Phe Asn
            20                  25                  30

<210> SEQ ID NO 30
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 30

Glu Val Gln Leu Val Glu Ser Gly Gly Gly Leu Ala Gln Pro Gly Gly
1               5                   10                  15

Ser Leu Gln Leu Ser Cys Ser Ala Pro Gly Phe Thr Leu Asp
            20                  25                  30

<210> SEQ ID NO 31
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 31

Ala Gln Glu Leu Glu Glu Ser Gly Gly Gly Leu Val Gln Ala Gly Gly
1               5                   10                  15

Ser Leu Arg Leu Ser Cys Ala Ala Ser Gly Arg Thr Phe Asn
            20                  25                  30

<210> SEQ ID NO 32
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 32

Val Glu Ser Gly Gly Gly Leu Val Gln Pro Gly Gly Ser Leu Arg Leu
1               5                   10                  15

Ser Cys Ala Ala Ser Gly
            20

<210> SEQ ID NO 33
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 33

Val Asp Ser Gly Gly Gly Leu Val Gln Ala Gly Asp Ser Leu Lys Leu
1               5                   10                  15

Ser Cys Ala Leu Thr Gly
            20

<210> SEQ ID NO 34
<211> LENGTH: 22
<212> TYPE: PRT
```

```
<213> ORGANISM: Artificial
<220> FEATURE:
<223> OTHER INFORMATION: KERE-class Nanobody FW1 sequence

<400> SEQUENCE: 34

Val Asp Ser Gly Gly Gly Leu Val Gln Ala Gly Asp Ser Leu Arg Leu
1               5                   10                  15

Ser Cys Ala Ala Ser Gly
            20

<210> SEQ ID NO 35
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 35

Val Asp Ser Gly Gly Gly Leu Val Glu Ala Gly Gly Ser Leu Arg Leu
1               5                   10                  15

Ser Cys Gln Val Ser Glu
            20

<210> SEQ ID NO 36
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 36

Gln Asp Ser Gly Gly Gly Ser Val Gln Ala Gly Gly Ser Leu Lys Leu
1               5                   10                  15

Ser Cys Ala Ala Ser Gly
            20

<210> SEQ ID NO 37
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 37

Val Gln Ser Gly Gly Arg Leu Val Gln Ala Gly Asp Ser Leu Arg Leu
1               5                   10                  15

Ser Cys Ala Ala Ser Glu
            20

<210> SEQ ID NO 38
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 38

Val Glu Ser Gly Gly Thr Leu Val Gln Ser Gly Asp Ser Leu Lys Leu
1               5                   10                  15

Ser Cys Ala Ser Ser Thr
            20

<210> SEQ ID NO 39
<211> LENGTH: 22
<212> TYPE: PRT
```

```
<213> ORGANISM: Artificial
<220> FEATURE:
<223> OTHER INFORMATION: KERE-class Nanobody FW1 sequence

<400> SEQUENCE: 39

Met Glu Ser Gly Gly Asp Ser Val Gln Ser Gly Gly Ser Leu Thr Leu
1               5                   10                  15

Ser Cys Val Ala Ser Gly
            20

<210> SEQ ID NO 40
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 40

Gln Ala Ser Gly Gly Gly Leu Val Gln Ala Gly Gly Ser Leu Arg Leu
1               5                   10                  15

Ser Cys Ser Ala Ser Val
            20

<210> SEQ ID NO 41
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 41

Trp Phe Arg Gln Ala Pro Gly Lys Glu Arg Glu Phe Val Ala
1               5                   10

<210> SEQ ID NO 42
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 42

Trp Phe Arg Gln Thr Pro Gly Arg Glu Arg Glu Phe Val Ala
1               5                   10

<210> SEQ ID NO 43
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 43

Trp Tyr Arg Gln Ala Pro Gly Lys Gln Arg Glu Met Val Ala
1               5                   10

<210> SEQ ID NO 44
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 44

Trp Tyr Arg Gln Gly Pro Gly Lys Gln Arg Glu Leu Val Ala
1               5                   10
```

<210> SEQ ID NO 45
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 45

Trp Ile Arg Gln Ala Pro Gly Lys Glu Arg Glu Gly Val Ser
1               5                   10

<210> SEQ ID NO 46
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 46

Trp Phe Arg Glu Ala Pro Gly Lys Glu Arg Glu Gly Ile Ser
1               5                   10

<210> SEQ ID NO 47
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 47

Trp Tyr Arg Gln Ala Pro Gly Lys Glu Arg Asp Leu Val Ala
1               5                   10

<210> SEQ ID NO 48
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 48

Trp Phe Arg Gln Ala Pro Gly Lys Gln Arg Glu Glu Val Ser
1               5                   10

<210> SEQ ID NO 49
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 49

Trp Phe Arg Gln Pro Pro Gly Lys Val Arg Glu Phe Val Gly
1               5                   10

<210> SEQ ID NO 50
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 50

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Arg Cys Tyr Phe
            20                  25                  30

<210> SEQ ID NO 51
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 51

Arg Phe Ala Ile Ser Arg Asp Asn Asn Lys Asn Thr Gly Tyr Leu Gln
1               5                   10                  15

Met Asn Ser Leu Glu Pro Glu Asp Thr Ala Val Tyr Tyr Cys Ala Ala
            20                  25                  30

<210> SEQ ID NO 52
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 52

Arg Phe Thr Val Ala Arg Asn Asn Ala Lys Asn Thr Val Asn Leu Glu
1               5                   10                  15

Met Asn Ser Leu Lys Pro Glu Asp Thr Ala Val Tyr Tyr Cys Ala Ala
            20                  25                  30

<210> SEQ ID NO 53
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 53

Arg Phe Thr Ile Ser Arg Asp Ile Ala Lys Asn Thr Val Asp Leu Leu
1               5                   10                  15

Met Asn Asn Leu Glu Pro Glu Asp Thr Ala Val Tyr Tyr Cys Ala Ala
            20                  25                  30

<210> SEQ ID NO 54
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 54

Arg Leu Thr Ile Ser Arg Asp Asn Ala Val Asp Thr Met Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 55
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 55

Arg Phe Thr Ile Ser Arg Asp Asn Ala Lys Asn Thr Val Tyr Leu Gln
1               5                   10                  15

Met Asp Asn Val Lys Pro Glu Asp Thr Ala Ile Tyr Tyr Cys Ala Ala
            20                  25                  30

```
<210> SEQ ID NO 56
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 56

Arg Phe Thr Ile Ser Lys Asp Ser Gly Lys Asn Thr Val Tyr Leu Gln
1               5                   10                  15

Met Thr Ser Leu Lys Pro Glu Asp Thr Ala Val Tyr Tyr Cys Ala Thr
            20                  25                  30

<210> SEQ ID NO 57
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 57

Arg Phe Thr Ile Ser Arg Asp Ser Ala Lys Asn Met Met Tyr Leu Gln
1               5                   10                  15

Met Asn Asn Leu Lys Pro Gln Asp Thr Ala Val Tyr Tyr Cys Ala Ala
            20                  25                  30

<210> SEQ ID NO 58
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 58

Arg Phe Thr Ile Ser Arg Glu Asn Asp Lys Ser Thr Val Tyr Leu Gln
1               5                   10                  15

Leu Asn Ser Leu Lys Pro Glu Asp Thr Ala Val Tyr Tyr Cys Ala Ala
            20                  25                  30

<210> SEQ ID NO 59
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 59

Arg Phe Thr Ile Ser Arg Asp Tyr Ala Gly Asn Thr Ala Tyr Leu Gln
1               5                   10                  15

Met Asn Ser Leu Lys Pro Glu Asp Thr Gly Val Tyr Tyr Cys Ala Thr
            20                  25                  30

<210> SEQ ID NO 60
<211> LENGTH: 11
<212> TYPE: PRT
<213> ORGANISM: Artificial
<220> FEATURE:
<223> OTHER INFORMATION: KERE-class Nanobody FW4 sequence

<400> SEQUENCE: 60

Trp Gly Gln Gly Thr Gln Val Thr Val Ser Ser
1               5                   10

<210> SEQ ID NO 61
```

```
<211> LENGTH: 11
<212> TYPE: PRT
<213> ORGANISM: Artificial
<220> FEATURE:
<223> OTHER INFORMATION: KERE-class Nanobody FW4 sequence

<400> SEQUENCE: 61

Trp Gly Lys Gly Thr Leu Val Thr Val Ser Ser
1               5                   10

<210> SEQ ID NO 62
<211> LENGTH: 11
<212> TYPE: PRT
<213> ORGANISM: Artificial
<220> FEATURE:
<223> OTHER INFORMATION: KERE-class Nanobody FW4 sequence

<400> SEQUENCE: 62

Arg Gly Gln Gly Thr Arg Val Thr Val Ser Ser
1               5                   10

<210> SEQ ID NO 63
<211> LENGTH: 11
<212> TYPE: PRT
<213> ORGANISM: Artificial
<220> FEATURE:
<223> OTHER INFORMATION: KERE-class Nanobody FW4 sequence

<400> SEQUENCE: 63

Trp Gly Leu Gly Thr Gln Val Thr Ile Ser Ser
1               5                   10

<210> SEQ ID NO 64
<211> LENGTH: 30
<212> TYPE: PRT
<213> ORGANISM: Artificial
<220> FEATURE:
<223> OTHER INFORMATION: GLEW-class Nanobody FW1 sequence

<400> SEQUENCE: 64

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 65
<211> LENGTH: 30
<212> TYPE: PRT
<213> ORGANISM: Artificial
<220> FEATURE:
<223> OTHER INFORMATION: GLEW-class Nanobody FW1 sequence

<400> SEQUENCE: 65

Glu Val His Leu Val Glu Ser Gly Gly Gly Leu Val Arg Pro Gly Gly
1               5                   10                  15

Ser Leu Arg Leu Ser Cys Ala Ala Phe Gly Phe Ile Phe Lys
            20                  25                  30

<210> SEQ ID NO 66
<211> LENGTH: 30
<212> TYPE: PRT
<213> ORGANISM: Artificial
<220> FEATURE:
<223> OTHER INFORMATION: GLEW-class Nanobody FW1 sequence

<400> SEQUENCE: 66

Gln Val Lys Leu Glu Glu Ser Gly Gly Gly Leu Ala Gln Pro Gly Gly
```

```
                1               5                   10                  15
Ser Leu Arg Leu Ser Cys Val Ala Ser Gly Phe Thr Phe Ser
            20                  25                  30
```

<210> SEQ ID NO 67
<211> LENGTH: 30
<212> TYPE: PRT
<213> ORGANISM: Artificial
<220> FEATURE:
<223> OTHER INFORMATION: GLEW-class Nanobody FW1 sequence

<400> SEQUENCE: 67

```
Glu Val Gln Leu Val Glu Ser Gly Gly Gly Leu Val Gln Pro Gly Gly
1               5                   10                  15
Ser Leu Arg Leu Ser Cys Val Cys Val Ser Ser Gly Cys Thr
            20                  25                  30
```

<210> SEQ ID NO 68
<211> LENGTH: 30
<212> TYPE: PRT
<213> ORGANISM: Artificial
<220> FEATURE:
<223> OTHER INFORMATION: GLEW-class Nanobody FW1 sequence

<400> SEQUENCE: 68

```
Glu Val Gln Leu Val Glu Ser Gly Gly Gly Leu Ala Leu Pro Gly Gly
1               5                   10                  15
Ser Leu Thr Leu Ser Cys Val Phe Ser Gly Ser Thr Phe Ser
            20                  25                  30
```

<210> SEQ ID NO 69
<211> LENGTH: 22
<212> TYPE: PRT
<213> ORGANISM: Artificial
<220> FEATURE:
<223> OTHER INFORMATION: GLEW-class Nanobody FW1 sequence

<400> SEQUENCE: 69

```
Val Glu Ser Gly Gly Gly Leu Val Gln Pro Gly Gly Ser Leu Arg Leu
1               5                   10                  15
Ser Cys Ala Ala Ser Gly
            20
```

<210> SEQ ID NO 70
<211> LENGTH: 22
<212> TYPE: PRT
<213> ORGANISM: Artificial
<220> FEATURE:
<223> OTHER INFORMATION: GLEW-class Nanobody FW1 sequence

<400> SEQUENCE: 70

```
Glu Glu Ser Gly Gly Gly Leu Ala Gln Pro Gly Gly Ser Leu Arg Leu
1               5                   10                  15
Ser Cys Val Ala Ser Gly
            20
```

<210> SEQ ID NO 71
<211> LENGTH: 22
<212> TYPE: PRT
<213> ORGANISM: Artificial
<220> FEATURE:
<223> OTHER INFORMATION: GLEW-class Nanobody FW1 sequence

<400> SEQUENCE: 71

```
Val Glu Ser Gly Gly Gly Leu Ala Leu Pro Gly Gly Ser Leu Thr Leu
```

```
1               5                  10                  15
Ser Cys Val Phe Ser Gly
                20

<210> SEQ ID NO 72
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 72

Trp Val Arg Gln Ala Pro Gly Lys Val Leu Glu Trp Val Ser
1               5                  10

<210> SEQ ID NO 73
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 73

Trp Val Arg Arg Pro Pro Gly Lys Gly Leu Glu Trp Val Ser
1               5                  10

<210> SEQ ID NO 74
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 74

Trp Val Arg Gln Ala Pro Gly Met Gly Leu Glu Trp Val Ser
1               5                  10

<210> SEQ ID NO 75
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 75

Trp Val Arg Gln Ala Pro Gly Lys Glu Pro Glu Trp Val Ser
1               5                  10

<210> SEQ ID NO 76
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 76

Trp Val Arg Gln Ala Pro Gly Lys Asp Gln Glu Trp Val Ser
1               5                  10

<210> SEQ ID NO 77
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 77
```

```
Trp Val Arg Gln Ala Pro Gly Lys Ala Glu Glu Trp Val Ser
1               5                   10
```

<210> SEQ ID NO 78
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 78

```
Trp Val Arg Gln Ala Pro Gly Lys Gly Leu Glu Trp Val Ala
1               5                   10
```

<210> SEQ ID NO 79
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 79

```
Trp Val Arg Gln Ala Pro Gly Arg Ala Thr Glu Trp Val Ser
1               5                   10
```

<210> SEQ ID NO 80
<211> LENGTH: 32
<212> TYPE: PRT
<213> ORGANISM: Artificial
<220> FEATURE:
<223> OTHER INFORMATION: GLEW-class Nanobody FW3 sequence

<400> SEQUENCE: 80

```
Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Val Tyr Tyr Cys Val Lys
                20                  25                  30
```

<210> SEQ ID NO 81
<211> LENGTH: 32
<212> TYPE: PRT
<213> ORGANISM: Artificial
<220> FEATURE:
<223> OTHER INFORMATION: GLEW-class Nanobody FW3 sequence

<400> SEQUENCE: 81

```
Arg Phe Thr Ile Ser Arg Asp Asn Ala Arg Asn Thr Leu Tyr Leu Gln
1               5                   10                  15

Met Asp Ser Leu Ile Pro Glu Asp Thr Ala Leu Tyr Tyr Cys Ala Arg
                20                  25                  30
```

<210> SEQ ID NO 82
<211> LENGTH: 32
<212> TYPE: PRT
<213> ORGANISM: Artificial
<220> FEATURE:
<223> OTHER INFORMATION: GLEW-class Nanobody FW3 sequence

<400> SEQUENCE: 82

```
Arg Phe Thr Ser Ser Arg Asp Asn Ala Lys Ser Thr Leu Tyr Leu Gln
1               5                   10                  15

Met Asn Asp Leu Lys Pro Glu Asp Thr Ala Leu Tyr Tyr Cys Ala Arg
                20                  25                  30
```

<210> SEQ ID NO 83
<211> LENGTH: 32

```
<212> TYPE: PRT
<213> ORGANISM: Artificial
<220> FEATURE:
<223> OTHER INFORMATION: GLEW-class Nanobody FW3 sequence

<400> SEQUENCE: 83

Arg Phe Ile Ile Ser Arg Asp Asn Ala Lys Asn Thr Leu Tyr Leu Gln
1               5                   10                  15
Met Asn Ser Leu Gly Pro Glu Asp Thr Ala Met Tyr Tyr Cys Gln Arg
            20                  25                  30

<210> SEQ ID NO 84
<211> LENGTH: 32
<212> TYPE: PRT
<213> ORGANISM: Artificial
<220> FEATURE:
<223> OTHER INFORMATION: GLEW-class Nanobody FW3 sequence

<400> SEQUENCE: 84

Arg Phe Thr Ala Ser Arg Asp Asn Ala Lys Asn Thr Leu Tyr Leu Gln
1               5                   10                  15
Met Asn Ser Leu Lys Ser Glu Asp Thr Ala Arg Tyr Tyr Cys Ala Arg
            20                  25                  30

<210> SEQ ID NO 85
<211> LENGTH: 32
<212> TYPE: PRT
<213> ORGANISM: Artificial
<220> FEATURE:
<223> OTHER INFORMATION: GLEW-class Nanobody FW3 sequence

<400> SEQUENCE: 85

Arg Phe Thr Ile Ser Arg Asp Asn Ala Lys Asn Thr Leu Tyr Leu Gln
1               5                   10                  15
Met Asp Asp Leu Gln Ser Glu Asp Thr Ala Met Tyr Tyr Cys Gly Arg
            20                  25                  30

<210> SEQ ID NO 86
<211> LENGTH: 11
<212> TYPE: PRT
<213> ORGANISM: Artificial
<220> FEATURE:
<223> OTHER INFORMATION: GLEW-class Nanobody FW4 sequence

<400> SEQUENCE: 86

Gly Ser Gln Gly Thr Gln Val Thr Val Ser Ser
1               5                   10

<210> SEQ ID NO 87
<211> LENGTH: 11
<212> TYPE: PRT
<213> ORGANISM: Artificial
<220> FEATURE:
<223> OTHER INFORMATION: GLEW-class Nanobody FW4 sequence

<400> SEQUENCE: 87

Leu Arg Gly Gly Thr Gln Val Thr Val Ser Ser
1               5                   10

<210> SEQ ID NO 88
<211> LENGTH: 11
<212> TYPE: PRT
<213> ORGANISM: Artificial
<220> FEATURE:
<223> OTHER INFORMATION: GLEW-class Nanobody FW4 sequence

<400> SEQUENCE: 88
```

```
Arg Gly Gln Gly Thr Leu Val Thr Val Ser Ser
 1               5                  10
```

<210> SEQ ID NO 89
<211> LENGTH: 11
<212> TYPE: PRT
<213> ORGANISM: Artificial
<220> FEATURE:
<223> OTHER INFORMATION: GLEW-class Nanobody FW4 sequence

<400> SEQUENCE: 89

```
Arg Ser Arg Gly Ile Gln Val Thr Val Ser Ser
 1               5                  10
```

<210> SEQ ID NO 90
<211> LENGTH: 11
<212> TYPE: PRT
<213> ORGANISM: Artificial
<220> FEATURE:
<223> OTHER INFORMATION: GLEW-class Nanobody FW4 sequence

<400> SEQUENCE: 90

```
Trp Gly Lys Gly Thr Gln Val Thr Val Ser Ser
 1               5                  10
```

<210> SEQ ID NO 91
<211> LENGTH: 11
<212> TYPE: PRT
<213> ORGANISM: Artificial
<220> FEATURE:
<223> OTHER INFORMATION: GLEW-class Nanobody FW4 sequence

<400> SEQUENCE: 91

```
Trp Gly Gln Gly Thr Gln Val Thr Val Ser Ser
 1               5                  10
```

<210> SEQ ID NO 92
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 92

```
Ala Val Gln Leu Val Glu Ser Gly Gly Gly Leu Val Gln Ala Gly Gly
 1               5                  10                  15
Ser Leu Arg Leu Ser Cys Ala Ala Ser Gly Arg Thr Phe Ser
            20                  25                  30
```

<210> SEQ ID NO 93
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 93

```
Gln Val Gln Leu Gln Glu Ser Gly Gly Gly Met Val Gln Pro Gly Gly
 1               5                  10                  15
Ser Leu Arg Leu Ser Cys Ala Ala Ser Gly Phe Asp Phe Gly
            20                  25                  30
```

<210> SEQ ID NO 94
<211> LENGTH: 30
<212> TYPE: PRT
<213> ORGANISM: Artificial

```
<220> FEATURE:
<223> OTHER INFORMATION: P,R,S 103-class Nanobody FW1 sequence

<400> SEQUENCE: 94

Glu Val His Leu Val Glu Ser Gly Gly Gly Leu Val Arg Pro Gly Gly
1               5                   10                  15

Ser Leu Arg Leu Ser Cys Ala Ala Phe Gly Phe Ile Phe Lys
            20                  25                  30

<210> SEQ ID NO 95
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 95

Gln Val Gln Leu Ala Glu Ser Gly Gly Gly Leu Val Gln Pro Gly Gly
1               5                   10                  15

Ser Leu Lys Leu Ser Cys Ala Ala Ser Arg Thr Ile Val Ser
            20                  25                  30

<210> SEQ ID NO 96
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 96

Gln Glu His Leu Val Glu Ser Gly Gly Gly Leu Val Asp Ile Gly Gly
1               5                   10                  15

Ser Leu Arg Leu Ser Cys Ala Ala Ser Glu Arg Ile Phe Ser
            20                  25                  30

<210> SEQ ID NO 97
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 97

Gln Val Lys Leu Glu Glu Ser Gly Gly Gly Leu Ala Gln Pro Gly Gly
1               5                   10                  15

Ser Leu Arg Leu Ser Cys Val Ala Ser Gly Phe Thr Phe Ser
            20                  25                  30

<210> SEQ ID NO 98
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 98

Glu Val Gln Leu Val Glu Ser Gly Gly Gly Leu Val Gln Pro Gly Gly
1               5                   10                  15

Ser Leu Arg Leu Ser Cys Val Cys Val Ser Ser Gly Cys Thr
            20                  25                  30

<210> SEQ ID NO 99
<211> LENGTH: 30
<212> TYPE: PRT
<213> ORGANISM: Artificial
```

```
<220> FEATURE:
<223> OTHER INFORMATION: P,R,S 103-class Nanobody FW1 sequence

<400> SEQUENCE: 99

Glu Val Gln Leu Val Glu Ser Gly Gly Gly Leu Ala Leu Pro Gly Gly
1               5                   10                  15

Ser Leu Thr Leu Ser Cys Val Phe Ser Gly Ser Thr Phe Ser
            20                  25                  30

<210> SEQ ID NO 100
<211> LENGTH: 22
<212> TYPE: PRT
<213> ORGANISM: Artificial
<220> FEATURE:
<223> OTHER INFORMATION: P,R,S 103-class Nanobody FW1 sequence

<400> SEQUENCE: 100

Val Glu Ser Gly Gly Gly Leu Val Gln Ala Gly Gly Ser Leu Arg Leu
1               5                   10                  15

Ser Cys Ala Ala Ser Gly
            20

<210> SEQ ID NO 101
<211> LENGTH: 22
<212> TYPE: PRT
<213> ORGANISM: Artificial
<220> FEATURE:
<223> OTHER INFORMATION: P,R,S 103-class Nanobody FW1 sequence

<400> SEQUENCE: 101

Ala Glu Ser Gly Gly Gly Leu Val Gln Pro Gly Gly Ser Leu Lys Leu
1               5                   10                  15

Ser Cys Ala Ala Ser Arg
            20

<210> SEQ ID NO 102
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 102

Trp Phe Arg Gln Ala Pro Gly Lys Glu Arg Glu Phe Val Ala
1               5                   10

<210> SEQ ID NO 103
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 103

Trp Val Arg Gln Ala Pro Gly Lys Val Leu Glu Trp Val Ser
1               5                   10

<210> SEQ ID NO 104
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 104

Trp Val Arg Arg Pro Pro Gly Lys Gly Leu Glu Trp Val Ser
```

```
1               5                  10
```

<210> SEQ ID NO 105
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 105

```
Trp Ile Arg Gln Ala Pro Gly Lys Glu Arg Glu Gly Val Ser
1               5                  10
```

<210> SEQ ID NO 106
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 106

```
Trp Val Arg Gln Tyr Pro Gly Lys Glu Pro Glu Trp Val Ser
1               5                  10
```

<210> SEQ ID NO 107
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 107

```
Trp Phe Arg Gln Pro Pro Gly Lys Glu His Glu Phe Val Ala
1               5                  10
```

<210> SEQ ID NO 108
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 108

```
Trp Tyr Arg Gln Ala Pro Gly Lys Arg Thr Glu Leu Val Ala
1               5                  10
```

<210> SEQ ID NO 109
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 109

```
Trp Leu Arg Gln Ala Pro Gly Gln Gly Leu Glu Trp Val Ser
1               5                  10
```

<210> SEQ ID NO 110
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 110

```
Trp Leu Arg Gln Thr Pro Gly Lys Gly Leu Glu Trp Val Gly
1               5                  10
```

```
<210> SEQ ID NO 111
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 111

Trp Val Arg Gln Ala Pro Gly Lys Ala Glu Glu Phe Val Ser
1               5                   10

<210> SEQ ID NO 112
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 112

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Ala Ala
                20                  25                  30

<210> SEQ ID NO 113
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 113

Arg Phe Thr Ile Ser Arg Asp Asn Ala Arg Asn Thr Leu Tyr Leu Gln
1               5                   10                  15

Met Asp Ser Leu Ile Pro Glu Asp Thr Ala Leu Tyr Tyr Cys Ala Arg
                20                  25                  30

<210> SEQ ID NO 114
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 114

Arg Phe Thr Ile Ser Arg Asp Asn Ala Lys Asn Glu Met Tyr Leu Gln
1               5                   10                  15

Met Asn Asn Leu Lys Thr Glu Asp Thr Gly Val Tyr Trp Cys Gly Ala
                20                  25                  30

<210> SEQ ID NO 115
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 115

Arg Phe Thr Ile Ser Ser Asp Ser Asn Arg Asn Met Ile Tyr Leu Gln
1               5                   10                  15

Met Asn Asn Leu Lys Pro Glu Asp Thr Ala Val Tyr Tyr Cys Ala Ala
                20                  25                  30

<210> SEQ ID NO 116
<211> LENGTH: 32
```

-continued

```
<212> TYPE: PRT
<213> ORGANISM: Artificial
<220> FEATURE:
<223> OTHER INFORMATION: P,R,S 103-class Nanobody FW3 sequence

<400> SEQUENCE: 116

Arg Phe Thr Ile Ser Arg Asp Asn Ala Lys Asn Met Leu Tyr Leu His
1               5                  10                  15

Leu Asn Asn Leu Lys Ser Glu Asp Thr Ala Val Tyr Tyr Cys Arg Arg
            20                  25                  30

<210> SEQ ID NO 117
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 117

Arg Phe Thr Ile Ser Arg Asp Asn Ala Lys Lys Thr Val Tyr Leu Arg
1               5                  10                  15

Leu Asn Ser Leu Asn Pro Glu Asp Thr Ala Val Tyr Ser Cys Asn Leu
            20                  25                  30

<210> SEQ ID NO 118
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 118

Arg Phe Lys Ile Ser Arg Asp Asn Ala Lys Lys Thr Leu Tyr Leu Gln
1               5                  10                  15

Met Asn Ser Leu Gly Pro Glu Asp Thr Ala Met Tyr Tyr Cys Gln Arg
            20                  25                  30

<210> SEQ ID NO 119
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 119

Arg Phe Thr Val Ser Arg Asp Asn Gly Lys Asn Thr Ala Tyr Leu Arg
1               5                  10                  15

Met Asn Ser Leu Lys Pro Glu Asp Thr Ala Asp Tyr Tyr Cys Ala Val
            20                  25                  30

<210> SEQ ID NO 120
<211> LENGTH: 11
<212> TYPE: PRT
<213> ORGANISM: Artificial
<220> FEATURE:
<223> OTHER INFORMATION: P,R,S 103-class Nanobody FW4 sequence

<400> SEQUENCE: 120

Arg Gly Gln Gly Thr Gln Val Thr Val Ser Ser
1               5                  10

<210> SEQ ID NO 121
<211> LENGTH: 11
<212> TYPE: PRT
<213> ORGANISM: Artificial
<220> FEATURE:
```

<223> OTHER INFORMATION: P,R,S 103-class Nanobody FW4 sequence

<400> SEQUENCE: 121

Leu Arg Gly Gly Thr Gln Val Thr Val Ser Ser
1               5                   10

<210> SEQ ID NO 122
<211> LENGTH: 11
<212> TYPE: PRT
<213> ORGANISM: Artificial
<220> FEATURE:
<223> OTHER INFORMATION: P,R,S 103-class Nanobody FW4 sequence

<400> SEQUENCE: 122

Gly Asn Lys Gly Thr Leu Val Thr Val Ser Ser
1               5                   10

<210> SEQ ID NO 123
<211> LENGTH: 11
<212> TYPE: PRT
<213> ORGANISM: Artificial
<220> FEATURE:
<223> OTHER INFORMATION: P,R,S 103-class Nanobody FW4 sequence

<400> SEQUENCE: 123

Ser Ser Pro Gly Thr Gln Val Thr Val Ser Ser
1               5                   10

<210> SEQ ID NO 124
<211> LENGTH: 11
<212> TYPE: PRT
<213> ORGANISM: Artificial
<220> FEATURE:
<223> OTHER INFORMATION: P,R,S 103-class Nanobody FW4 sequence

<400> SEQUENCE: 124

Ser Ser Gln Gly Thr Leu Val Thr Val Ser Ser
1               5                   10

<210> SEQ ID NO 125
<211> LENGTH: 11
<212> TYPE: PRT
<213> ORGANISM: Artificial
<220> FEATURE:
<223> OTHER INFORMATION: P,R,S 103-class Nanobody FW4 sequence

<400> SEQUENCE: 125

Arg Ser Arg Gly Ile Gln Val Thr Val Ser Ser
1               5                   10

<210> SEQ ID NO 126
<211> LENGTH: 30
<212> TYPE: PRT
<213> ORGANISM: Artificial
<220> FEATURE:
<223> OTHER INFORMATION: Nanobody, nanobody fragment or nanobody
      construct

<400> SEQUENCE: 126

Glu Val Gln Leu Val Glu Ser Gly Gly Gly Leu Val Gln Ala Gly Gly
1               5                   10                  15

Ser Leu Arg Leu Ser Cys Ile Ala Ser Gly Asp Thr Ser Glu
            20                  25                  30

<210> SEQ ID NO 127
<211> LENGTH: 30
<212> TYPE: PRT

```
<213> ORGANISM: Artificial
<220> FEATURE:
<223> OTHER INFORMATION: Nanobody, nanobody fragment or nanobody
      construct
<220> FEATURE:
<221> NAME/KEY: misc_feature
<222> LOCATION: (27)..(28)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid

<400> SEQUENCE: 127

Glu Val Gln Leu Val Glu Ser Gly Gly Gly Leu Val Gln Ala Gly Gly
1               5                   10                  15

Ser Leu Arg Leu Ser Cys Ala Ala Ser Gly Xaa Xaa Phe Xaa
            20                  25                  30

<210> SEQ ID NO 128
<211> LENGTH: 30
<212> TYPE: PRT
<213> ORGANISM: Artificial
<220> FEATURE:
<223> OTHER INFORMATION: Nanobody, nanobody fragment or nanobody
      construct

<400> SEQUENCE: 128

Glu Val Gln Leu Val Glu Ser Gly Gly Gly Leu Val Gln Ala Gly Gly
1               5                   10                  15

Ser Leu Arg Leu Ser Cys Val Ala Ser Gly Asp Thr Ser Glu
            20                  25                  30

<210> SEQ ID NO 129
<211> LENGTH: 30
<212> TYPE: PRT
<213> ORGANISM: Artificial
<220> FEATURE:
<223> OTHER INFORMATION: Nanobody, nanobody fragment or nanobody
      construct

<400> SEQUENCE: 129

Glu Val Gln Leu Val Glu Ser Gly Gly Gly Leu Val Gln Ala Gly Gly
1               5                   10                  15

Ser Leu Arg Leu Ser Cys Val Ala Ser Gly Asp Thr Ser Glu
            20                  25                  30

<210> SEQ ID NO 130
<211> LENGTH: 30
<212> TYPE: PRT
<213> ORGANISM: Artificial
<220> FEATURE:
<223> OTHER INFORMATION: Nanobody, nanobody fragment or nanobody
      construct

<400> SEQUENCE: 130

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Asp Phe Ser
            20                  25                  30

<210> SEQ ID NO 131
<211> LENGTH: 30
<212> TYPE: PRT
<213> ORGANISM: Artificial
<220> FEATURE:
<223> OTHER INFORMATION: Nanobody, nanobody fragment or nanobody
      construct
```

```
<400> SEQUENCE: 131

Glu Val Gln Leu Val Glu Ser Gly Gly Gly Leu Val Gln Ser Gly Gly
1               5                   10                  15

Ser Leu Ser Leu Ser Cys Ala Ala Ser Gly Ser Val Leu Arg
            20                  25                  30

<210> SEQ ID NO 132
<211> LENGTH: 30
<212> TYPE: PRT
<213> ORGANISM: Artificial
<220> FEATURE:
<223> OTHER INFORMATION: Nanobody, nanobody fragment or nanobody
      construct

<400> SEQUENCE: 132

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp
            20                  25                  30

<210> SEQ ID NO 133
<211> LENGTH: 30
<212> TYPE: PRT
<213> ORGANISM: Artificial
<220> FEATURE:
<223> OTHER INFORMATION: Nanobody, nanobody fragment or nanobody
      construct

<400> SEQUENCE: 133

Glu Val Gln Leu Val Glu Ser Gly Gly Gly Leu Val Gln Pro Gly Gly
1               5                   10                  15

Ser Leu Arg Leu Ser Cys Ala Thr Ser Gly Val Ile Phe Ser
            20                  25                  30

<210> SEQ ID NO 134
<211> LENGTH: 30
<212> TYPE: PRT
<213> ORGANISM: Artificial
<220> FEATURE:
<223> OTHER INFORMATION: Nanobody, nanobody fragment or nanobody
      construct

<400> SEQUENCE: 134

Glu Val Gln Leu Val Lys Ser Gly Gly Gly Leu Val Gln Pro Gly Gly
1               5                   10                  15

Ser Leu Arg Leu Ser Cys Ala Ala Ser Gly Ser Ile Val Ser
            20                  25                  30

<210> SEQ ID NO 135
<211> LENGTH: 30
<212> TYPE: PRT
<213> ORGANISM: Artificial
<220> FEATURE:
<223> OTHER INFORMATION: Nanobody, nanobody fragment or nanobody
      construct

<400> SEQUENCE: 135

Glu Val Gln Leu Val Glu Ser Gly Gly Gly Leu Val Gln Pro Gly Gly
1               5                   10                  15

Ser Leu Arg Leu Ser Cys Ala Thr Ser Gly Val Ile Phe Ser
            20                  25                  30

<210> SEQ ID NO 136
<211> LENGTH: 30
```

```
<212> TYPE: PRT
<213> ORGANISM: Artificial
<220> FEATURE:
<223> OTHER INFORMATION: Nanobody, nanobody fragment or nanobody
      construct

<400> SEQUENCE: 136

Glu Val Gln Leu Val Glu Ser Gly Gly Gly Leu Val Gln Pro Gly Gly
1               5                  10                  15

Ser Leu Arg Leu Ser Cys Ala Ala Ser Gly Arg Thr Ser Ser
            20                  25                  30

<210> SEQ ID NO 137
<211> LENGTH: 30
<212> TYPE: PRT
<213> ORGANISM: Artificial
<220> FEATURE:
<223> OTHER INFORMATION: Nanobody, nanobody fragment or nanobody
      construct

<400> SEQUENCE: 137

Glu Val Gln Leu Val Glu Ser Gly Gly Asp Leu Val Gln Pro Gly Gly
1               5                  10                  15

Ser Leu Arg Leu Ser Cys Ala Ala Ser Gly Thr Val Phe Ser
            20                  25                  30

<210> SEQ ID NO 138
<211> LENGTH: 30
<212> TYPE: PRT
<213> ORGANISM: Artificial
<220> FEATURE:
<223> OTHER INFORMATION: Nanobody, nanobody fragment or nanobody
      construct

<400> SEQUENCE: 138

Glu Val Gln Leu Val Glu Ser Gly Gly Asp Leu Val Gln Pro Gly Gly
1               5                  10                  15

Ser Leu Arg Leu Ser Cys Ala Ala Ser Gly Thr Val Phe Ser
            20                  25                  30

<210> SEQ ID NO 139
<211> LENGTH: 30
<212> TYPE: PRT
<213> ORGANISM: Artificial
<220> FEATURE:
<223> OTHER INFORMATION: Nanobody, nanobody fragment or nanobody
      construct

<400> SEQUENCE: 139

Glu Val Gln Leu Val Glu Ser Gly Gly Asp Leu Val Gln Pro Gly Gly
1               5                  10                  15

Ser Leu Arg Leu Ser Cys Ala Ala Ser Arg Thr Val Phe Ser
            20                  25                  30

<210> SEQ ID NO 140
<211> LENGTH: 30
<212> TYPE: PRT
<213> ORGANISM: Artificial
<220> FEATURE:
<223> OTHER INFORMATION: Nanobody, nanobody fragment or nanobody
      construct

<400> SEQUENCE: 140

Glu Val Gln Leu Val Glu Ser Gly Gly Gly Leu Val Gln Ala Gly Gly
1               5                  10                  15

Ser Leu Arg Leu Ser Cys Ala Ala Ser Gly Gly Ile Phe Gly
```

20 25 30

<210> SEQ ID NO 141
<211> LENGTH: 30
<212> TYPE: PRT
<213> ORGANISM: Artificial
<220> FEATURE:
<223> OTHER INFORMATION: Nanobody, nanobody fragment or nanobody
    construct

<400> SEQUENCE: 141

Glu Val Gln Leu Val Glu Ser Gly Gly Asp Leu Val Gln Pro Gly Gly
1               5                   10                  15

Ser Leu Arg Leu Ser Cys Thr Thr Ser Gly Thr Val Phe Ser
            20                  25                  30

<210> SEQ ID NO 142
<211> LENGTH: 30
<212> TYPE: PRT
<213> ORGANISM: Artificial
<220> FEATURE:
<223> OTHER INFORMATION: Nanobody, nanobody fragment or nanobody
    construct

<400> SEQUENCE: 142

Glu Val Gln Leu Val Glu Ser Gly Gly Gly Leu Val Gln Ala Gly Asp
1               5                   10                  15

Ser Leu Arg Leu Ser Cys Ala Val Ser Gly Gly Ser Phe Ser
            20                  25                  30

<210> SEQ ID NO 143
<211> LENGTH: 30
<212> TYPE: PRT
<213> ORGANISM: Artificial
<220> FEATURE:
<223> OTHER INFORMATION: Nanobody, nanobody fragment or nanobody
    construct

<400> SEQUENCE: 143

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Ser Ser
            20                  25                  30

<210> SEQ ID NO 144
<211> LENGTH: 30
<212> TYPE: PRT
<213> ORGANISM: Artificial
<220> FEATURE:
<223> OTHER INFORMATION: Nanobody, nanobody fragment or nanobody
    construct

<400> SEQUENCE: 144

Glu Val Gln Leu Val Glu Ser Gly Gly Asp Leu Val Gln Pro Gly Gly
1               5                   10                  15

Ser Leu Arg Leu Ser Cys Ala Ala Ser Ala Thr Val Phe Ser
            20                  25                  30

<210> SEQ ID NO 145
<211> LENGTH: 30
<212> TYPE: PRT
<213> ORGANISM: Artificial
<220> FEATURE:
<223> OTHER INFORMATION: Nanobody, nanobody fragment or nanobody
    construct

<400> SEQUENCE: 145

-continued

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser
            20                  25                  30

<210> SEQ ID NO 146
<211> LENGTH: 30
<212> TYPE: PRT
<213> ORGANISM: Artificial
<220> FEATURE:
<223> OTHER INFORMATION: Nanobody, nanobody fragment or nanobody
      construct

<400> SEQUENCE: 146

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ile Asn Ser
            20                  25                  30

<210> SEQ ID NO 147
<211> LENGTH: 30
<212> TYPE: PRT
<213> ORGANISM: Artificial
<220> FEATURE:
<223> OTHER INFORMATION: Nanobody, nanobody fragment or nanobody
      construct

<400> SEQUENCE: 147

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly
            20                  25                  30

<210> SEQ ID NO 148
<211> LENGTH: 30
<212> TYPE: PRT
<213> ORGANISM: Artificial
<220> FEATURE:
<223> OTHER INFORMATION: Nanobody, nanobody fragment or nanobody
      construct

<400> SEQUENCE: 148

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Met Ser Ser
            20                  25                  30

<210> SEQ ID NO 149
<211> LENGTH: 30
<212> TYPE: PRT
<213> ORGANISM: Artificial
<220> FEATURE:
<223> OTHER INFORMATION: Nanobody, nanobody fragment or nanobody
      construct

<400> SEQUENCE: 149

Glu Val Gln Leu Val Glu Ser Gly Gly Ala Leu Val Gln Ala Gly Gly
1               5                   10                  15

Ser Leu Arg Leu Ser Cys Val Ala Ser Gly Ser Ser Phe Ser
            20                  25                  30

<210> SEQ ID NO 150
<211> LENGTH: 30
<212> TYPE: PRT
<213> ORGANISM: Artificial

<220> FEATURE:
<223> OTHER INFORMATION: Nanobody, nanobody fragment or nanobody
      construct

<400> SEQUENCE: 150

Glu Val Lys Leu Val Glu Ser Gly Gly Gly Leu Val Gln Pro Gly Gly
1               5                   10                  15

Ser Leu Arg Leu Ser Cys Ala Ala Ser Gly Ser Ile Phe Arg
            20                  25                  30

<210> SEQ ID NO 151
<211> LENGTH: 30
<212> TYPE: PRT
<213> ORGANISM: Artificial
<220> FEATURE:
<223> OTHER INFORMATION: Nanobody, nanobody fragment or nanobody
      construct

<400> SEQUENCE: 151

Glu Val Gln Leu Val Glu Ser Gly Gly Gly Leu Val Gln Ala Gly Gly
1               5                   10                  15

Ser Leu Arg Leu Ser Cys Val Val Ser Gly Ser Ile Leu Ser
            20                  25                  30

<210> SEQ ID NO 152
<211> LENGTH: 30
<212> TYPE: PRT
<213> ORGANISM: Artificial
<220> FEATURE:
<223> OTHER INFORMATION: Nanobody, nanobody fragment or nanobody
      construct

<400> SEQUENCE: 152

Glu Val Gln Leu Val Glu Ser Gly Gly Gly Leu Val Gln Ala Gly Gly
1               5                   10                  15

Ser Leu Arg Leu Ser Cys Ala Ala Ser Gly Met Thr Thr Ile
            20                  25                  30

<210> SEQ ID NO 153
<211> LENGTH: 30
<212> TYPE: PRT
<213> ORGANISM: Artificial
<220> FEATURE:
<223> OTHER INFORMATION: Nanobody, nanobody fragment or nanobody
      construct

<400> SEQUENCE: 153

Glu Val Gln Leu Val Glu Ser Gly Gly Gly Leu Val Gln Ala Gly Gly
1               5                   10                  15

Ser Leu Arg Leu Ser Cys Ala Ala Ser Gly Met Thr Thr Ile
            20                  25                  30

<210> SEQ ID NO 154
<211> LENGTH: 30
<212> TYPE: PRT
<213> ORGANISM: Artificial
<220> FEATURE:
<223> OTHER INFORMATION: Nanobody, nanobody fragment or nanobody
      construct

<400> SEQUENCE: 154

Glu Val Gln Leu Val Glu Ser Gly Gly Gly Leu Val Gln Ala Gly Gly
1               5                   10                  15

Ser Leu Arg Leu Ser Cys Ala Ala Ser Gly Met Thr Thr Ile
            20                  25                  30

```
<210> SEQ ID NO 155
<211> LENGTH: 5
<212> TYPE: PRT
<213> ORGANISM: Artificial
<220> FEATURE:
<223> OTHER INFORMATION: Nanobody, nanobody fragment or nanobody
      construct

<400> SEQUENCE: 155

Ile Tyr Asp Met Gly
1               5

<210> SEQ ID NO 156
<211> LENGTH: 5
<212> TYPE: PRT
<213> ORGANISM: Artificial
<220> FEATURE:
<223> OTHER INFORMATION: Nanobody, nanobody fragment or nanobody
      construct

<400> SEQUENCE: 156

Ser Asp Val Met Gly
1               5

<210> SEQ ID NO 157
<211> LENGTH: 5
<212> TYPE: PRT
<213> ORGANISM: Artificial
<220> FEATURE:
<223> OTHER INFORMATION: Nanobody, nanobody fragment or nanobody
      construct

<400> SEQUENCE: 157

Ile Tyr Asp Met Gly
1               5

<210> SEQ ID NO 158
<211> LENGTH: 5
<212> TYPE: PRT
<213> ORGANISM: Artificial
<220> FEATURE:
<223> OTHER INFORMATION: Nanobody, nanobody fragment or nanobody
      construct

<400> SEQUENCE: 158

Ile Tyr Asp Met Gly
1               5

<210> SEQ ID NO 159
<211> LENGTH: 5
<212> TYPE: PRT
<213> ORGANISM: Artificial
<220> FEATURE:
<223> OTHER INFORMATION: Nanobody, nanobody fragment or nanobody
      construct

<400> SEQUENCE: 159

Gly Phe Leu Leu Gly
1               5

<210> SEQ ID NO 160
<211> LENGTH: 5
<212> TYPE: PRT
<213> ORGANISM: Artificial
<220> FEATURE:
<223> OTHER INFORMATION: Nanobody, nanobody fragment or nanobody
      construct

<400> SEQUENCE: 160
```

```
Ile Asn Asp Met Gly
1               5

<210> SEQ ID NO 161
<211> LENGTH: 5
<212> TYPE: PRT
<213> ORGANISM: Artificial
<220> FEATURE:
<223> OTHER INFORMATION: Nanobody, nanobody fragment or nanobody
      construct

<400> SEQUENCE: 161

Asp Tyr Ala Ile Gly
1               5

<210> SEQ ID NO 162
<211> LENGTH: 5
<212> TYPE: PRT
<213> ORGANISM: Artificial
<220> FEATURE:
<223> OTHER INFORMATION: Nanobody, nanobody fragment or nanobody
      construct

<400> SEQUENCE: 162

Thr Ala Ala Met Gly
1               5

<210> SEQ ID NO 163
<211> LENGTH: 5
<212> TYPE: PRT
<213> ORGANISM: Artificial
<220> FEATURE:
<223> OTHER INFORMATION: Nanobody, nanobody fragment or nanobody
      construct

<400> SEQUENCE: 163

Ala Asn Leu Ile Gly
1               5

<210> SEQ ID NO 164
<211> LENGTH: 5
<212> TYPE: PRT
<213> ORGANISM: Artificial
<220> FEATURE:
<223> OTHER INFORMATION: Nanobody, nanobody fragment or nanobody
      construct

<400> SEQUENCE: 164

Thr Ala Ala Met Gly
1               5

<210> SEQ ID NO 165
<211> LENGTH: 5
<212> TYPE: PRT
<213> ORGANISM: Artificial
<220> FEATURE:
<223> OTHER INFORMATION: Nanobody, nanobody fragment or nanobody
      construct

<400> SEQUENCE: 165

Pro Ile Ala Met Gly
1               5

<210> SEQ ID NO 166
<211> LENGTH: 5
<212> TYPE: PRT
<213> ORGANISM: Artificial
<220> FEATURE:
```

<223> OTHER INFORMATION: Nanobody, nanobody fragment or nanobody
      construct

<400> SEQUENCE: 166

Asn Asn Asp Met Gly
1               5

<210> SEQ ID NO 167
<211> LENGTH: 5
<212> TYPE: PRT
<213> ORGANISM: Artificial
<220> FEATURE:
<223> OTHER INFORMATION: Nanobody, nanobody fragment or nanobody
      construct

<400> SEQUENCE: 167

Asn Asn Asp Met Gly
1               5

<210> SEQ ID NO 168
<211> LENGTH: 5
<212> TYPE: PRT
<213> ORGANISM: Artificial
<220> FEATURE:
<223> OTHER INFORMATION: Nanobody, nanobody fragment or nanobody
      construct

<400> SEQUENCE: 168

Ile Ser Asp Met Gly
1               5

<210> SEQ ID NO 169
<211> LENGTH: 5
<212> TYPE: PRT
<213> ORGANISM: Artificial
<220> FEATURE:
<223> OTHER INFORMATION: Nanobody, nanobody fragment or nanobody
      construct

<400> SEQUENCE: 169

Ile Asn Ala Val Ala
1               5

<210> SEQ ID NO 170
<211> LENGTH: 5
<212> TYPE: PRT
<213> ORGANISM: Artificial
<220> FEATURE:
<223> OTHER INFORMATION: Nanobody, nanobody fragment or nanobody
      construct

<400> SEQUENCE: 170

Ile Asn Asp Met Gly
1               5

<210> SEQ ID NO 171
<211> LENGTH: 5
<212> TYPE: PRT
<213> ORGANISM: Artificial
<220> FEATURE:
<223> OTHER INFORMATION: Nanobody, nanobody fragment or nanobody
      construct

<400> SEQUENCE: 171

Ser Tyr Thr Met Gly
1               5

<210> SEQ ID NO 172

```
<211> LENGTH: 5
<212> TYPE: PRT
<213> ORGANISM: Artificial
<220> FEATURE:
<223> OTHER INFORMATION: Nanobody, nanobody fragment or nanobody
      construct

<400> SEQUENCE: 172

Pro Ile Ala Met Gly
1               5

<210> SEQ ID NO 173
<211> LENGTH: 5
<212> TYPE: PRT
<213> ORGANISM: Artificial
<220> FEATURE:
<223> OTHER INFORMATION: Nanobody, nanobody fragment or nanobody
      construct

<400> SEQUENCE: 173

Asn Ser Asp Met Gly
1               5

<210> SEQ ID NO 174
<211> LENGTH: 5
<212> TYPE: PRT
<213> ORGANISM: Artificial
<220> FEATURE:
<223> OTHER INFORMATION: Nanobody, nanobody fragment or nanobody
      construct

<400> SEQUENCE: 174

Ile Thr Glu Met Asp
1               5

<210> SEQ ID NO 175

<400> SEQUENCE: 175

000

<210> SEQ ID NO 176
<211> LENGTH: 5
<212> TYPE: PRT
<213> ORGANISM: Artificial
<220> FEATURE:
<223> OTHER INFORMATION: Nanobody, nanobody fragment or nanobody
      construct

<400> SEQUENCE: 176

Asp Tyr Ala Met Asn
1               5

<210> SEQ ID NO 177
<211> LENGTH: 5
<212> TYPE: PRT
<213> ORGANISM: Artificial
<220> FEATURE:
<223> OTHER INFORMATION: Nanobody, nanobody fragment or nanobody
      construct

<400> SEQUENCE: 177

Ile Asn Ala Met Arg
1               5

<210> SEQ ID NO 178
<211> LENGTH: 5
<212> TYPE: PRT
<213> ORGANISM: Artificial
```

```
<220> FEATURE:
<223> OTHER INFORMATION: Nanobody, nanobody fragment or nanobody
      construct

<400> SEQUENCE: 178

Ile Asn Asp Met Asp
1               5

<210> SEQ ID NO 179
<211> LENGTH: 5
<212> TYPE: PRT
<213> ORGANISM: Artificial
<220> FEATURE:
<223> OTHER INFORMATION: Nanobody, nanobody fragment or nanobody
      construct

<400> SEQUENCE: 179

Phe Asn Gly Val Asp
1               5

<210> SEQ ID NO 180
<211> LENGTH: 5
<212> TYPE: PRT
<213> ORGANISM: Artificial
<220> FEATURE:
<223> OTHER INFORMATION: Nanobody, nanobody fragment or nanobody
      construct

<400> SEQUENCE: 180

Ile Asn Thr Met Asp
1               5

<210> SEQ ID NO 181
<211> LENGTH: 4
<212> TYPE: PRT
<213> ORGANISM: Artificial
<220> FEATURE:
<223> OTHER INFORMATION: Nanobody, nanobody fragment or nanobody
      construct

<400> SEQUENCE: 181

Gly Pro Met Gly
1

<210> SEQ ID NO 182
<211> LENGTH: 4
<212> TYPE: PRT
<213> ORGANISM: Artificial
<220> FEATURE:
<223> OTHER INFORMATION: Nanobody, nanobody fragment or nanobody
      construct

<400> SEQUENCE: 182

Gly Pro Met Gly
1

<210> SEQ ID NO 183
<211> LENGTH: 4
<212> TYPE: PRT
<213> ORGANISM: Artificial
<220> FEATURE:
<223> OTHER INFORMATION: Nanobody, nanobody fragment or nanobody
      construct

<400> SEQUENCE: 183

Gly Pro Met Gly
1
```

```
<210> SEQ ID NO 184
<211> LENGTH: 14
<212> TYPE: PRT
<213> ORGANISM: Artificial
<220> FEATURE:
<223> OTHER INFORMATION: Nanobody, nanobody fragment or nanobody
      construct

<400> SEQUENCE: 184

Trp Phe Arg Gln Ala Pro Gly Lys Glu Arg Glu Phe Val Ser
1               5                   10

<210> SEQ ID NO 185
<211> LENGTH: 14
<212> TYPE: PRT
<213> ORGANISM: Artificial
<220> FEATURE:
<223> OTHER INFORMATION: Nanobody, nanobody fragment or nanobody
      construct

<400> SEQUENCE: 185

Trp Phe Arg Arg Ala Pro Gly Lys Glu Arg Glu Phe Val Ala
1               5                   10

<210> SEQ ID NO 186
<211> LENGTH: 14
<212> TYPE: PRT
<213> ORGANISM: Artificial
<220> FEATURE:
<223> OTHER INFORMATION: Nanobody, nanobody fragment or nanobody
      construct

<400> SEQUENCE: 186

Trp Phe Arg Gln Ala Pro Gly Lys Glu Arg Glu Phe Val Ser
1               5                   10

<210> SEQ ID NO 187
<211> LENGTH: 14
<212> TYPE: PRT
<213> ORGANISM: Artificial
<220> FEATURE:
<223> OTHER INFORMATION: Nanobody, nanobody fragment or nanobody
      construct

<400> SEQUENCE: 187

Trp Phe Arg Gln Ala Pro Gly Lys Glu Arg Glu Phe Val Ser
1               5                   10

<210> SEQ ID NO 188
<211> LENGTH: 14
<212> TYPE: PRT
<213> ORGANISM: Artificial
<220> FEATURE:
<223> OTHER INFORMATION: Nanobody, nanobody fragment or nanobody
      construct

<400> SEQUENCE: 188

Trp Tyr Arg Gln Pro Pro Gly Lys Gln Arg Glu Leu Ile Ala
1               5                   10

<210> SEQ ID NO 189
<211> LENGTH: 14
<212> TYPE: PRT
<213> ORGANISM: Artificial
<220> FEATURE:
<223> OTHER INFORMATION: Nanobody, nanobody fragment or nanobody
      construct

<400> SEQUENCE: 189
```

```
Trp Tyr Arg Gln Ala Pro Gly Lys Thr Arg Glu Met Val Ala
1               5                   10
```

<210> SEQ ID NO 190
<211> LENGTH: 14
<212> TYPE: PRT
<213> ORGANISM: Artificial
<220> FEATURE:
<223> OTHER INFORMATION: Nanobody, nanobody fragment or nanobody
      construct

<400> SEQUENCE: 190

```
Trp Phe Arg Gln Ala Pro Gly Lys Glu Arg Glu Gly Val Ser
1               5                   10
```

<210> SEQ ID NO 191
<211> LENGTH: 14
<212> TYPE: PRT
<213> ORGANISM: Artificial
<220> FEATURE:
<223> OTHER INFORMATION: Nanobody, nanobody fragment or nanobody
      construct

<400> SEQUENCE: 191

```
Trp Tyr Arg Gln Ala Pro Gly Lys Ser Arg Val Leu Val Ala
1               5                   10
```

<210> SEQ ID NO 192
<211> LENGTH: 14
<212> TYPE: PRT
<213> ORGANISM: Artificial
<220> FEATURE:
<223> OTHER INFORMATION: Nanobody, nanobody fragment or nanobody
      construct

<400> SEQUENCE: 192

```
Trp Tyr Arg Gln Ala Pro Gly Lys Gln Arg Glu Gly Val Ala
1               5                   10
```

<210> SEQ ID NO 193
<211> LENGTH: 14
<212> TYPE: PRT
<213> ORGANISM: Artificial
<220> FEATURE:
<223> OTHER INFORMATION: Nanobody, nanobody fragment or nanobody
      construct

<400> SEQUENCE: 193

```
Trp Tyr Arg Gln Ala Pro Gly Lys Ser Arg Val Leu Val Ala
1               5                   10
```

<210> SEQ ID NO 194
<211> LENGTH: 14
<212> TYPE: PRT
<213> ORGANISM: Artificial
<220> FEATURE:
<223> OTHER INFORMATION: Nanobody, nanobody fragment or nanobody
      construct

<400> SEQUENCE: 194

```
Trp Phe Arg Gln Ala Pro Gly Lys Glu Arg Glu Phe Val Ser
1               5                   10
```

<210> SEQ ID NO 195
<211> LENGTH: 14
<212> TYPE: PRT
<213> ORGANISM: Artificial
<220> FEATURE:
<223> OTHER INFORMATION: Nanobody, nanobody fragment or nanobody -continued

<400> SEQUENCE: 195

Trp Ser Arg Gln Ala Pro Gly Lys Glu Arg Glu Leu Val Ala
1               5                   10

<210> SEQ ID NO 196
<211> LENGTH: 14
<212> TYPE: PRT
<213> ORGANISM: Artificial
<220> FEATURE:
<223> OTHER INFORMATION: Nanobody, nanobody fragment or nanobody
      construct

<400> SEQUENCE: 196

Trp Ser Arg Gln Ala Pro Gly Lys Glu Arg Glu Leu Val Ala
1               5                   10

<210> SEQ ID NO 197
<211> LENGTH: 14
<212> TYPE: PRT
<213> ORGANISM: Artificial
<220> FEATURE:
<223> OTHER INFORMATION: Nanobody, nanobody fragment or nanobody
      construct

<400> SEQUENCE: 197

Trp Ser Arg Gln Ala Pro Gly Lys Glu Arg Glu Leu Val Ala
1               5                   10

<210> SEQ ID NO 198
<211> LENGTH: 14
<212> TYPE: PRT
<213> ORGANISM: Artificial
<220> FEATURE:
<223> OTHER INFORMATION: Nanobody, nanobody fragment or nanobody
      construct

<400> SEQUENCE: 198

Trp Tyr Arg Gln Ala Pro Gly Lys Glu Arg Asp Trp Val Ala
1               5                   10

<210> SEQ ID NO 199
<211> LENGTH: 14
<212> TYPE: PRT
<213> ORGANISM: Artificial
<220> FEATURE:
<223> OTHER INFORMATION: Nanobody, nanobody fragment or nanobody
      construct

<400> SEQUENCE: 199

Trp Ser Arg Gln Ala Pro Gly Lys Gly Arg Glu Leu Val Ala
1               5                   10

<210> SEQ ID NO 200
<211> LENGTH: 14
<212> TYPE: PRT
<213> ORGANISM: Artificial
<220> FEATURE:
<223> OTHER INFORMATION: Nanobody, nanobody fragment or nanobody
      construct

<400> SEQUENCE: 200

Trp Val Arg Gln Ala Pro Gly Lys Glu Arg Glu Ala Val Ala
1               5                   10

<210> SEQ ID NO 201
<211> LENGTH: 14

```
<212> TYPE: PRT
<213> ORGANISM: Artificial
<220> FEATURE:
<223> OTHER INFORMATION: Nanobody, nanobody fragment or nanobody
      construct

<400> SEQUENCE: 201

Trp Phe Arg Gln Ala Pro Gly Lys Glu Arg Glu Phe Val Ser
1               5                   10

<210> SEQ ID NO 202
<211> LENGTH: 14
<212> TYPE: PRT
<213> ORGANISM: Artificial
<220> FEATURE:
<223> OTHER INFORMATION: Nanobody, nanobody fragment or nanobody
      construct

<400> SEQUENCE: 202

Trp Ser Arg Gln Ala Pro Gly Lys Glu Arg Glu Leu Val Ala
1               5                   10

<210> SEQ ID NO 203
<211> LENGTH: 14
<212> TYPE: PRT
<213> ORGANISM: Artificial
<220> FEATURE:
<223> OTHER INFORMATION: Nanobody, nanobody fragment or nanobody
      construct

<400> SEQUENCE: 203

Trp Tyr Arg Gln Ala Pro Gly Lys Gln Arg Glu Trp Val Ala
1               5                   10

<210> SEQ ID NO 204
<211> LENGTH: 14
<212> TYPE: PRT
<213> ORGANISM: Artificial
<220> FEATURE:
<223> OTHER INFORMATION: Nanobody, nanobody fragment or nanobody
      construct

<400> SEQUENCE: 204

Trp Tyr His Gln Ala Pro Gly Lys Glu Arg Glu Trp Val Ala
1               5                   10

<210> SEQ ID NO 205
<211> LENGTH: 14
<212> TYPE: PRT
<213> ORGANISM: Artificial
<220> FEATURE:
<223> OTHER INFORMATION: Nanobody, nanobody fragment or nanobody
      construct

<400> SEQUENCE: 205

Trp Val Arg Gln Ala Pro Gly Lys Gly Leu Glu Trp Val Ser
1               5                   10

<210> SEQ ID NO 206
<211> LENGTH: 14
<212> TYPE: PRT
<213> ORGANISM: Artificial
<220> FEATURE:
<223> OTHER INFORMATION: Nanobody, nanobody fragment or nanobody
      construct

<400> SEQUENCE: 206

Trp Tyr Arg Gln Ala Ser Gly Lys Gln Arg Glu Pro Val Ala
1               5                   10
```

```
<210> SEQ ID NO 207
<211> LENGTH: 14
<212> TYPE: PRT
<213> ORGANISM: Artificial
<220> FEATURE:
<223> OTHER INFORMATION: Nanobody, nanobody fragment or nanobody
      construct

<400> SEQUENCE: 207

Trp Tyr Arg Gln Ala Pro Gly Lys Thr Arg Glu Trp Val Ala
1               5                   10

<210> SEQ ID NO 208
<211> LENGTH: 14
<212> TYPE: PRT
<213> ORGANISM: Artificial
<220> FEATURE:
<223> OTHER INFORMATION: Nanobody, nanobody fragment or nanobody
      construct

<400> SEQUENCE: 208

Trp Tyr Arg Gln Ala Pro Gly Ala Glu Arg Glu Trp Val Ala
1               5                   10

<210> SEQ ID NO 209
<211> LENGTH: 14
<212> TYPE: PRT
<213> ORGANISM: Artificial
<220> FEATURE:
<223> OTHER INFORMATION: Nanobody, nanobody fragment or nanobody
      construct

<400> SEQUENCE: 209

Trp Tyr Arg Gln Ala Pro Gly Asn Glu Arg Glu Trp Val Gly
1               5                   10

<210> SEQ ID NO 210
<211> LENGTH: 14
<212> TYPE: PRT
<213> ORGANISM: Artificial
<220> FEATURE:
<223> OTHER INFORMATION: Nanobody, nanobody fragment or nanobody
      construct

<400> SEQUENCE: 210

Trp Tyr Arg Gln Gly Pro Gly Lys Gln Arg Glu Leu Val Ala
1               5                   10

<210> SEQ ID NO 211
<211> LENGTH: 14
<212> TYPE: PRT
<213> ORGANISM: Artificial
<220> FEATURE:
<223> OTHER INFORMATION: Nanobody, nanobody fragment or nanobody
      construct

<400> SEQUENCE: 211

Trp Tyr Arg Gln Gly Pro Gly Lys Gln Arg Glu Leu Val Ala
1               5                   10

<210> SEQ ID NO 212
<211> LENGTH: 14
<212> TYPE: PRT
<213> ORGANISM: Artificial
<220> FEATURE:
<223> OTHER INFORMATION: Nanobody, nanobody fragment or nanobody
      construct
```

```
<400> SEQUENCE: 212

Trp Tyr Arg Gln Gly Pro Gly Lys Gln Arg Glu Leu Val Ala
1               5                   10

<210> SEQ ID NO 213
<211> LENGTH: 17
<212> TYPE: PRT
<213> ORGANISM: Artificial
<220> FEATURE:
<223> OTHER INFORMATION: Nanobody, nanobody fragment or nanobody
      construct

<400> SEQUENCE: 213

Ser Ile His Trp Arg Gly Arg Gly Thr Asn Tyr Thr Asp Ser Val Glu
1               5                   10                  15

Gly

<210> SEQ ID NO 214
<211> LENGTH: 16
<212> TYPE: PRT
<213> ORGANISM: Artificial
<220> FEATURE:
<223> OTHER INFORMATION: Nanobody, nanobody fragment or nanobody
      construct

<400> SEQUENCE: 214

Ser Ile Thr Thr Thr Gly Asn Glu Tyr Tyr Glu Asp Ser Leu Lys Gly
1               5                   10                  15

<210> SEQ ID NO 215
<211> LENGTH: 17
<212> TYPE: PRT
<213> ORGANISM: Artificial
<220> FEATURE:
<223> OTHER INFORMATION: Nanobody, nanobody fragment or nanobody
      construct

<400> SEQUENCE: 215

Ser Ile His Trp Gly Gly Arg Gly Thr Asn Tyr Thr Asp Ser Val Lys
1               5                   10                  15

Gly

<210> SEQ ID NO 216
<211> LENGTH: 17
<212> TYPE: PRT
<213> ORGANISM: Artificial
<220> FEATURE:
<223> OTHER INFORMATION: Nanobody, nanobody fragment or nanobody
      construct

<400> SEQUENCE: 216

Ser Ile His Trp Gly Gly Arg Gly Thr Asn Tyr Thr Asp Ser Val Lys
1               5                   10                  15

Gly

<210> SEQ ID NO 217
<211> LENGTH: 16
<212> TYPE: PRT
<213> ORGANISM: Artificial
<220> FEATURE:
<223> OTHER INFORMATION: Nanobody, nanobody fragment or nanobody
      construct

<400> SEQUENCE: 217

Gln Thr Thr Asp Gly Gly Arg Thr Asn Tyr Gly Asp Ser Val Lys Gly
1               5                   10                  15
```

```
<210> SEQ ID NO 218
<211> LENGTH: 16
<212> TYPE: PRT
<213> ORGANISM: Artificial
<220> FEATURE:
<223> OTHER INFORMATION: Nanobody, nanobody fragment or nanobody
      construct

<400> SEQUENCE: 218

Thr Ile Thr Arg Ser Gly Val Leu Asn Tyr Thr Asp Ser Val Lys Gly
1               5                   10                  15

<210> SEQ ID NO 219
<211> LENGTH: 17
<212> TYPE: PRT
<213> ORGANISM: Artificial
<220> FEATURE:
<223> OTHER INFORMATION: Nanobody, nanobody fragment or nanobody
      construct

<400> SEQUENCE: 219

Cys Met Arg Gly Arg Asp Gly Ser Thr Tyr Tyr Ala Asp Ser Val Asn
1               5                   10                  15

Gly

<210> SEQ ID NO 220
<211> LENGTH: 16
<212> TYPE: PRT
<213> ORGANISM: Artificial
<220> FEATURE:
<223> OTHER INFORMATION: Nanobody, nanobody fragment or nanobody
      construct

<400> SEQUENCE: 220

Arg Met Phe Ser Asp Gly Arg Thr Ile Tyr Ala Glu Ser Val Lys Arg
1               5                   10                  15

<210> SEQ ID NO 221
<211> LENGTH: 16
<212> TYPE: PRT
<213> ORGANISM: Artificial
<220> FEATURE:
<223> OTHER INFORMATION: Nanobody, nanobody fragment or nanobody
      construct

<400> SEQUENCE: 221

Phe Ile Thr Ser Gly Gly Ala Ile Asn Tyr Ala Asp Ser Val Lys Gly
1               5                   10                  15

<210> SEQ ID NO 222
<211> LENGTH: 16
<212> TYPE: PRT
<213> ORGANISM: Artificial
<220> FEATURE:
<223> OTHER INFORMATION: Nanobody, nanobody fragment or nanobody
      construct

<400> SEQUENCE: 222

Arg Met Phe Ser Asp Gly Arg Thr Ile Tyr Ala Glu Ser Val Lys Arg
1               5                   10                  15

<210> SEQ ID NO 223
<211> LENGTH: 17
<212> TYPE: PRT
<213> ORGANISM: Artificial
<220> FEATURE:
<223> OTHER INFORMATION: Nanobody, nanobody fragment or nanobody
```

-continued

```
<400> SEQUENCE: 223

Gly Ile Thr Trp Ser Gly Ala Tyr Thr His Tyr Ala Asn Ser Val Lys
1               5                   10                  15
Gly

<210> SEQ ID NO 224
<211> LENGTH: 16
<212> TYPE: PRT
<213> ORGANISM: Artificial
<220> FEATURE:
<223> OTHER INFORMATION: Nanobody, nanobody fragment or nanobody
      construct

<400> SEQUENCE: 224

Ser Phe Thr Ser Gly Gly Asn Thr Val Tyr Ala Asp Ala Ala Lys Gly
1               5                   10                  15

<210> SEQ ID NO 225
<211> LENGTH: 16
<212> TYPE: PRT
<213> ORGANISM: Artificial
<220> FEATURE:
<223> OTHER INFORMATION: Nanobody, nanobody fragment or nanobody
      construct

<400> SEQUENCE: 225

Ser Phe Thr Ser Gly Gly Asn Thr Val Tyr Ala Asp Ala Ala Lys Gly
1               5                   10                  15

<210> SEQ ID NO 226
<211> LENGTH: 16
<212> TYPE: PRT
<213> ORGANISM: Artificial
<220> FEATURE:
<223> OTHER INFORMATION: Nanobody, nanobody fragment or nanobody
      construct

<400> SEQUENCE: 226

Ser Ile Ser Ser Asp Asn Tyr Thr Val Tyr Ala Asp Ala Ala Lys Gly
1               5                   10                  15

<210> SEQ ID NO 227
<211> LENGTH: 16
<212> TYPE: PRT
<213> ORGANISM: Artificial
<220> FEATURE:
<223> OTHER INFORMATION: Nanobody, nanobody fragment or nanobody
      construct

<400> SEQUENCE: 227

Leu Ile Val Gly Glu Ala Ile Thr Arg Tyr Thr Asp Ser Val Ser Gly
1               5                   10                  15

<210> SEQ ID NO 228
<211> LENGTH: 16
<212> TYPE: PRT
<213> ORGANISM: Artificial
<220> FEATURE:
<223> OTHER INFORMATION: Nanobody, nanobody fragment or nanobody
      construct

<400> SEQUENCE: 228

Ser Ile Ser Ser Glu Gly Thr Thr Ile Tyr Ala Asp Ala Ala Lys Gly
1               5                   10                  15
```

```
<210> SEQ ID NO 229
<211> LENGTH: 17
<212> TYPE: PRT
<213> ORGANISM: Artificial
<220> FEATURE:
<223> OTHER INFORMATION: Nanobody, nanobody fragment or nanobody
      construct

<400> SEQUENCE: 229

Ser Ile Trp Arg Ser Gly Gly Asn Thr Tyr Tyr Ala Asp Ser Val Lys
1               5                   10                  15

Gly

<210> SEQ ID NO 230
<211> LENGTH: 17
<212> TYPE: PRT
<213> ORGANISM: Artificial
<220> FEATURE:
<223> OTHER INFORMATION: Nanobody, nanobody fragment or nanobody
      construct

<400> SEQUENCE: 230

Gly Ile Thr Trp Ser Gly Ala Tyr Thr His Tyr Ala Asn Ser Val Lys
1               5                   10                  15

Gly

<210> SEQ ID NO 231
<211> LENGTH: 16
<212> TYPE: PRT
<213> ORGANISM: Artificial
<220> FEATURE:
<223> OTHER INFORMATION: Nanobody, nanobody fragment or nanobody
      construct

<400> SEQUENCE: 231

Ser Ile Thr Thr Asp Gly Asn Thr Leu Tyr Ala Asp Ala Ala Lys Gly
1               5                   10                  15

<210> SEQ ID NO 232
<211> LENGTH: 16
<212> TYPE: PRT
<213> ORGANISM: Artificial
<220> FEATURE:
<223> OTHER INFORMATION: Nanobody, nanobody fragment or nanobody
      construct

<400> SEQUENCE: 232

Gly Glu Thr Ser Asp Gly Ser Thr Asn Tyr Ala Asp Ser Val Lys Gly
1               5                   10                  15

<210> SEQ ID NO 233
<211> LENGTH: 16
<212> TYPE: PRT
<213> ORGANISM: Artificial
<220> FEATURE:
<223> OTHER INFORMATION: Nanobody, nanobody fragment or nanobody
      construct

<400> SEQUENCE: 233

Ser Ile Thr Ser Ser Gly Thr Ala Ile Tyr Ala Asp Ser Val Lys Gly
1               5                   10                  15

<210> SEQ ID NO 234
<211> LENGTH: 17
<212> TYPE: PRT
<213> ORGANISM: Artificial
<220> FEATURE:
<223> OTHER INFORMATION: Nanobody, nanobody fragment or nanobody
```

```
                              -continued
    construct

<400> SEQUENCE: 234

Ser Ile Ser Ala Gly Gly Tyr Ser Thr Thr Tyr Ala Asp Ser Val Lys
1               5                   10                  15
Gly

<210> SEQ ID NO 235
<211> LENGTH: 16
<212> TYPE: PRT
<213> ORGANISM: Artificial
<220> FEATURE:
<223> OTHER INFORMATION: Nanobody, nanobody fragment or nanobody
      construct

<400> SEQUENCE: 235

Glu Ile Thr Ser Glu Gly Thr Ile Ile Tyr Ala Asp Ser Val Lys Gly
1               5                   10                  15

<210> SEQ ID NO 236
<211> LENGTH: 16
<212> TYPE: PRT
<213> ORGANISM: Artificial
<220> FEATURE:
<223> OTHER INFORMATION: Nanobody, nanobody fragment or nanobody
      construct

<400> SEQUENCE: 236

Gly Ile Asn Glu Tyr Gly Gly Arg Asn Tyr Ala Asn Ser Val Lys Asp
1               5                   10                  15

<210> SEQ ID NO 237
<211> LENGTH: 16
<212> TYPE: PRT
<213> ORGANISM: Artificial
<220> FEATURE:
<223> OTHER INFORMATION: Nanobody, nanobody fragment or nanobody
      construct

<400> SEQUENCE: 237

Gly Phe Gly Ser Gly Gly Thr Thr Asn Tyr Ala Asp Ser Val Lys Gly
1               5                   10                  15

<210> SEQ ID NO 238
<211> LENGTH: 16
<212> TYPE: PRT
<213> ORGANISM: Artificial
<220> FEATURE:
<223> OTHER INFORMATION: Nanobody, nanobody fragment or nanobody
      construct

<400> SEQUENCE: 238

Gly Ile Thr Asp Gly Gly Arg Ser Asn Tyr Ala Asp Ser Val Lys Asp
1               5                   10                  15

<210> SEQ ID NO 239
<211> LENGTH: 16
<212> TYPE: PRT
<213> ORGANISM: Artificial
<220> FEATURE:
<223> OTHER INFORMATION: Nanobody, nanobody fragment or nanobody
      construct

<400> SEQUENCE: 239

Arg Ile Thr Gly Gly Gly Ser Thr Asn Tyr Val Asp Ser Ala Lys Gly
1               5                   10                  15
```

```
<210> SEQ ID NO 240
<211> LENGTH: 16
<212> TYPE: PRT
<213> ORGANISM: Artificial
<220> FEATURE:
<223> OTHER INFORMATION: Nanobody, nanobody fragment or nanobody
      construct

<400> SEQUENCE: 240

Arg Ile Thr Gly Gly Gly Ser Thr Asn Tyr Val Asp Ser Ala Lys Gly
1               5                   10                  15

<210> SEQ ID NO 241
<211> LENGTH: 16
<212> TYPE: PRT
<213> ORGANISM: Artificial
<220> FEATURE:
<223> OTHER INFORMATION: Nanobody, nanobody fragment or nanobody
      construct

<400> SEQUENCE: 241

Arg Ile Thr Gly Gly Gly Ser Thr Asn Tyr Val Asp Ser Ala Lys Gly
1               5                   10                  15

<210> SEQ ID NO 242
<211> LENGTH: 32
<212> TYPE: PRT
<213> ORGANISM: Artificial
<220> FEATURE:
<223> OTHER INFORMATION: Nanobody, nanobody fragment or nanobody
      construct

<400> SEQUENCE: 242

Arg Phe Thr Ile Ser Lys Asp Asn Ala Lys Asn Met Val Tyr Leu Gln
1               5                   10                  15

Met Asn Ser Leu Lys Pro Glu Asp Thr Ala Val Tyr Tyr Cys Ala Ala
                20                  25                  30

<210> SEQ ID NO 243
<211> LENGTH: 32
<212> TYPE: PRT
<213> ORGANISM: Artificial
<220> FEATURE:
<223> OTHER INFORMATION: Nanobody, nanobody fragment or nanobody
      construct

<400> SEQUENCE: 243

Arg Phe Thr Val Ser Arg Asp Ile Ala Glu Asn Thr Met Tyr Leu Glu
1               5                   10                  15

Met Thr Asn Leu Lys Pro Glu Asp Thr Ala Glu Tyr Ser Cys Ala Gly
                20                  25                  30

<210> SEQ ID NO 244
<211> LENGTH: 32
<212> TYPE: PRT
<213> ORGANISM: Artificial
<220> FEATURE:
<223> OTHER INFORMATION: Nanobody, nanobody fragment or nanobody
      construct

<400> SEQUENCE: 244

Arg Phe Thr Ile Ser Lys Asp Asn Ala Lys Asn Met Val His Leu Gln
1               5                   10                  15

Met Asn Ser Leu Lys Pro Glu Asp Thr Ala Val Tyr Tyr Cys Ala Ala
                20                  25                  30

<210> SEQ ID NO 245
```

```
<211> LENGTH: 32
<212> TYPE: PRT
<213> ORGANISM: Artificial
<220> FEATURE:
<223> OTHER INFORMATION: Nanobody, nanobody fragment or nanobody
      construct

<400> SEQUENCE: 245

Arg Phe Thr Ile Ser Lys Asp Asn Ala Lys Asn Met Val Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 246
<211> LENGTH: 32
<212> TYPE: PRT
<213> ORGANISM: Artificial
<220> FEATURE:
<223> OTHER INFORMATION: Nanobody, nanobody fragment or nanobody
      construct

<400> SEQUENCE: 246

Arg Phe Thr Ile Ser Arg Asp Asn Ala Lys Asn Thr Trp Tyr Leu Gln
1               5                   10                  15

Met Asp Ser Leu Lys Pro Glu Asp Thr Gly Val Tyr Tyr Cys Asn Thr
            20                  25                  30

<210> SEQ ID NO 247
<211> LENGTH: 32
<212> TYPE: PRT
<213> ORGANISM: Artificial
<220> FEATURE:
<223> OTHER INFORMATION: Nanobody, nanobody fragment or nanobody
      construct

<400> SEQUENCE: 247

Arg Phe Thr Val Ser Arg Asp Asp Ala Lys Asn Thr Val Tyr Leu Gln
1               5                   10                  15

Met Ser Ser Leu Lys Pro Glu Asp Thr Ala Val Tyr Ser Cys Phe Ala
            20                  25                  30

<210> SEQ ID NO 248
<211> LENGTH: 32
<212> TYPE: PRT
<213> ORGANISM: Artificial
<220> FEATURE:
<223> OTHER INFORMATION: Nanobody, nanobody fragment or nanobody
      construct

<400> SEQUENCE: 248

Arg Phe Thr Ile Ser Ser Asp Asn Ala Lys Asn Thr Val Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 249
<211> LENGTH: 32
<212> TYPE: PRT
<213> ORGANISM: Artificial
<220> FEATURE:
<223> OTHER INFORMATION: Nanobody, nanobody fragment or nanobody
      construct

<400> SEQUENCE: 249

Arg Phe Thr Ile Ser Arg Asp Asn Ala Lys Asn Thr Val Tyr Leu Gln
1               5                   10                  15
```

Met Asn Ser Leu Glu Pro Glu Asp Thr Ala Val Tyr Tyr Cys Asn Ala
            20                  25                  30

<210> SEQ ID NO 250
<211> LENGTH: 32
<212> TYPE: PRT
<213> ORGANISM: Artificial
<220> FEATURE:
<223> OTHER INFORMATION: Nanobody, nanobody fragment or nanobody
      construct

<400> SEQUENCE: 250

Arg Phe Thr Ile Ser Arg Asp Asp Ala Lys Asn Thr Val Tyr Leu Gln
1               5                   10                  15

Met Asn Ser Leu Lys Pro Glu Asp Thr Ala Ile Tyr Tyr Cys Asn Leu
            20                  25                  30

<210> SEQ ID NO 251
<211> LENGTH: 32
<212> TYPE: PRT
<213> ORGANISM: Artificial
<220> FEATURE:
<223> OTHER INFORMATION: Nanobody, nanobody fragment or nanobody
      construct

<400> SEQUENCE: 251

Arg Phe Thr Ile Ser Arg Asp Asn Ala Lys Asn Thr Val Tyr Leu Gln
1               5                   10                  15

Met Asn Ser Leu Glu Pro Glu Asp Thr Ala Val Tyr Tyr Cys Asn Ala
            20                  25                  30

<210> SEQ ID NO 252
<211> LENGTH: 32
<212> TYPE: PRT
<213> ORGANISM: Artificial
<220> FEATURE:
<223> OTHER INFORMATION: Nanobody, nanobody fragment or nanobody
      construct

<400> SEQUENCE: 252

Arg Phe Thr Ile Ser Arg Asp Ser Ala Lys Asn Thr Val Tyr Leu Gln
1               5                   10                  15

Met Asn Ser Leu Lys Pro Glu Asp Thr Ala Val Tyr Tyr Cys Thr Thr
            20                  25                  30

<210> SEQ ID NO 253
<211> LENGTH: 32
<212> TYPE: PRT
<213> ORGANISM: Artificial
<220> FEATURE:
<223> OTHER INFORMATION: Nanobody, nanobody fragment or nanobody
      construct

<400> SEQUENCE: 253

Arg Phe Thr Ile Ser Arg Asp Asn Ser Lys Asn Thr Val Tyr Leu Glu
1               5                   10                  15

Met Asn Ser Leu Lys Pro Asp Asp Thr Ala Val Tyr Tyr Cys Arg Val
            20                  25                  30

<210> SEQ ID NO 254
<211> LENGTH: 32
<212> TYPE: PRT
<213> ORGANISM: Artificial
<220> FEATURE:
<223> OTHER INFORMATION: Nanobody, nanobody fragment or nanobody
      construct

<400> SEQUENCE: 254

Arg Phe Thr Ile Ser Arg Asp Asn Ser Lys Asn Thr Val Tyr Leu Glu
1               5                   10                  15

Met Asn Ser Leu Lys Pro Asp Asp Thr Ala Val Tyr Tyr Cys Arg Val
            20                  25                  30

<210> SEQ ID NO 255
<211> LENGTH: 32
<212> TYPE: PRT
<213> ORGANISM: Artificial
<220> FEATURE:
<223> OTHER INFORMATION: Nanobody, nanobody fragment or nanobody
      construct

<400> SEQUENCE: 255

Arg Phe Thr Ile Ser Arg Asp Asn Ser Lys Asn Thr Val Tyr Leu Glu
1               5                   10                  15

Met Asn Ser Leu Lys Pro Asp Asp Thr Ala Val Tyr Tyr Cys Arg Val
            20                  25                  30

<210> SEQ ID NO 256
<211> LENGTH: 32
<212> TYPE: PRT
<213> ORGANISM: Artificial
<220> FEATURE:
<223> OTHER INFORMATION: Nanobody, nanobody fragment or nanobody
      construct

<400> SEQUENCE: 256

Arg Phe Thr Ile Ser Arg Asp Asn Ala Lys Asn Thr Val Tyr Leu Glu
1               5                   10                  15

Met Asn Ser Leu Lys Pro Asp Asp Thr Ala Val Tyr Tyr Cys Arg Val
            20                  25                  30

<210> SEQ ID NO 257
<211> LENGTH: 32
<212> TYPE: PRT
<213> ORGANISM: Artificial
<220> FEATURE:
<223> OTHER INFORMATION: Nanobody, nanobody fragment or nanobody
      construct

<400> SEQUENCE: 257

Arg Phe Thr Ile Ser Arg Asp Asn Ser Lys Asn Thr Val Tyr Leu Glu
1               5                   10                  15

Met Asn Ser Leu Lys Pro Asp Asp Thr Ala Val Tyr Tyr Cys Arg Val
            20                  25                  30

<210> SEQ ID NO 258
<211> LENGTH: 32
<212> TYPE: PRT
<213> ORGANISM: Artificial
<220> FEATURE:
<223> OTHER INFORMATION: Nanobody, nanobody fragment or nanobody
      construct

<400> SEQUENCE: 258

Arg Phe Thr Val Ser Arg Asp Asn Ala Lys His Thr Val Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 259
<211> LENGTH: 32
<212> TYPE: PRT

<213> ORGANISM: Artificial
<220> FEATURE:
<223> OTHER INFORMATION: Nanobody, nanobody fragment or nanobody
      construct

<400> SEQUENCE: 259

Arg Phe Thr Ile Ser Arg Asp Ser Ala Lys Asn Thr Val Tyr Leu Gln
1               5                   10                  15
Met Asn Ser Leu Lys Pro Glu Asp Thr Ala Val Tyr Tyr Cys Thr Thr
            20                  25                  30

<210> SEQ ID NO 260
<211> LENGTH: 32
<212> TYPE: PRT
<213> ORGANISM: Artificial
<220> FEATURE:
<223> OTHER INFORMATION: Nanobody, nanobody fragment or nanobody
      construct

<400> SEQUENCE: 260

Arg Phe Ala Ile Tyr Arg Asp Asn Ser Lys Asn Thr Val Tyr Leu Glu
1               5                   10                  15
Met Asn Ser Leu Lys Pro Asp Asp Thr Ala Val Tyr Tyr Cys Arg Val
            20                  25                  30

<210> SEQ ID NO 261
<211> LENGTH: 32
<212> TYPE: PRT
<213> ORGANISM: Artificial
<220> FEATURE:
<223> OTHER INFORMATION: Nanobody, nanobody fragment or nanobody
      construct

<400> SEQUENCE: 261

Arg Phe Thr Ile Ser Arg Asp Asn Ala Asn Asn Ala Val Tyr Leu Gln
1               5                   10                  15
Met Asn Arg Leu Lys Pro Glu Asp Thr Ala Val Tyr His Cys Ala Ala
            20                  25                  30

<210> SEQ ID NO 262
<211> LENGTH: 32
<212> TYPE: PRT
<213> ORGANISM: Artificial
<220> FEATURE:
<223> OTHER INFORMATION: Nanobody, nanobody fragment or nanobody
      construct

<400> SEQUENCE: 262

Arg Ile Thr Ile Ser Arg Asp Asn Ala Lys Asn Thr Val Tyr Leu Gln
1               5                   10                  15
Met Asn Ser Leu Lys Thr Glu Asp Thr Gly Val Tyr Tyr Cys Ala Ala
            20                  25                  30

<210> SEQ ID NO 263
<211> LENGTH: 32
<212> TYPE: PRT
<213> ORGANISM: Artificial
<220> FEATURE:
<223> OTHER INFORMATION: Nanobody, nanobody fragment or nanobody
      construct

<400> SEQUENCE: 263

Arg Phe Thr Ile Ser Arg Asp Asn Ala Lys Asn Thr Leu Tyr Leu Gln
1               5                   10                  15
Met Asn Ser Leu Asn Pro Glu Asp Thr Ala Val Tyr Tyr Cys Ala Arg
            20                  25                  30

```
<210> SEQ ID NO 264
<211> LENGTH: 32
<212> TYPE: PRT
<213> ORGANISM: Artificial
<220> FEATURE:
<223> OTHER INFORMATION: Nanobody, nanobody fragment or nanobody
      construct

<400> SEQUENCE: 264

Arg Phe Thr Thr Ser Arg Asp Asn Ala Lys Asn Thr Val Tyr Leu Gln
1               5                   10                  15

Met Asn Ser Leu Lys Pro Glu Asp Thr Gly Val Tyr Tyr Cys Ala Ala
            20                  25                  30

<210> SEQ ID NO 265
<211> LENGTH: 32
<212> TYPE: PRT
<213> ORGANISM: Artificial
<220> FEATURE:
<223> OTHER INFORMATION: Nanobody, nanobody fragment or nanobody
      construct

<400> SEQUENCE: 265

Arg Phe Thr Ile Ser Thr Asp Asn Ala Lys Asn Thr Val Tyr Leu Gln
1               5                   10                  15

Met Asn Ser Leu Lys Pro Glu Asp Thr Gly Val Tyr Tyr Cys Ala Ala
            20                  25                  30

<210> SEQ ID NO 266
<211> LENGTH: 32
<212> TYPE: PRT
<213> ORGANISM: Artificial
<220> FEATURE:
<223> OTHER INFORMATION: Nanobody, nanobody fragment or nanobody
      construct

<400> SEQUENCE: 266

Arg Phe Ile Val Ser Arg Asp Asn Ala Glu Asn Thr Val Phe Leu Gln
1               5                   10                  15

Met Asn Ser Leu Lys Pro Glu Asp Ser Ala Val Tyr Phe Cys Ala Ala
            20                  25                  30

<210> SEQ ID NO 267
<211> LENGTH: 32
<212> TYPE: PRT
<213> ORGANISM: Artificial
<220> FEATURE:
<223> OTHER INFORMATION: Nanobody, nanobody fragment or nanobody
      construct

<400> SEQUENCE: 267

Arg Phe Thr Ile Tyr Arg Ala Asn Ala Lys Asn Thr Val Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 268
<211> LENGTH: 32
<212> TYPE: PRT
<213> ORGANISM: Artificial
<220> FEATURE:
<223> OTHER INFORMATION: Nanobody, nanobody fragment or nanobody
      construct

<400> SEQUENCE: 268
```

Arg Phe Thr Ile Ser Arg Asp Asn Ala Lys Asn Ala Val Tyr Leu Gln
1               5                   10                  15

Met Asn Asn Leu Lys Leu Asp Asp Thr Ala Val Tyr Tyr Cys Asn Ala
            20                  25                  30

<210> SEQ ID NO 269
<211> LENGTH: 32
<212> TYPE: PRT
<213> ORGANISM: Artificial
<220> FEATURE:
<223> OTHER INFORMATION: Nanobody, nanobody fragment or nanobody
      construct

<400> SEQUENCE: 269

Arg Phe Thr Ile Ser Arg Asp Asn Ala Lys Asn Met Gly Tyr Leu Gln
1               5                   10                  15

Met Asn Asn Leu Lys Leu Asp Asp Thr Ala Ile Tyr Tyr Cys Tyr Ala
            20                  25                  30

<210> SEQ ID NO 270
<211> LENGTH: 32
<212> TYPE: PRT
<213> ORGANISM: Artificial
<220> FEATURE:
<223> OTHER INFORMATION: Nanobody, nanobody fragment or nanobody
      construct

<400> SEQUENCE: 270

Arg Phe Thr Ile Ser Arg His Asn Ala Lys Asn Met Val Tyr Leu Gln
1               5                   10                  15

Met Asn Asn Leu Lys Leu Asp Asp Thr Ala Val Tyr Tyr Cys Asn Ala
            20                  25                  30

<210> SEQ ID NO 271
<211> LENGTH: 16
<212> TYPE: PRT
<213> ORGANISM: Artificial
<220> FEATURE:
<223> OTHER INFORMATION: Nanobody, nanobody fragment or nanobody
      construct

<400> SEQUENCE: 271

Thr Arg Leu Ile Val Tyr Thr Pro Thr Gly Phe Arg Gln Tyr Phe Asp
1               5                   10                  15

<210> SEQ ID NO 272
<211> LENGTH: 14
<212> TYPE: PRT
<213> ORGANISM: Artificial
<220> FEATURE:
<223> OTHER INFORMATION: Nanobody, nanobody fragment or nanobody
      construct

<400> SEQUENCE: 272

Arg Leu Leu Gly Ser Thr Ile Arg Ser His Glu Tyr Arg Tyr
1               5                   10

<210> SEQ ID NO 273
<211> LENGTH: 16
<212> TYPE: PRT
<213> ORGANISM: Artificial
<220> FEATURE:
<223> OTHER INFORMATION: Nanobody, nanobody fragment or nanobody
      construct

<400> SEQUENCE: 273

Thr Arg Leu Ile Val Tyr Thr Pro Thr Gly Phe Arg Gln Tyr Phe Asp 1               5                   10                  15

<210> SEQ ID NO 274
<211> LENGTH: 16
<212> TYPE: PRT
<213> ORGANISM: Artificial
<220> FEATURE:
<223> OTHER INFORMATION: Nanobody, nanobody fragment or nanobody
      construct

<400> SEQUENCE: 274

Thr Arg Leu Ile Val Tyr Thr Pro Thr Gly Phe Arg Gln Tyr Phe Asp
1               5                   10                  15

<210> SEQ ID NO 275
<211> LENGTH: 5
<212> TYPE: PRT
<213> ORGANISM: Artificial
<220> FEATURE:
<223> OTHER INFORMATION: Nanobody, nanobody fragment or nanobody
      construct

<400> SEQUENCE: 275

Phe Pro Leu Thr Ser
1               5

<210> SEQ ID NO 276
<211> LENGTH: 13
<212> TYPE: PRT
<213> ORGANISM: Artificial
<220> FEATURE:
<223> OTHER INFORMATION: Nanobody, nanobody fragment or nanobody
      construct

<400> SEQUENCE: 276

Asn Ile Val Ile Arg Ser Ser Gly Tyr Phe Asn Arg Tyr
1               5                   10

<210> SEQ ID NO 277
<211> LENGTH: 19
<212> TYPE: PRT
<213> ORGANISM: Artificial
<220> FEATURE:
<223> OTHER INFORMATION: Nanobody, nanobody fragment or nanobody
      construct

<400> SEQUENCE: 277

His Thr Asp Phe Ala Cys Tyr Ile Gly Tyr Tyr Ser Asp Tyr Asp Pro
1               5                   10                  15

His Asp Tyr

<210> SEQ ID NO 278
<211> LENGTH: 7
<212> TYPE: PRT
<213> ORGANISM: Artificial
<220> FEATURE:
<223> OTHER INFORMATION: Nanobody, nanobody fragment or nanobody
      construct

<400> SEQUENCE: 278

Leu Gln Phe Gly Ala Val Tyr
1               5

<210> SEQ ID NO 279
<211> LENGTH: 7
<212> TYPE: PRT
<213> ORGANISM: Artificial
<220> FEATURE:

<223> OTHER INFORMATION: Nanobody, nanobody fragment or nanobody
      construct

<400> SEQUENCE: 279

Arg Gln Leu Gly Asn Val Tyr
1               5

<210> SEQ ID NO 280
<211> LENGTH: 7
<212> TYPE: PRT
<213> ORGANISM: Artificial
<220> FEATURE:
<223> OTHER INFORMATION: Nanobody, nanobody fragment or nanobody
      construct

<400> SEQUENCE: 280

Leu Gln Phe Gly Ala Val Tyr
1               5

<210> SEQ ID NO 281
<211> LENGTH: 10
<212> TYPE: PRT
<213> ORGANISM: Artificial
<220> FEATURE:
<223> OTHER INFORMATION: Nanobody, nanobody fragment or nanobody
      construct

<400> SEQUENCE: 281

Ala Thr Asn Ser Thr Thr Gly Tyr Asp Tyr
1               5                   10

<210> SEQ ID NO 282
<211> LENGTH: 9
<212> TYPE: PRT
<213> ORGANISM: Artificial
<220> FEATURE:
<223> OTHER INFORMATION: Nanobody, nanobody fragment or nanobody
      construct

<400> SEQUENCE: 282

Val Asp Leu Leu Arg Gly Lys Leu Tyr
1               5

<210> SEQ ID NO 283
<211> LENGTH: 9
<212> TYPE: PRT
<213> ORGANISM: Artificial
<220> FEATURE:
<223> OTHER INFORMATION: Nanobody, nanobody fragment or nanobody
      construct

<400> SEQUENCE: 283

Val Asp Leu Leu Arg Gly Lys Leu Tyr
1               5

<210> SEQ ID NO 284
<211> LENGTH: 9
<212> TYPE: PRT
<213> ORGANISM: Artificial
<220> FEATURE:
<223> OTHER INFORMATION: Nanobody, nanobody fragment or nanobody
      construct

<400> SEQUENCE: 284

Val Asp Pro Leu Arg Gly Lys Leu Tyr
1               5

<210> SEQ ID NO 285

```
<211> LENGTH: 9
<212> TYPE: PRT
<213> ORGANISM: Artificial
<220> FEATURE:
<223> OTHER INFORMATION: Nanobody, nanobody fragment or nanobody
      construct

<400> SEQUENCE: 285

Val Asp Pro Leu Arg Gly Lys Leu Tyr
1               5

<210> SEQ ID NO 286
<211> LENGTH: 9
<212> TYPE: PRT
<213> ORGANISM: Artificial
<220> FEATURE:
<223> OTHER INFORMATION: Nanobody, nanobody fragment or nanobody
      construct

<400> SEQUENCE: 286

Val Asp Pro Leu Arg Gly Lys Leu Tyr
1               5

<210> SEQ ID NO 287
<211> LENGTH: 12
<212> TYPE: PRT
<213> ORGANISM: Artificial
<220> FEATURE:
<223> OTHER INFORMATION: Nanobody, nanobody fragment or nanobody
      construct

<400> SEQUENCE: 287

Ala Ser Phe Ala Pro Gly Ser Arg Gly Tyr Asp Tyr
1               5                   10

<210> SEQ ID NO 288
<211> LENGTH: 10
<212> TYPE: PRT
<213> ORGANISM: Artificial
<220> FEATURE:
<223> OTHER INFORMATION: Nanobody, nanobody fragment or nanobody
      construct

<400> SEQUENCE: 288

Ala Thr Asn Ser Thr Thr Gly Tyr Asp Tyr
1               5                   10

<210> SEQ ID NO 289
<211> LENGTH: 9
<212> TYPE: PRT
<213> ORGANISM: Artificial
<220> FEATURE:
<223> OTHER INFORMATION: Nanobody, nanobody fragment or nanobody
      construct

<400> SEQUENCE: 289

Val Asp Leu Leu Arg Gly Lys Leu Tyr
1               5

<210> SEQ ID NO 290
<211> LENGTH: 13
<212> TYPE: PRT
<213> ORGANISM: Artificial
<220> FEATURE:
<223> OTHER INFORMATION: Nanobody, nanobody fragment or nanobody
      construct

<400> SEQUENCE: 290

Ser Leu Arg Asn Ser Gly Ser Asn Val Glu Gly Arg Tyr
```

<210> SEQ ID NO 291
<211> LENGTH: 9
<212> TYPE: PRT
<213> ORGANISM: Artificial
<220> FEATURE:
<223> OTHER INFORMATION: Nanobody, nanobody fragment or nanobody construct

<400> SEQUENCE: 291

Asn Leu Gln Asn Ala Arg Gly Ser Tyr
1               5

<210> SEQ ID NO 292
<211> LENGTH: 7
<212> TYPE: PRT
<213> ORGANISM: Artificial
<220> FEATURE:
<223> OTHER INFORMATION: Nanobody, nanobody fragment or nanobody construct

<400> SEQUENCE: 292

Gly Asp Trp Arg Tyr Gly Ser
1               5

<210> SEQ ID NO 293
<211> LENGTH: 8
<212> TYPE: PRT
<213> ORGANISM: Artificial
<220> FEATURE:
<223> OTHER INFORMATION: Nanobody, nanobody fragment or nanobody construct

<400> SEQUENCE: 293

Asp Asp Gly Ala Arg Gly Ser Tyr
1               5

<210> SEQ ID NO 294
<211> LENGTH: 9
<212> TYPE: PRT
<213> ORGANISM: Artificial
<220> FEATURE:
<223> OTHER INFORMATION: Nanobody, nanobody fragment or nanobody construct

<400> SEQUENCE: 294

Thr Leu Ala Lys Gly Gly Gly Arg Tyr
1               5

<210> SEQ ID NO 295
<211> LENGTH: 9
<212> TYPE: PRT
<213> ORGANISM: Artificial
<220> FEATURE:
<223> OTHER INFORMATION: Nanobody, nanobody fragment or nanobody construct

<400> SEQUENCE: 295

Ser Ile Glu Gly Val Ser Gly Arg Tyr
1               5

<210> SEQ ID NO 296
<211> LENGTH: 12
<212> TYPE: PRT
<213> ORGANISM: Artificial
<220> FEATURE:
<223> OTHER INFORMATION: Nanobody, nanobody fragment or nanobody construct

<400> SEQUENCE: 296

Asp Leu Arg Gly Gly Ile Ala Thr Thr Gly Arg Tyr
1               5                   10

<210> SEQ ID NO 297
<211> LENGTH: 12
<212> TYPE: PRT
<213> ORGANISM: Artificial
<220> FEATURE:
<223> OTHER INFORMATION: Nanobody, nanobody fragment or nanobody
      construct

<400> SEQUENCE: 297

Tyr Gly Ser Gly Ser Asp Tyr Leu Pro Ile Asp Tyr
1               5                   10

<210> SEQ ID NO 298
<211> LENGTH: 12
<212> TYPE: PRT
<213> ORGANISM: Artificial
<220> FEATURE:
<223> OTHER INFORMATION: Nanobody, nanobody fragment or nanobody
      construct

<400> SEQUENCE: 298

Tyr Gly Ser Gly Ser Asp Tyr Leu Pro Thr Asp Tyr
1               5                   10

<210> SEQ ID NO 299
<211> LENGTH: 12
<212> TYPE: PRT
<213> ORGANISM: Artificial
<220> FEATURE:
<223> OTHER INFORMATION: Nanobody, nanobody fragment or nanobody
      construct

<400> SEQUENCE: 299

Tyr Gly Ser Gly Ser Asp Tyr Leu Pro Met Asp Tyr
1               5                   10

<210> SEQ ID NO 300
<211> LENGTH: 11
<212> TYPE: PRT
<213> ORGANISM: Artificial
<220> FEATURE:
<223> OTHER INFORMATION: Nanobody, nanobody fragment or nanobody
      construct

<400> SEQUENCE: 300

Trp Gly Gln Gly Ala Gln Val Thr Val Ser Ser
1               5                   10

<210> SEQ ID NO 301
<211> LENGTH: 11
<212> TYPE: PRT
<213> ORGANISM: Artificial
<220> FEATURE:
<223> OTHER INFORMATION: Nanobody, nanobody fragment or nanobody
      construct

<400> SEQUENCE: 301

Trp Gly Gln Gly Thr Gln Val Thr Val Ser Ser
1               5                   10

<210> SEQ ID NO 302
<211> LENGTH: 11
<212> TYPE: PRT

```
<213> ORGANISM: Artificial
<220> FEATURE:
<223> OTHER INFORMATION: Nanobody, nanobody fragment or nanobody
      construct

<400> SEQUENCE: 302

Trp Gly Gln Gly Thr Gln Val Thr Val Ser Ser
1               5                   10

<210> SEQ ID NO 303
<211> LENGTH: 11
<212> TYPE: PRT
<213> ORGANISM: Artificial
<220> FEATURE:
<223> OTHER INFORMATION: Nanobody, nanobody fragment or nanobody
      construct

<400> SEQUENCE: 303

Trp Gly Gln Gly Thr Gln Val Thr Val Ser Ser
1               5                   10

<210> SEQ ID NO 304
<211> LENGTH: 11
<212> TYPE: PRT
<213> ORGANISM: Artificial
<220> FEATURE:
<223> OTHER INFORMATION: Nanobody, nanobody fragment or nanobody
      construct

<400> SEQUENCE: 304

Trp Gly Gln Gly Thr Gln Val Thr Val Ser Ser
1               5                   10

<210> SEQ ID NO 305
<211> LENGTH: 11
<212> TYPE: PRT
<213> ORGANISM: Artificial
<220> FEATURE:
<223> OTHER INFORMATION: Nanobody, nanobody fragment or nanobody
      construct

<400> SEQUENCE: 305

Trp Gly Gln Gly Thr Leu Val Thr Val Ser Ser
1               5                   10

<210> SEQ ID NO 306
<211> LENGTH: 11
<212> TYPE: PRT
<213> ORGANISM: Artificial
<220> FEATURE:
<223> OTHER INFORMATION: Nanobody, nanobody fragment or nanobody
      construct

<400> SEQUENCE: 306

Trp Gly Gln Gly Thr Gln Val Thr Val Ser Ser
1               5                   10

<210> SEQ ID NO 307
<211> LENGTH: 11
<212> TYPE: PRT
<213> ORGANISM: Artificial
<220> FEATURE:
<223> OTHER INFORMATION: Nanobody, nanobody fragment or nanobody
      construct

<400> SEQUENCE: 307

Trp Gly Gln Gly Thr Gln Val Thr Val Ser Ser
1               5                   10
```

```
<210> SEQ ID NO 308
<211> LENGTH: 11
<212> TYPE: PRT
<213> ORGANISM: Artificial
<220> FEATURE:
<223> OTHER INFORMATION: Nanobody, nanobody fragment or nanobody
      construct

<400> SEQUENCE: 308

Trp Ala Gln Gly Thr Gln Val Thr Val Ser Ser
1               5                   10

<210> SEQ ID NO 309
<211> LENGTH: 11
<212> TYPE: PRT
<213> ORGANISM: Artificial
<220> FEATURE:
<223> OTHER INFORMATION: Nanobody, nanobody fragment or nanobody
      construct

<400> SEQUENCE: 309

Trp Gly Gln Gly Thr Gln Val Thr Val Ser Ser
1               5                   10

<210> SEQ ID NO 310
<211> LENGTH: 11
<212> TYPE: PRT
<213> ORGANISM: Artificial
<220> FEATURE:
<223> OTHER INFORMATION: Nanobody, nanobody fragment or nanobody
      construct

<400> SEQUENCE: 310

Trp Gly Gln Gly Thr Gln Val Thr Val Ser Ser
1               5                   10

<210> SEQ ID NO 311
<211> LENGTH: 11
<212> TYPE: PRT
<213> ORGANISM: Artificial
<220> FEATURE:
<223> OTHER INFORMATION: Nanobody, nanobody fragment or nanobody
      construct

<400> SEQUENCE: 311

Trp Gly Gln Gly Thr Gln Val Thr Val Ser Ser
1               5                   10

<210> SEQ ID NO 312
<211> LENGTH: 11
<212> TYPE: PRT
<213> ORGANISM: Artificial
<220> FEATURE:
<223> OTHER INFORMATION: Nanobody, nanobody fragment or nanobody
      construct

<400> SEQUENCE: 312

Trp Gly Gln Gly Thr Gln Val Thr Val Ser Ser
1               5                   10

<210> SEQ ID NO 313
<211> LENGTH: 11
<212> TYPE: PRT
<213> ORGANISM: Artificial
<220> FEATURE:
<223> OTHER INFORMATION: Nanobody, nanobody fragment or nanobody
      construct

<400> SEQUENCE: 313
```

Trp Gly Gln Gly Thr Gln Val Thr Val Ser Ser
1               5                   10

<210> SEQ ID NO 314
<211> LENGTH: 11
<212> TYPE: PRT
<213> ORGANISM: Artificial
<220> FEATURE:
<223> OTHER INFORMATION: Nanobody, nanobody fragment or nanobody
      construct

<400> SEQUENCE: 314

Trp Gly Gln Gly Thr Gln Val Thr Val Ser Ser
1               5                   10

<210> SEQ ID NO 315
<211> LENGTH: 11
<212> TYPE: PRT
<213> ORGANISM: Artificial
<220> FEATURE:
<223> OTHER INFORMATION: Nanobody, nanobody fragment or nanobody
      construct

<400> SEQUENCE: 315

Trp Gly Gln Gly Thr Gln Val Thr Val Ser Ser
1               5                   10

<210> SEQ ID NO 316
<211> LENGTH: 11
<212> TYPE: PRT
<213> ORGANISM: Artificial
<220> FEATURE:
<223> OTHER INFORMATION: Nanobody, nanobody fragment or nanobody
      construct

<400> SEQUENCE: 316

Trp Gly Gln Gly Thr Gln Val Thr Val Ser Ser
1               5                   10

<210> SEQ ID NO 317
<211> LENGTH: 11
<212> TYPE: PRT
<213> ORGANISM: Artificial
<220> FEATURE:
<223> OTHER INFORMATION: Nanobody, nanobody fragment or nanobody
      construct

<400> SEQUENCE: 317

Trp Gly Gln Gly Thr Gln Val Thr Val Ser Ser
1               5                   10

<210> SEQ ID NO 318
<211> LENGTH: 11
<212> TYPE: PRT
<213> ORGANISM: Artificial
<220> FEATURE:
<223> OTHER INFORMATION: Nanobody, nanobody fragment or nanobody
      construct

<400> SEQUENCE: 318

Trp Gly Gln Gly Thr Gln Val Thr Val Ser Ser
1               5                   10

<210> SEQ ID NO 319
<211> LENGTH: 11
<212> TYPE: PRT
<213> ORGANISM: Artificial
<220> FEATURE:

<223> OTHER INFORMATION: Nanobody, nanobody fragment or nanobody
      construct

<400> SEQUENCE: 319

Trp Gly Gln Gly Thr Gln Val Thr Val Ser Ser
1               5                   10

<210> SEQ ID NO 320
<211> LENGTH: 11
<212> TYPE: PRT
<213> ORGANISM: Artificial
<220> FEATURE:
<223> OTHER INFORMATION: Nanobody, nanobody fragment or nanobody
      construct

<400> SEQUENCE: 320

Tyr Gly Gln Gly Thr Gln Val Thr Val Ser Ser
1               5                   10

<210> SEQ ID NO 321
<211> LENGTH: 11
<212> TYPE: PRT
<213> ORGANISM: Artificial
<220> FEATURE:
<223> OTHER INFORMATION: Nanobody, nanobody fragment or nanobody
      construct

<400> SEQUENCE: 321

Arg Gly Gln Gly Thr Gln Val Thr Val Ser Ser
1               5                   10

<210> SEQ ID NO 322
<211> LENGTH: 11
<212> TYPE: PRT
<213> ORGANISM: Artificial
<220> FEATURE:
<223> OTHER INFORMATION: Nanobody, nanobody fragment or nanobody
      construct

<400> SEQUENCE: 322

Tyr Gly Gln Gly Thr Gln Val Thr Val Ser Ser
1               5                   10

<210> SEQ ID NO 323
<211> LENGTH: 11
<212> TYPE: PRT
<213> ORGANISM: Artificial
<220> FEATURE:
<223> OTHER INFORMATION: Nanobody, nanobody fragment or nanobody
      construct

<400> SEQUENCE: 323

Trp Gly Gln Gly Thr Pro Val Thr Val Ser Ser
1               5                   10

<210> SEQ ID NO 324
<211> LENGTH: 11
<212> TYPE: PRT
<213> ORGANISM: Artificial
<220> FEATURE:
<223> OTHER INFORMATION: Nanobody, nanobody fragment or nanobody
      construct

<400> SEQUENCE: 324

Tyr Gly Gln Gly Thr Gln Val Thr Val Ser Ser
1               5                   10

<210> SEQ ID NO 325

```
<211> LENGTH: 11
<212> TYPE: PRT
<213> ORGANISM: Artificial
<220> FEATURE:
<223> OTHER INFORMATION: Nanobody, nanobody fragment or nanobody
      construct

<400> SEQUENCE: 325

Trp Gly Gln Gly Thr Gln Val Thr Val Ser Ser
1               5                   10

<210> SEQ ID NO 326
<211> LENGTH: 11
<212> TYPE: PRT
<213> ORGANISM: Artificial
<220> FEATURE:
<223> OTHER INFORMATION: Nanobody, nanobody fragment or nanobody
      construct

<400> SEQUENCE: 326

Trp Gly Gln Gly Thr Gln Val Thr Val Ser Ser
1               5                   10

<210> SEQ ID NO 327
<211> LENGTH: 11
<212> TYPE: PRT
<213> ORGANISM: Artificial
<220> FEATURE:
<223> OTHER INFORMATION: Nanobody, nanobody fragment or nanobody
      construct

<400> SEQUENCE: 327

Trp Gly Gln Gly Thr Gln Val Thr Val Ser Ser
1               5                   10

<210> SEQ ID NO 328
<211> LENGTH: 11
<212> TYPE: PRT
<213> ORGANISM: Artificial
<220> FEATURE:
<223> OTHER INFORMATION: Nanobody, nanobody fragment or nanobody
      construct

<400> SEQUENCE: 328

Trp Gly Gln Gly Thr Gln Val Thr Val Ser Ser
1               5                   10

<210> SEQ ID NO 329
<211> LENGTH: 125
<212> TYPE: PRT
<213> ORGANISM: Artificial
<220> FEATURE:
<223> OTHER INFORMATION: Nanobody, nanobody fragment or nanobody
      construct

<400> SEQUENCE: 329

Glu Val Gln Leu Val Glu Ser Gly Gly Gly Leu Val Gln Ala Gly Gly
1               5                   10                  15

Ser Leu Arg Leu Ser Cys Ile Ala Ser Gly Asp Thr Ser Glu Ile Tyr
            20                  25                  30

Asp Met Gly Trp Phe Arg Gln Ala Pro Gly Lys Glu Arg Glu Phe Val
        35                  40                  45

Ser Ser Ile His Trp Arg Gly Arg Gly Thr Asn Tyr Thr Asp Ser Val
    50                  55                  60

Glu Gly Arg Phe Thr Ile Ser Lys Asp Asn Ala Lys Asn Met Val Tyr
65                  70                  75                  80
```

```
Leu Gln Met Asn Ser Leu Lys Pro Glu Asp Thr Ala Val Tyr Tyr Cys
                 85                  90                  95

Ala Ala Thr Arg Leu Ile Val Tyr Thr Pro Thr Gly Phe Arg Gln Tyr
            100                 105                 110

Phe Asp Trp Gly Gln Gly Ala Gln Val Thr Val Ser Ser
        115                 120                 125

<210> SEQ ID NO 330
<211> LENGTH: 122
<212> TYPE: PRT
<213> ORGANISM: Artificial
<220> FEATURE:
<223> OTHER INFORMATION: Nanobody, nanobody fragment or nanobody
      construct
<220> FEATURE:
<221> NAME/KEY: misc_feature
<222> LOCATION: (27)..(28)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid

<400> SEQUENCE: 330

Glu Val Gln Leu Val Glu Ser Gly Gly Gly Leu Val Gln Ala Gly Gly
1               5                   10                  15

Ser Leu Arg Leu Ser Cys Ala Ala Ser Gly Xaa Xaa Phe Xaa Ser Asp
            20                  25                  30

Val Met Gly Trp Phe Arg Arg Ala Pro Gly Lys Glu Arg Glu Phe Val
        35                  40                  45

Ala Ser Ile Thr Thr Thr Gly Asn Glu Tyr Tyr Glu Asp Ser Leu Lys
    50                  55                  60

Gly Arg Phe Thr Val Ser Arg Asp Ile Ala Glu Asn Thr Met Tyr Leu
65                  70                  75                  80

Glu Met Thr Asn Leu Lys Pro Glu Asp Thr Ala Glu Tyr Ser Cys Ala
                85                  90                  95

Gly Arg Leu Leu Gly Ser Thr Ile Arg Ser His Glu Tyr Arg Tyr Trp
            100                 105                 110

Gly Gln Gly Thr Gln Val Thr Val Ser Ser
        115                 120

<210> SEQ ID NO 331
<211> LENGTH: 125
<212> TYPE: PRT
<213> ORGANISM: Artificial
<220> FEATURE:
<223> OTHER INFORMATION: Nanobody, nanobody fragment or nanobody
      construct

<400> SEQUENCE: 331

Glu Val Gln Leu Val Glu Ser Gly Gly Gly Leu Val Gln Ala Gly Gly
1               5                   10                  15

Ser Leu Arg Leu Ser Cys Val Ala Ser Gly Asp Thr Ser Glu Ile Tyr
            20                  25                  30

Asp Met Gly Trp Phe Arg Gln Ala Pro Gly Lys Glu Arg Glu Phe Val
        35                  40                  45

Ser Ser Ile His Trp Gly Gly Arg Gly Thr Asn Tyr Thr Asp Ser Val
    50                  55                  60

Lys Gly Arg Phe Thr Ile Ser Lys Asp Asn Ala Lys Asn Met Val His
65                  70                  75                  80

Leu Gln Met Asn Ser Leu Lys Pro Glu Asp Thr Ala Val Tyr Tyr Cys
                85                  90                  95
```

```
Ala Ala Thr Arg Leu Ile Val Tyr Thr Pro Thr Gly Phe Arg Gln Tyr
            100                 105                 110

Phe Asp Trp Gly Gln Gly Thr Gln Val Thr Val Ser Ser
            115                 120                 125

<210> SEQ ID NO 332
<211> LENGTH: 125
<212> TYPE: PRT
<213> ORGANISM: Artificial
<220> FEATURE:
<223> OTHER INFORMATION: Nanobody, nanobody fragment or nanobody
      construct

<400> SEQUENCE: 332

Glu Val Gln Leu Val Glu Ser Gly Gly Gly Leu Val Gln Ala Gly Gly
1               5                   10                  15

Ser Leu Arg Leu Ser Cys Val Ala Ser Gly Asp Thr Ser Glu Ile Tyr
            20                  25                  30

Asp Met Gly Trp Phe Arg Gln Ala Pro Gly Lys Glu Arg Glu Phe Val
            35                  40                  45

Ser Ser Ile His Trp Gly Gly Arg Gly Thr Asn Tyr Thr Asp Ser Val
        50                  55                  60

Lys Gly Arg Phe Thr Ile Ser Lys Asp Asn Ala Lys Asn Met Val Tyr
65                  70                  75                  80

Leu Gln Met Asn Ser Leu Lys Pro Glu Asp Thr Ala Val Tyr Tyr Cys
                85                  90                  95

Ala Ala Thr Arg Leu Ile Val Tyr Thr Pro Thr Gly Phe Arg Gln Tyr
            100                 105                 110

Phe Asp Trp Gly Gln Gly Thr Gln Val Thr Val Ser Ser
            115                 120                 125

<210> SEQ ID NO 333
<211> LENGTH: 113
<212> TYPE: PRT
<213> ORGANISM: Artificial
<220> FEATURE:
<223> OTHER INFORMATION: Nanobody, nanobody fragment or nanobody
      construct

<400> SEQUENCE: 333

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Asp Phe Ser Gly Phe
            20                  25                  30

Leu Leu Gly Trp Tyr Arg Gln Pro Pro Gly Lys Gln Arg Glu Leu Ile
            35                  40                  45

Ala Gln Thr Thr Asp Gly Gly Arg Thr Asn Tyr Gly Asp Ser Val Lys
        50                  55                  60

Gly Arg Phe Thr Ile Ser Arg Asp Asn Ala Lys Asn Thr Trp Tyr Leu
65                  70                  75                  80

Gln Met Asp Ser Leu Lys Pro Glu Asp Thr Gly Val Tyr Tyr Cys Asn
                85                  90                  95

Thr Phe Pro Leu Thr Ser Trp Gly Gln Gly Thr Gln Val Thr Val Ser
            100                 105                 110

Ser

<210> SEQ ID NO 334
<211> LENGTH: 121
<212> TYPE: PRT
```

<213> ORGANISM: Artificial
<220> FEATURE:
<223> OTHER INFORMATION: Nanobody, nanobody fragment or nanobody construct

<400> SEQUENCE: 334

Glu Val Gln Leu Val Glu Ser Gly Gly Gly Leu Val Gln Ser Gly Gly
1               5                   10                  15

Ser Leu Ser Leu Ser Cys Ala Ala Ser Gly Ser Val Leu Arg Ile Asn
            20                  25                  30

Asp Met Gly Trp Tyr Arg Gln Ala Pro Gly Lys Thr Arg Glu Met Val
        35                  40                  45

Ala Thr Ile Thr Arg Ser Gly Val Leu Asn Tyr Thr Asp Ser Val Lys
    50                  55                  60

Gly Arg Phe Thr Val Ser Arg Asp Asp Ala Lys Asn Thr Val Tyr Leu
65                  70                  75                  80

Gln Met Ser Ser Leu Lys Pro Glu Asp Thr Ala Val Tyr Ser Cys Phe
                85                  90                  95

Ala Asn Ile Val Ile Arg Ser Ser Gly Tyr Phe Asn Arg Tyr Trp Gly
            100                 105                 110

Gln Gly Thr Leu Val Thr Val Ser Ser
        115                 120

<210> SEQ ID NO 335
<211> LENGTH: 128
<212> TYPE: PRT
<213> ORGANISM: Artificial
<220> FEATURE:
<223> OTHER INFORMATION: Nanobody, nanobody fragment or nanobody construct

<400> SEQUENCE: 335

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Gly Val
        35                  40                  45

Ser Cys Met Arg Gly Arg Asp Gly Ser Thr Tyr Tyr Ala Asp Ser Val
    50                  55                  60

Asn Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala His Thr Asp Phe Ala Cys Tyr Ile Gly Tyr Tyr Ser Asp Tyr
            100                 105                 110

Asp Pro His Asp Tyr Trp Gly Gln Gly Thr Gln Val Thr Val Ser Ser
        115                 120                 125

<210> SEQ ID NO 336
<211> LENGTH: 115
<212> TYPE: PRT
<213> ORGANISM: Artificial
<220> FEATURE:
<223> OTHER INFORMATION: Nanobody, nanobody fragment or nanobody construct

<400> SEQUENCE: 336

Glu Val Gln Leu Val Glu Ser Gly Gly Gly Leu Val Gln Pro Gly Gly
1               5                   10                  15

```
Ser Leu Arg Leu Ser Cys Ala Thr Ser Gly Val Ile Phe Ser Thr Ala
            20                  25                  30

Ala Met Gly Trp Tyr Arg Gln Ala Pro Gly Lys Ser Arg Val Leu Val
        35                  40                  45

Ala Arg Met Phe Ser Asp Gly Arg Thr Ile Tyr Ala Glu Ser Val Lys
50                  55                  60

Arg Arg Phe Thr Ile Ser Arg Asp Asn Ala Lys Asn Thr Val Tyr Leu
65                  70                  75                  80

Gln Met Asn Ser Leu Glu Pro Glu Asp Thr Ala Val Tyr Tyr Cys Asn
                85                  90                  95

Ala Leu Gln Phe Gly Ala Val Tyr Trp Gly Gln Gly Thr Gln Val Thr
            100                 105                 110

Val Ser Ser
    115

<210> SEQ ID NO 337
<211> LENGTH: 115
<212> TYPE: PRT
<213> ORGANISM: Artificial
<220> FEATURE:
<223> OTHER INFORMATION: Nanobody, nanobody fragment or nanobody
      construct

<400> SEQUENCE: 337

Glu Val Gln Leu Val Lys Ser Gly Gly Gly Leu Val Gln Pro Gly Gly
1               5                   10                  15

Ser Leu Arg Leu Ser Cys Ala Ala Ser Gly Ser Ile Val Ser Ala Asn
            20                  25                  30

Leu Ile Gly Trp Tyr Arg Gln Ala Pro Gly Lys Gln Arg Glu Gly Val
        35                  40                  45

Ala Phe Ile Thr Ser Gly Gly Ala Ile Asn Tyr Ala Asp Ser Val Lys
50                  55                  60

Gly Arg Phe Thr Ile Ser Arg Asp Asp Ala Lys Asn Thr Val Tyr Leu
65                  70                  75                  80

Gln Met Asn Ser Leu Lys Pro Glu Asp Thr Ala Ile Tyr Tyr Cys Asn
                85                  90                  95

Leu Arg Gln Leu Gly Asn Val Tyr Trp Ala Gln Gly Thr Gln Val Thr
            100                 105                 110

Val Ser Ser
    115

<210> SEQ ID NO 338
<211> LENGTH: 115
<212> TYPE: PRT
<213> ORGANISM: Artificial
<220> FEATURE:
<223> OTHER INFORMATION: Nanobody, nanobody fragment or nanobody
      construct

<400> SEQUENCE: 338

Glu Val Gln Leu Val Glu Ser Gly Gly Gly Leu Val Gln Pro Gly Gly
1               5                   10                  15

Ser Leu Arg Leu Ser Cys Ala Thr Ser Gly Val Ile Phe Ser Thr Ala
            20                  25                  30

Ala Met Gly Trp Tyr Arg Gln Ala Pro Gly Lys Ser Arg Val Leu Val
        35                  40                  45

Ala Arg Met Phe Ser Asp Gly Arg Thr Ile Tyr Ala Glu Ser Val Lys
50                  55                  60

Arg Arg Phe Thr Ile Ser Arg Asp Asn Ala Lys Asn Thr Val Tyr Leu
```

-continued

```
                65                  70                  75                  80
Gln Met Asn Ser Leu Glu Pro Glu Asp Thr Ala Val Tyr Tyr Cys Asn
                    85                  90                  95

Ala Leu Gln Phe Gly Ala Val Tyr Trp Gly Gln Gly Thr Gln Val Thr
                    100                 105                 110

Val Ser Ser
        115

<210> SEQ ID NO 339
<211> LENGTH: 119
<212> TYPE: PRT
<213> ORGANISM: Artificial
<220> FEATURE:
<223> OTHER INFORMATION: Nanobody, nanobody fragment or nanobody
      construct

<400> SEQUENCE: 339

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Ser Ser Pro Ile
                20                  25                  30

Ala Met Gly Trp Phe Arg Gln Ala Pro Gly Lys Glu Arg Glu Phe Val
            35                  40                  45

Ser Gly Ile Thr Trp Ser Gly Ala Tyr Thr His Tyr Ala Asn Ser Val
        50                  55                  60

Lys Gly Arg Phe Thr Ile Ser Arg Asp Ser Ala Lys Asn Thr Val Tyr
65                  70                  75                  80

Leu Gln Met Asn Ser Leu Lys Pro Glu Asp Thr Ala Val Tyr Tyr Cys
                85                  90                  95

Thr Thr Ala Thr Asn Ser Thr Thr Gly Tyr Asp Tyr Trp Gly Gln Gly
            100                 105                 110

Thr Gln Val Thr Val Ser Ser
        115

<210> SEQ ID NO 340
<211> LENGTH: 117
<212> TYPE: PRT
<213> ORGANISM: Artificial
<220> FEATURE:
<223> OTHER INFORMATION: Nanobody, nanobody fragment or nanobody
      construct

<400> SEQUENCE: 340

Glu Val Gln Leu Val Glu Ser Gly Gly Asp Leu Val Gln Pro Gly Gly
1               5                   10                  15

Ser Leu Arg Leu Ser Cys Ala Ala Ser Gly Thr Val Phe Ser Asn Asn
                20                  25                  30

Asp Met Gly Trp Ser Arg Gln Ala Pro Gly Lys Glu Arg Glu Leu Val
            35                  40                  45

Ala Ser Phe Thr Ser Gly Gly Asn Thr Val Tyr Ala Asp Ala Ala Lys
        50                  55                  60

Gly Arg Phe Thr Ile Ser Arg Asp Asn Ser Lys Asn Thr Val Tyr Leu
65                  70                  75                  80

Glu Met Asn Ser Leu Lys Pro Asp Asp Thr Ala Val Tyr Tyr Cys Arg
                85                  90                  95

Val Val Asp Leu Leu Arg Gly Lys Leu Tyr Trp Gly Gln Gly Thr Gln
            100                 105                 110

Val Thr Val Ser Ser
        115
```

<210> SEQ ID NO 341
<211> LENGTH: 117
<212> TYPE: PRT
<213> ORGANISM: Artificial
<220> FEATURE:
<223> OTHER INFORMATION: Nanobody, nanobody fragment or nanobody construct

<400> SEQUENCE: 341

Glu Val Gln Leu Val Glu Ser Gly Gly Asp Leu Val Gln Pro Gly Gly
1               5                   10                  15

Ser Leu Arg Leu Ser Cys Ala Ala Ser Gly Thr Val Phe Ser Asn Asn
            20                  25                  30

Asp Met Gly Trp Ser Arg Gln Ala Pro Gly Lys Glu Arg Glu Leu Val
        35                  40                  45

Ala Ser Phe Thr Ser Gly Gly Asn Thr Val Tyr Ala Asp Ala Ala Lys
    50                  55                  60

Gly Arg Phe Thr Ile Ser Arg Asp Asn Ser Lys Asn Thr Val Tyr Leu
65                  70                  75                  80

Glu Met Asn Ser Leu Lys Pro Asp Asp Thr Ala Val Tyr Tyr Cys Arg
                85                  90                  95

Val Val Asp Leu Leu Arg Gly Lys Leu Tyr Trp Gly Gln Gly Thr Gln
            100                 105                 110

Val Thr Val Ser Ser
        115

<210> SEQ ID NO 342
<211> LENGTH: 117
<212> TYPE: PRT
<213> ORGANISM: Artificial
<220> FEATURE:
<223> OTHER INFORMATION: Nanobody, nanobody fragment or nanobody construct

<400> SEQUENCE: 342

Glu Val Gln Leu Val Glu Ser Gly Gly Asp Leu Val Gln Pro Gly Gly
1               5                   10                  15

Ser Leu Arg Leu Ser Cys Ala Ala Ser Arg Thr Val Phe Ser Ile Ser
            20                  25                  30

Asp Met Gly Trp Ser Arg Gln Ala Pro Gly Lys Glu Arg Glu Leu Val
        35                  40                  45

Ala Ser Ile Ser Ser Asp Asn Tyr Thr Val Tyr Ala Asp Ala Ala Lys
    50                  55                  60

Gly Arg Phe Thr Ile Ser Arg Asp Asn Ser Lys Asn Thr Val Tyr Leu
65                  70                  75                  80

Glu Met Asn Ser Leu Lys Pro Asp Asp Thr Ala Val Tyr Tyr Cys Arg
                85                  90                  95

Val Val Asp Pro Leu Arg Gly Lys Leu Tyr Trp Gly Gln Gly Thr Gln
            100                 105                 110

Val Thr Val Ser Ser
        115

<210> SEQ ID NO 343
<211> LENGTH: 117
<212> TYPE: PRT
<213> ORGANISM: Artificial
<220> FEATURE:
<223> OTHER INFORMATION: Nanobody, nanobody fragment or nanobody construct -continued

<400> SEQUENCE: 343

Glu Val Gln Leu Val Glu Ser Gly Gly Gly Leu Val Gln Ala Gly Gly
1               5                   10                  15

Ser Leu Arg Leu Ser Cys Ala Ala Ser Gly Gly Ile Phe Gly Ile Asn
            20                  25                  30

Ala Val Ala Trp Tyr Arg Gln Ala Pro Gly Lys Glu Arg Asp Trp Val
        35                  40                  45

Ala Leu Ile Val Gly Glu Ala Ile Thr Arg Tyr Thr Asp Ser Val Ser
    50                  55                  60

Gly Arg Phe Thr Ile Ser Arg Asp Asn Ala Lys Asn Thr Val Tyr Leu
65                  70                  75                  80

Glu Met Asn Ser Leu Lys Pro Asp Asp Thr Ala Val Tyr Tyr Cys Arg
                85                  90                  95

Val Val Asp Pro Leu Arg Gly Lys Leu Tyr Trp Gly Gln Gly Thr Gln
            100                 105                 110

Val Thr Val Ser Ser
        115

<210> SEQ ID NO 344
<211> LENGTH: 117
<212> TYPE: PRT
<213> ORGANISM: Artificial
<220> FEATURE:
<223> OTHER INFORMATION: Nanobody, nanobody fragment or nanobody
      construct

<400> SEQUENCE: 344

Glu Val Gln Leu Val Glu Ser Gly Gly Asp Leu Val Gln Pro Gly Gly
1               5                   10                  15

Ser Leu Arg Leu Ser Cys Thr Thr Ser Gly Thr Val Phe Ser Ile Asn
            20                  25                  30

Asp Met Gly Trp Ser Arg Gln Ala Pro Gly Lys Gly Arg Glu Leu Val
        35                  40                  45

Ala Ser Ile Ser Ser Glu Gly Thr Thr Ile Tyr Ala Asp Ala Ala Lys
    50                  55                  60

Gly Arg Phe Thr Ile Ser Arg Asp Asn Ser Lys Asn Thr Val Tyr Leu
65                  70                  75                  80

Glu Met Asn Ser Leu Lys Pro Asp Asp Thr Ala Val Tyr Tyr Cys Arg
                85                  90                  95

Val Val Asp Pro Leu Arg Gly Lys Leu Tyr Trp Gly Gln Gly Thr Gln
            100                 105                 110

Val Thr Val Ser Ser
        115

<210> SEQ ID NO 345
<211> LENGTH: 121
<212> TYPE: PRT
<213> ORGANISM: Artificial
<220> FEATURE:
<223> OTHER INFORMATION: Nanobody, nanobody fragment or nanobody
      construct

<400> SEQUENCE: 345

Glu Val Gln Leu Val Glu Ser Gly Gly Gly Leu Val Gln Ala Gly Asp
1               5                   10                  15

Ser Leu Arg Leu Ser Cys Ala Val Ser Gly Gly Ser Phe Ser Ser Tyr
            20                  25                  30

Thr Met Gly Trp Val Arg Gln Ala Pro Gly Lys Glu Arg Glu Ala Val
        35                  40                  45

Ala Ser Ile Trp Arg Ser Gly Gly Asn Thr Tyr Tyr Ala Asp Ser Val
        50                  55                  60

Lys Gly Arg Phe Thr Val Ser Arg Asp Asn Ala Lys His Thr Val Tyr
 65                  70                  75                  80

Leu Gln Met Asn Ser Leu Lys Pro Glu Asp Thr Ala Val Tyr Tyr Cys
                 85                  90                  95

Ala Ala Ala Ser Phe Ala Pro Gly Ser Arg Gly Tyr Asp Tyr Trp Gly
            100                 105                 110

Gln Gly Thr Gln Val Thr Val Ser Ser
        115                 120

<210> SEQ ID NO 346
<211> LENGTH: 119
<212> TYPE: PRT
<213> ORGANISM: Artificial
<220> FEATURE:
<223> OTHER INFORMATION: Nanobody, nanobody fragment or nanobody
      construct

<400> SEQUENCE: 346

Glu Val Gln Leu Val Glu Ser Gly Gly Gly Leu Val Gln Pro Gly Gly
 1               5                  10                  15

Ser Leu Arg Leu Ser Cys Ala Ala Ser Gly Arg Thr Ser Ser Pro Ile
             20                  25                  30

Ala Met Gly Trp Phe Arg Gln Ala Pro Gly Lys Glu Arg Glu Phe Val
         35                  40                  45

Ser Gly Ile Thr Trp Ser Gly Ala Tyr Thr His Tyr Ala Asn Ser Val
     50                  55                  60

Lys Gly Arg Phe Thr Ile Ser Arg Asp Ser Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Thr Thr Ala Thr Asn Ser Thr Thr Gly Tyr Asp Tyr Trp Gly Gln Gly
            100                 105                 110

Thr Gln Val Thr Val Ser Ser
        115

<210> SEQ ID NO 347
<211> LENGTH: 117
<212> TYPE: PRT
<213> ORGANISM: Artificial
<220> FEATURE:
<223> OTHER INFORMATION: Nanobody, nanobody fragment or nanobody
      construct

<400> SEQUENCE: 347

Glu Val Gln Leu Val Glu Ser Gly Gly Asp Leu Val Gln Pro Gly Gly
 1               5                  10                  15

Ser Leu Arg Leu Ser Cys Ala Ala Ser Ala Thr Val Phe Ser Asn Ser
             20                  25                  30

Asp Met Gly Trp Ser Arg Gln Ala Pro Gly Lys Glu Arg Glu Leu Val
         35                  40                  45

Ala Ser Ile Thr Thr Asp Gly Asn Thr Leu Tyr Ala Asp Ala Ala Lys
     50                  55                  60

Gly Arg Phe Ala Ile Tyr Arg Asp Asn Ser Lys Asn Thr Val Tyr Leu
 65                  70                  75                  80

Glu Met Asn Ser Leu Lys Pro Asp Asp Thr Ala Val Tyr Tyr Cys Arg
                 85                  90                  95

Val Val Asp Leu Leu Arg Gly Lys Leu Tyr Trp Gly Gln Gly Thr Gln
            100                 105                 110

Val Thr Val Ser Ser
        115

<210> SEQ ID NO 348
<211> LENGTH: 121
<212> TYPE: PRT
<213> ORGANISM: Artificial
<220> FEATURE:
<223> OTHER INFORMATION: Nanobody, nanobody fragment or nanobody
      construct

<400> SEQUENCE: 348

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser Ile Thr
            20                  25                  30

Glu Met Asp Trp Tyr Arg Gln Ala Pro Gly Lys Gln Arg Glu Trp Val
        35                  40                  45

Ala Gly Glu Thr Ser Asp Gly Ser Thr Asn Tyr Ala Asp Ser Val Lys
50                  55                  60

Gly Arg Phe Thr Ile Ser Arg Asp Asn Ala Asn Asn Ala Val Tyr Leu
65                  70                  75                  80

Gln Met Asn Arg Leu Lys Pro Glu Asp Thr Ala Val Tyr His Cys Ala
            85                  90                  95

Ala Ser Leu Arg Asn Ser Gly Ser Asn Val Glu Gly Arg Tyr Trp Gly
            100                 105                 110

Gln Gly Thr Gln Val Thr Val Ser Ser
        115                 120

<210> SEQ ID NO 349
<211> LENGTH: 114
<212> TYPE: PRT
<213> ORGANISM: Artificial
<220> FEATURE:
<223> OTHER INFORMATION: Nanobody, nanobody fragment or nanobody
      construct

<400> SEQUENCE: 349

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ile Asn Ser Met Asn
            20                  25                  30

Trp Tyr His Gln Ala Pro Gly Lys Glu Arg Glu Trp Val Ala Ser Ile
        35                  40                  45

Thr Ser Ser Gly Thr Ala Ile Tyr Ala Asp Ser Val Lys Gly Arg Ile
    50                  55                  60

Thr Ile Ser Arg Asp Asn Ala Lys Asn Thr Val Tyr Leu Gln Met Asn
65                  70                  75                  80

Ser Leu Lys Thr Glu Asp Thr Gly Val Tyr Tyr Cys Ala Ala Asn Leu
            85                  90                  95

Gln Asn Ala Arg Gly Ser Tyr Tyr Gly Gln Gly Thr Gln Val Thr Val
            100                 105                 110

Ser Ser

<210> SEQ ID NO 350
<211> LENGTH: 116
<212> TYPE: PRT
<213> ORGANISM: Artificial -continued

```
<220> FEATURE:
<223> OTHER INFORMATION: Nanobody, nanobody fragment or nanobody
      construct

<400> SEQUENCE: 350

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Asp Tyr
            20                  25                  30

Ala Met Asn Trp Val Arg Gln Ala Pro Gly Lys Gly Leu Glu Trp Val
        35                  40                  45

Ser Ser Ile Ser Ala Gly Gly Tyr Ser Thr Thr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Asn Pro Glu Asp Thr Ala Val Tyr Tyr Cys
                85                  90                  95

Ala Arg Gly Asp Trp Arg Tyr Gly Ser Arg Gly Gln Gly Thr Gln Val
            100                 105                 110

Thr Val Ser Ser
        115

<210> SEQ ID NO 351
<211> LENGTH: 116
<212> TYPE: PRT
<213> ORGANISM: Artificial
<220> FEATURE:
<223> OTHER INFORMATION: Nanobody, nanobody fragment or nanobody
      construct

<400> SEQUENCE: 351

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Met Ser Ile Asn
            20                  25                  30

Ala Met Arg Trp Tyr Arg Gln Ala Ser Gly Lys Gln Arg Glu Pro Val
        35                  40                  45

Ala Glu Ile Thr Ser Glu Gly Thr Ile Ile Tyr Ala Asp Ser Val Lys
    50                  55                  60

Gly Arg Phe Thr Thr Ser Arg Asp Asn Ala Lys Asn Thr Val Tyr Leu
65                  70                  75                  80

Gln Met Asn Ser Leu Lys Pro Glu Asp Thr Gly Val Tyr Tyr Cys Ala
                85                  90                  95

Ala Asp Asp Gly Ala Arg Gly Ser Tyr Tyr Gly Gln Gly Thr Gln Val
            100                 105                 110

Thr Val Ser Ser
        115

<210> SEQ ID NO 352
<211> LENGTH: 117
<212> TYPE: PRT
<213> ORGANISM: Artificial
<220> FEATURE:
<223> OTHER INFORMATION: Nanobody, nanobody fragment or nanobody
      construct

<400> SEQUENCE: 352

Glu Val Gln Leu Val Glu Ser Gly Gly Ala Leu Val Gln Ala Gly Gly
1               5                   10                  15

Ser Leu Arg Leu Ser Cys Val Ala Ser Gly Ser Ser Phe Ser Ile Asn
```

-continued

```
                    20                  25                  30
Asp Met Asp Trp Tyr Arg Gln Ala Pro Gly Lys Thr Arg Glu Trp Val
            35                  40                  45
Ala Gly Ile Asn Glu Tyr Gly Gly Arg Asn Tyr Ala Asn Ser Val Lys
        50                  55                  60
Asp Arg Phe Thr Ile Ser Thr Asp Asn Ala Lys Asn Thr Val Tyr Leu
65                  70                  75                  80
Gln Met Asn Ser Leu Lys Pro Glu Asp Thr Gly Val Tyr Tyr Cys Ala
                85                  90                  95
Ala Thr Leu Ala Lys Gly Gly Arg Tyr Trp Gly Gln Gly Thr Pro
            100                 105                 110
Val Thr Val Ser Ser
            115

<210> SEQ ID NO 353
<211> LENGTH: 117
<212> TYPE: PRT
<213> ORGANISM: Artificial
<220> FEATURE:
<223> OTHER INFORMATION: Nanobody, nanobody fragment or nanobody
      construct

<400> SEQUENCE: 353

Glu Val Lys Leu Val Glu Ser Gly Gly Leu Val Gln Pro Gly Gly
1               5                   10                  15
Ser Leu Arg Leu Ser Cys Ala Ala Ser Gly Ser Ile Phe Arg Phe Asn
            20                  25                  30
Gly Val Asp Trp Tyr Arg Gln Ala Pro Gly Ala Glu Arg Glu Trp Val
            35                  40                  45
Ala Gly Phe Gly Ser Gly Gly Thr Thr Asn Tyr Ala Asp Ser Val Lys
        50                  55                  60
Gly Arg Phe Ile Val Ser Arg Asp Asn Ala Glu Asn Thr Val Phe Leu
65                  70                  75                  80
Gln Met Asn Ser Leu Lys Pro Glu Asp Ser Ala Val Tyr Phe Cys Ala
                85                  90                  95
Ala Ser Ile Glu Gly Val Ser Gly Arg Tyr Tyr Gly Gln Gly Thr Gln
            100                 105                 110
Val Thr Val Ser Ser
            115

<210> SEQ ID NO 354
<211> LENGTH: 120
<212> TYPE: PRT
<213> ORGANISM: Artificial
<220> FEATURE:
<223> OTHER INFORMATION: Nanobody, nanobody fragment or nanobody
      construct

<400> SEQUENCE: 354

Glu Val Gln Leu Val Glu Ser Gly Gly Gly Leu Val Gln Ala Gly Gly
1               5                   10                  15
Ser Leu Arg Leu Ser Cys Val Val Ser Gly Ser Ile Leu Ser Ile Asn
            20                  25                  30
Thr Met Asp Trp Tyr Arg Gln Ala Pro Gly Asn Glu Arg Glu Trp Val
            35                  40                  45
Gly Gly Ile Thr Asp Gly Gly Arg Ser Asn Tyr Ala Asp Ser Val Lys
        50                  55                  60
Asp Arg Phe Thr Ile Tyr Arg Ala Asn Ala Lys Asn Thr Val Tyr Leu
65                  70                  75                  80
```

```
Gln Met Asn Ser Leu Lys Pro Glu Asp Thr Ala Val Tyr Tyr Cys Ala
                85                  90                  95

Ala Asp Leu Arg Gly Gly Ile Ala Thr Thr Gly Arg Tyr Trp Gly Gln
            100                 105                 110

Gly Thr Gln Val Thr Val Ser Ser
        115                 120

<210> SEQ ID NO 355
<211> LENGTH: 119
<212> TYPE: PRT
<213> ORGANISM: Artificial
<220> FEATURE:
<223> OTHER INFORMATION: Nanobody, nanobody fragment or nanobody
      construct

<400> SEQUENCE: 355

Glu Val Gln Leu Val Glu Ser Gly Gly Gly Leu Val Gln Ala Gly Gly
1               5                   10                  15

Ser Leu Arg Leu Ser Cys Ala Ala Ser Gly Met Thr Thr Ile Gly Pro
            20                  25                  30

Met Gly Trp Tyr Arg Gln Gly Pro Gly Lys Gln Arg Glu Leu Val Ala
        35                  40                  45

Arg Ile Thr Gly Gly Gly Ser Thr Asn Tyr Val Asp Ser Ala Lys Gly
    50                  55                  60

Arg Phe Thr Ile Ser Arg Asp Asn Ala Lys Asn Ala Val Tyr Leu Gln
65                  70                  75                  80

Met Asn Asn Leu Lys Leu Asp Asp Thr Ala Val Tyr Tyr Cys Asn Ala
                85                  90                  95

Tyr Gly Ser Gly Ser Asp Tyr Leu Pro Ile Asp Tyr Trp Gly Gln Gly
            100                 105                 110

Thr Gln Val Thr Val Ser Ser
        115

<210> SEQ ID NO 356
<211> LENGTH: 119
<212> TYPE: PRT
<213> ORGANISM: Artificial
<220> FEATURE:
<223> OTHER INFORMATION: Nanobody, nanobody fragment or nanobody
      construct

<400> SEQUENCE: 356

Glu Val Gln Leu Val Glu Ser Gly Gly Gly Leu Val Gln Ala Gly Gly
1               5                   10                  15

Ser Leu Arg Leu Ser Cys Ala Ala Ser Gly Met Thr Thr Ile Gly Pro
            20                  25                  30

Met Gly Trp Tyr Arg Gln Gly Pro Gly Lys Gln Arg Glu Leu Val Ala
        35                  40                  45

Arg Ile Thr Gly Gly Gly Ser Thr Asn Tyr Val Asp Ser Ala Lys Gly
    50                  55                  60

Arg Phe Thr Ile Ser Arg Asp Asn Ala Lys Asn Met Gly Tyr Leu Gln
65                  70                  75                  80

Met Asn Asn Leu Lys Leu Asp Asp Thr Ala Ile Tyr Tyr Cys Tyr Ala
                85                  90                  95

Tyr Gly Ser Gly Ser Asp Tyr Leu Pro Thr Asp Tyr Trp Gly Gln Gly
            100                 105                 110

Thr Gln Val Thr Val Ser Ser
        115
```

<210> SEQ ID NO 357
<211> LENGTH: 119
<212> TYPE: PRT
<213> ORGANISM: Artificial
<220> FEATURE:
<223> OTHER INFORMATION: Nanobody, nanobody fragment or nanobody
      construct

<400> SEQUENCE: 357

Glu Val Gln Leu Val Glu Ser Gly Gly Gly Leu Val Gln Ala Gly Gly
1               5                   10                  15

Ser Leu Arg Leu Ser Cys Ala Ala Ser Gly Met Thr Thr Ile Gly Pro
            20                  25                  30

Met Gly Trp Tyr Arg Gln Gly Pro Gly Lys Gln Arg Glu Leu Val Ala
        35                  40                  45

Arg Ile Thr Gly Gly Gly Ser Thr Asn Tyr Val Asp Ser Ala Lys Gly
    50                  55                  60

Arg Phe Thr Ile Ser Arg His Asn Ala Lys Asn Met Val Tyr Leu Gln
65                  70                  75                  80

Met Asn Asn Leu Lys Leu Asp Asp Thr Ala Val Tyr Tyr Cys Asn Ala
                85                  90                  95

Tyr Gly Ser Gly Ser Asp Tyr Leu Pro Met Asp Tyr Trp Gly Gln Gly
            100                 105                 110

Thr Gln Val Thr Val Ser Ser
        115

<210> SEQ ID NO 358
<211> LENGTH: 120
<212> TYPE: PRT
<213> ORGANISM: Artificial
<220> FEATURE:
<223> OTHER INFORMATION: Nanobody, nanobody fragment or nanobody
      construct

<400> SEQUENCE: 358

Glu Val Gln Leu Val Glu Ser Gly Gly Gly Leu Val Gln Ala Gly Gly
1               5                   10                  15

Ser Leu Arg Leu Ser Cys Val Val Ser Gly Ser Ile Leu Ser Ile Asn
            20                  25                  30

Thr Met Asp Trp Tyr Arg Gln Ala Pro Gly Lys Gln Arg Glu Trp Phe
        35                  40                  45

Ala Gly Leu Ser Asp Gly Gly Arg Ala Asn Tyr Ala Asp Ser Val Lys
    50                  55                  60

Asp Arg Phe Thr Ile Ala Arg Asp Asn Ala Lys Asn Thr Val Tyr Leu
65                  70                  75                  80

Gln Met Asn Ser Leu Lys Pro Gly Asp Thr Ala Ile Tyr Tyr Cys Ala
                85                  90                  95

Ala Asp Leu Trp Asp Arg Gly Ala Thr Thr Gly Arg Tyr Trp Gly Gln
            100                 105                 110

Gly Thr Gln Val Thr Val Ser Ser
        115                 120

<210> SEQ ID NO 359
<211> LENGTH: 114
<212> TYPE: PRT
<213> ORGANISM: Artificial
<220> FEATURE:
<223> OTHER INFORMATION: Nanobody, nanobody fragment or nanobody
      construct

<400> SEQUENCE: 359

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ile Asn Ser Met Asn
            20                  25                  30

Trp Tyr Arg Gln Ala Pro Gly Lys Glu Arg Glu Trp Val Ala Ser Ile
        35                  40                  45

Thr Ser Ser Gly Thr Thr Ile Tyr Ala Asp Ser Val Lys Gly Arg Ile
    50                  55                  60

Thr Ile Ser Glu Asp Asn Ala Lys Asn Thr Val Tyr Leu Gln Met Asn
65                  70                  75                  80

Ser Leu Lys Thr Glu Asp Thr Gly Val Tyr Tyr Cys Ala Ala Asn Leu
            85                  90                  95

Arg Asn Ala Arg Gly Ser Tyr Tyr Gly Gln Gly Thr Gln Val Thr Val
            100                 105                 110

Ser Ser

<210> SEQ ID NO 360
<211> LENGTH: 116
<212> TYPE: PRT
<213> ORGANISM: Artificial
<220> FEATURE:
<223> OTHER INFORMATION: Nanobody, nanobody fragment or nanobody
      construct

<400> SEQUENCE: 360

Glu Val Gln Leu Val Glu Ser Gly Gly Gly Leu Val Gln Ala Gly Gly
1               5                   10                  15

Ser Leu Arg Leu Ser Cys Ala Ala Ser Thr Asn Val Ser Ser Phe Asn
            20                  25                  30

Thr Met Ser Trp Tyr Arg Gln Ser Pro Arg Lys Gln Arg Glu Trp Val
        35                  40                  45

Ala Thr Ile Thr Asp Gly Asp Asn Thr His Tyr Ala Asp Ser Val Lys
    50                  55                  60

Gly Arg Phe Thr Thr Ser Arg Asp Asn Ala Lys Asn Leu Leu Tyr Leu
65                  70                  75                  80

Gln Met Asn Ser Leu Lys Pro Glu Asp Thr Ala Val Tyr Tyr Cys Thr
            85                  90                  95

Gly Trp Arg Ala Thr Ser Gly Gly Ser Tyr Gly Gln Gly Thr Gln Val
            100                 105                 110

Thr Val Ser Ser
        115

<210> SEQ ID NO 361
<211> LENGTH: 116
<212> TYPE: PRT
<213> ORGANISM: Artificial
<220> FEATURE:
<223> OTHER INFORMATION: Nanobody, nanobody fragment or nanobody
      construct

<400> SEQUENCE: 361

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Asp Tyr
            20                  25                  30

Ala Met Asn Trp Val Arg Gln Ala Pro Gly Lys Gly Leu Glu Trp Val
        35                  40                  45

Ser Ser Ile Ser Ala Gly Gly Tyr Ser Thr Thr Tyr Ala Asp Ser Val

```
                    50                  55                  60
Lys Gly Arg Phe Thr Ile Ser Arg Asp Asn Ala Lys Asn Thr Leu Tyr
 65                  70                  75                  80

Leu Gln Met Asn Ser Leu Asn Pro Glu Asp Thr Ala Val Tyr Tyr Cys
                 85                  90                  95

Ala Arg Gly Asp Trp Arg Tyr Gly Ser Arg Gly Gln Gly Thr Gln Val
            100                 105                 110

Thr Val Ser Ser
            115

<210> SEQ ID NO 362
<211> LENGTH: 124
<212> TYPE: PRT
<213> ORGANISM: Artificial
<220> FEATURE:
<223> OTHER INFORMATION: Nanobody, nanobody fragment or nanobody
      construct

<400> SEQUENCE: 362

Glu Val Gln Leu Val Glu Ser Gly Gly Asp Leu Val Gln Pro Gly Gly
  1               5                  10                  15

Ser Leu Arg Leu Ser Cys Ala Ala Ser Gly Phe Thr Phe Ser Thr Tyr
             20                  25                  30

Tyr Met Ser Trp Val Arg Gln Ala Pro Gly Lys Gly Leu Glu Trp Val
         35                  40                  45

Ser Gly Ile Tyr Ser Asp Gly Ser Asn Thr Tyr Tyr Ala Asp Ser Val
     50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Ser Glu Asp Thr Ala Val Tyr Tyr Cys
                 85                  90                  95

Thr Arg Pro Val Val Val Ala Gly Ser Pro Val Ser Tyr Glu Tyr Asp
            100                 105                 110

Tyr Ile Gly Gln Gly Thr Gln Val Thr Val Ser Ser
            115                 120

<210> SEQ ID NO 363
<211> LENGTH: 124
<212> TYPE: PRT
<213> ORGANISM: Artificial
<220> FEATURE:
<223> OTHER INFORMATION: Nanobody, nanobody fragment or nanobody
      construct

<400> SEQUENCE: 363

Glu Val Gln Leu Val Glu Ser Gly Gly Asp Leu Val Gln Pro Gly Gly
  1               5                  10                  15

Ser Leu Arg Leu Ser Cys Ala Ala Ser Gly Phe Thr Phe Ser Thr Tyr
             20                  25                  30

Tyr Met Ser Trp Val Arg Gln Ala Pro Gly Lys Gly Leu Glu Trp Val
         35                  40                  45

Ser Gly Ile Tyr Ser Asp Gly Ser Asn Thr Tyr Tyr Ala Asp Ser Val
     50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Ser Glu Asp Thr Ala Val Tyr Tyr Cys
                 85                  90                  95

Thr Arg Pro Val Val Val Ala Gly Ser Pro Val Ser Tyr Glu Tyr Asp
            100                 105                 110
```

```
Tyr Ile Gly Gln Gly Thr Gln Val Thr Val Ser Ser
        115                 120

<210> SEQ ID NO 364
<211> LENGTH: 117
<212> TYPE: PRT
<213> ORGANISM: Artificial
<220> FEATURE:
<223> OTHER INFORMATION: Nanobody, nanobody fragment or nanobody
      construct

<400> SEQUENCE: 364

Glu Val Gln Leu Val Glu Ser Gly Gly Asp Leu Val Gln Pro Gly Gly
1               5                   10                  15

Ser Leu Arg Leu Ser Cys Thr Thr Ser Gly Thr Val Phe Ser Ile Asn
            20                  25                  30

Asp Met Gly Trp Ser Arg Gln Ala Pro Gly Lys Gly Arg Glu Leu Val
        35                  40                  45

Ala Ser Ile Ser Ser Glu Gly Thr Thr Ile Tyr Ala Asp Ala Ala Lys
    50                  55                  60

Gly Arg Phe Thr Ile Ser Arg Asp Asn Ser Lys Asn Thr Val Tyr Leu
65                  70                  75                  80

Glu Met Asn Ser Leu Lys Pro Asp Asp Thr Ala Val Tyr Tyr Cys Arg
                85                  90                  95

Val Val Asp Pro Leu Arg Gly Lys Leu Tyr Trp Gly Gln Gly Thr Gln
            100                 105                 110

Val Thr Val Ser Ser
        115

<210> SEQ ID NO 365
<211> LENGTH: 114
<212> TYPE: PRT
<213> ORGANISM: Artificial
<220> FEATURE:
<223> OTHER INFORMATION: Nanobody, nanobody fragment or nanobody
      construct

<400> SEQUENCE: 365

Glu Val Gln Leu Val Glu Ser Gly Gly Gly Leu Val Gln Ala Gly Gly
1               5                   10                  15

Ser Leu Arg Leu Ser Cys Ala Thr Ser Gly Phe Thr Phe Ser Arg Phe
            20                  25                  30

Asp Met Ser Trp Phe Arg Gln Ala Pro Gly Lys Gln Arg Glu Phe Ile
        35                  40                  45

Ala Thr Ile Phe Ser Gly Gly Asp Thr Asp Tyr Ile Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Cys
                85                  90                  95

Pro Leu Gly Ile Glu Tyr Ala Trp Gly Gln Gly Thr Gln Val Thr Val
            100                 105                 110

Ser Ser
```